United States Patent
Jang et al.

(10) Patent No.: US 10,505,125 B2
(45) Date of Patent: Dec. 10, 2019

(54) COMPOUND FOR ORGANIC OPTOELECTRONIC DIODE, ORGANIC OPTOELECTRONIC DIODE COMPRISING SAME, AND DISPLAY DEVICE

(71) Applicant: SAMSUNG SDI CO., LTD., Yongin-si, Gyeonggi-do (KR)

(72) Inventors: Kipo Jang, Suwon-si (KR); Youngkwon Kim, Suwon-si (KR); Byungku Kim, Suwon-si (KR); Byoungkwan Lee, Suwon-si (KR); Jinhyun Lui, Suwon-si (KR); Eun Sun Yu, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 111 days.

(21) Appl. No.: 15/541,810

(22) PCT Filed: Feb. 17, 2016

(86) PCT No.: PCT/KR2016/001612
§ 371 (c)(1),
(2) Date: Jul. 6, 2017

(87) PCT Pub. No.: WO2016/182174
PCT Pub. Date: Nov. 17, 2016

(65) Prior Publication Data
US 2018/0006242 A1   Jan. 4, 2018

(30) Foreign Application Priority Data
May 13, 2015   (KR) .................. 10-2015-0066839

(51) Int. Cl.
*H01L 51/00*  (2006.01)
*C07D 495/04*  (2006.01)
(Continued)

(52) U.S. Cl.
CPC ........ *H01L 51/0072* (2013.01); *C07D 239/70* (2013.01); *C07D 403/04* (2013.01);
(Continued)

(58) Field of Classification Search
None
See application file for complete search history.

(56) References Cited

U.S. PATENT DOCUMENTS 7,807,687 B2   10/2010  Salbeck et al.
2013/0207047 A1   8/2013  Suda et al.
(Continued)

FOREIGN PATENT DOCUMENTS

CN   101348484 A   1/2009
CN   101490008 A   7/2009
(Continued)

OTHER PUBLICATIONS

Machine English translation of Choi et al. (KR 10-2015-0080966). Dec. 18, 2018.*
(Continued)

*Primary Examiner* — Jay Yang
(74) *Attorney, Agent, or Firm* — Lee & Morse, P.C.

(57) ABSTRACT

The present invention relates to: a compound for an organic optoelectronic diode, represented by a combination of chemical formulas 1 and 2; an organic optoelectronic diode comprising the same; and a display device comprising the organic optoelectronic diode. The detailed contents of formulas 1 and 2 are the same as those defined in the specification.

16 Claims, 1 Drawing Sheet

(51) Int. Cl.
- *C07F 7/08* (2006.01)
- *C07D 403/14* (2006.01)
- *C07D 491/048* (2006.01)
- *C09K 11/02* (2006.01)
- *H01L 51/56* (2006.01)
- *H01L 51/50* (2006.01)
- *H01L 51/52* (2006.01)
- *C09K 11/06* (2006.01)
- *C07D 403/04* (2006.01)
- *C07D 403/10* (2006.01)
- *C07D 409/04* (2006.01)
- *C07D 239/70* (2006.01)
- *C07D 519/00* (2006.01)

(52) U.S. Cl.
CPC ......... *C07D 403/10* (2013.01); *C07D 403/14* (2013.01); *C07D 409/04* (2013.01); *C07D 491/048* (2013.01); *C07D 495/04* (2013.01); *C07D 519/00* (2013.01); *C07F 7/0816* (2013.01); *C09K 11/025* (2013.01); *C09K 11/06* (2013.01); *H01L 51/0054* (2013.01); *H01L 51/0071* (2013.01); *H01L 51/0094* (2013.01); *H01L 51/001* (2013.01); *H01L 51/0073* (2013.01); *H01L 51/0074* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01); *H01L 51/56* (2013.01)

(56) References Cited

U.S. PATENT DOCUMENTS

| | | |
|---|---|---|
| 2014/0131663 A1 | 5/2014 | Beers |
| 2015/0034938 A1 | 2/2015 | Kang et al. |

FOREIGN PATENT DOCUMENTS

| | | |
|---|---|---|
| KR | 10-2005-0089993 A | 9/2005 |
| KR | 20090035637 A | 4/2009 |
| KR | 20130067274 A | 6/2013 |
| KR | 20130114785 A | 10/2013 |
| KR | 20130119740 A | 11/2013 |
| KR | 20130127567 A | 11/2013 |
| KR | 20140067914 A | 6/2014 |
| KR | 20140074858 A | 6/2014 |
| KR | 20140080205 A | 6/2014 |
| KR | 20140083907 A | 7/2014 |
| KR | 20140145355 A | 12/2014 |
| KR | 20150080966 A | 7/2015 |
| KR | 20150111106 A | 10/2015 |
| KR | 10-2016-0025777 A | 3/2016 |
| KR | 10-2016-0089655 A | 7/2016 |

OTHER PUBLICATIONS

Johnson et al. (J. Het. Chem. 1977, 14(7), p. 1209).*
Iveta Wiedermannova et al. "Oxo Derivatives of Quinoxaline II* of," Etc., AUPO, Chemica 38, 83 1999.
Judith Johnson et al., "Antimalarial drugs, Part 37, Synthesis and Antimalarial Effects of [1] Benzothieno [3, 2-f] quinazoline-1, 3-diamine", Journal of Heterocyclic Chemistry, vol. 14, No. 7, pp. 1209-1214, Dec. 31, 1977.
Chinese Office Action dated Aug. 3, 2018, and/or the accompanying Search Report dated Jul. 25, 2018, of the corresponding Chinese Patent Application No. 201680004850.6.

* cited by examiner

[Fig. 1]
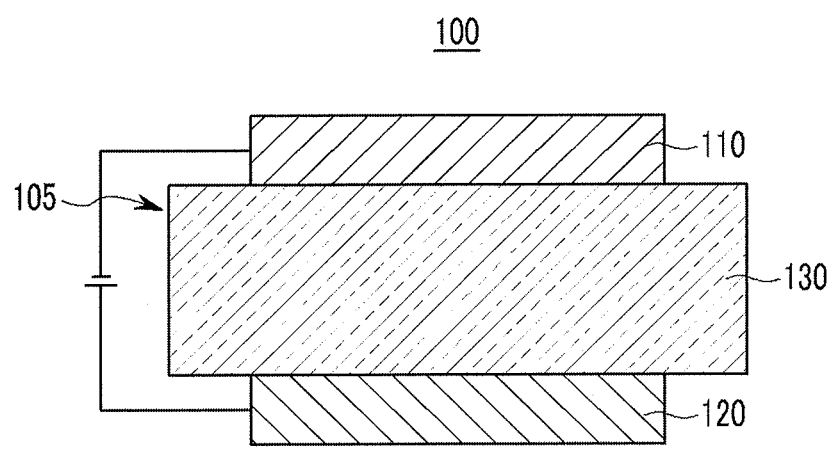
[Fig. 2]
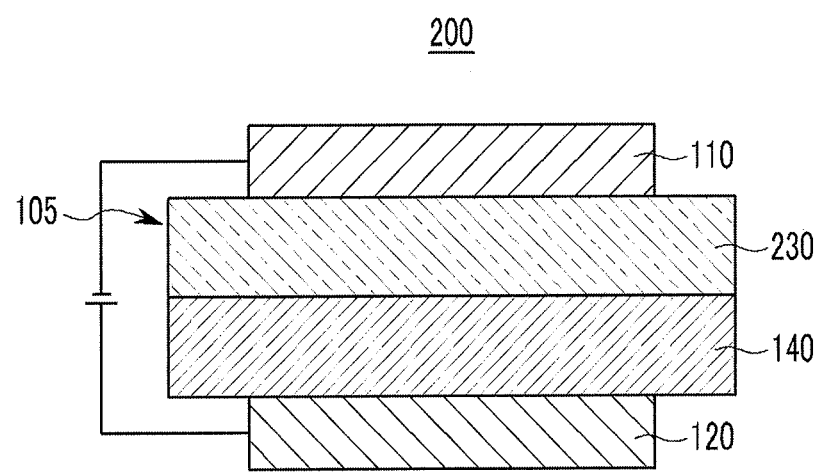

COMPOUND FOR ORGANIC OPTOELECTRONIC DIODE, ORGANIC OPTOELECTRONIC DIODE COMPRISING SAME, AND DISPLAY DEVICE

CROSS-REFERENCE TO RELATED APPLICATION

This is the U.S. national phase application based on PCT Application No. PCT/KR2016/001612, filed Feb. 17, 2016, which is based on Korean Patent Application No. 10-2015-0066839, filed May 13, 2015, the entire contents of all of which are hereby incorporated by reference.

TECHNICAL FIELD

A compound for an organic optoelectronic diode, an organic optoelectronic diode, and a display device are disclosed.

BACKGROUND ART

An organic optoelectronic diode is a device that converts electrical energy into photoenergy, and vice versa.

An organic optoelectronic diode may be classified as follows in accordance with its driving principles. One is a photoelectric diode where excitons are generated by photoenergy, separated into electrons and holes, and are transferred to different electrodes to generate electrical energy, and the other is a light emitting diode where a voltage or a current is supplied to an electrode to generate photoenergy from electrical energy.

Examples of the organic optoelectronic diode may be an organic photoelectric diode, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be, for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides a compound for an organic optoelectronic diode capable of realizing an organic optoelectronic diode having high efficiency and a long life-span.

Another embodiment provides an organic optoelectronic diode including the compound for an organic optoelectronic diode.

Yet another embodiment provides a display device including the organic optoelectronic diode.

Technical Solution

In an embodiment of the present invention, a compound for an organic optoelectronic diode represented by a combination of Chemical Formula 1 and Chemical Formula 2 is provided.

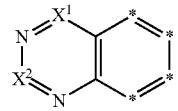

[Chemical Formula 1]

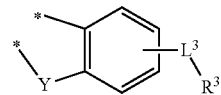

[Chemical Formula 2]

In Chemical Formulas 1 and 2, $X^1$ is N, or C-$L^1$-$R^1$, $X^2$ is N, or C-$L^2$-$R^2$, Y is O, S, $CR^aR^b$, or $SiR^cR^d$, $L^1$ to $L^3$ are independently a single bond, C6 to C30 arylene group, a substituted or unsubstituted C2 to C30 heteroarylene group, or a combination thereof, $R^1$ to $R^3$ and $R^a$ to $R^d$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heterocyclic group, a substituted or unsubstituted C6 to C30 arylamine group, a substituted or unsubstituted C1 to C30 alkoxy group, a substituted or unsubstituted C3 to C40 silyl group, a halogen, a halogen-containing group, a cyano group, a hydroxyl group, an amino group, a nitro group, a carboxyl group, a ferrocenyl group, or a combination thereof, and adjacent two *'s of Chemical Formula 1 are linked with *'s of Chemical Formula 2 to form a fused ring, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

In another embodiment of the present invention, an organic optoelectronic diode includes an anode and a cathode facing each other and at least one organic layer disposed between the anode and the cathode, wherein the organic layer includes the compound for an organic optoelectronic diode.

In yet another embodiment of the present invention, a display device including the organic optoelectronic diode is provided.

Advantageous Effects

An organic optoelectronic diode having high efficiency and a long life-span may be realized.

DESCRIPTION OF THE DRAWINGS

FIGS. 1 and 2 are cross-sectional views showing various embodiments of organic light emitting diode according to an embodiment of the present invention.

MODE FOR INVENTION

Hereinafter, embodiments of the present invention are described in detail. However, these embodiments are exemplary, the present invention is not limited thereto and the present invention is defined by the scope of claims.

In the present specification when a definition is not otherwise provided, "substituted" refers to replacement of at least one hydrogen of a substituent or a compound by deuterium, a halogen, a hydroxy group, an amino group, a C1 to C30 amine group, a nitro group, a C1 to C40 silyl group, a C1 to C30 alkyl group, C1 to C10 alkylsilyl group, a C3 to C30 cycloalkyl group, a C3 to C30 heterocycloalkyl group, a C6 to C30 aryl group, a C6 to C30 heteroaryl group, a C1 to C20 alkoxy group, a fluoro group, a C1 to C10 trifluoroalkyl group such as a trifluoromethyl group, or a cyano group.

In the present specification, when a definition is not otherwise provided, "hetero" refers to one including one to three heteroatoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C20 alkyl group. More specifically, the alkyl group may be a C1 to C10 alkyl group or a C1 to C6 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, a "heteroaryl group" may refer to an aryl group including at least one heteroatom selected from N, O, S, P, and Si instead of carbon (C). Two or more heteroaryl groups are linked by a sigma bond directly, or when the C2 to C60 heteroaryl group includes two or more rings, the two or more rings may be fused. When the heteroaryl group is a fused ring, each ring may include one to three heteroatoms.

Specific examples of the heteroaryl group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrylene group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridinyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted carbazolyl group, a substituted or unsubstituted dibenzofuranyl group, a substituted or unsubstituted dibenzothiophenyl group, a combination thereof, or a combined fused ring of the foregoing groups, but are not limited thereto.

In the present specification, a single bond refers to a direct bond not by carbon or a hetero atom except carbon, and specifically the meaning that L is a single bond means that a substituent linked to L directly bonds with a central core. That is, in the present specification, the single bond does not refer to methylene that is bonded via carbon.

In the specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic diode according to an embodiment is described.

In an embodiment of the present invention, a compound for an organic optoelectronic diode represented by a combination of Chemical Formula 1 and Chemical Formula 2 is provided.

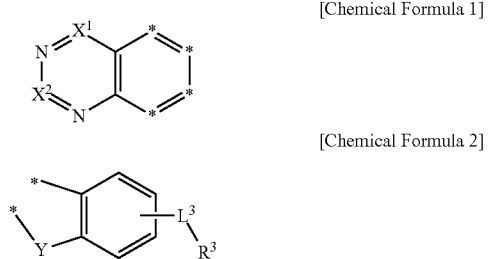

[Chemical Formula 1]

[Chemical Formula 2]

In Chemical Formulas 1 and 2.
$X^1$ is N, or $C-L^1-R^1$,
$X^2$ is N, or $C-L^2-R^2$,
Y is O, S, $CR^aR^b$, or $SiR^cR^d$,
$L^1$ to $L^3$ are independently a single bond, C6 to C30 arylene group, a substituted or unsubstituted C2 to C30 heteroarylene group, or a combination thereof,
$R^1$ to $R^3$ and $R^a$ to $R^d$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heterocyclic group, a substituted or unsubstituted C6 to C30 arylamine group, a substituted or unsubstituted C1 to C30 alkoxy group, a substituted or unsubstituted C3 to C40 silyl group, a halogen, a halogen-containing group, a cyano group, a hydroxyl group, an amino group, a nitro group, a carboxyl group, a ferrocenyl group, or a combination thereof, and
adjacent two *'s of Chemical Formula 1 are linked with *'s of Chemical Formula 2 to form a fused ring,
wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

The compound for an organic optoelectronic diode represented by a combination of Chemical Formulas 1 and 2 has a form where a ring is additionally fused with a quinazoline structure, and this core may disperse electrons in a wider and flatter molecular structure and thereby, secure stability about electrons and expand LUMO and flatness and thus bring about an effect of improving electron mobility and the like. The compound may be used as an electron transport material, an electron injection material, and a light emitting material due to strong electron characteristics of the core, and particularly, when used as the light emitting material, an effect of increasing efficiency and a life-span and decreasing a driving voltage by improving electron mobility may be obtained.

The core includes at least two N's and thus has a lower LUMO energy of −1.9 eV to −2.1 eV and accordingly, may show strong electron injection and transport characteristics and thus be more appropriate for a low driving/high efficiency material in ETL or HOST compared with a structure including one N (LUMO of −1.3 eV to −1.7 eV).

The compound for an organic optoelectronic diode represented by a combination of Chemical Formulas 1 and 2 may be represented by one of Chemical Formulas 3 to 8 according to a fusion position of additional ring fused with the quinazoline structure.

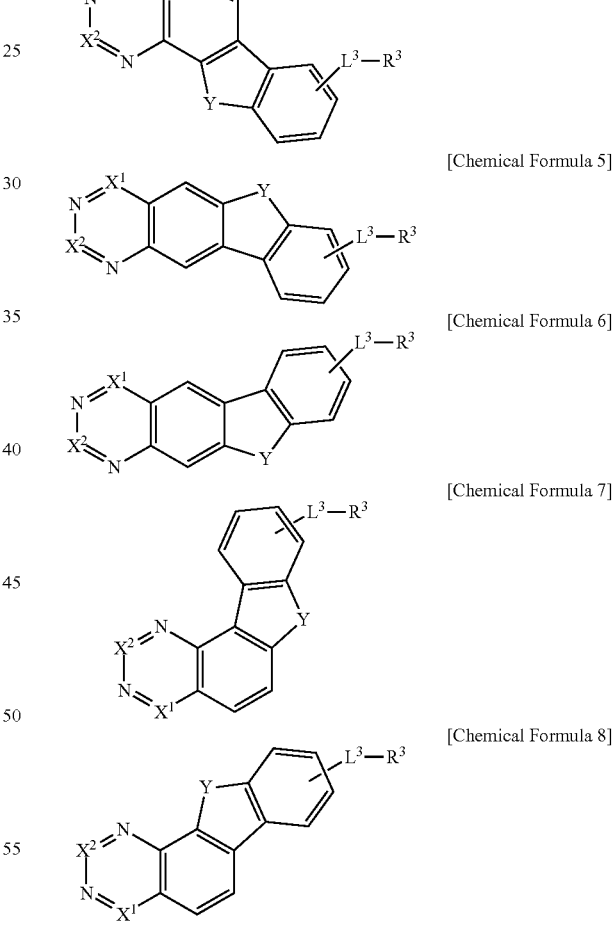

[Chemical Formula 3]

[Chemical Formula 4]

[Chemical Formula 5]

[Chemical Formula 6]

[Chemical Formula 7]

[Chemical Formula 8]

In Chemical Formulas 3 to 8, $X^1$, $X^2$, Y, $L^3$, and $R^3$ are the same as described above.

As shown in Chemical Formulas 3 to 8, a compound for an organic optoelectronic diode according to one embodiment of the present invention may be expressed as six kinds of structure depending on a fusion point.

The structures of Chemical Formulas 3 to 8 may play a role of an ET core of compounds respectively including the corresponding structures. Accordingly, since a HOMO energy level is determined by an additionally substituted substituent, but a LUMO energy level is in a range of −1.9 eV to −2.1 eV, the compounds may show an equal/equivalent function effect in an organic optoelectronic diode.

In an embodiment of the present invention, in Chemical Formula 1, 2 or Chemical Formula 3 to Chemical Formula 8, the $X^1$ may be C-$L^1$-$R^1$ and $X^2$ may be C-$L^2$-$R^2$.

In another embodiment of the present invention, the $R^1$ to $R^3$ are independently hydrogen, deuterium, a substituted or unsubstituted C6 to C30 arylamine group, a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted triphenylene group, a substituted or unsubstituted fluorenyl group, a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted azaphenanthrenyl group, a substituted or unsubstituted phenanthrolinyl group, a substituted or unsubstituted phenazinyl group, a substituted or unsubstituted carbazolyl group, a substituted or unsubstituted dibenzofuranyl group, a substituted or unsubstituted dibenzothiophenyl group, a substituted or unsubstituted benzofuropyrimidinyl group, a substituted or unsubstituted benzothienopyrimidinyl group, a substituted or unsubstituted benzocarbazolyl group, a substituted or unsubstituted benzofurocarbazolyl group, a substituted or unsubstituted indolocarbazolyl group, a substituted or unsubstituted benzofurofluorenyl group, a substituted or unsubstituted benzothienofluorenyl group, a substituted or unsubstituted indolodibenzofuranyl group, a substituted or unsubstituted benzoindolocarbazole group, or a combination thereof. Specifically, the $R^3$ may be hydrogen, the $R^1$ and $R^2$ may independently be selected from hydrogen, deuterium, or groups of Group I.

[Group 1]

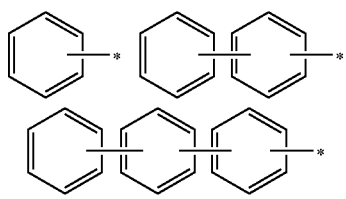

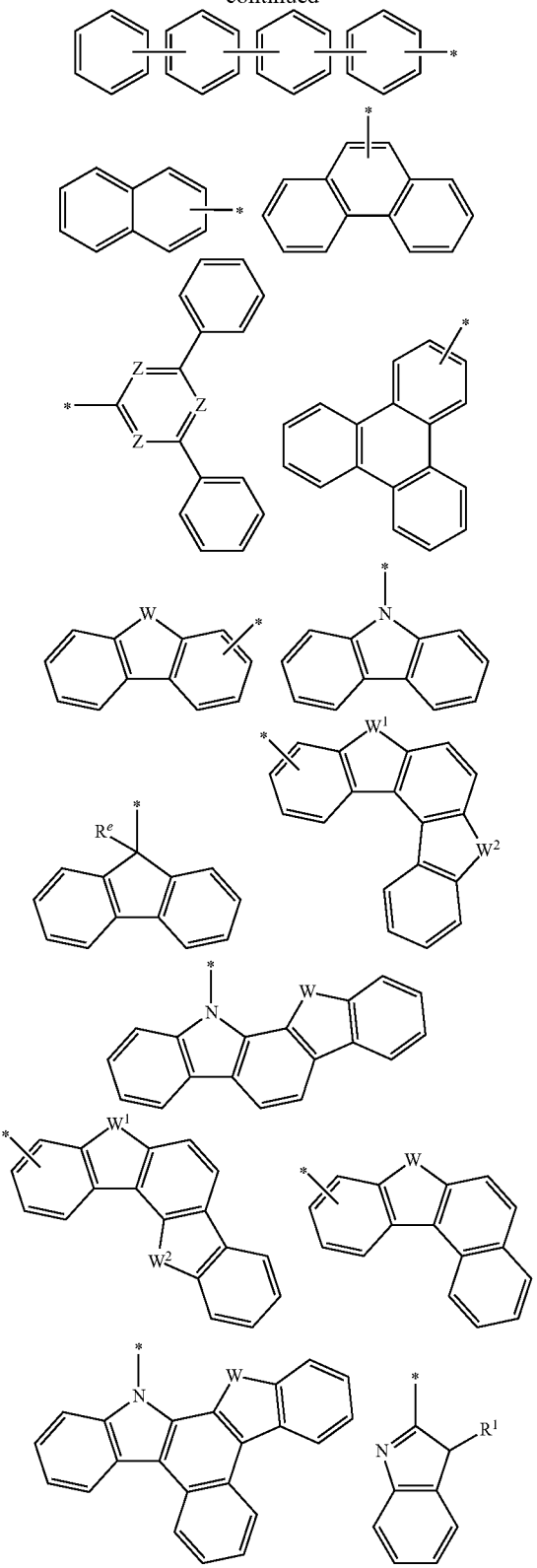

In Group I,
Z is N, or CR$^g$, W, $W^1$, and $W^2$ are independently O, S, NR$^h$, CR$^i$R$^j$, wherein R$^e$ to R$^j$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, or a substituted or unsubstituted C2 to C30 heteroaryl group, and * is a linking point and may be positioned at one element of elements consisting of the functional group.

For example, the substituted or unsubstituted groups of Group I may be represented by one of groups of Group I-1, but is not limited thereto.

[Group I-1]

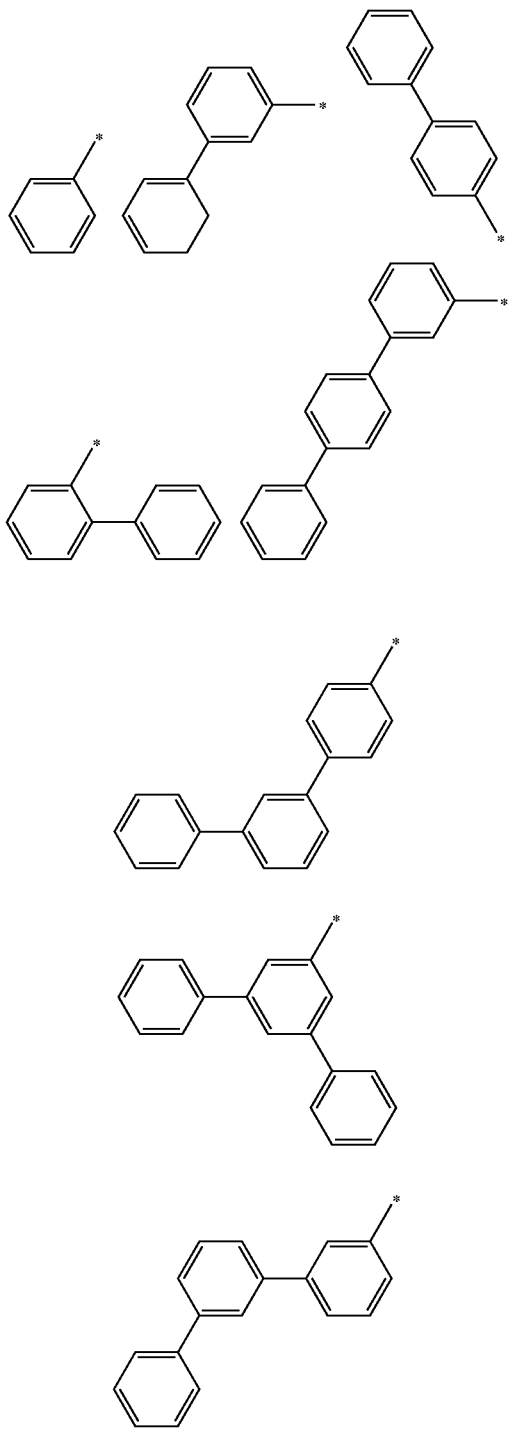

-continued

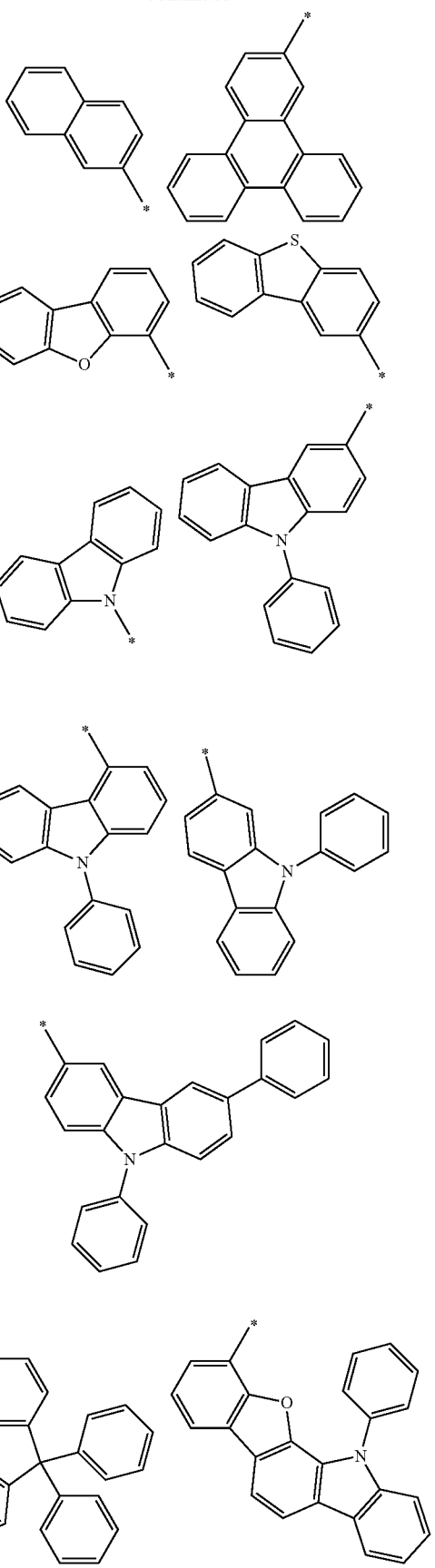

-continued

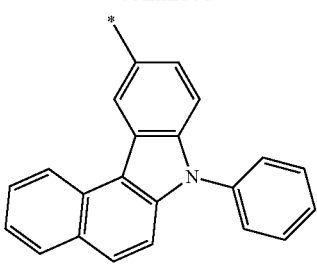
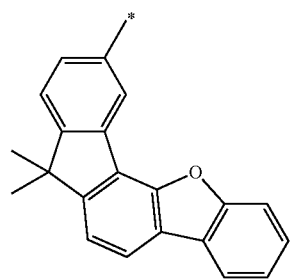
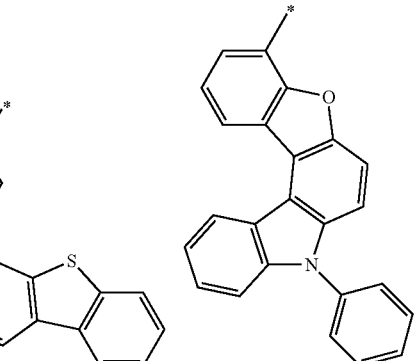
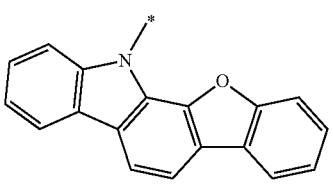
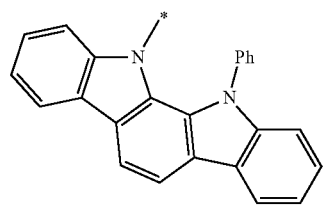
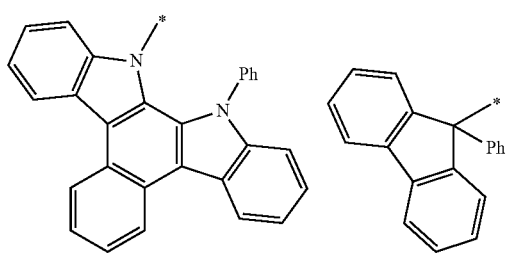

-continued

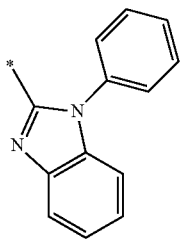
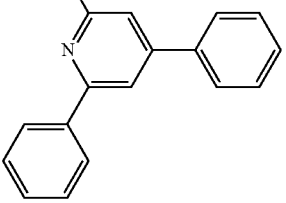

In addition, the $L^1$ to $L^3$ may independently be a single bond, a substituted or unsubstituted C6 to C30 arylene group, or a substituted or unsubstituted C2 to C30 heteroarylene group. Specifically, the $L^1$ to $L^3$ may independently be a single bond, a substituted or unsubstituted phenylene group, a substituted or unsubstituted biphenylene group, a substituted or unsubstituted terphenylene group, or a substituted or unsubstituted carbazolylene group.

For example, the $L^1$ to $L^3$ may independently be a single bond, or a group selected from substituted or unsubstituted groups of Group II, but are not limited thereto.

[Group II]

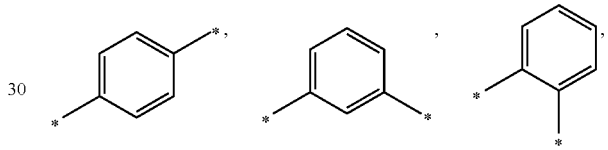
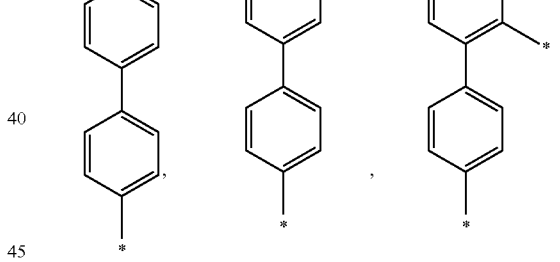
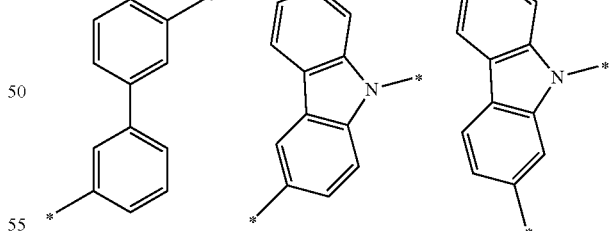

In Group II,
* is a linking point,
wherein "substituted" refers to replacement of at least one hydrogen by deuterium, a C1 to C40 silyl group, a C1 to C30 alkyl group, a C3 to C30 cycloalkyl group, a C2 to C30 heterocycloalkyl group, a C6 to C30 aryl group, carbazolyl group, a dibenzofuranyl group, a dibenzothiophenyl group, or a fluorenyl group.

In an example embodiment of the present invention, in Chemical Formulas 3 to 8, the L¹ to L³ may independently be a single bond, a substituted or unsubstituted phenylene group, a substituted or unsubstituted biphenylene group, a substituted or unsubstituted terphenylene group, a substituted or unsubstituted carbazolylene group, or a substituted or unsubstituted fluorenyl group, the R³ may be hydrogen, and the R¹ and R² may independently be hydrogen, deuterium, or one selected from groups of Group I.

[Group 1]

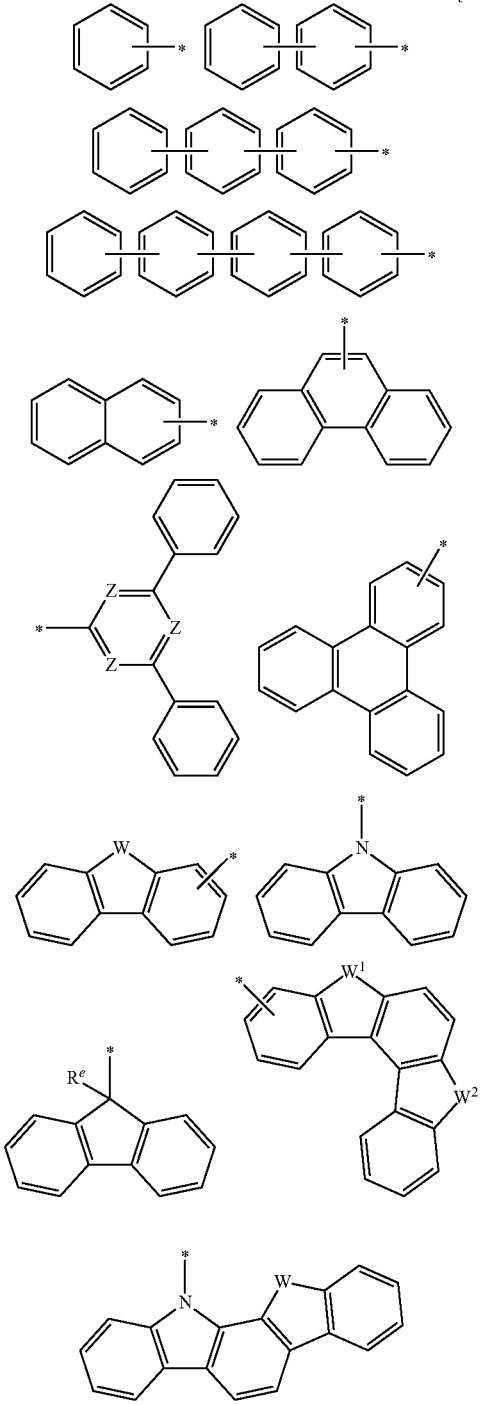

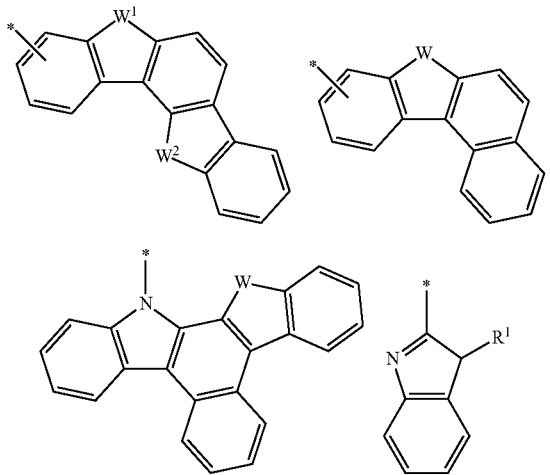

In Group I, Z is N, or CR$^g$, W, W¹, and W² are independently O, S, NR$^h$, or CR$^i$R$^j$, R$^e$ to R$^j$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, or a substituted or unsubstituted C2 to C30 heteroaryl group, and * is a linking point and may be positioned at one element of elements consisting of the functional group.

The compound for an organic optoelectronic diode represented by a combination of Chemical Formulas 1 and 2 may be for example the following compounds, but is not limited thereto.

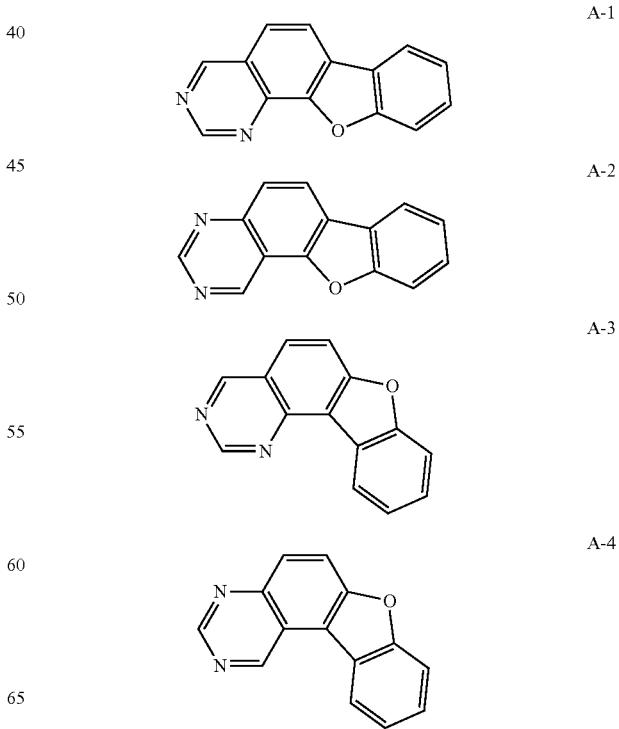

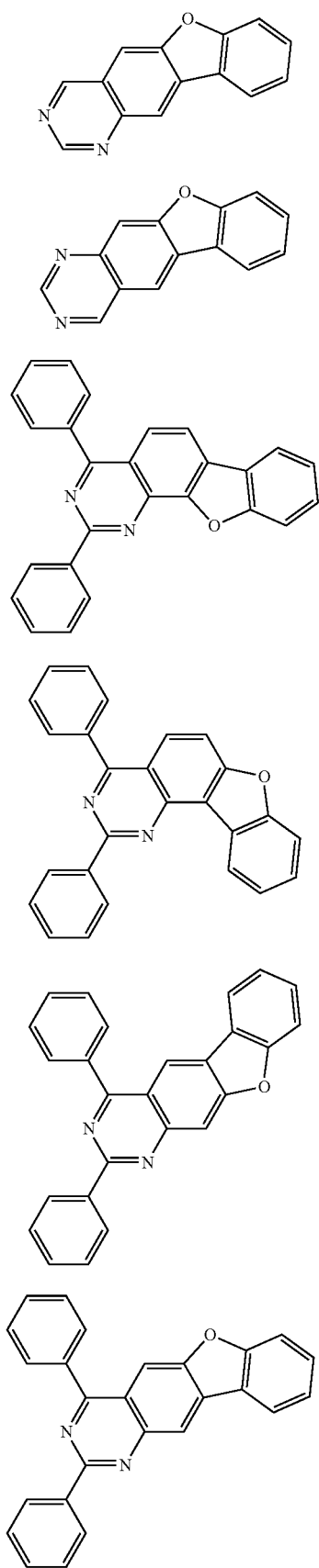
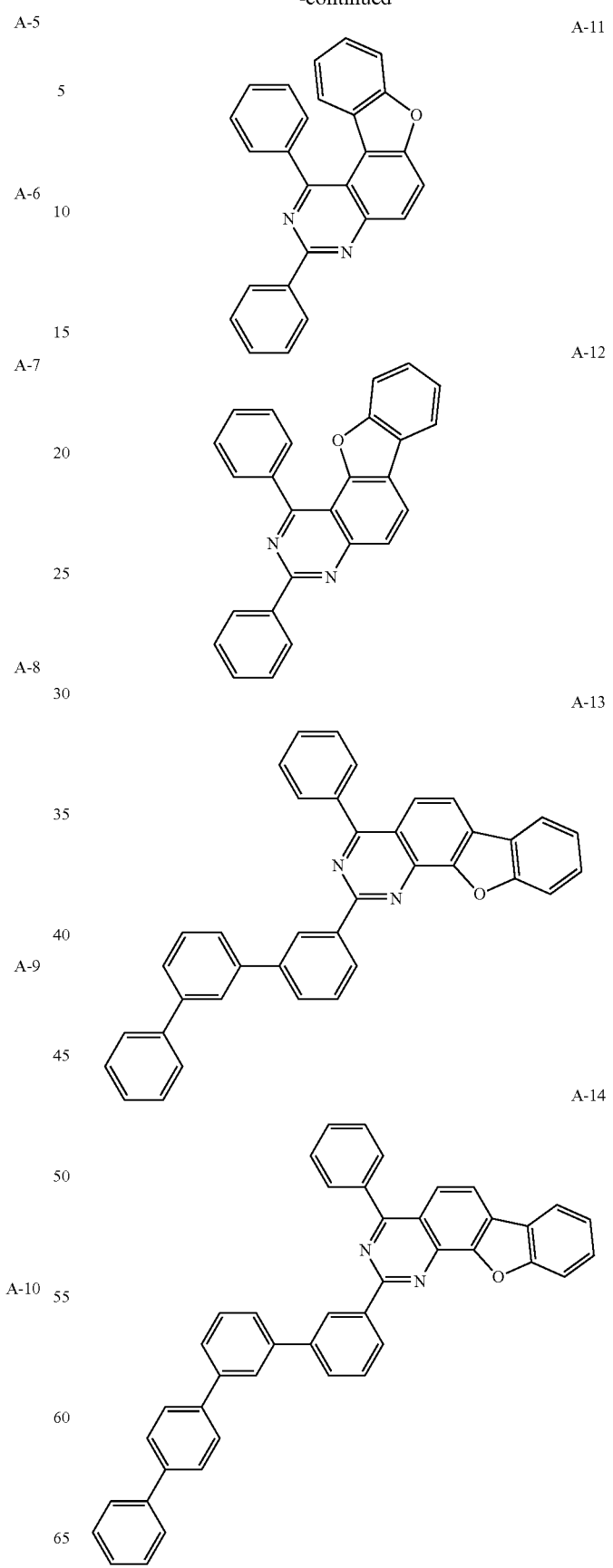

A-15
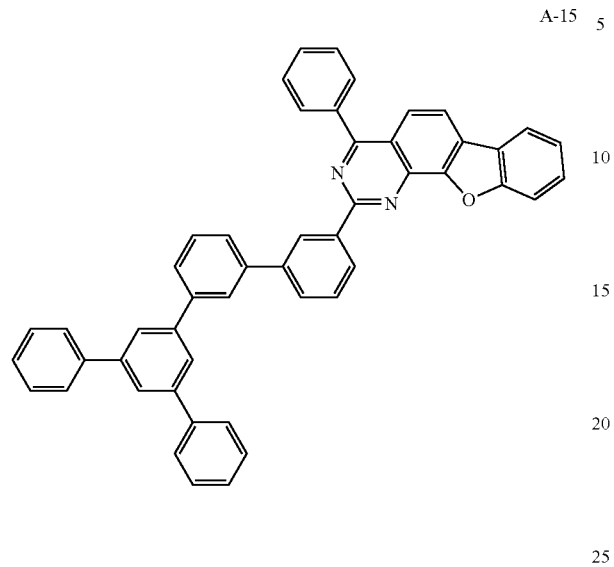
A-18
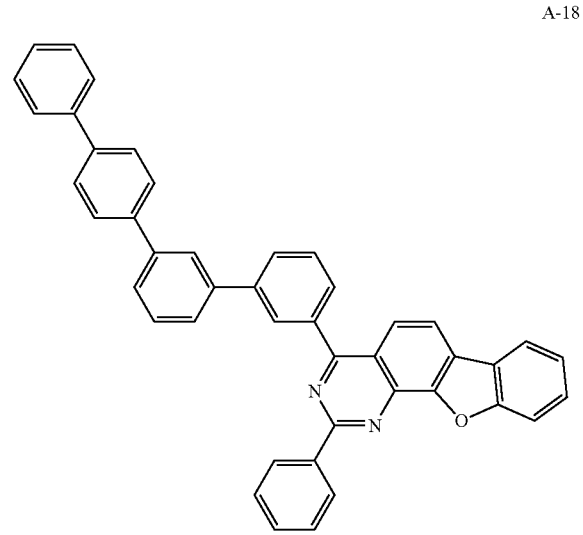
A-16
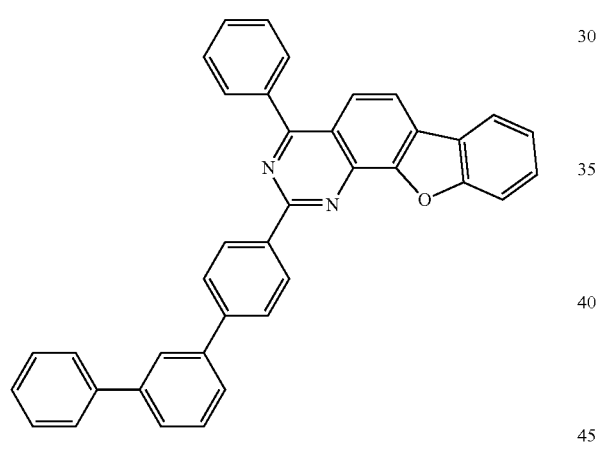
A-19
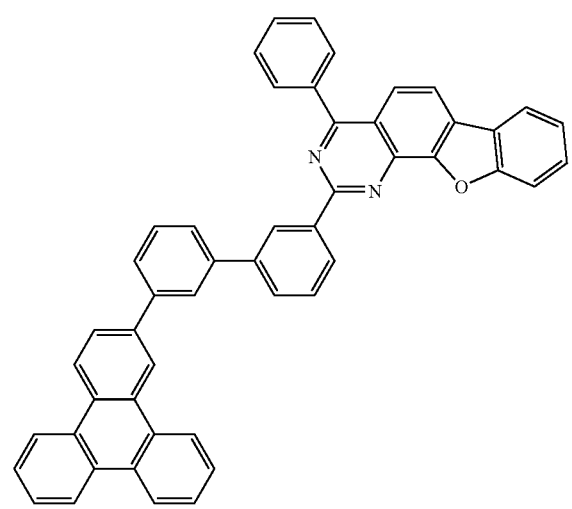
A-17
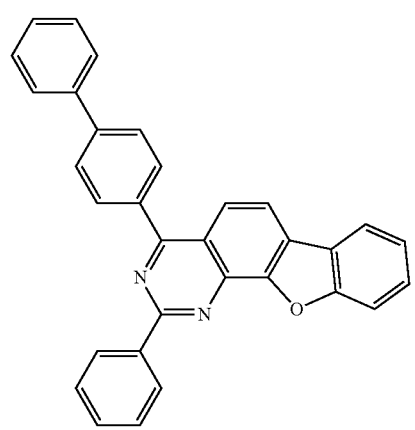
A-20
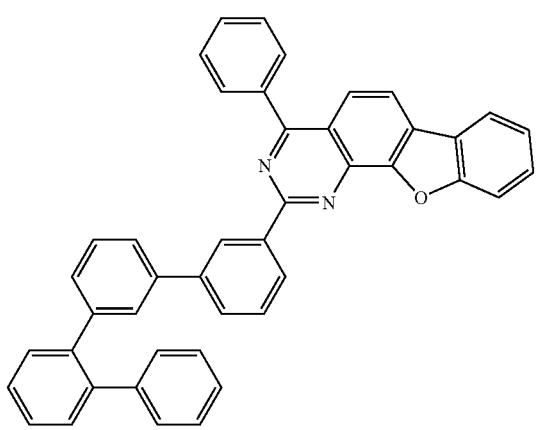

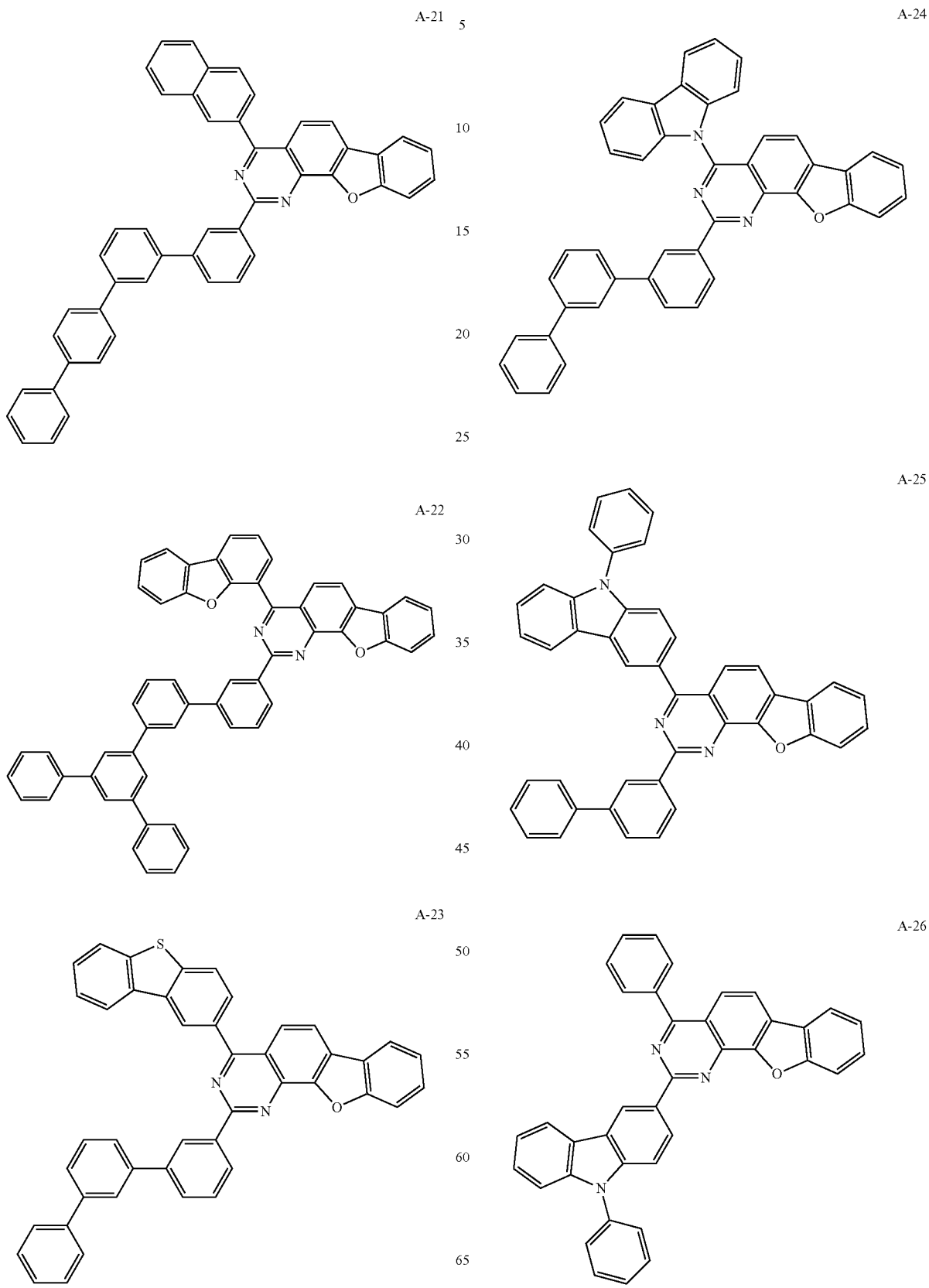

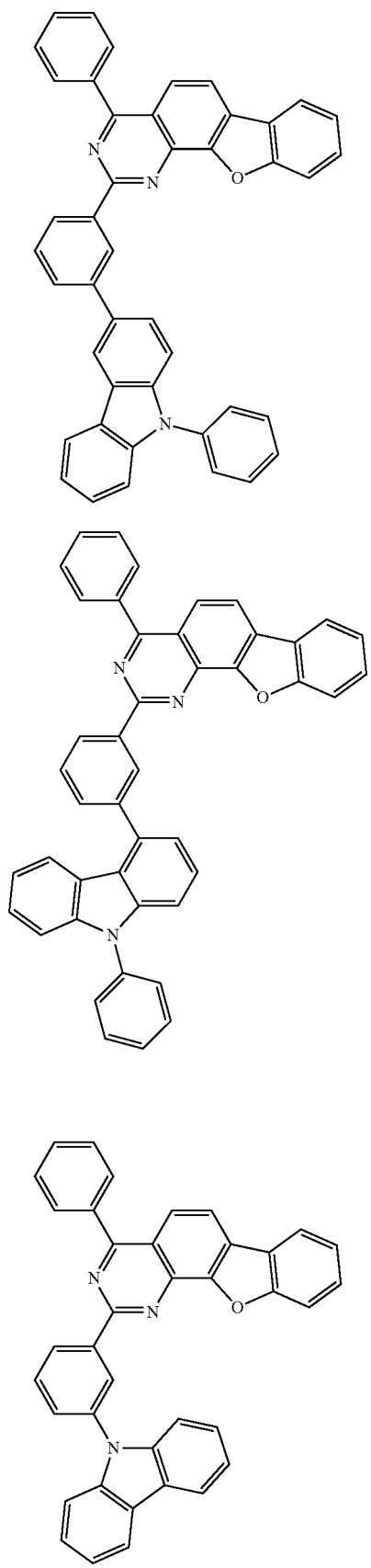
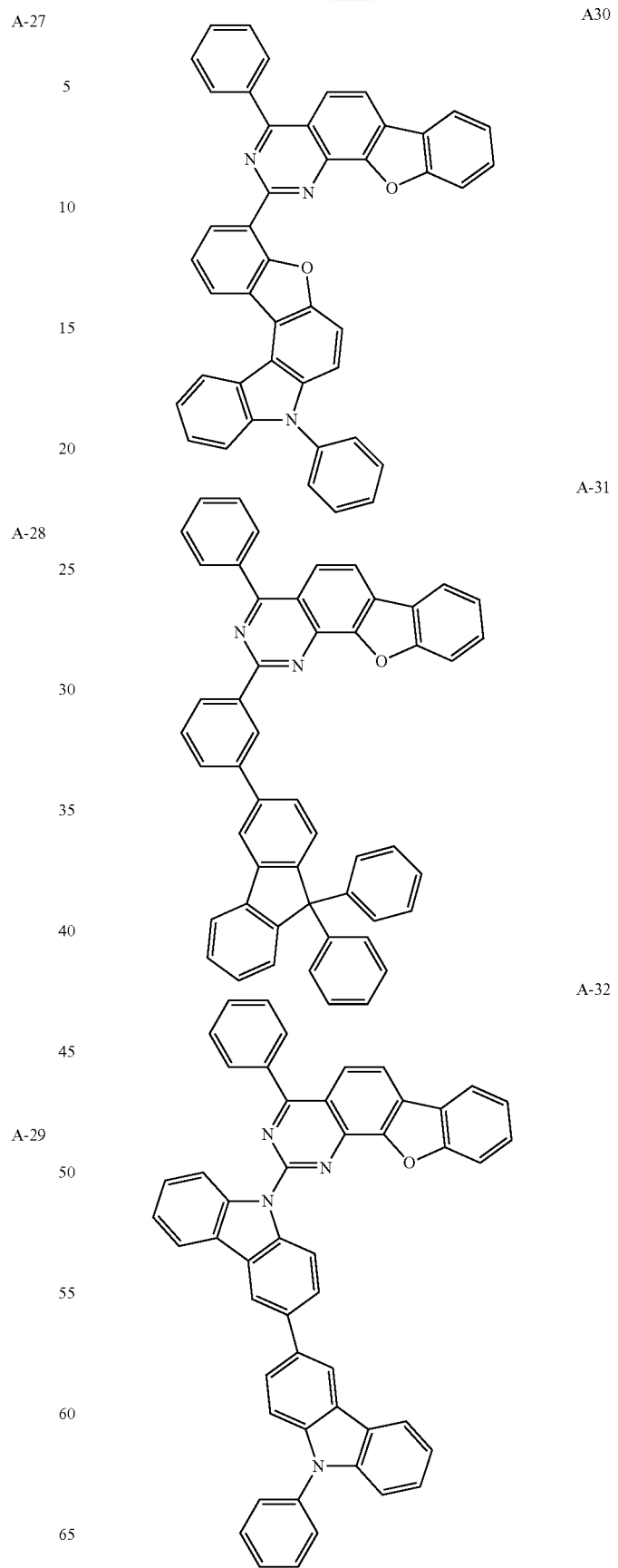

A-33
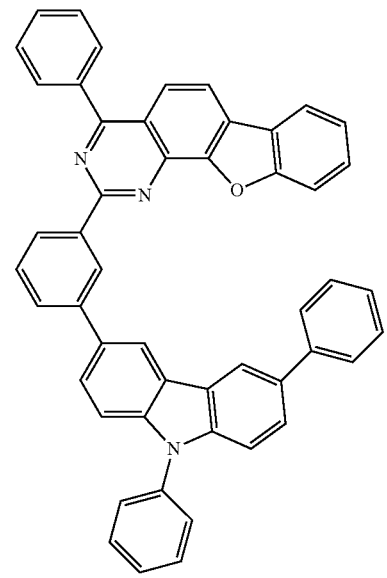
A-34
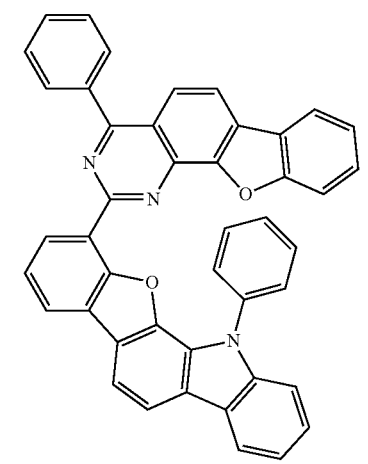
A-35
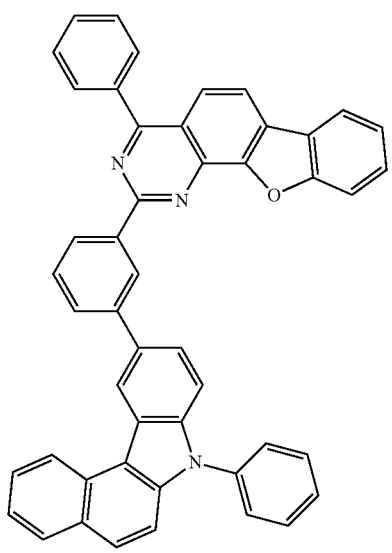
A-36
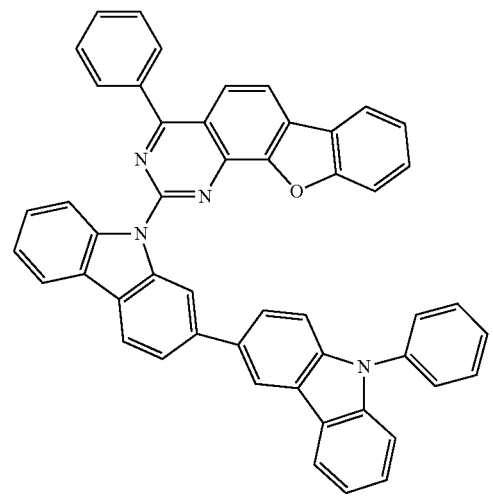
A-37
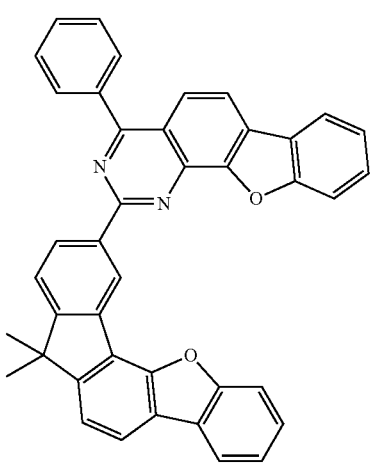
A-38
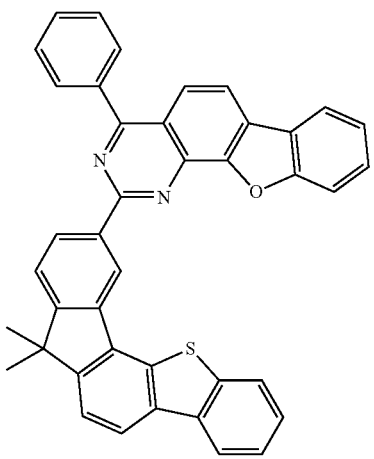

A-39
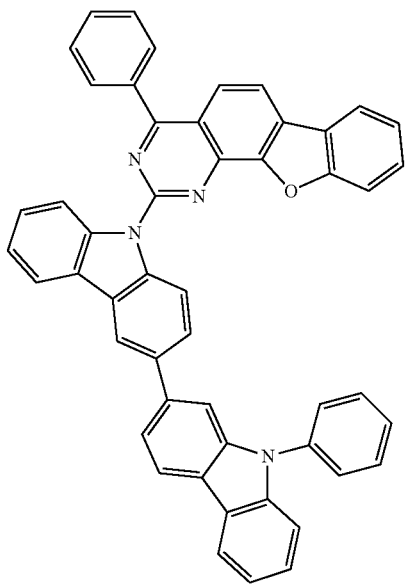
A-40
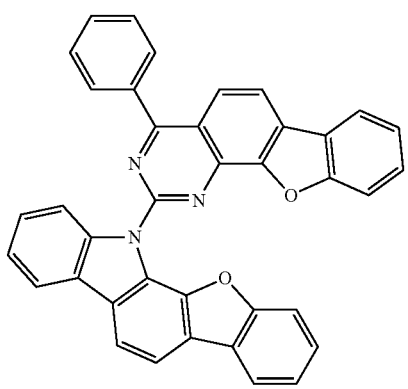
A-41
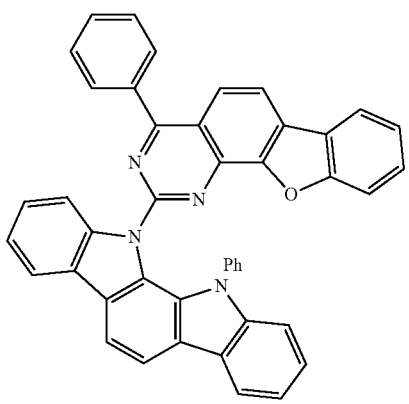
A-42
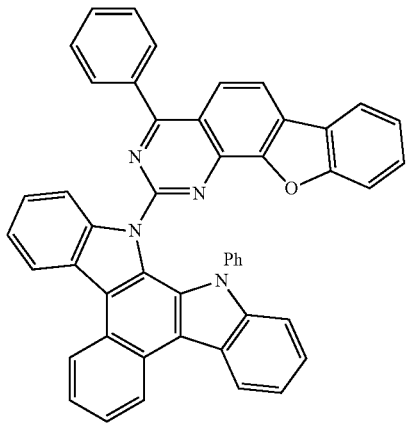
A-43
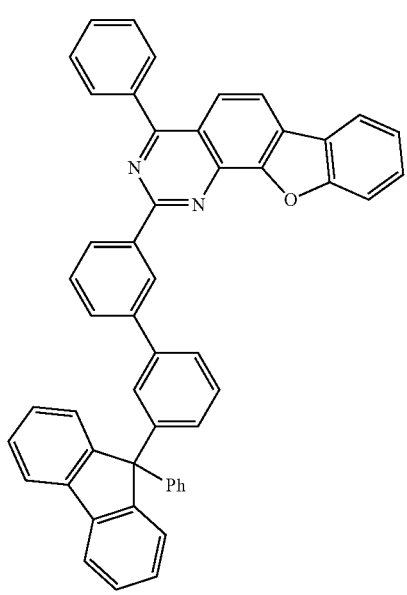
A-44
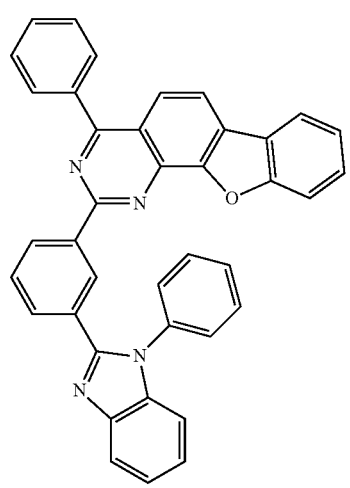

-continued
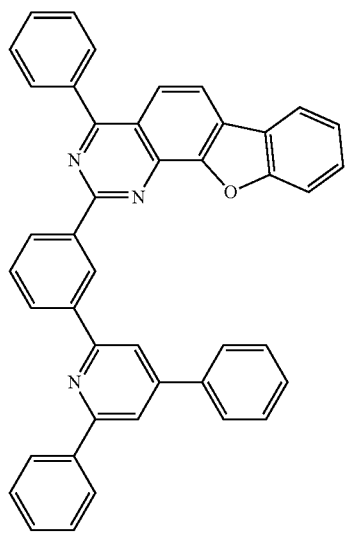
A-45
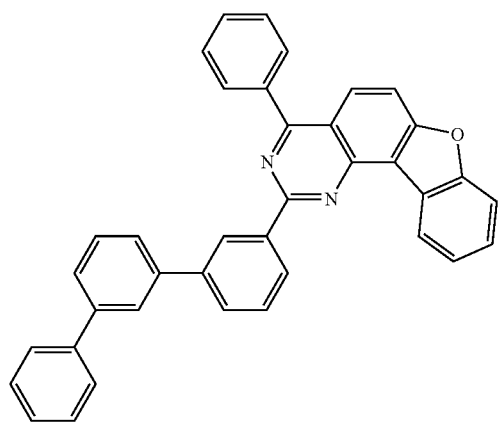
A-46
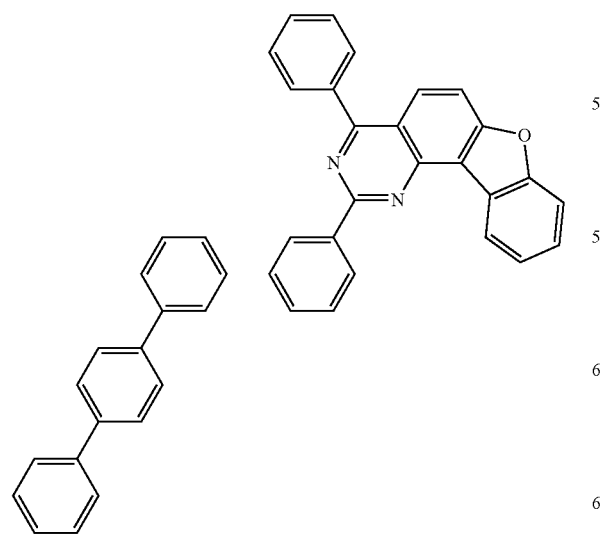
A-47
-continued
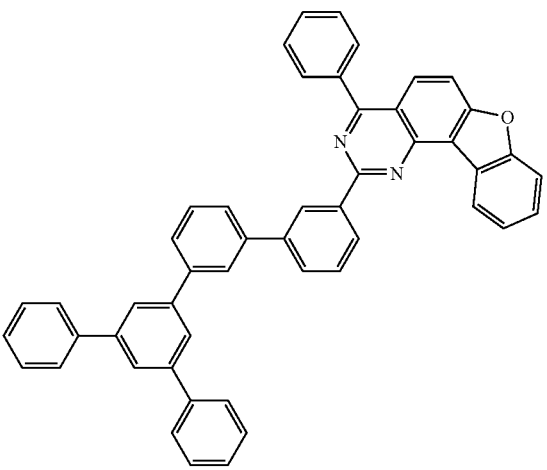
A-48
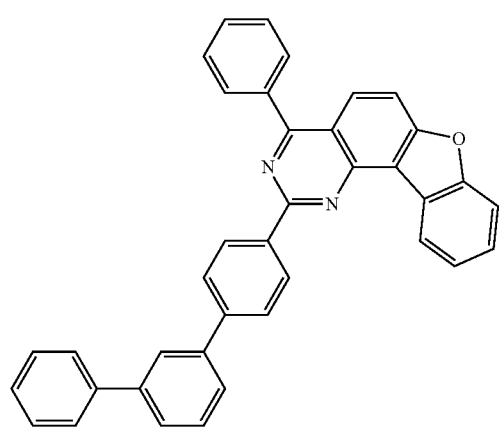
A-49
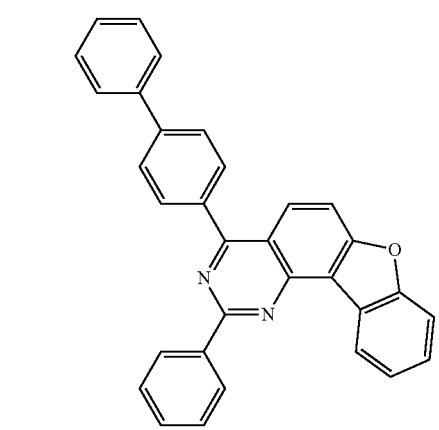
A-50

A-51
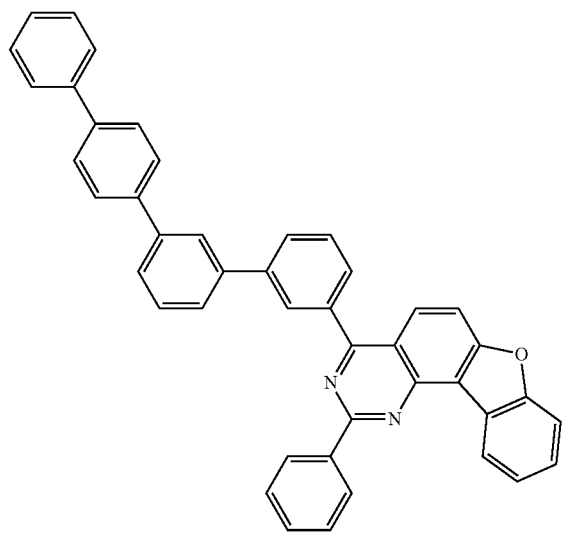
A-52
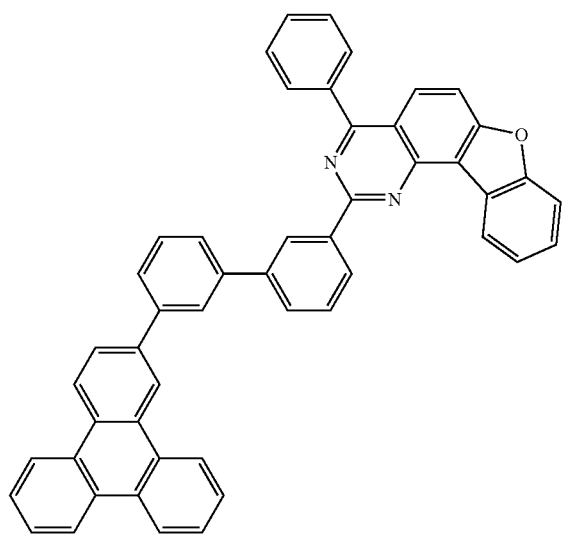
A-53
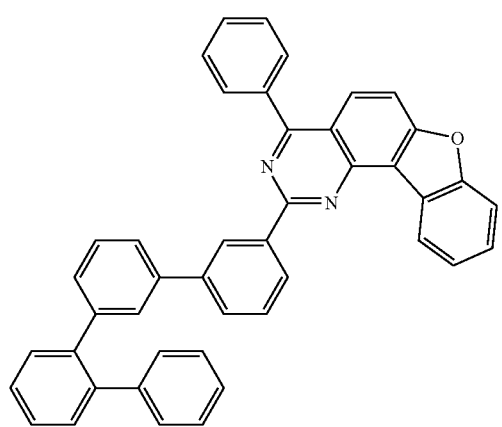
A-54
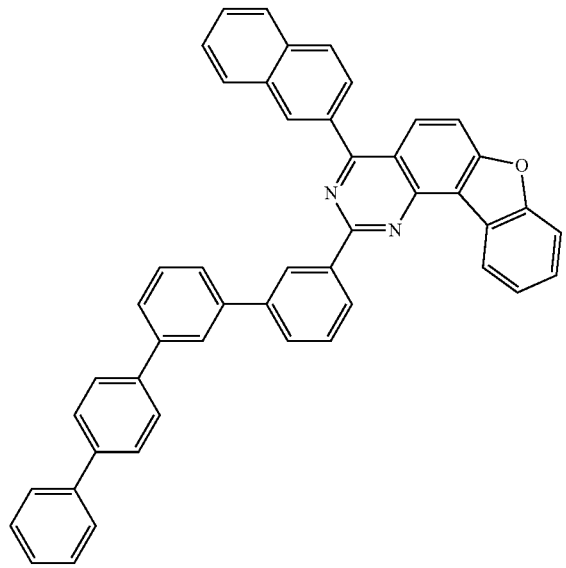
A-55
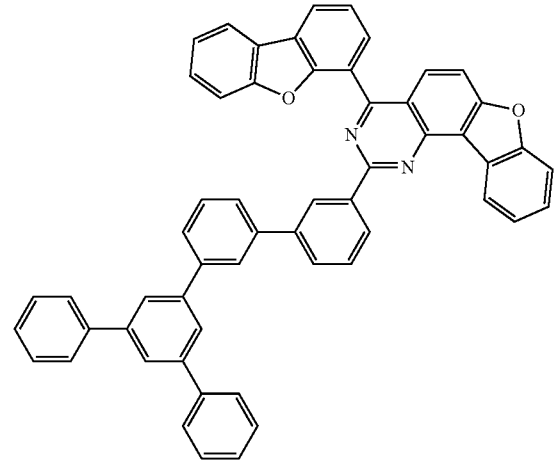
A-56
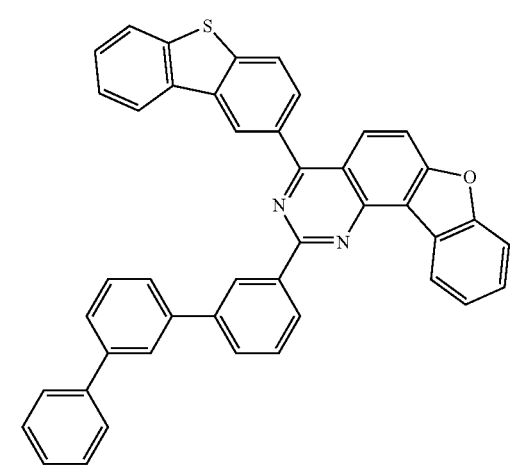

A-57
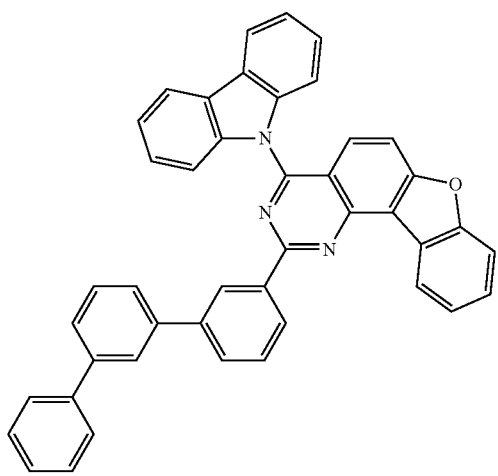
A-58
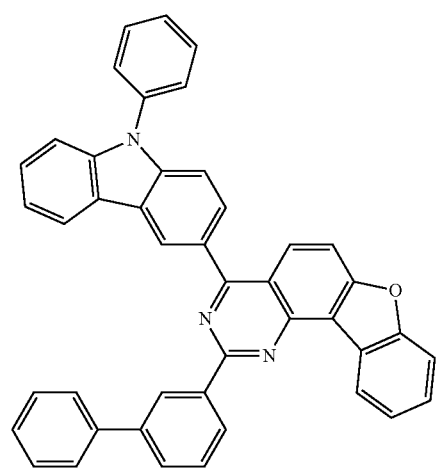
A-59
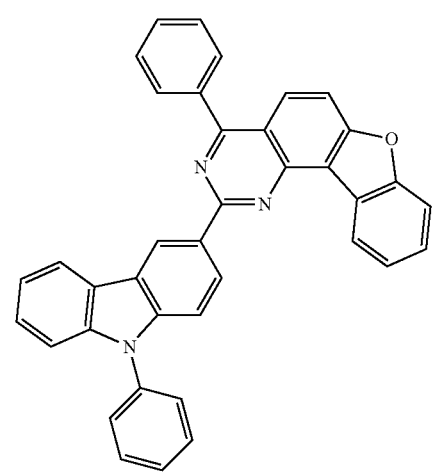
A-60
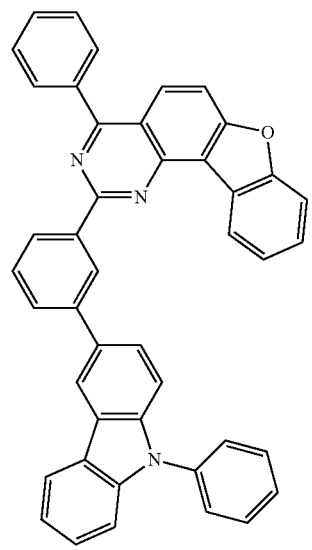
A-61
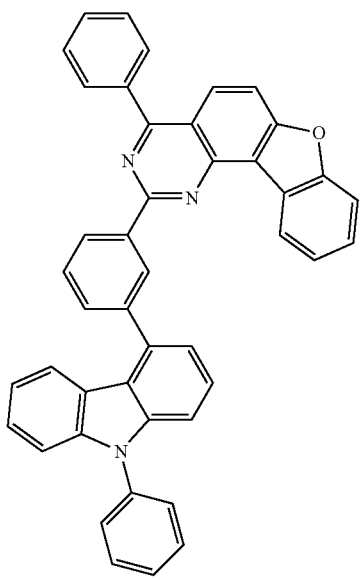
A-62
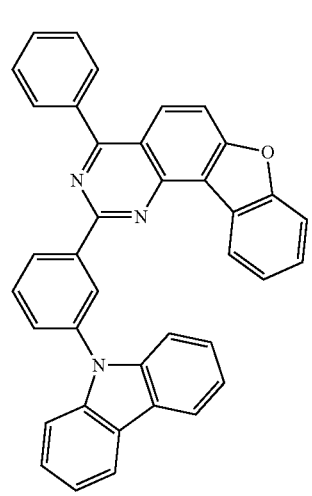

A-63
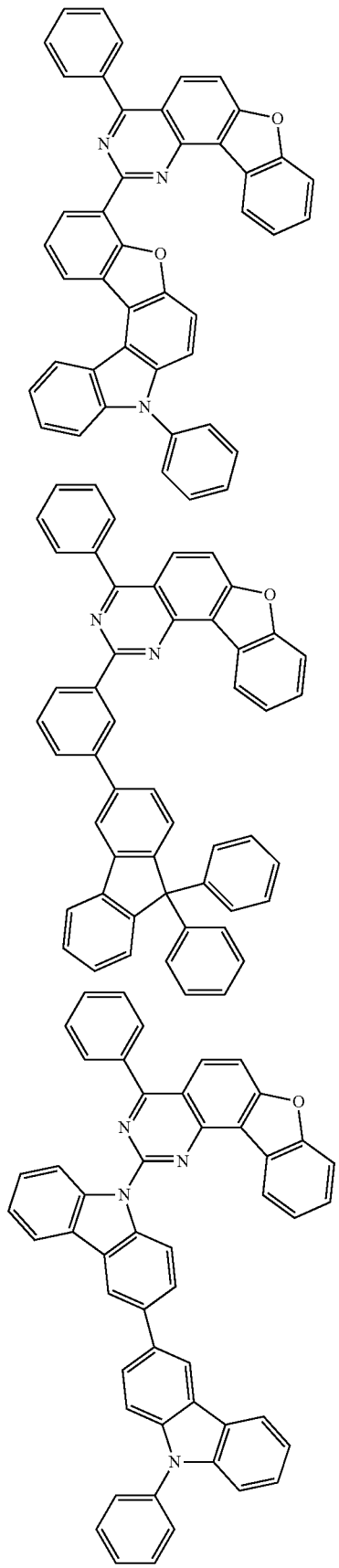
A-64
A-65
A-66
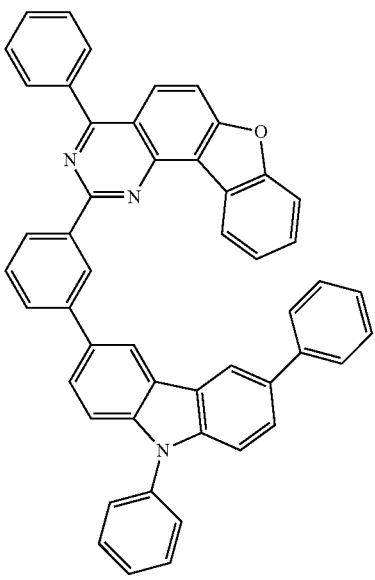
A-67
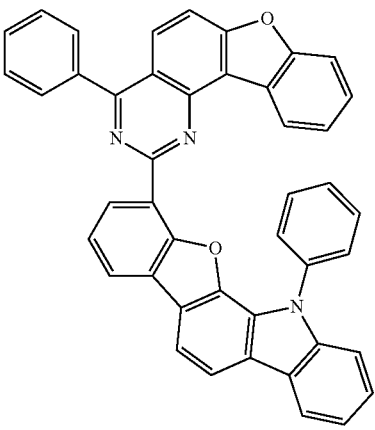
A-68
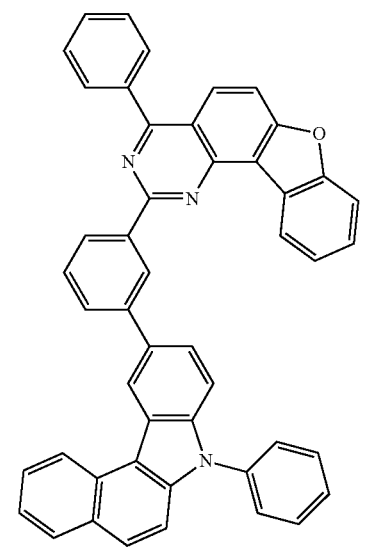

A-69
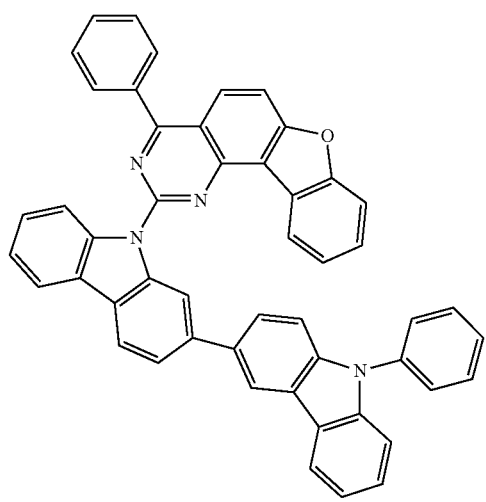
A-70
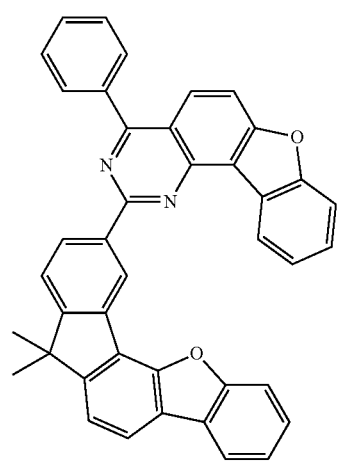
A-71
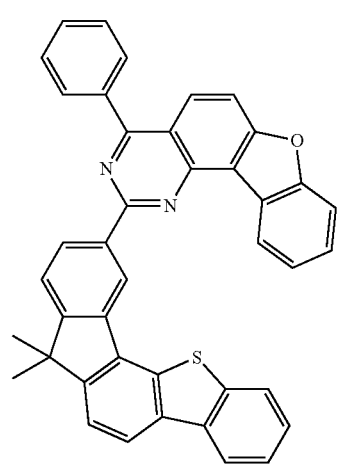
A-72
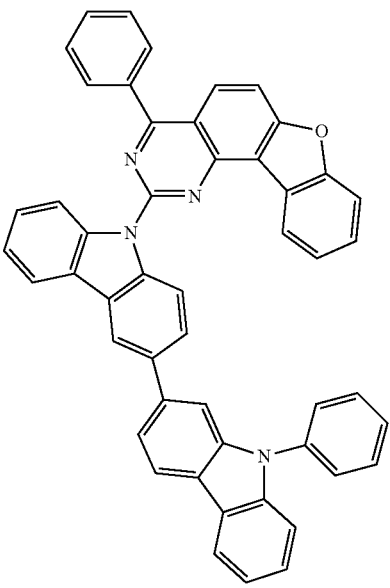
A-73
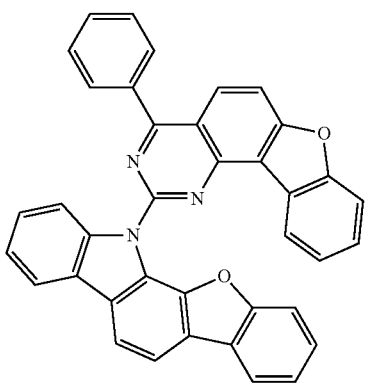
A-74
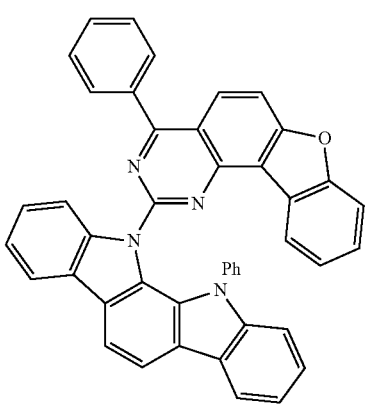

A-75 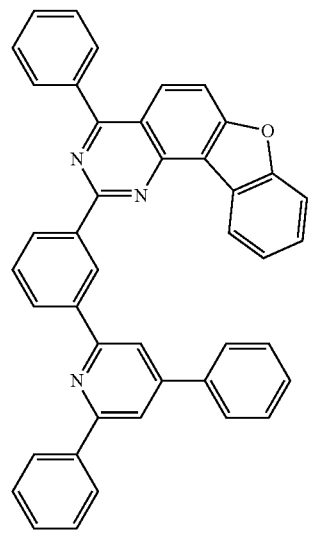
A-78 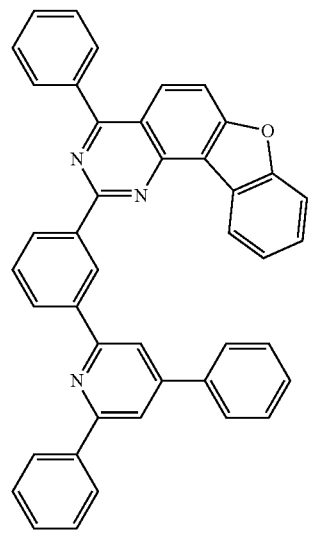
A-76 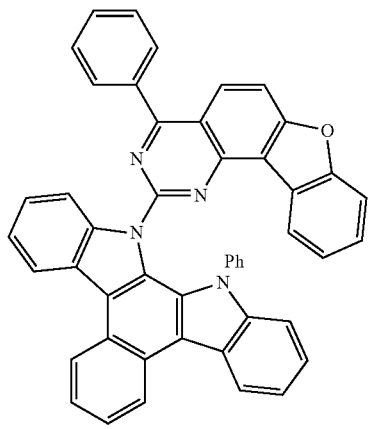
A-79 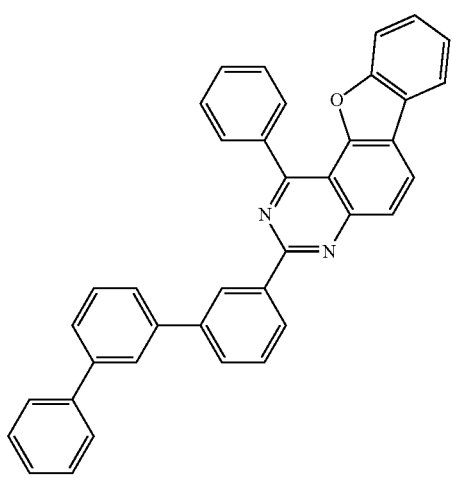
A-77 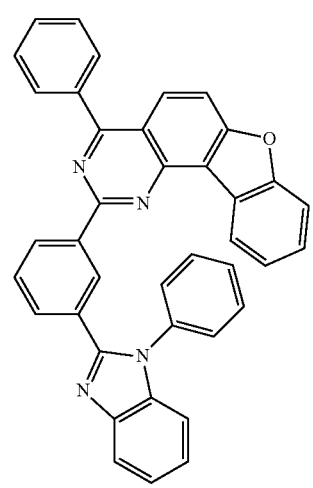
A-80 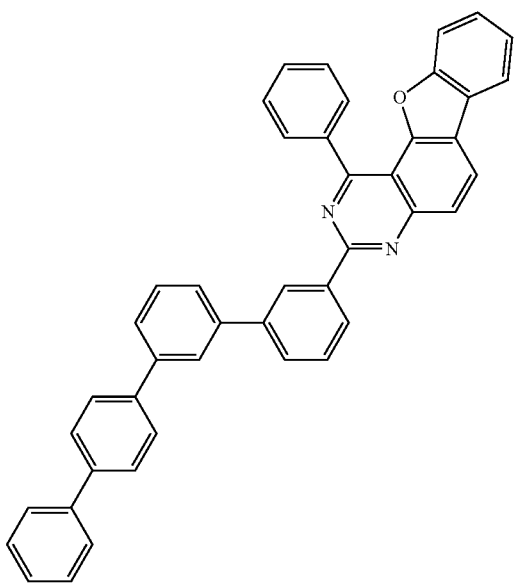

A-81
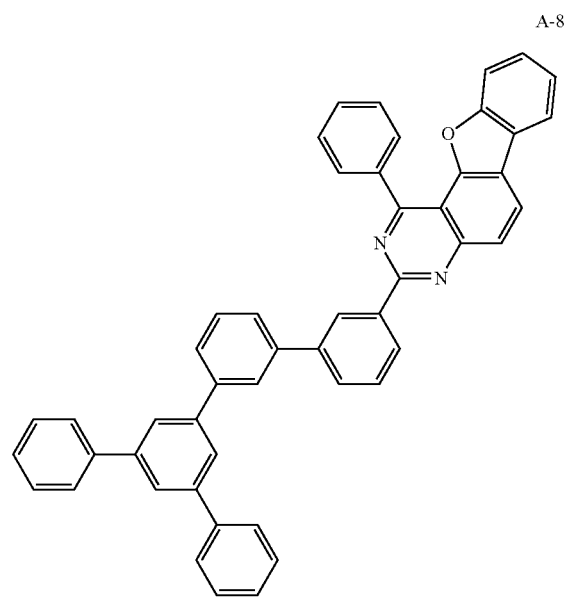
A-82
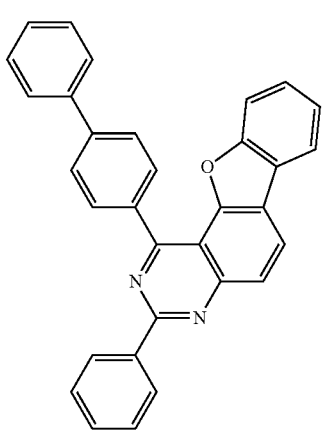
A-83
A-84
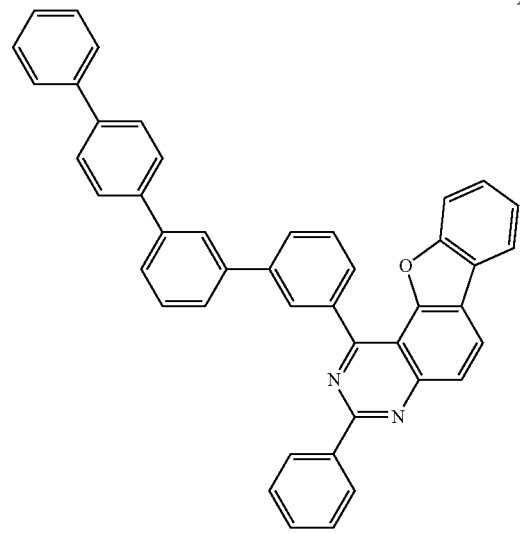
A-85
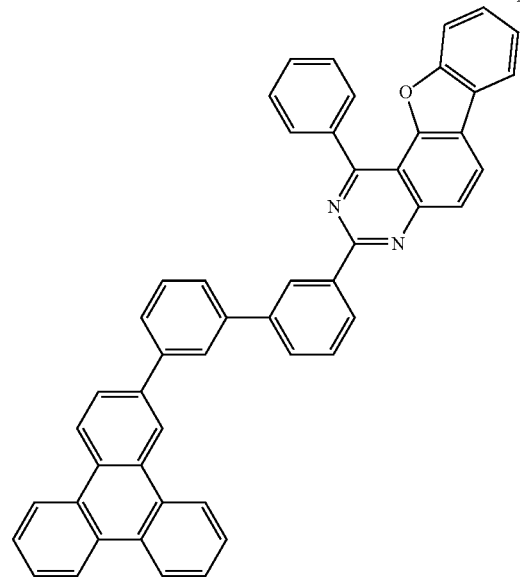
A-86
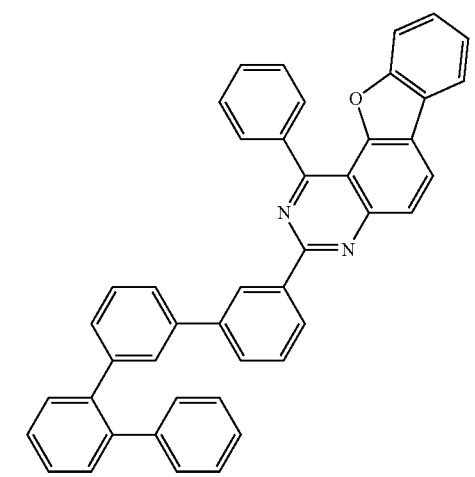

A-87
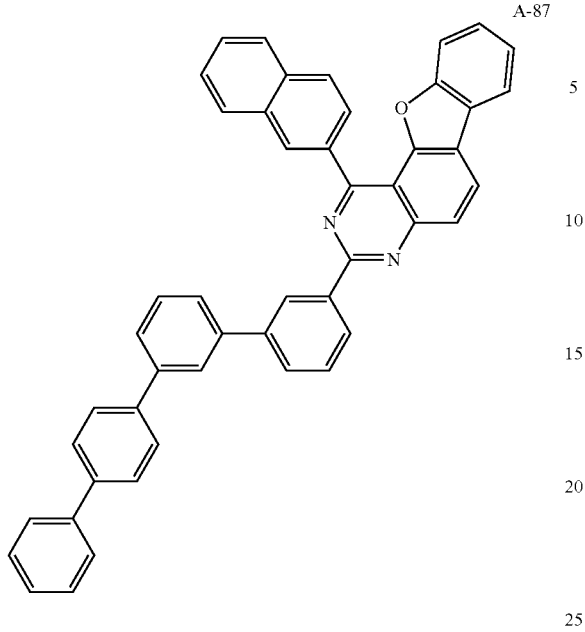
A-88
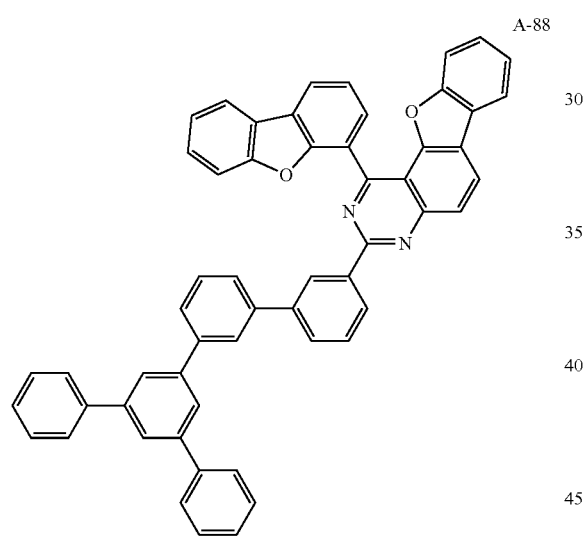
A-89
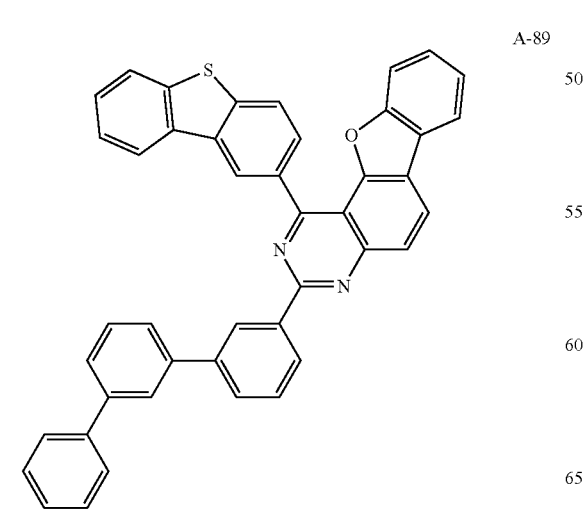
A-90
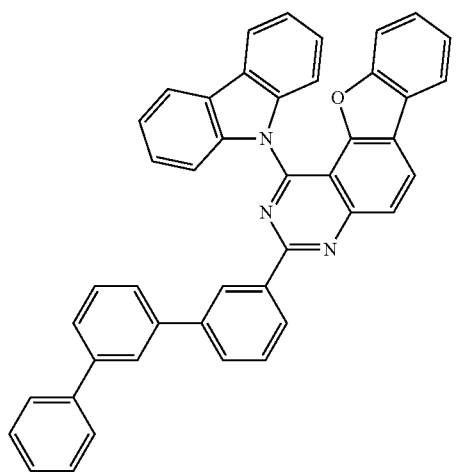
A-91
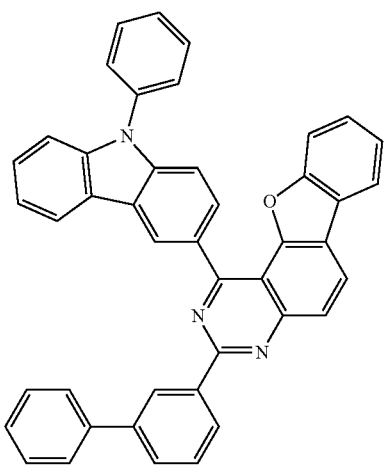
A-92
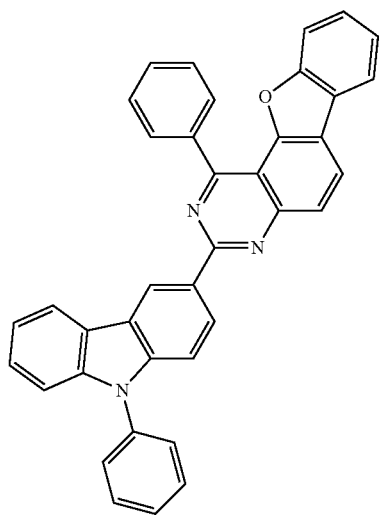

A-93
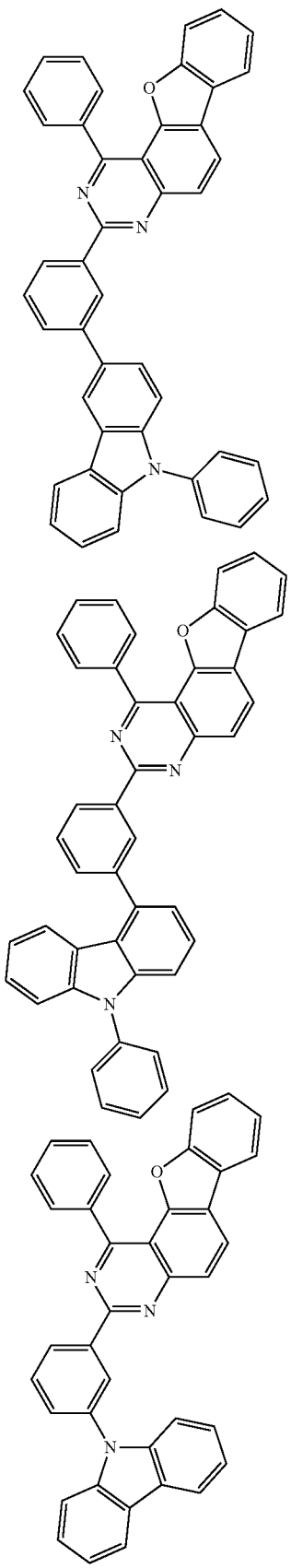
A-94
A-95
A-96
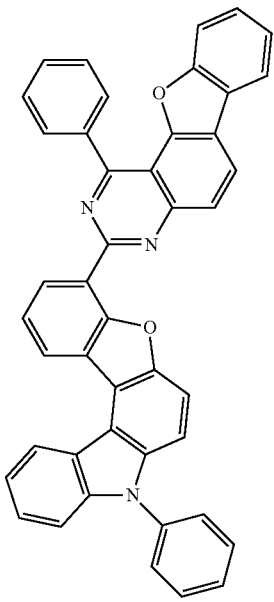
A-97
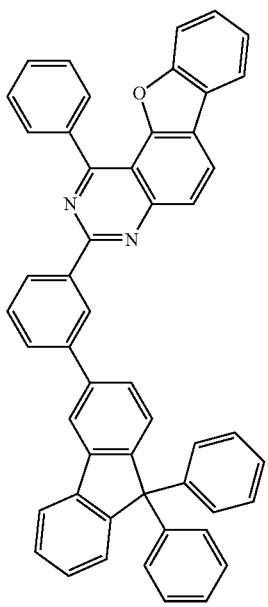

A-98
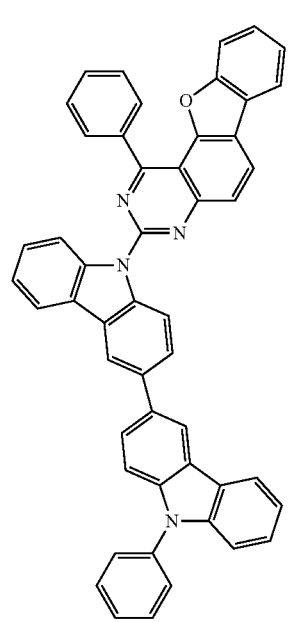
A-100
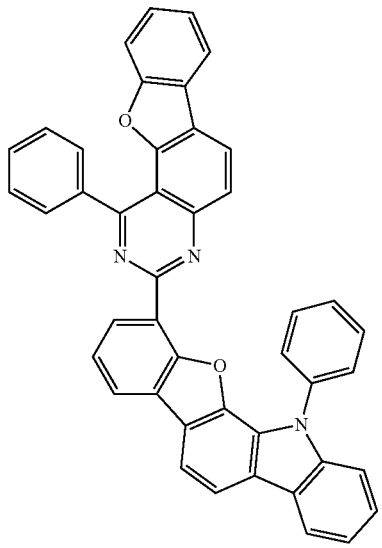
A-99
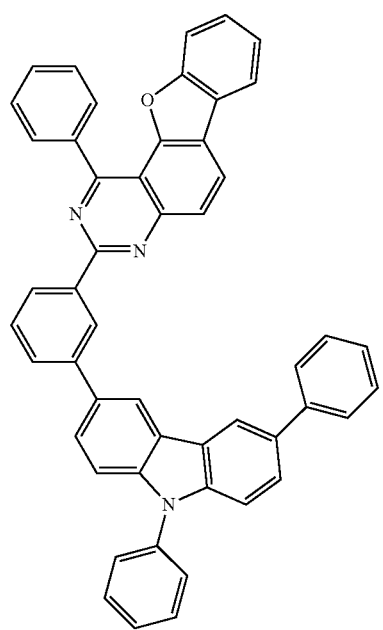
A-101
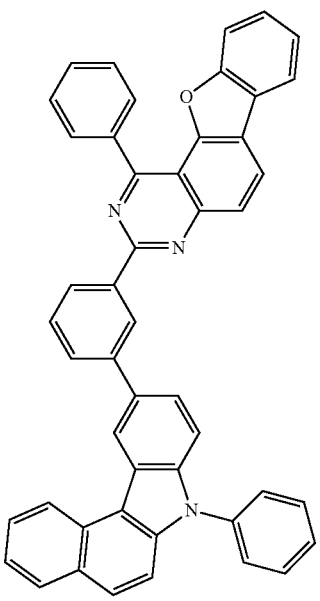

A-102
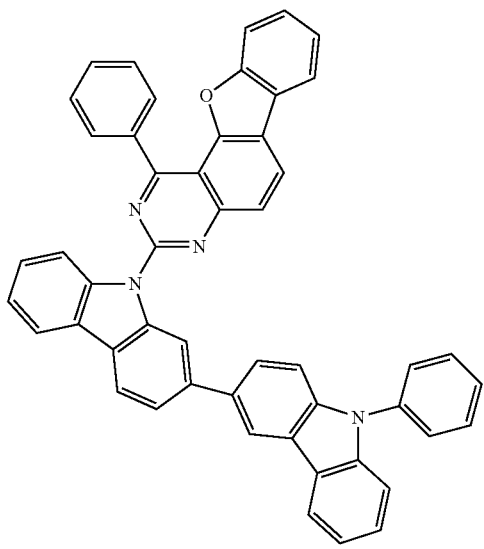
A-103
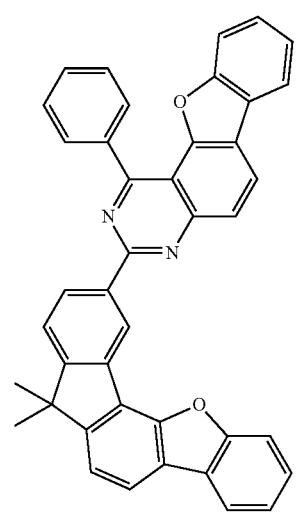
A-104
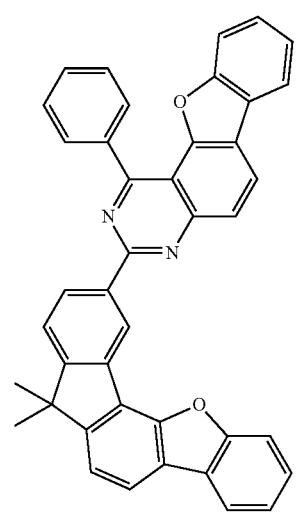
A-105
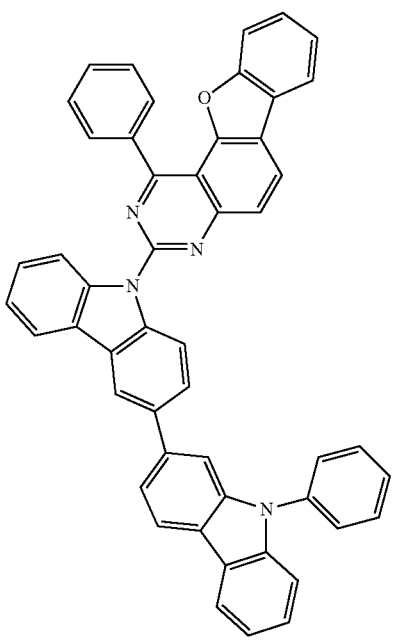
A-106
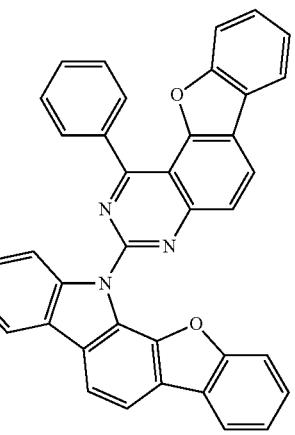
A-107
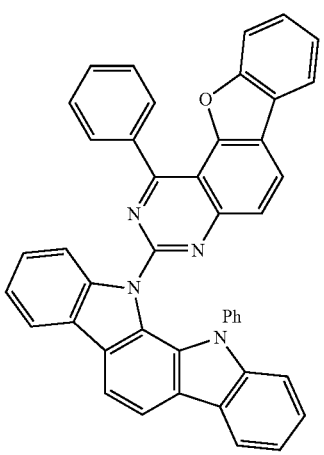

A-108
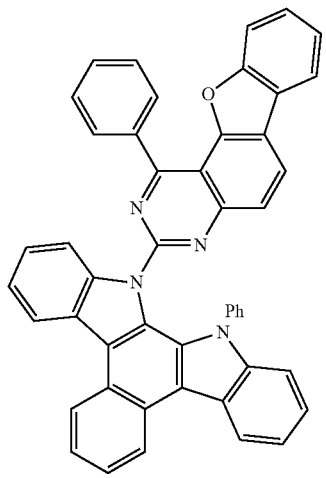
A-109
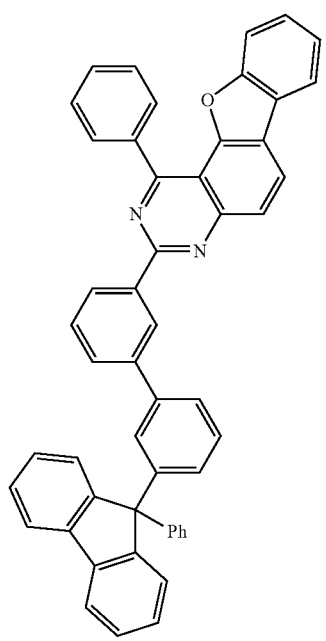
A-110
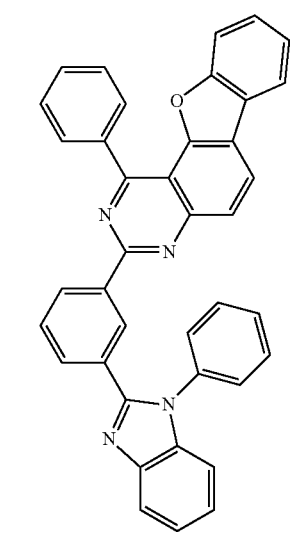
A-111
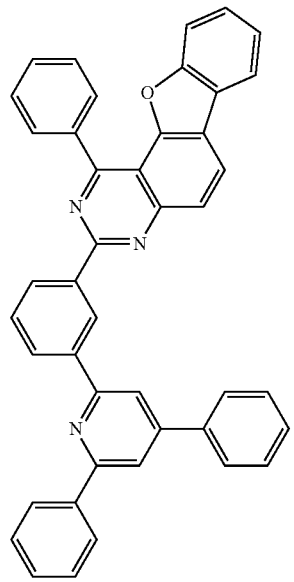
A-112
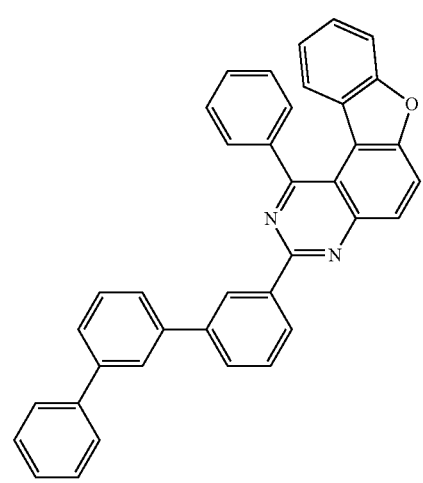
A-113
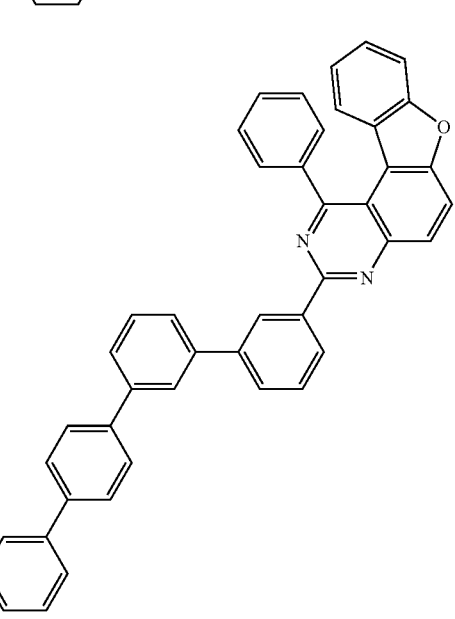

A-114
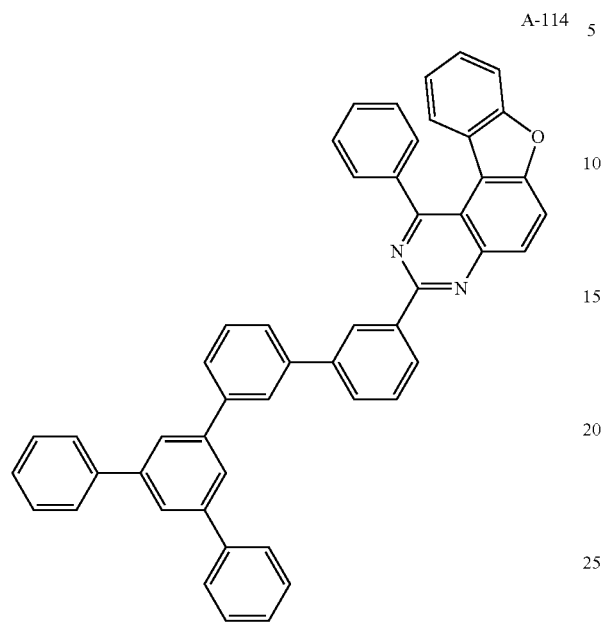
A-115
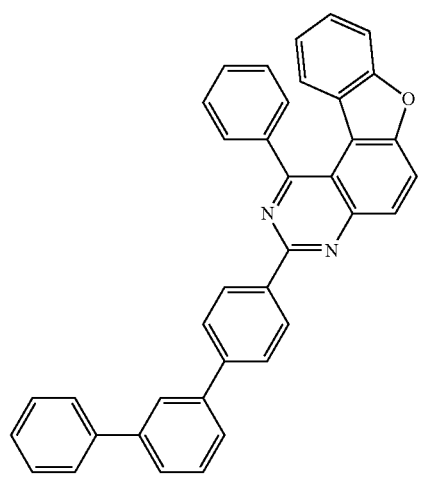
A-116
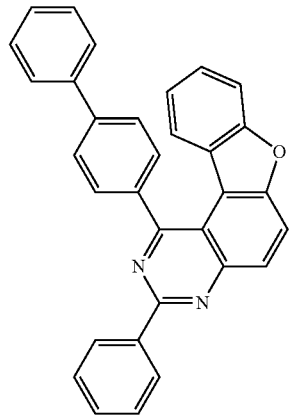
A-117
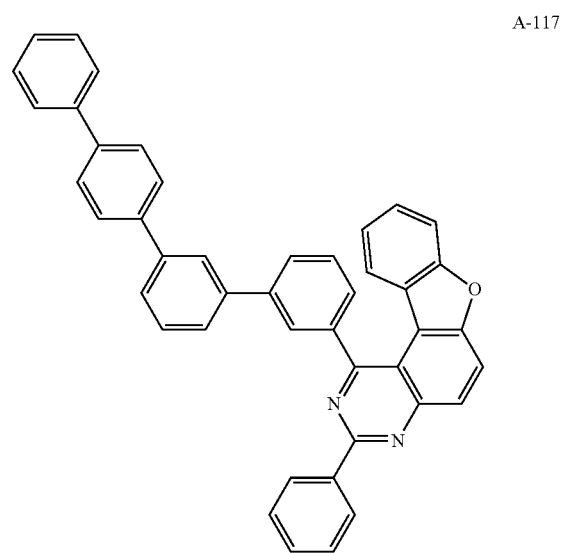
A-118
A-119

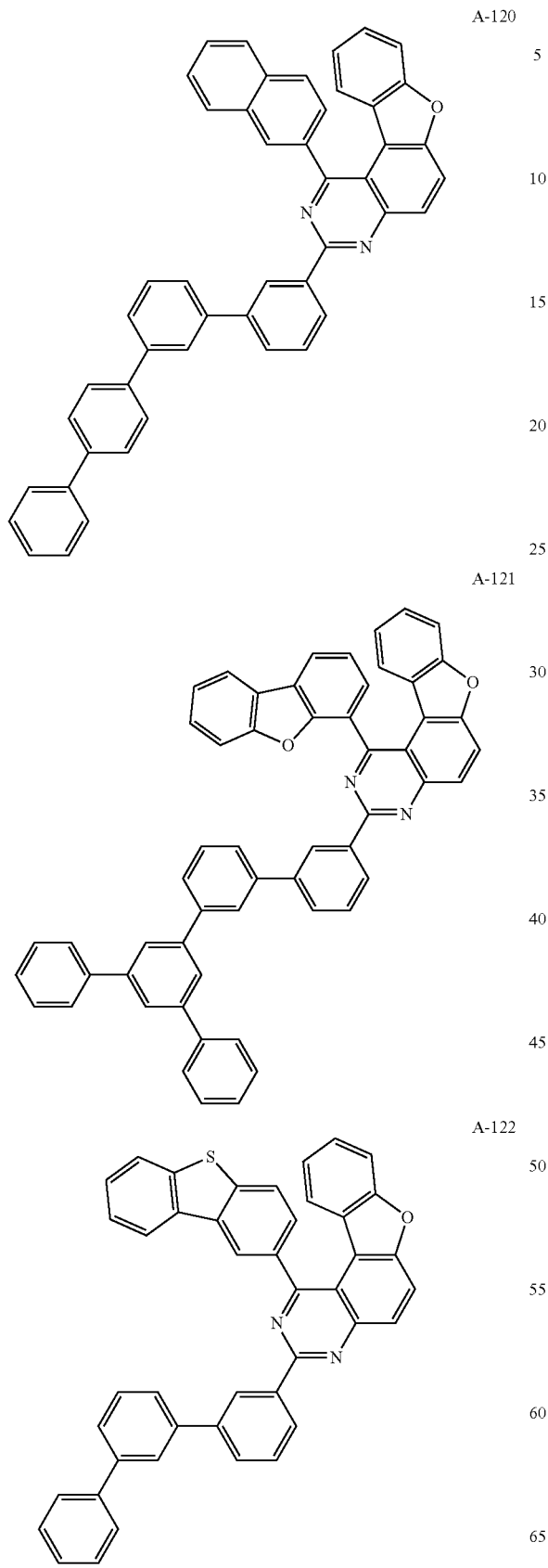
A-120
A-121
A-122
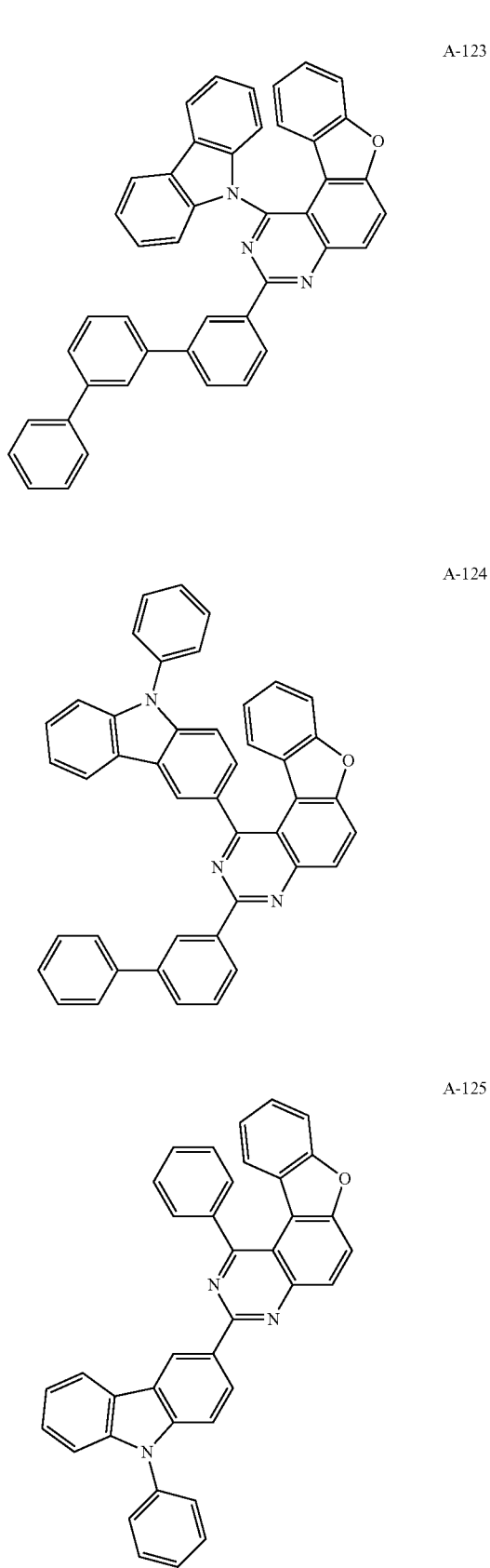
A-123
A-124
A-125

-continued
A-126
A-127
A-128
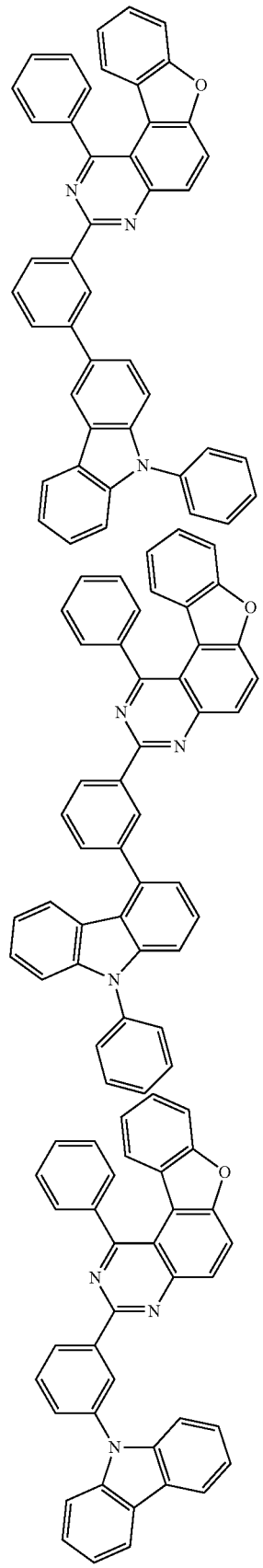
-continued
A-129
A-130

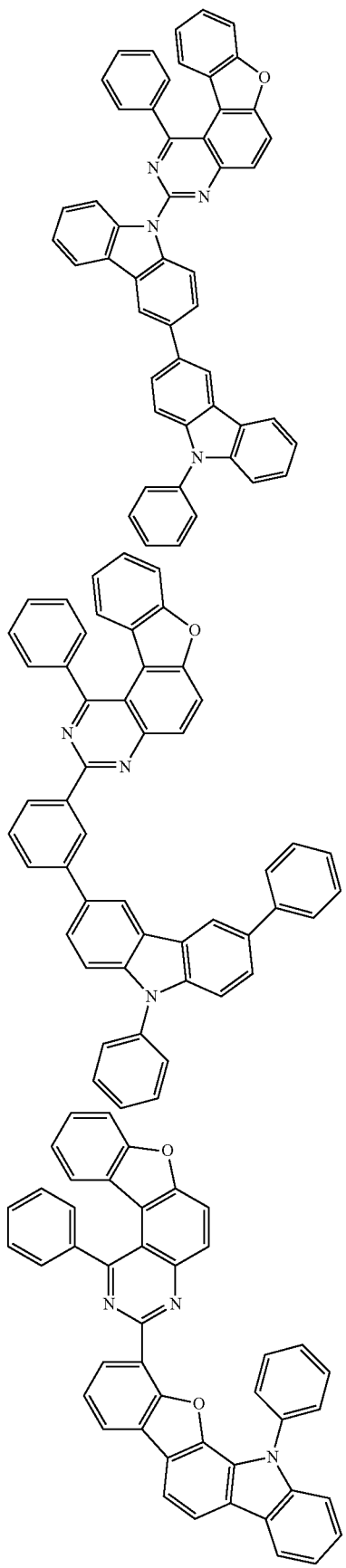
A-131
A-132
A-133
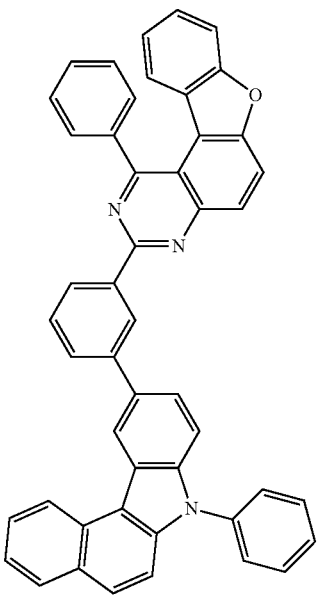
A-134
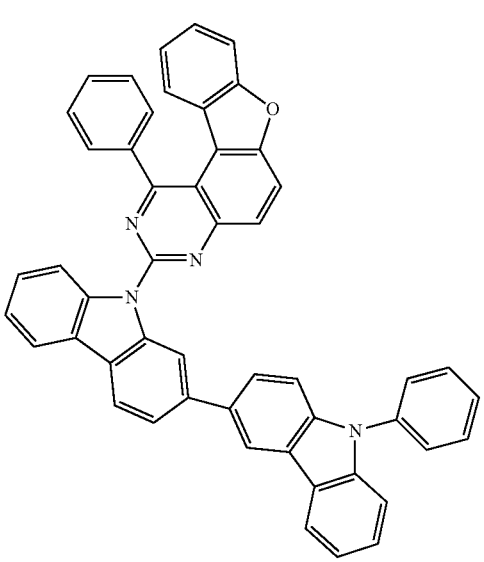
A-135
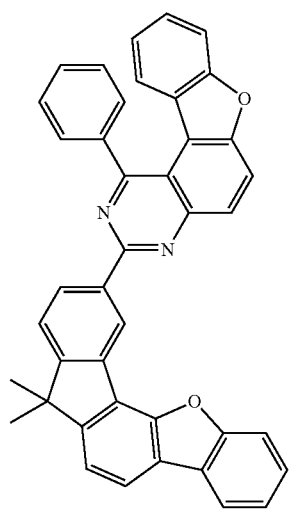
A-136

A-137
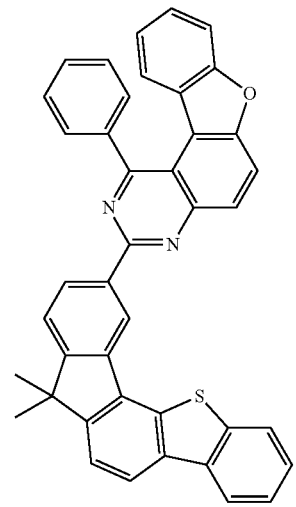
A-138
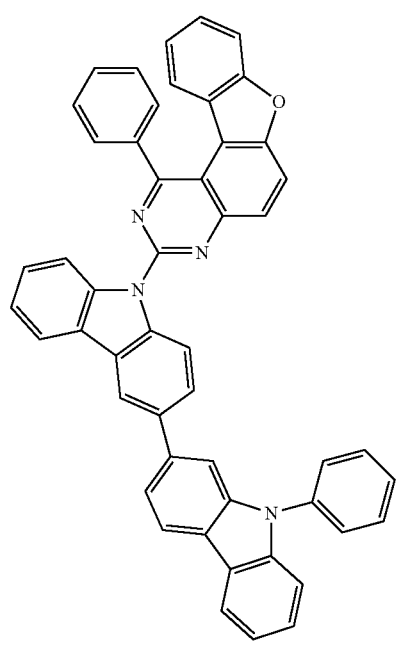
A-139
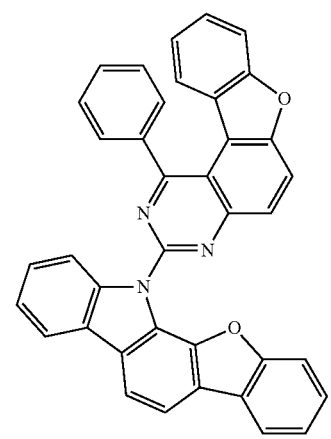
A-140
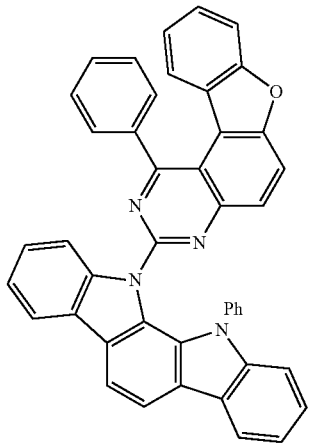
A-141
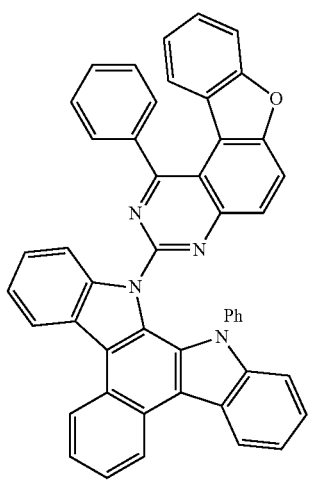
A-142
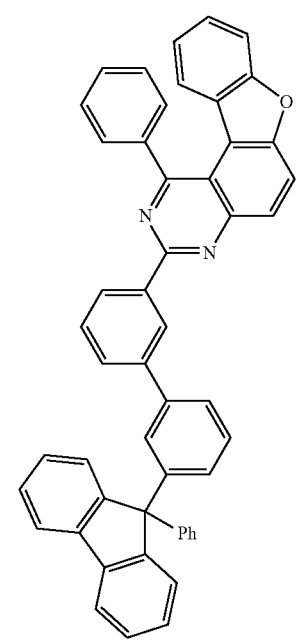

A-143
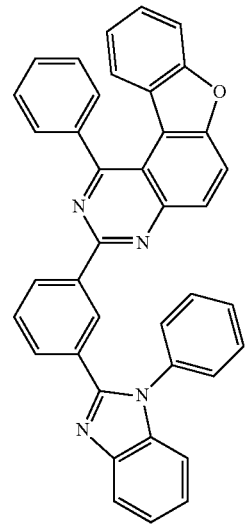
A-144
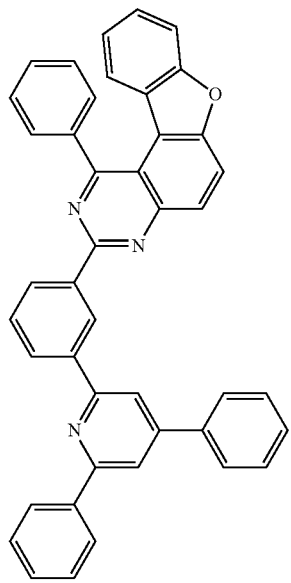
A-145
A-146
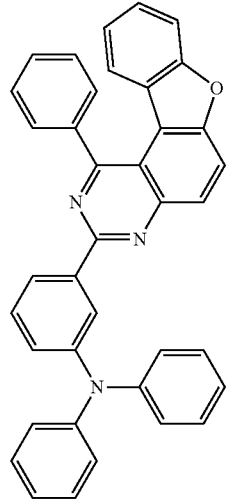
A-147
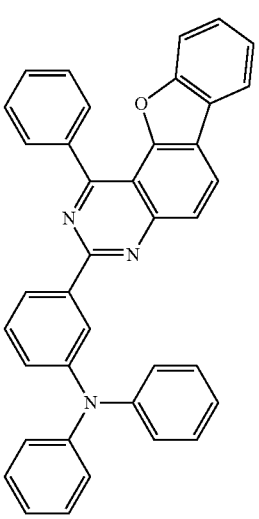
A-148
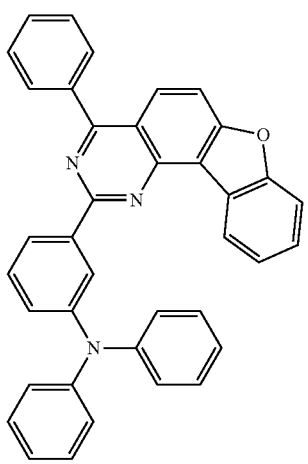

-continued
A-149
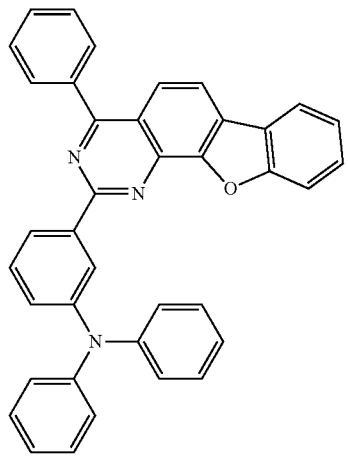
A-150
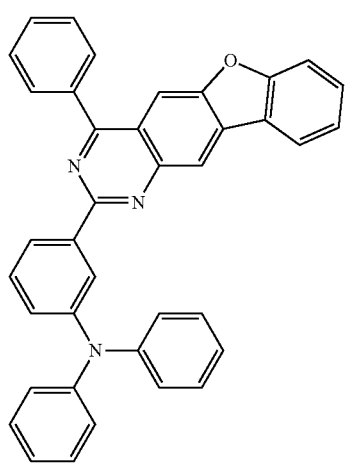
-continued
B-5
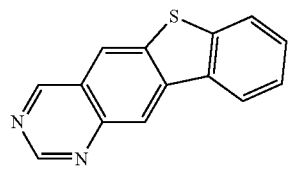
B-6
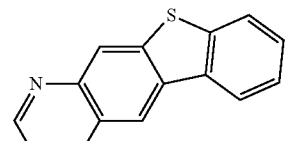
B-7
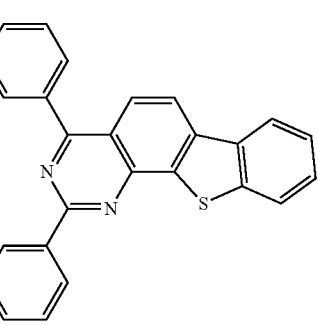
B-8
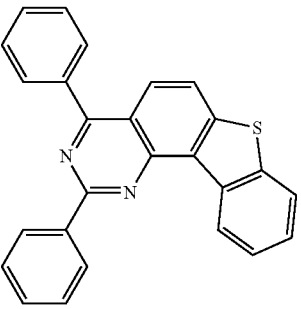
B-9
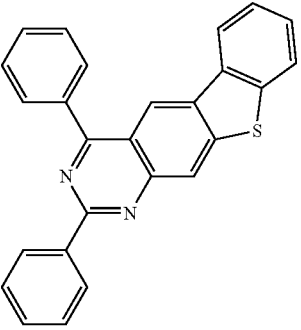
B-10
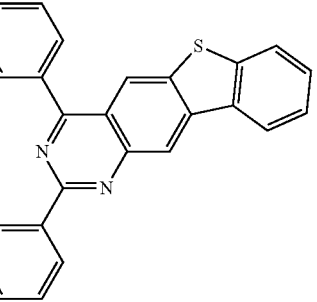

B-11
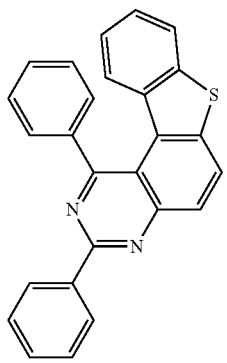
B-12
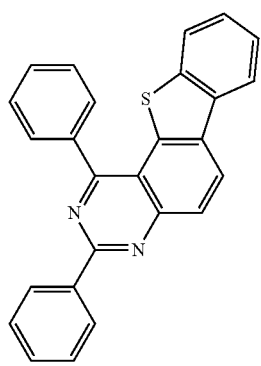
B-13
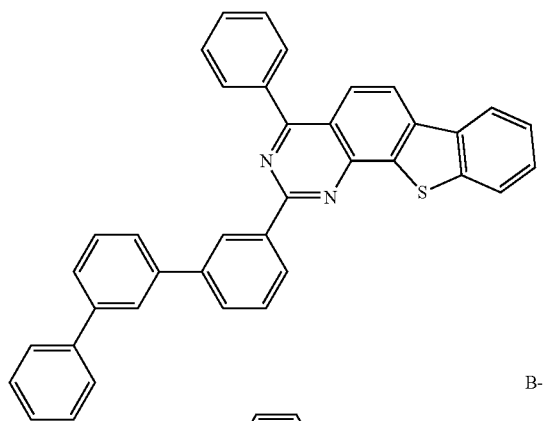
B-14
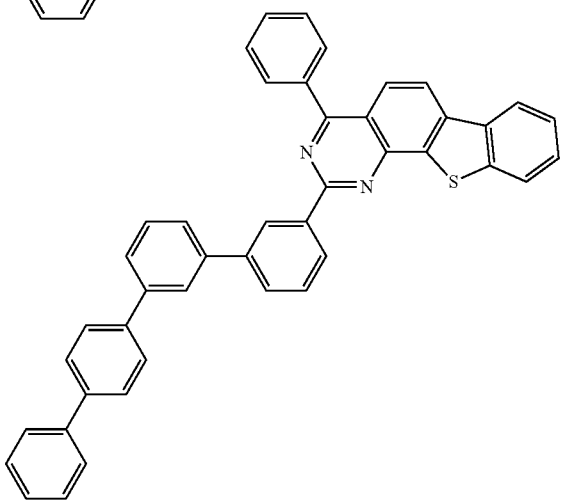
B-15
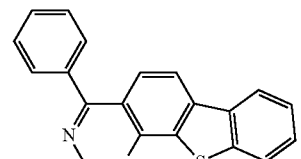
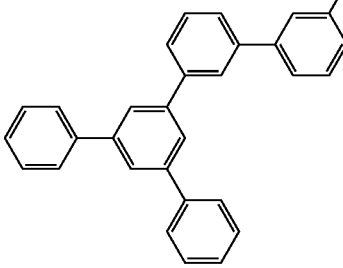
B-16
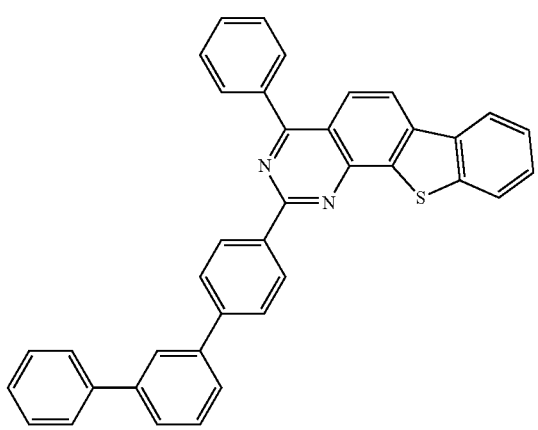
B-17
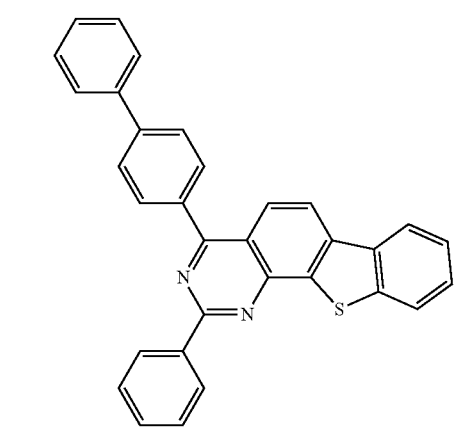

-continued
B-18
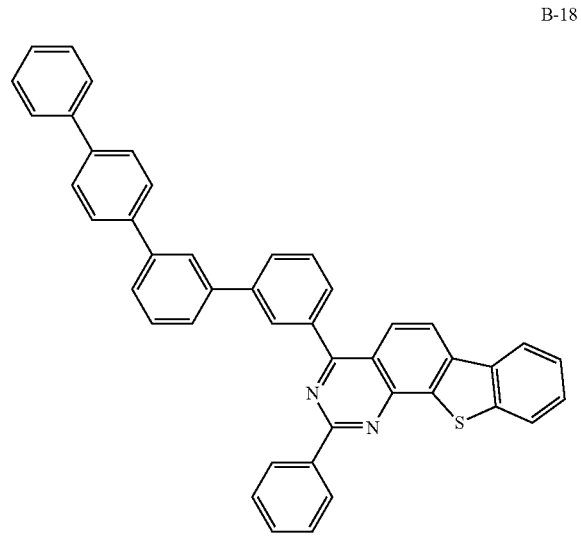
B-19
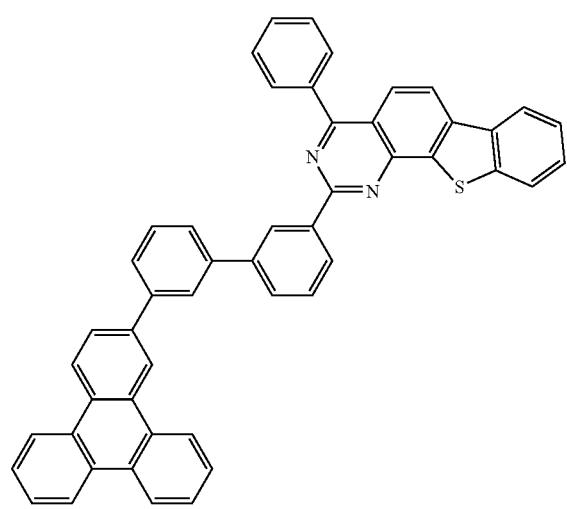
B-20
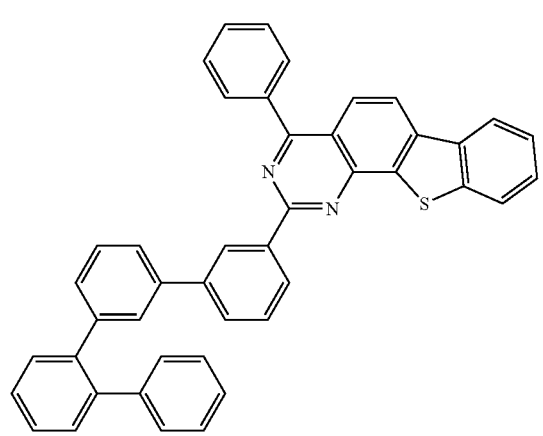
B-21
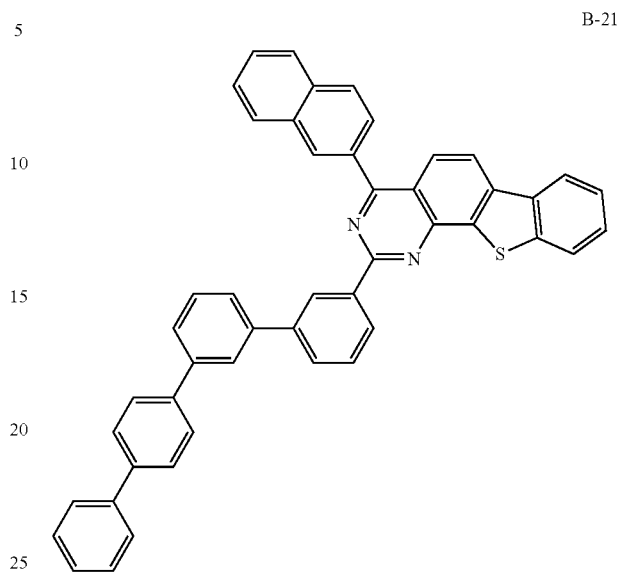
B-22
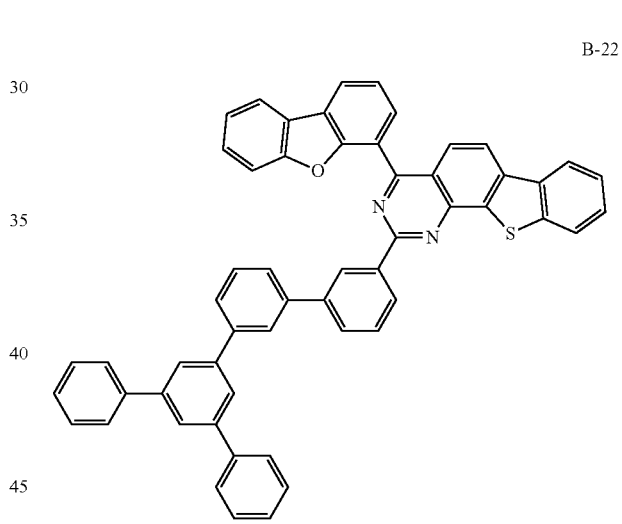
B-23
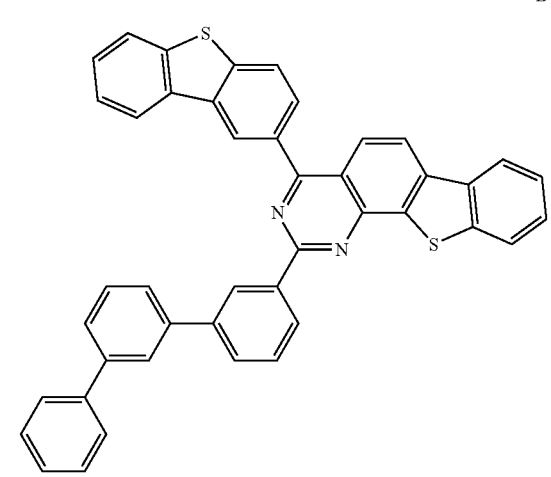

B-24
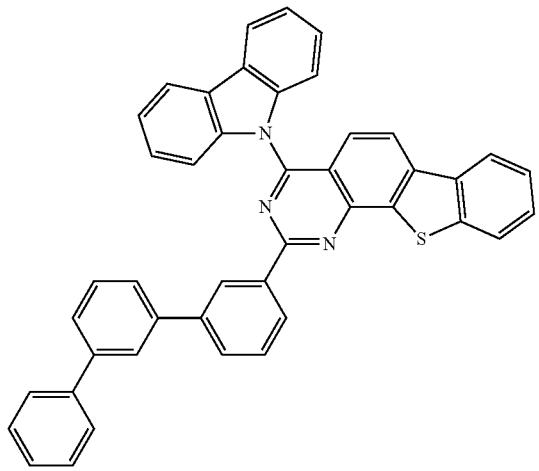
B-25
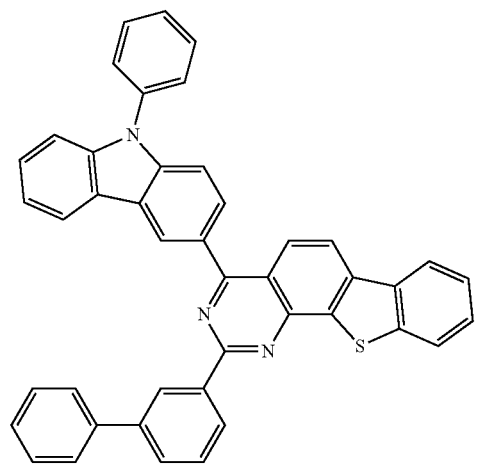
B-26
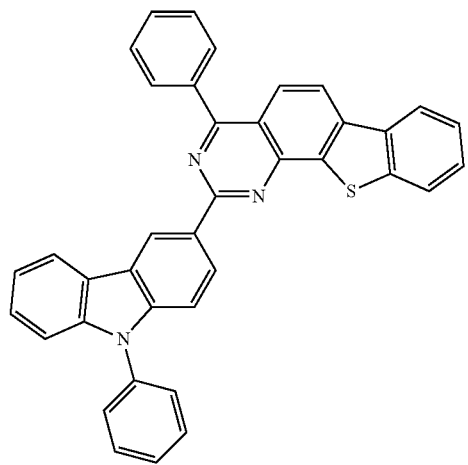
B-27
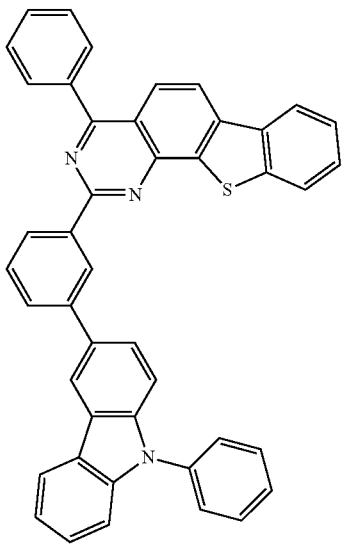
B-28
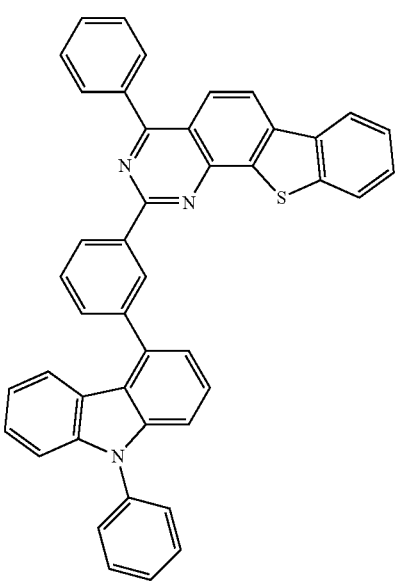
B-29
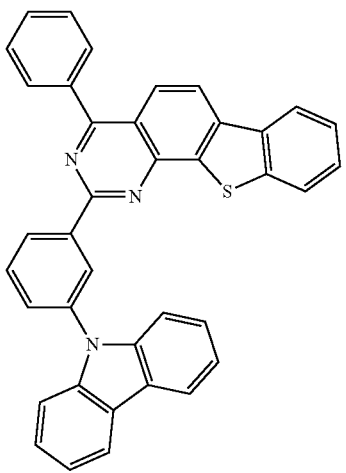

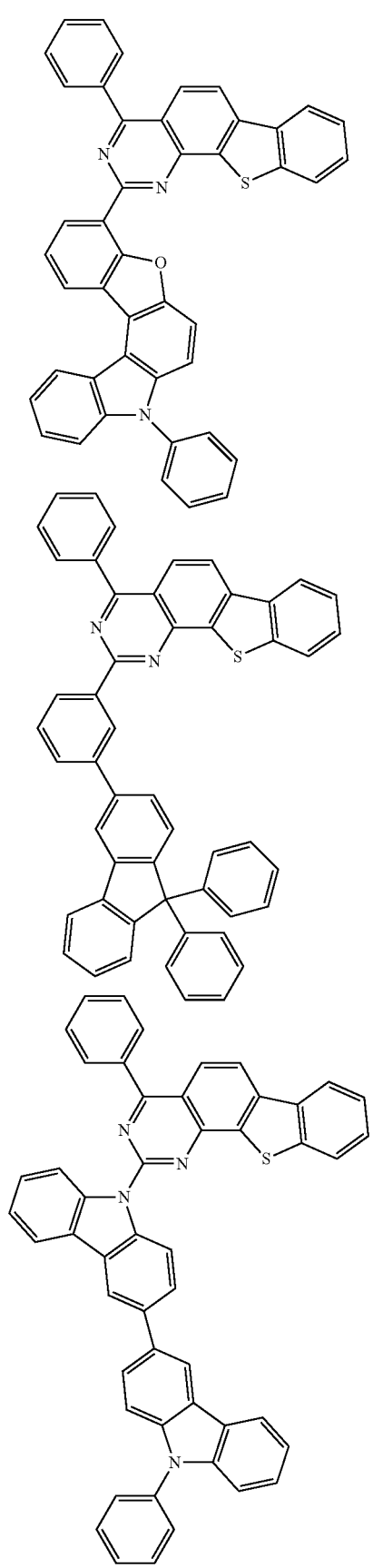
B-30
B-31
B-32
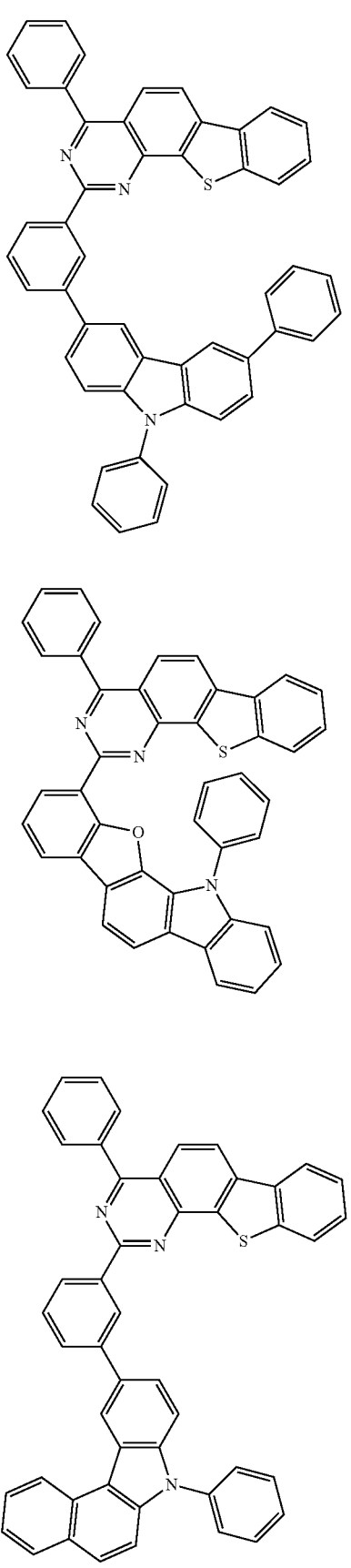
B-33
B-34
B-35

B-36
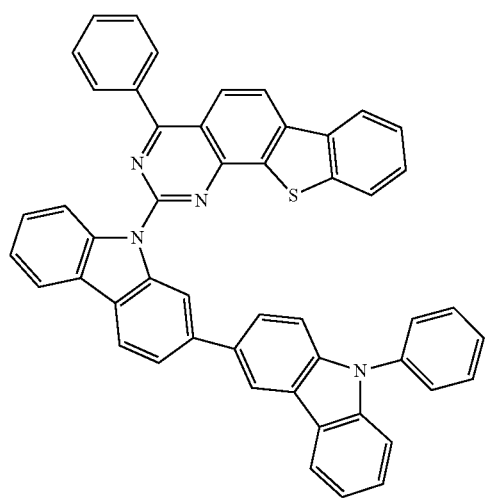
B-37
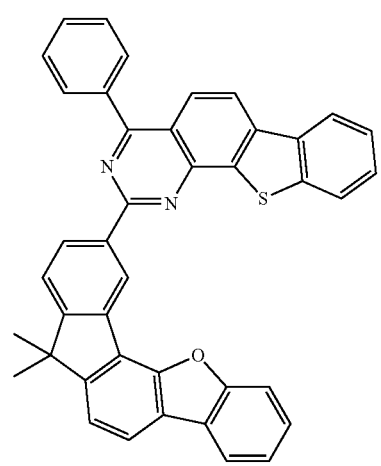
B-38
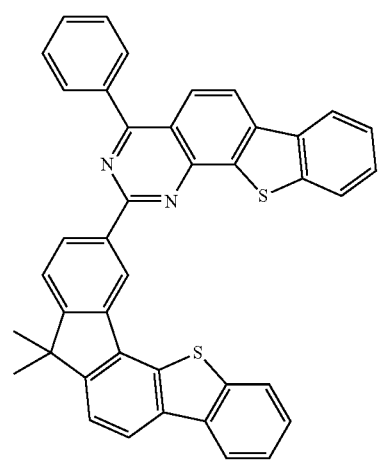
B-39
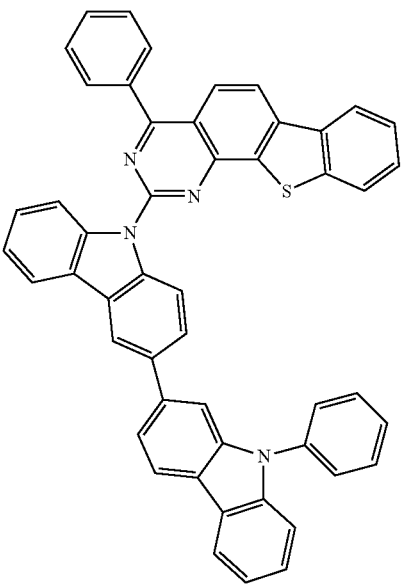
B-40
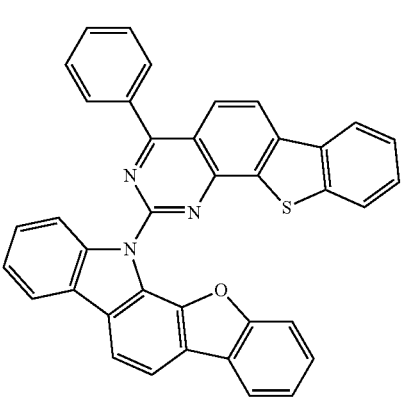
B-41
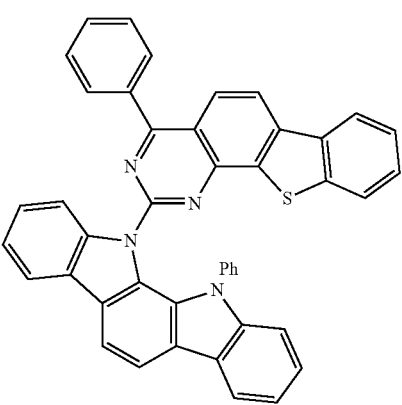

B-42
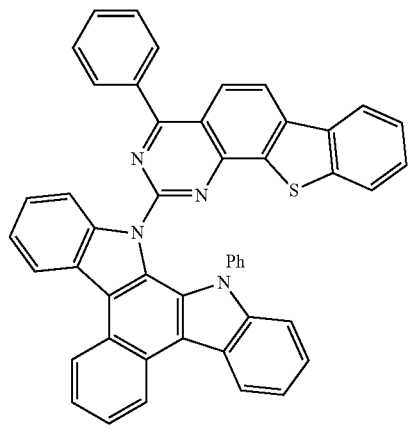
B-43
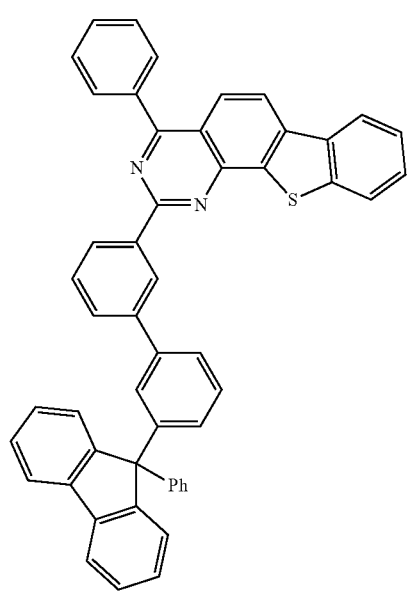
B-44
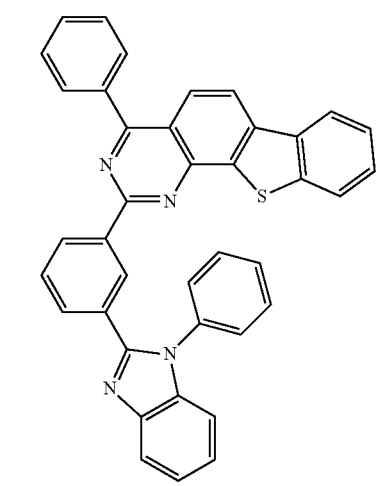
B-45
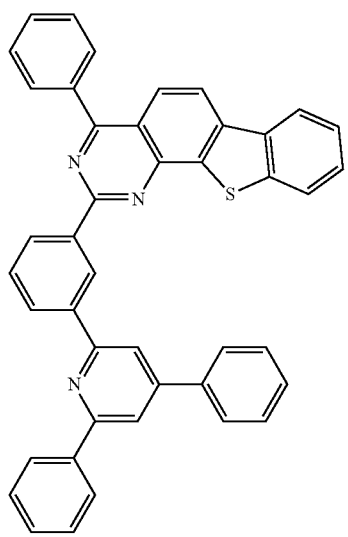
B-46
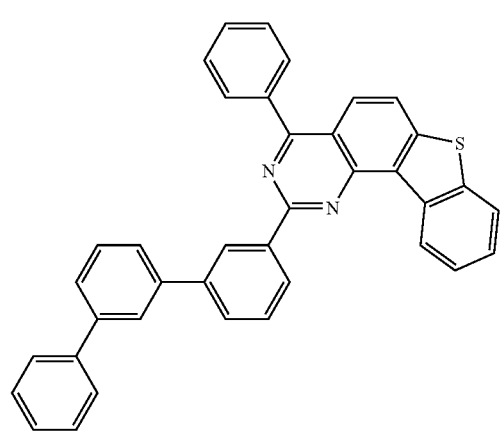
B-47
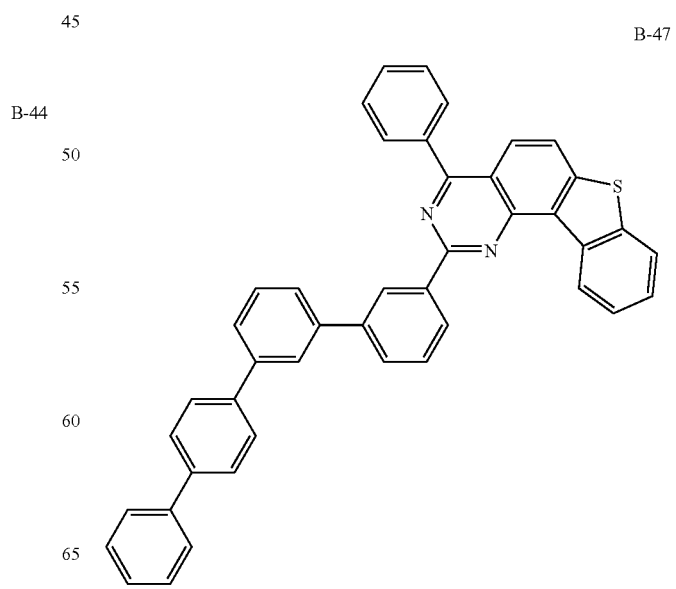

B-48
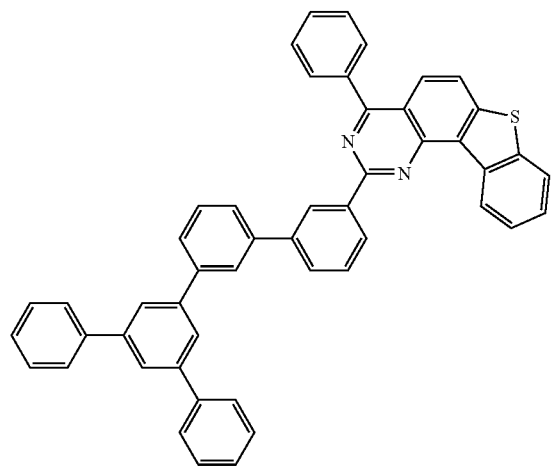
B-51
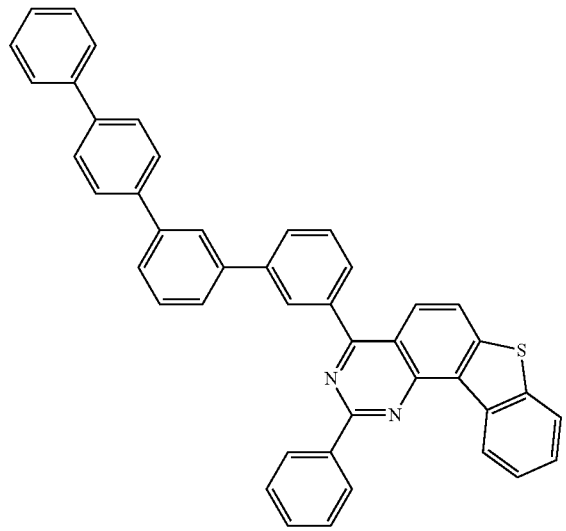
B-49
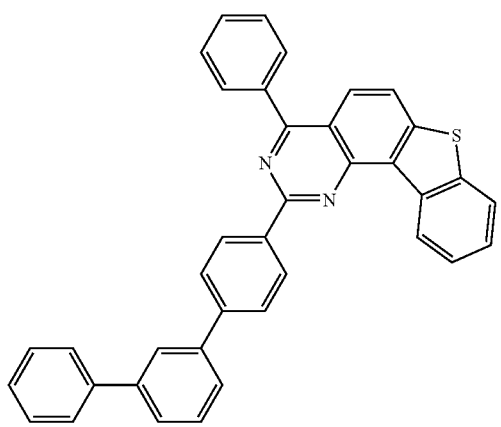
B-52
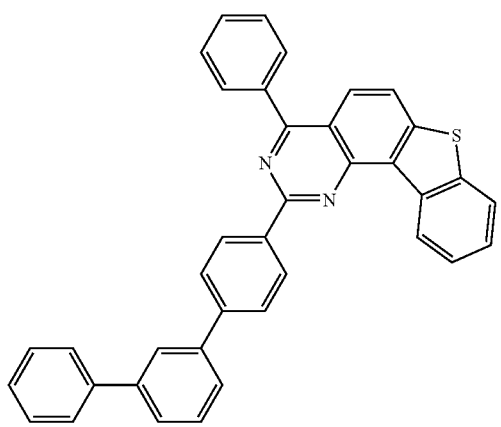
B-50
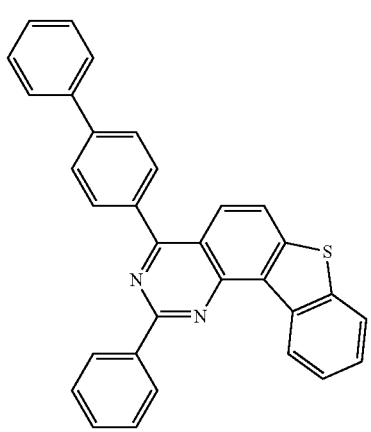
B-53
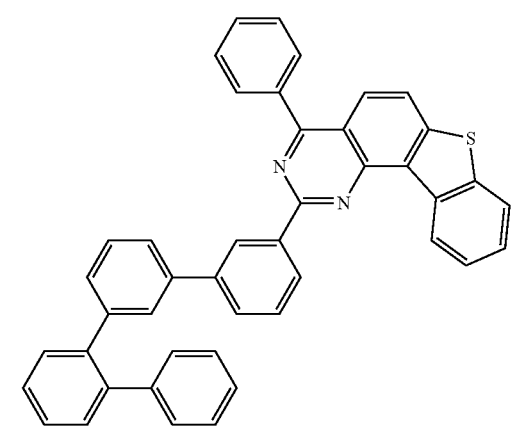

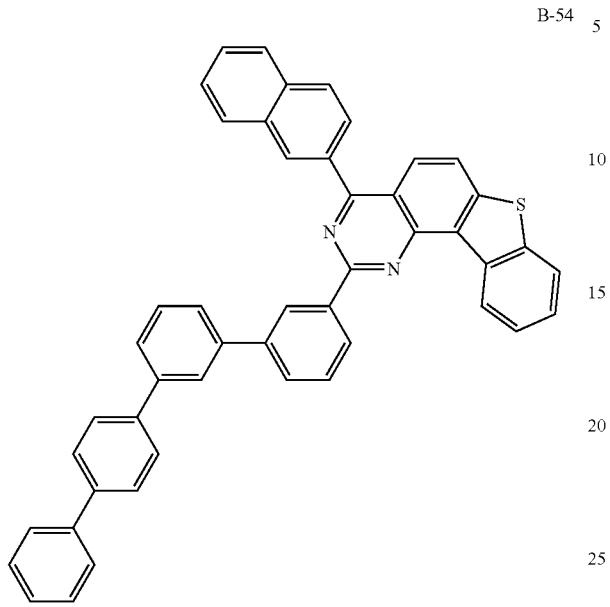
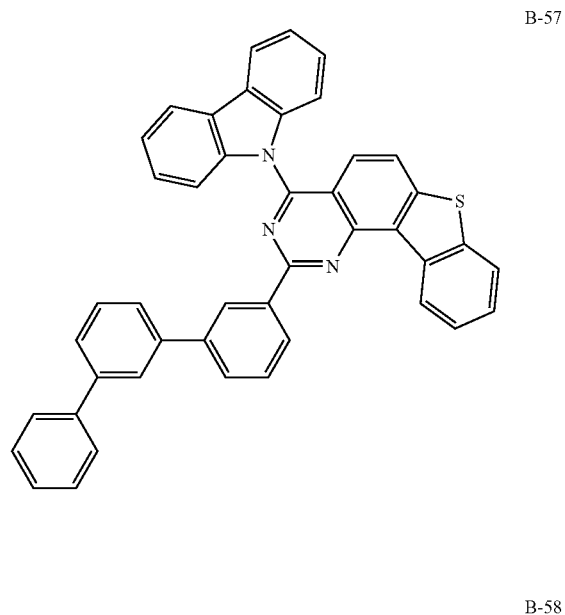
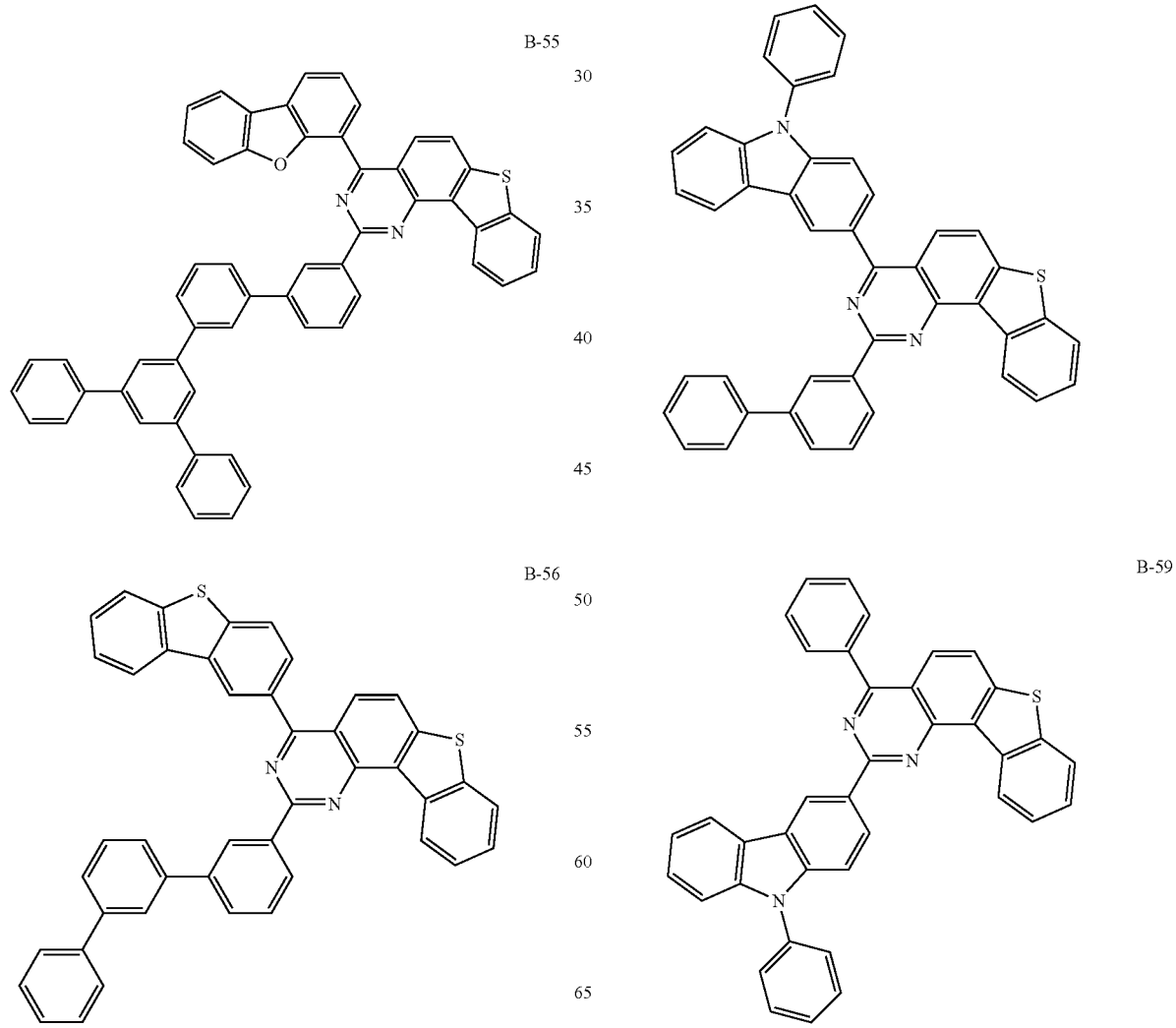

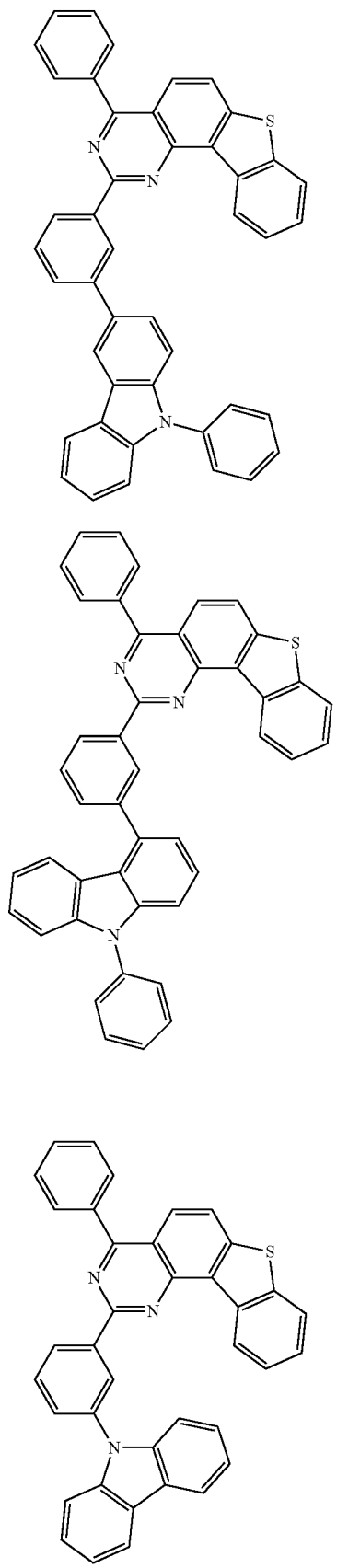
B-60
B-61
B-62
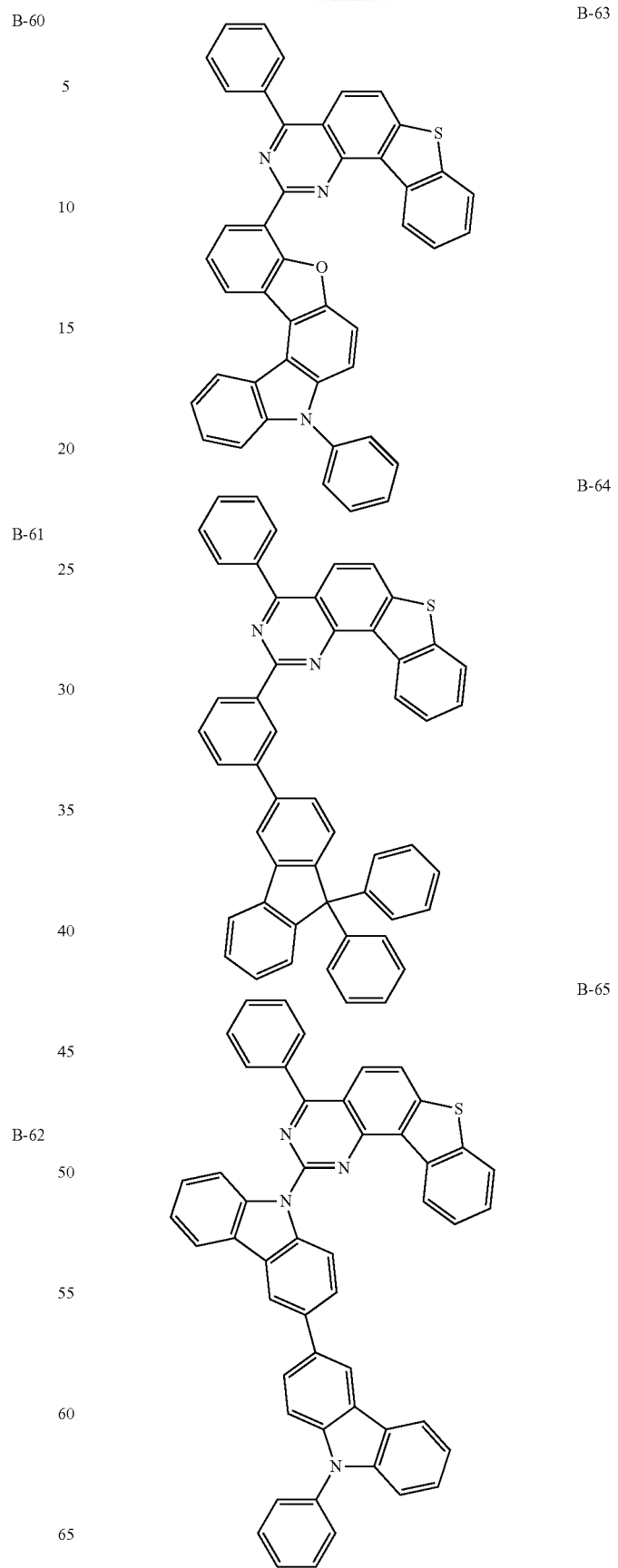
B-63
B-64
B-65

B-66
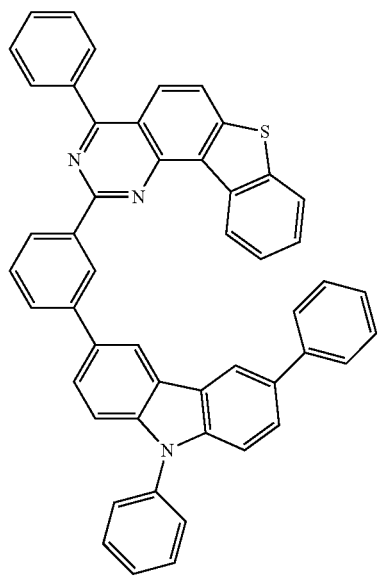
B-67
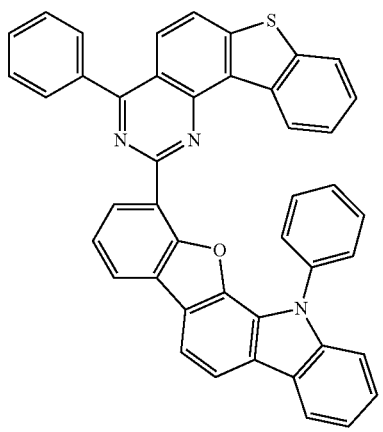
B-68
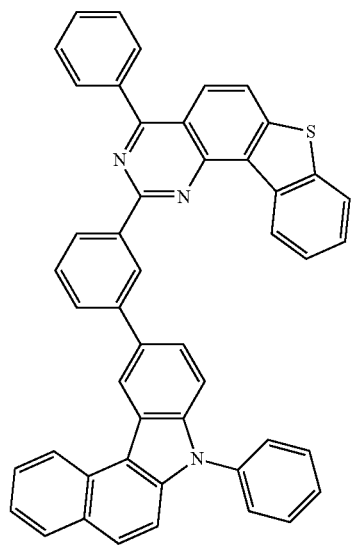
B-69
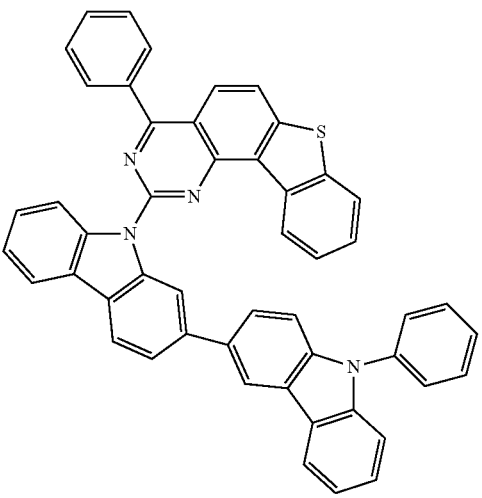
B-70
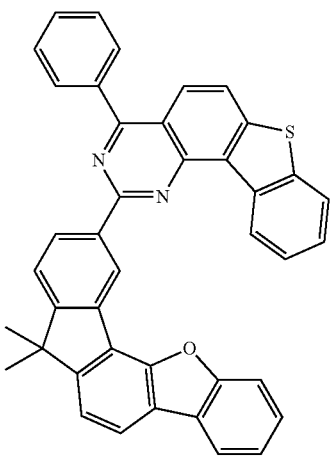
B-71
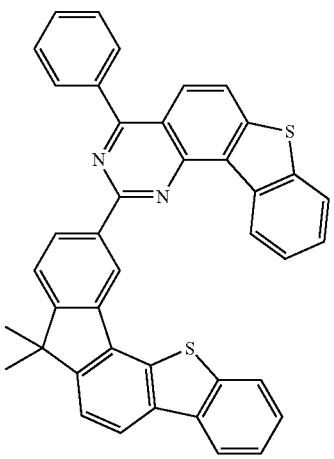

B-72
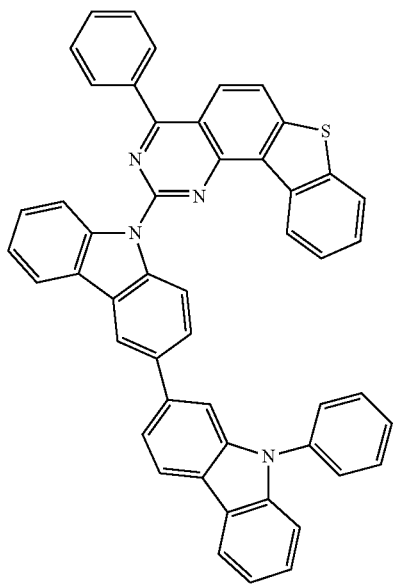
B-73
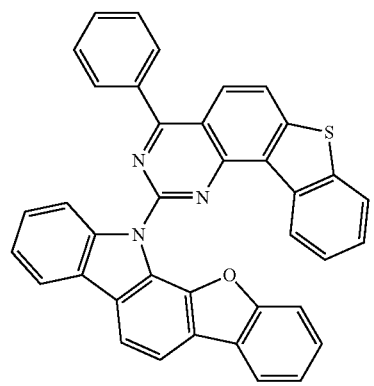
B-74
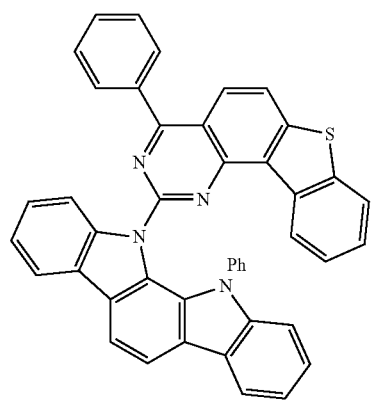
B-75
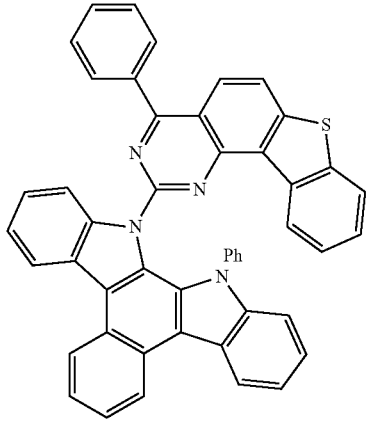
B-76
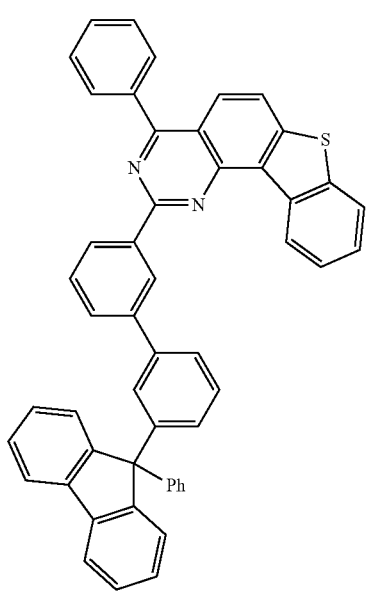
B-77
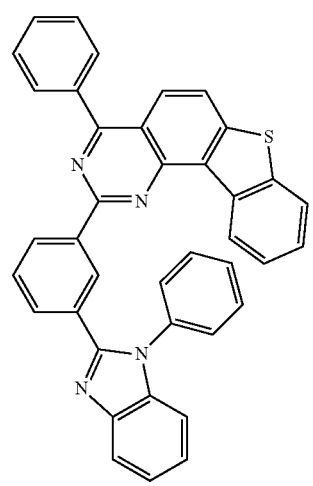

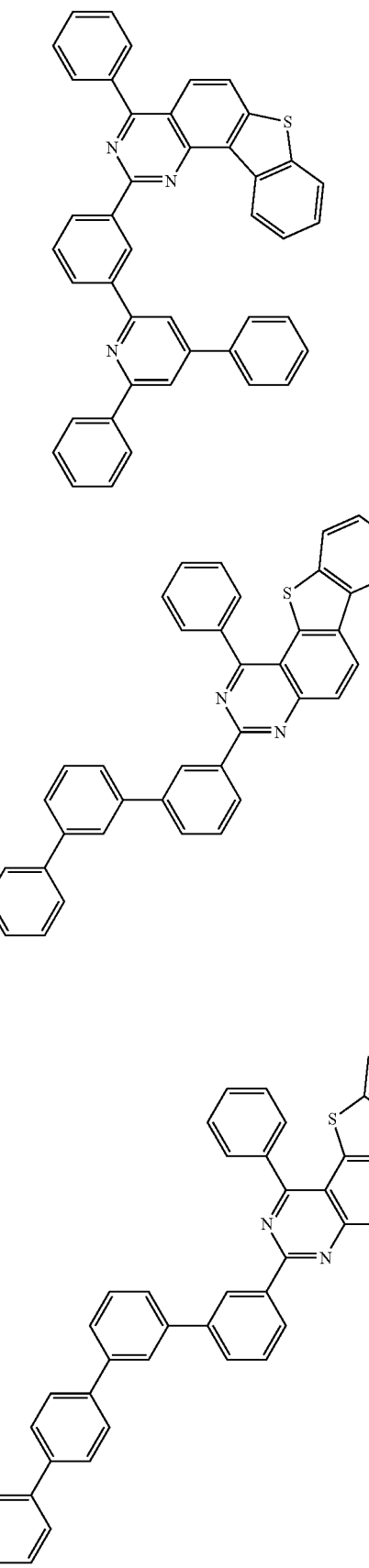
B-78
B-79
B-80
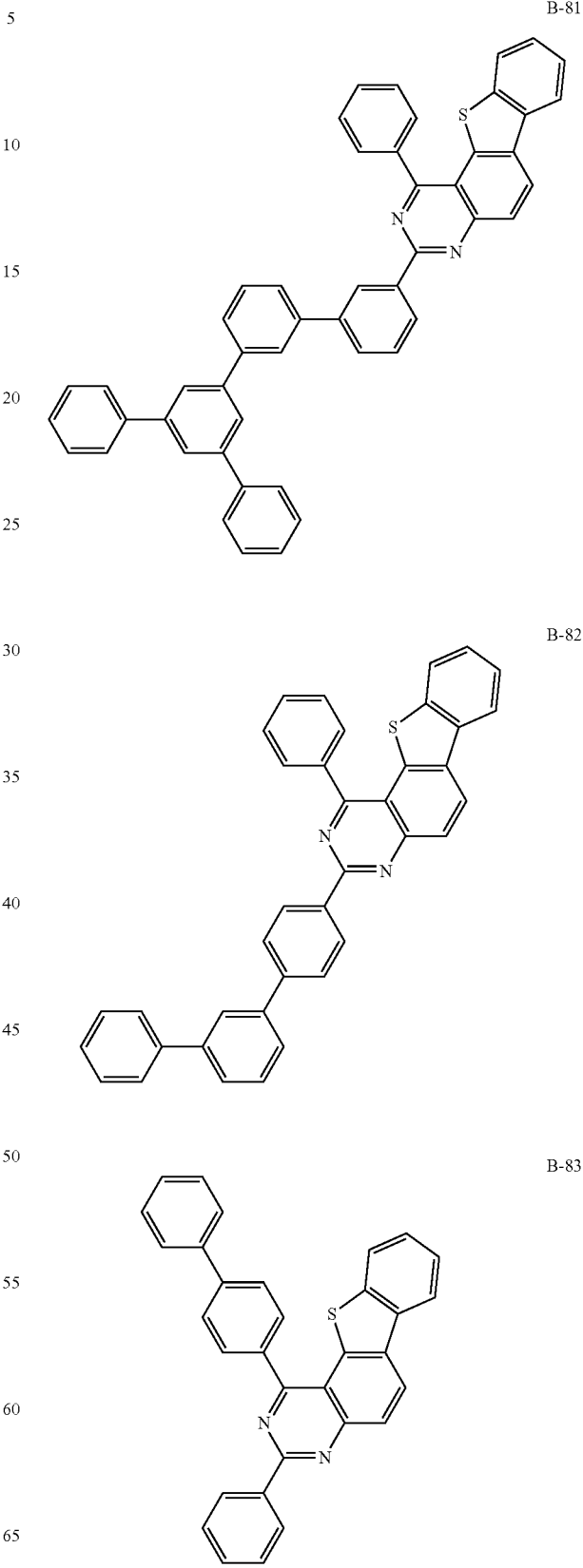
B-81
B-82
B-83

B-84
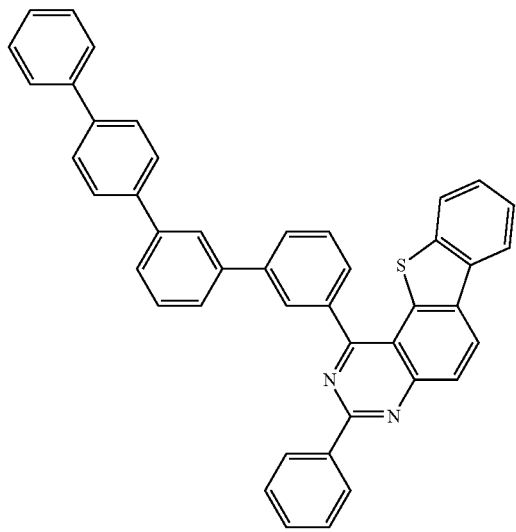
B-85
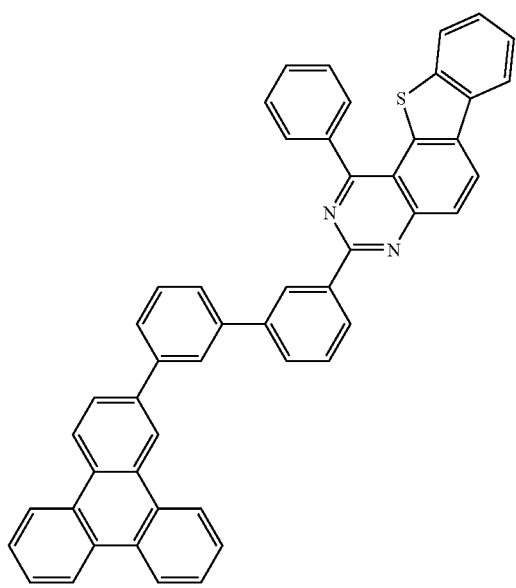
B-87
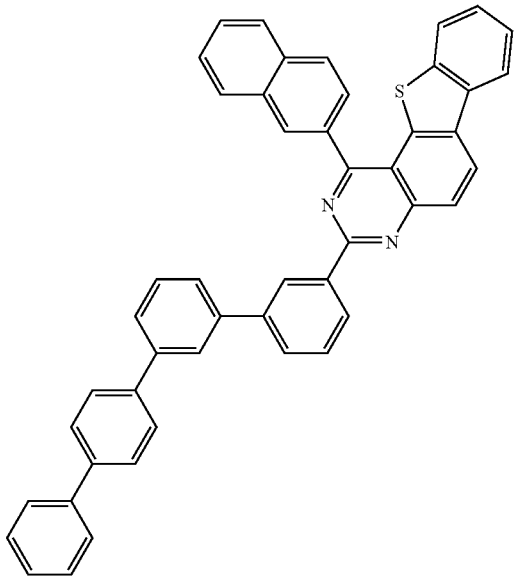
B-88
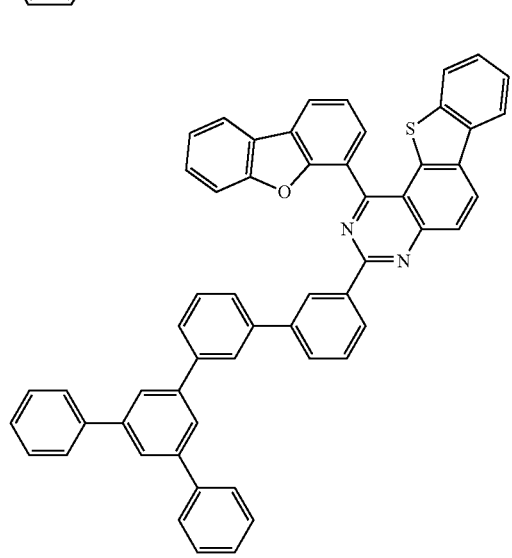
B-86
B-89
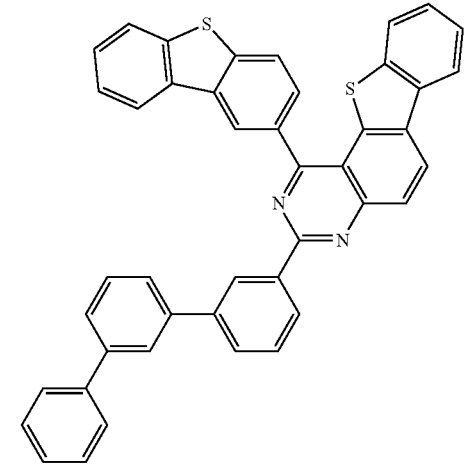

-continued
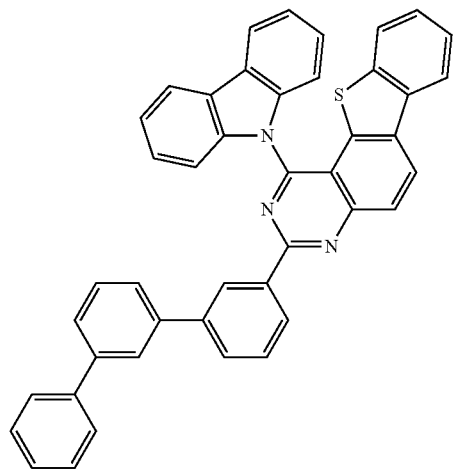
B-90
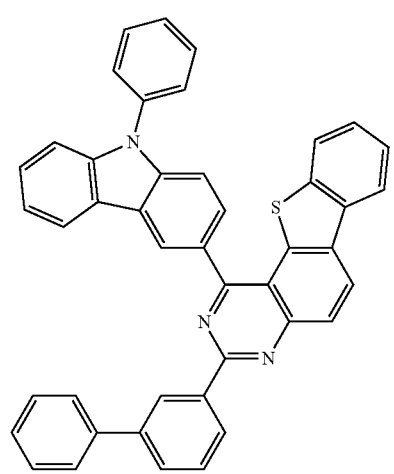
B-91
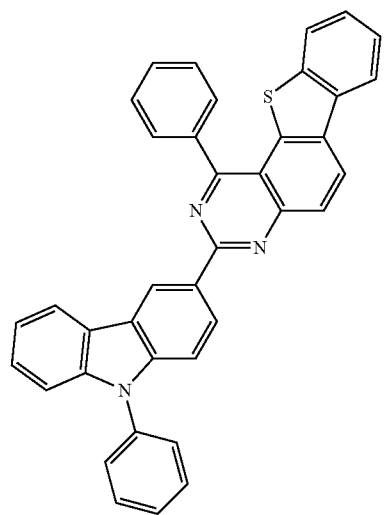
B-92
-continued
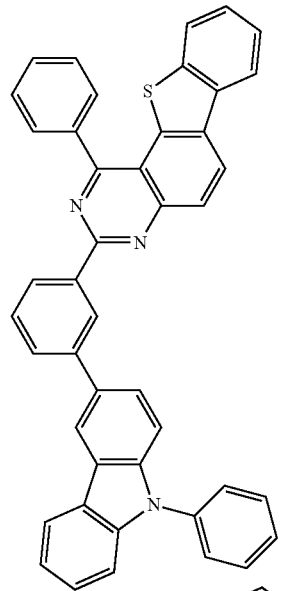
B-93
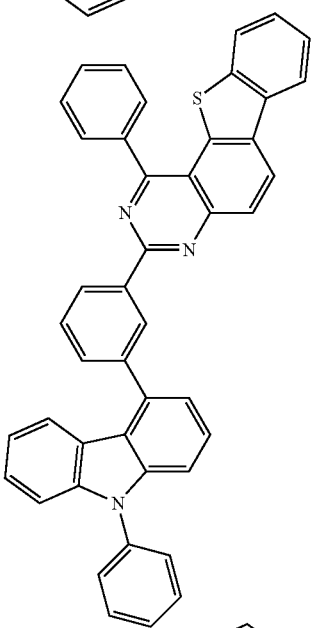
B-94
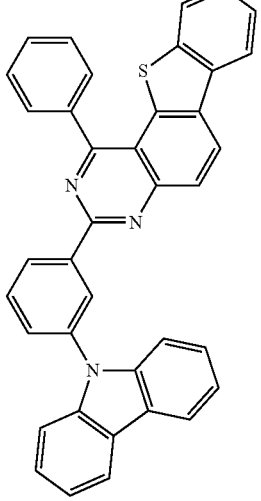
B-95

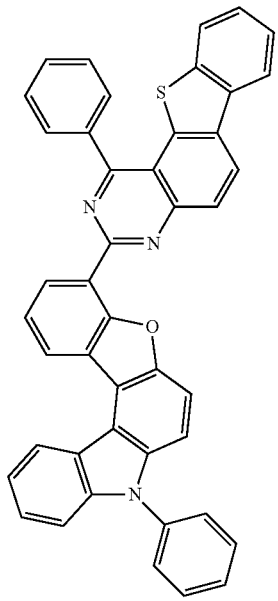
B-96
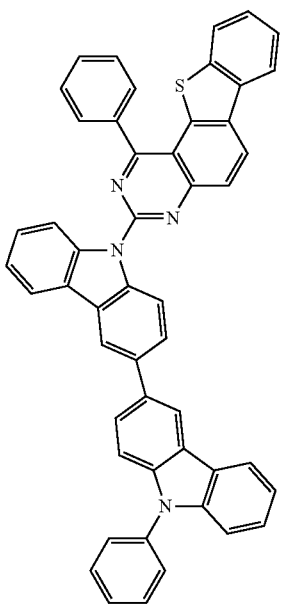
B-98
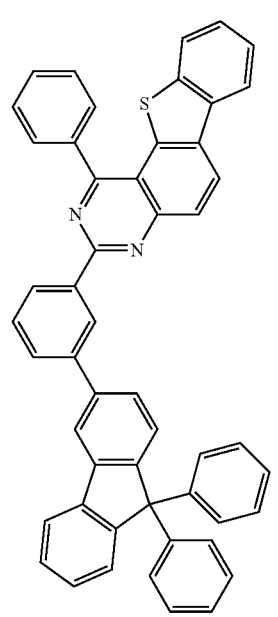
B-97
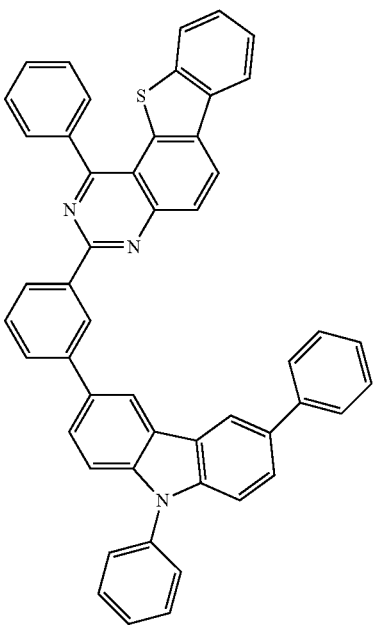
B-99

B-100
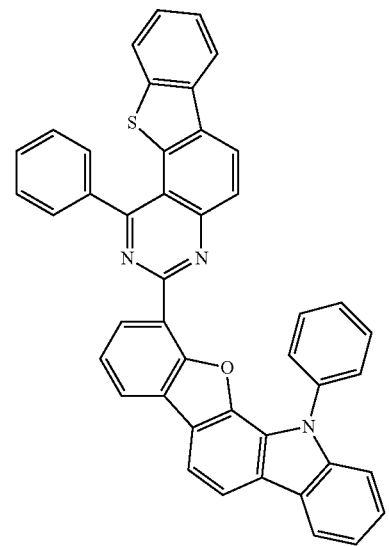
B-101
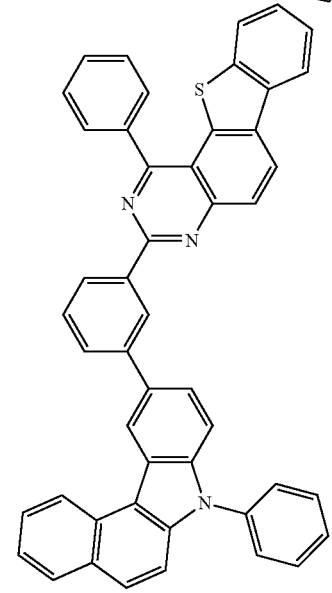
B-102
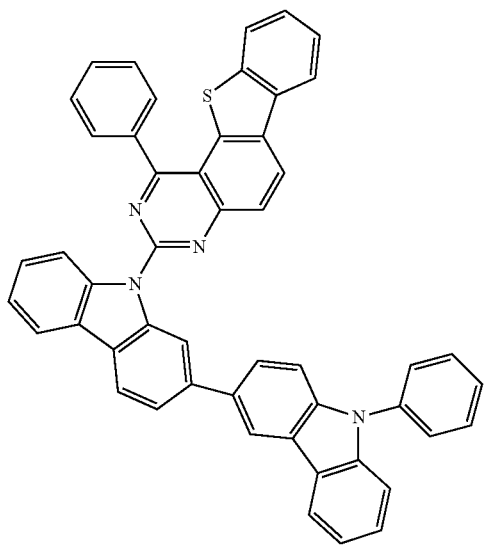
B-103
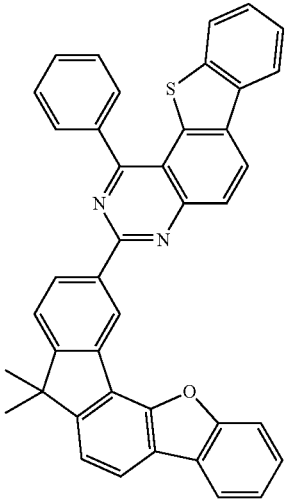
B-104
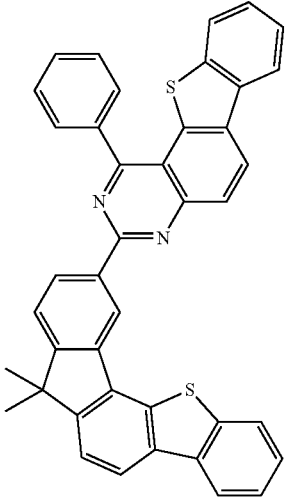
B-105
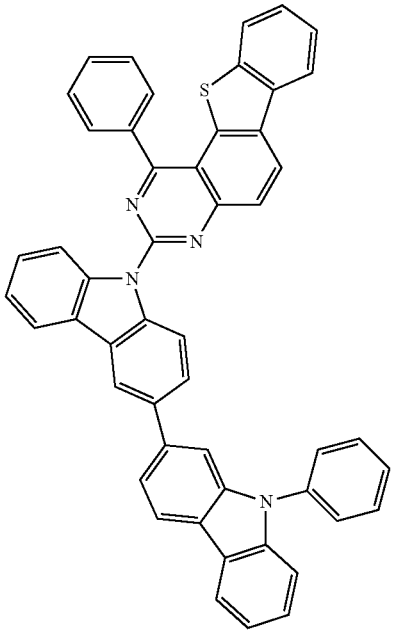

B-106
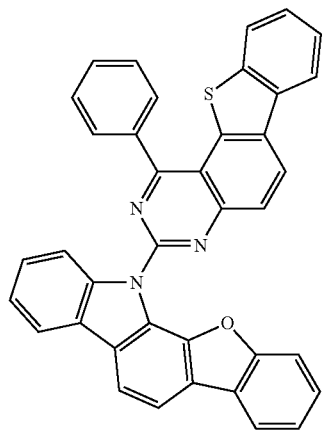
B-107
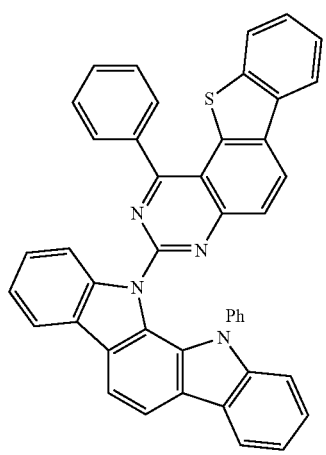
B-108
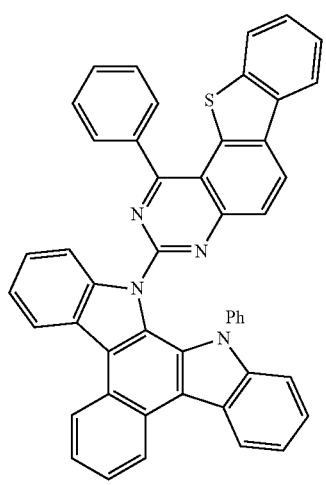
B-109
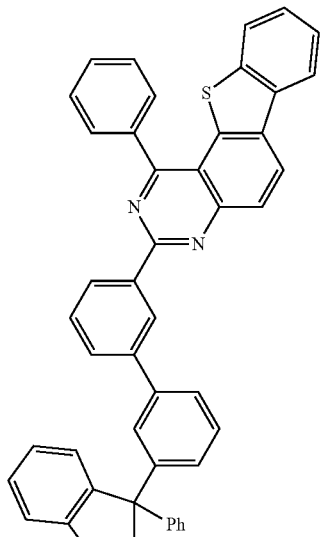
B-110
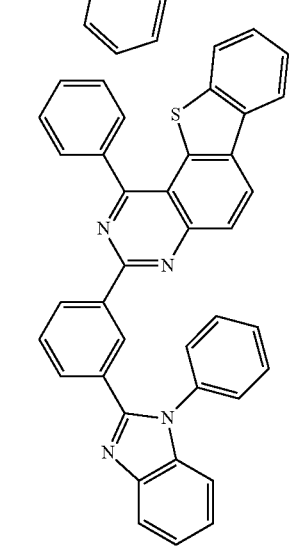
B-111
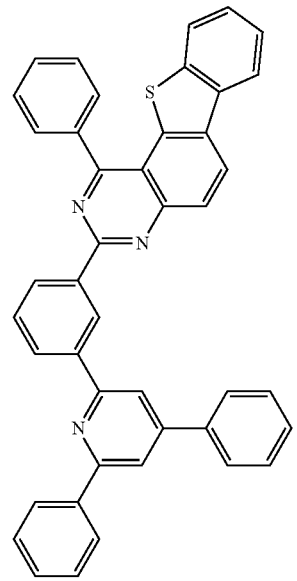

B-112
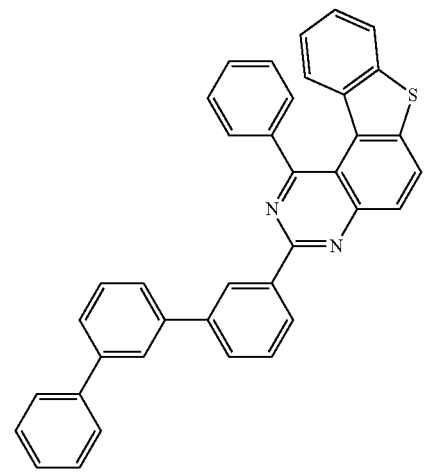
B-113
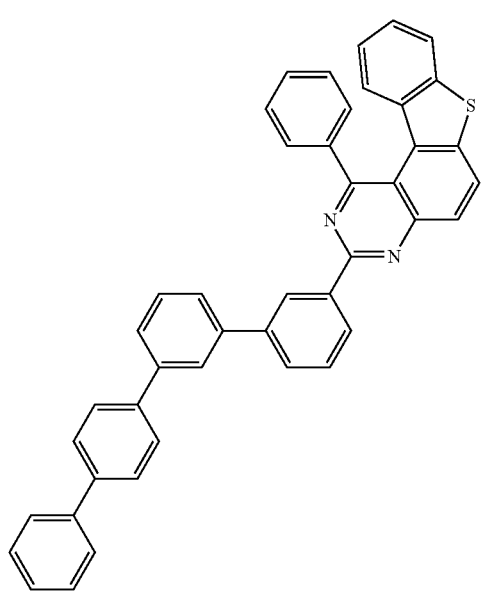
B-114
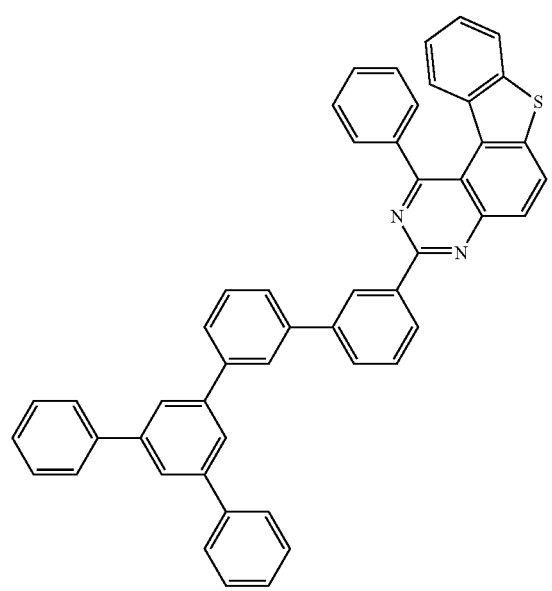
B-115
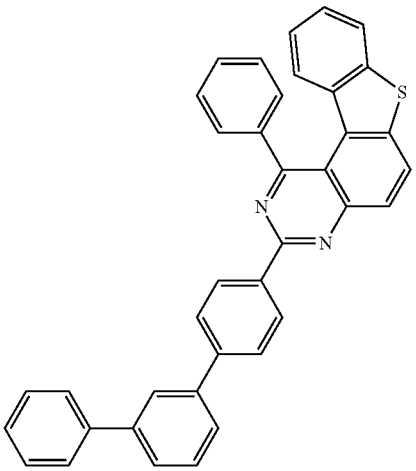
B-116
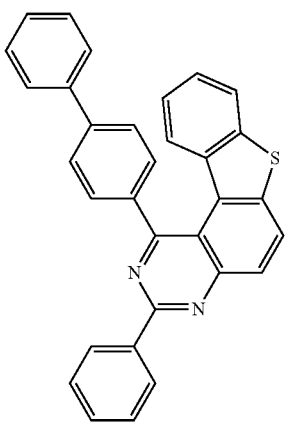
B-117
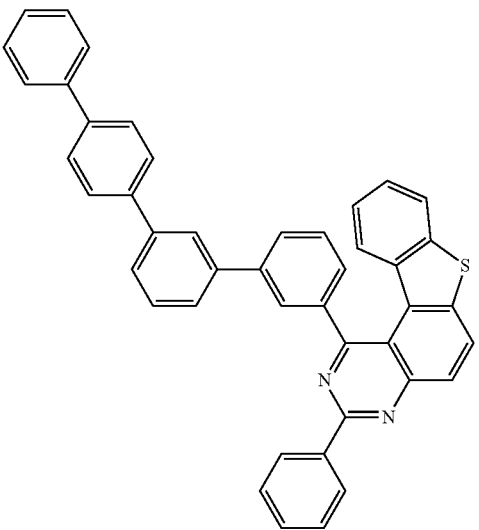

B-118
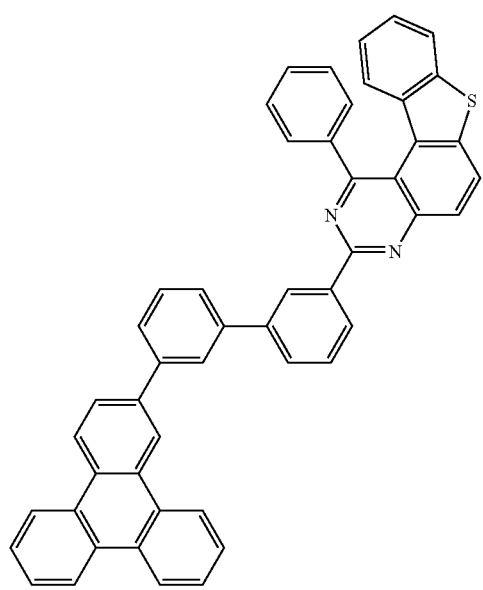
B-119
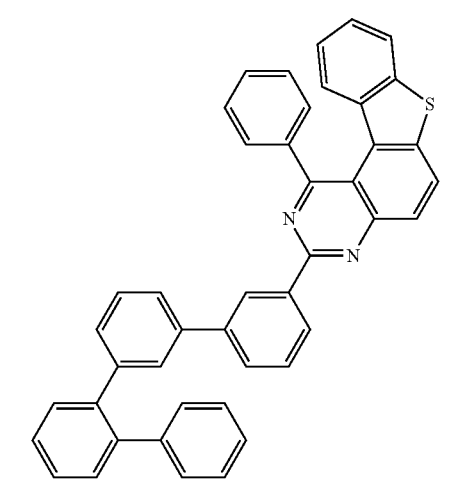
B-120
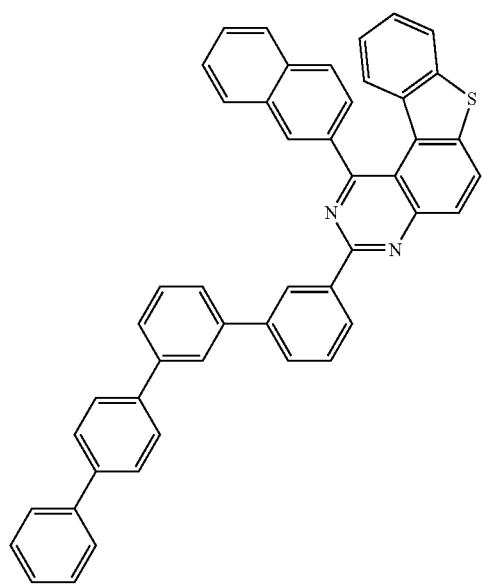
B-121
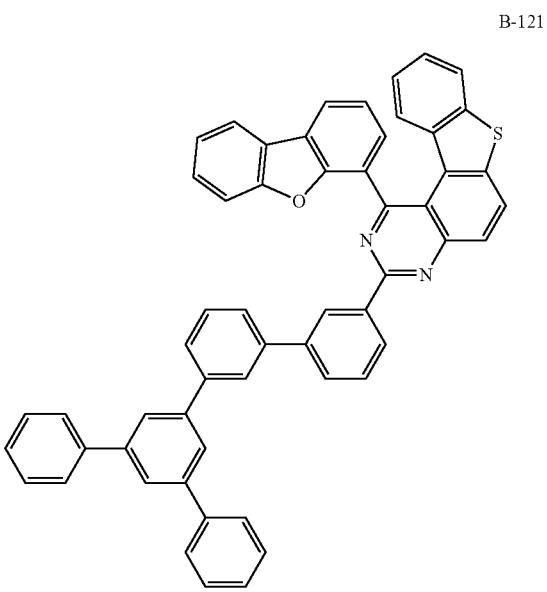
B-122
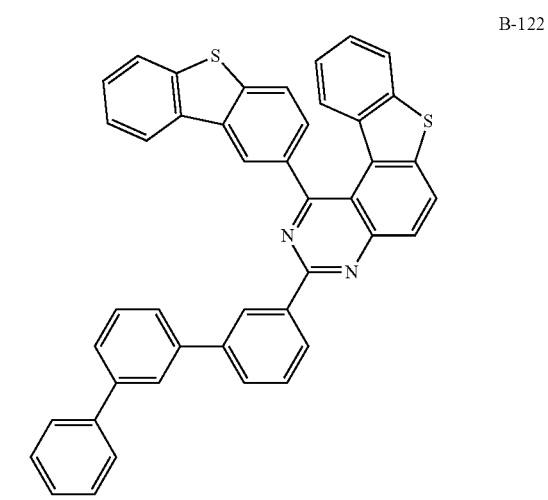
B-123
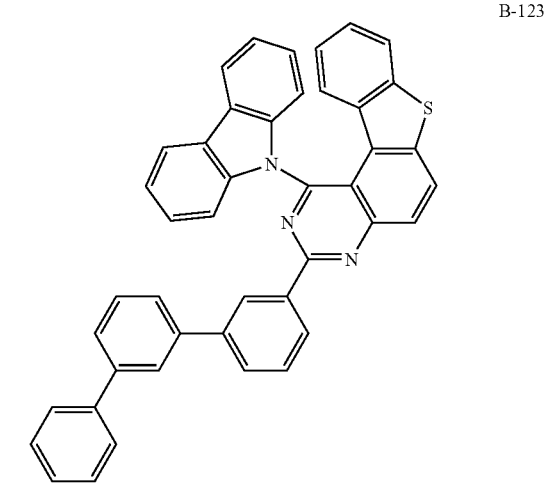

B-124
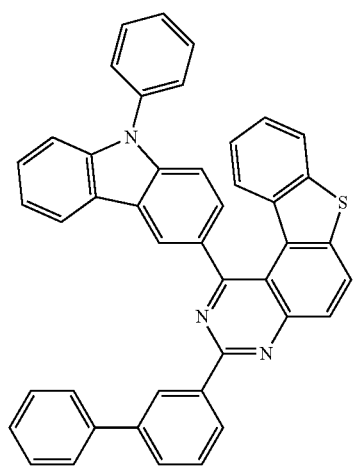
B-125
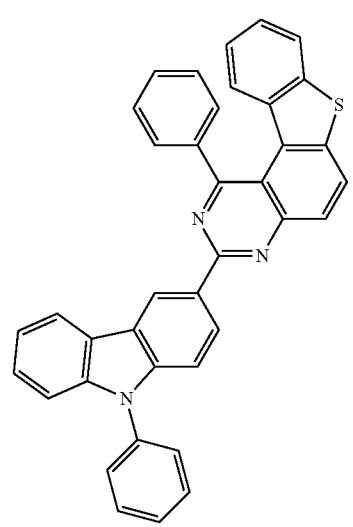
B-126
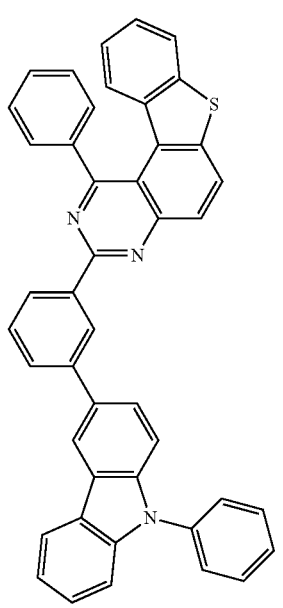
B-127
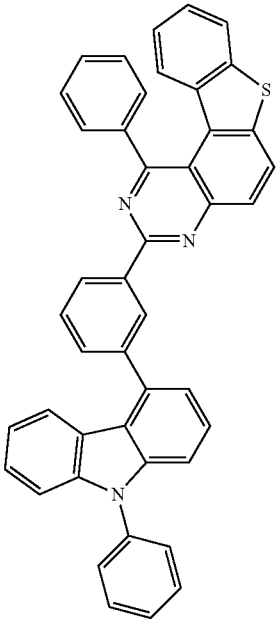
B-128
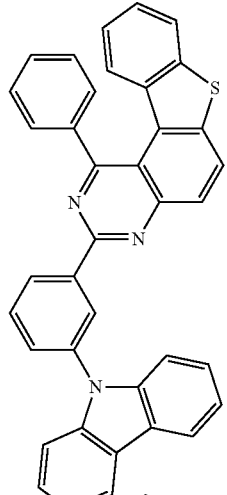
B-129
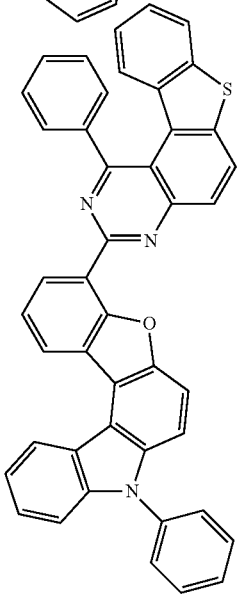

B-130
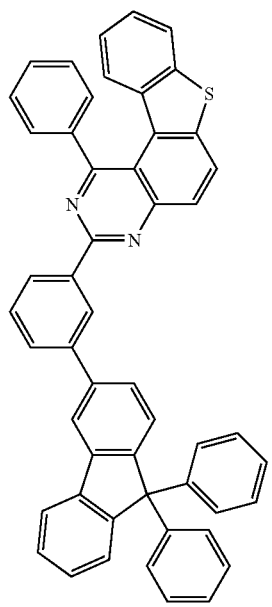
B-131
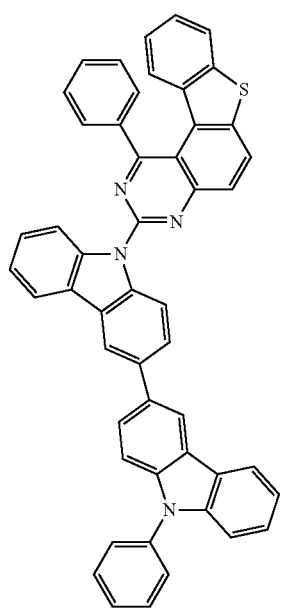
B-132
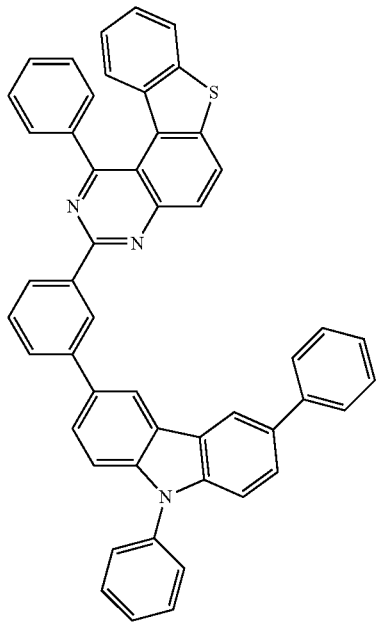
B-133
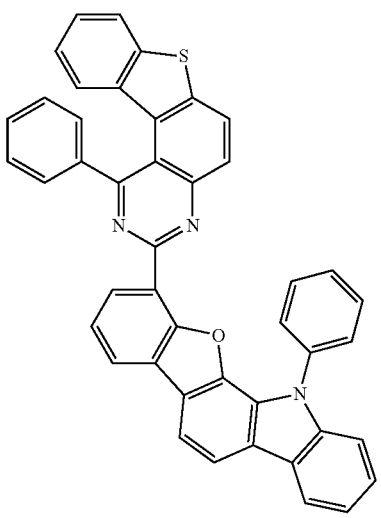

B-134
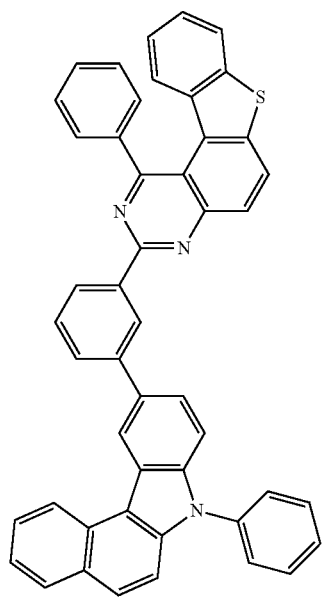
B-135
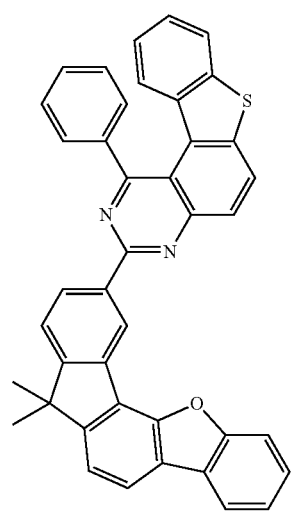
B-136
B-137
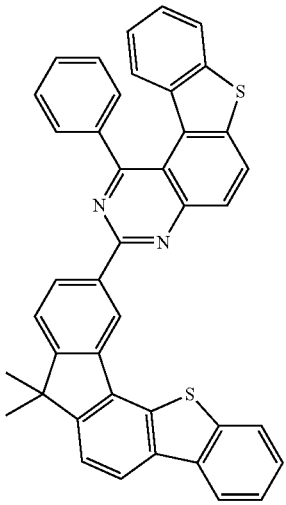
B-138
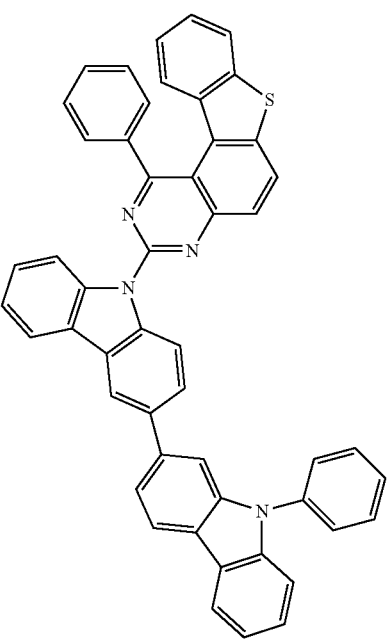
B-139
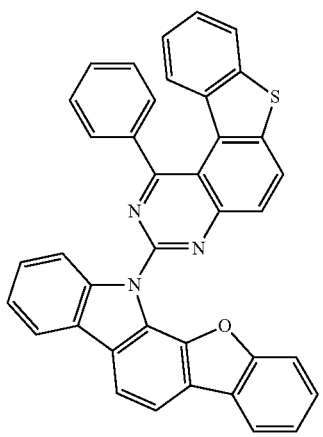

-continued
B-140
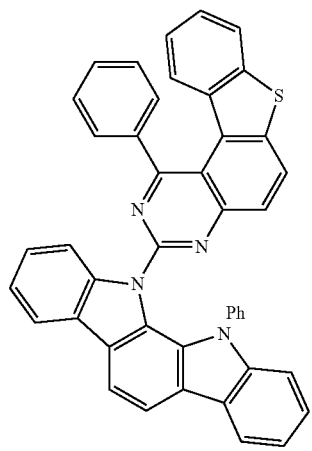
B-141
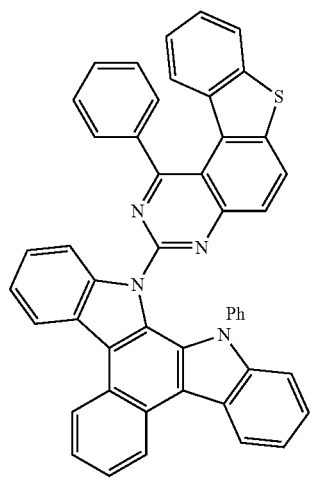
B-142
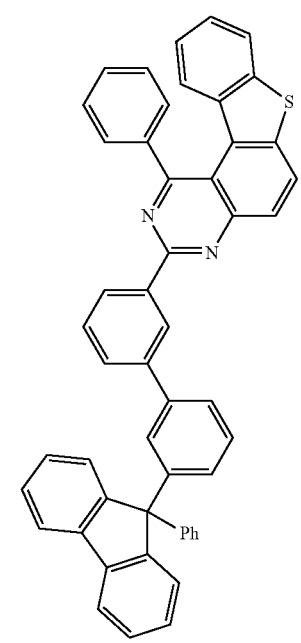
-continued
B-143
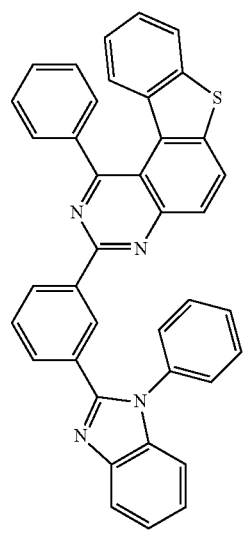
B-144
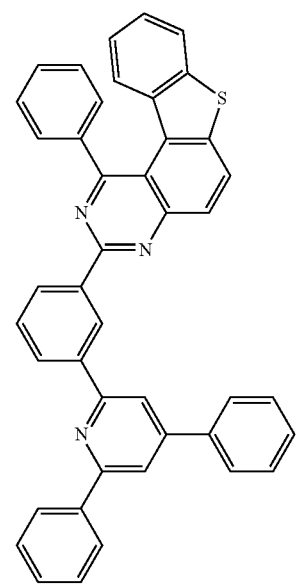
B-145
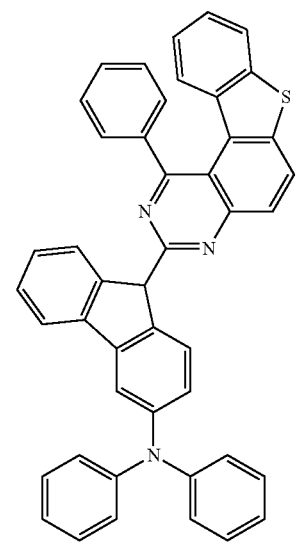

111
-continued
B-146
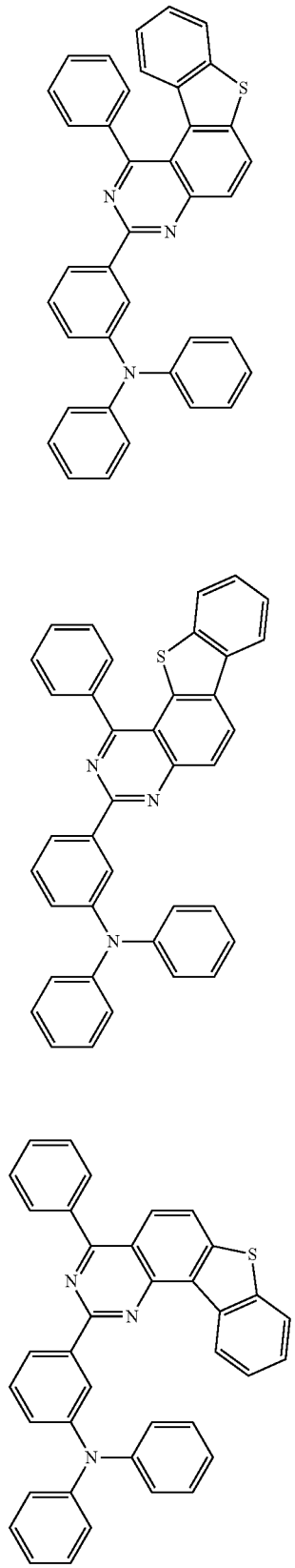
B-147
B-148
112
-continued
B-149
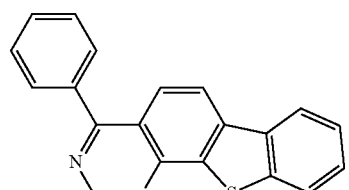
B-150
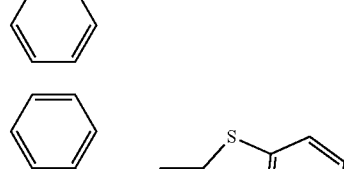
C-1
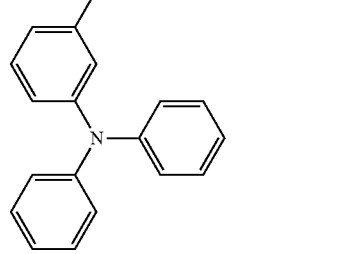
C-2
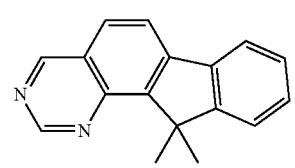
C-3
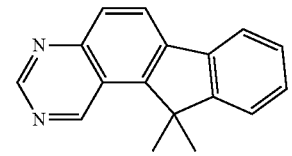
C-4
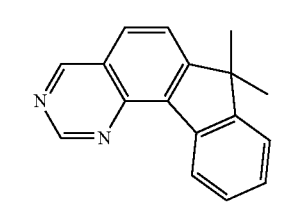
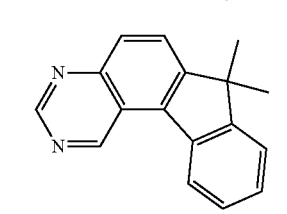

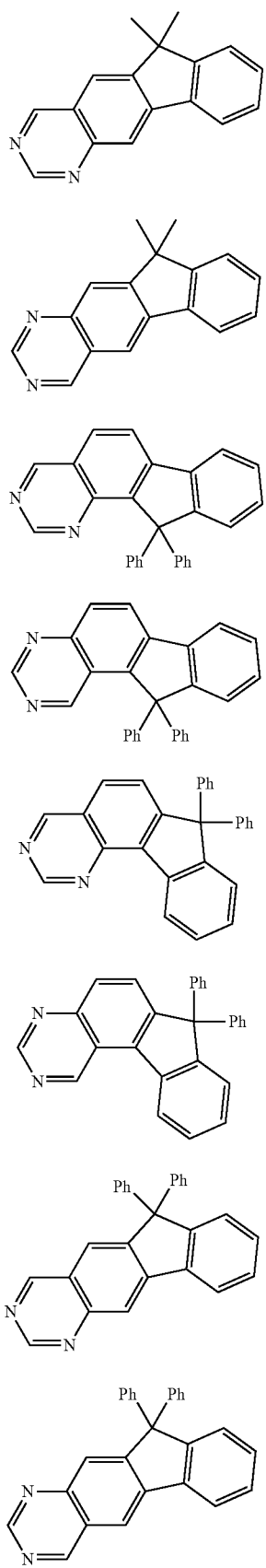
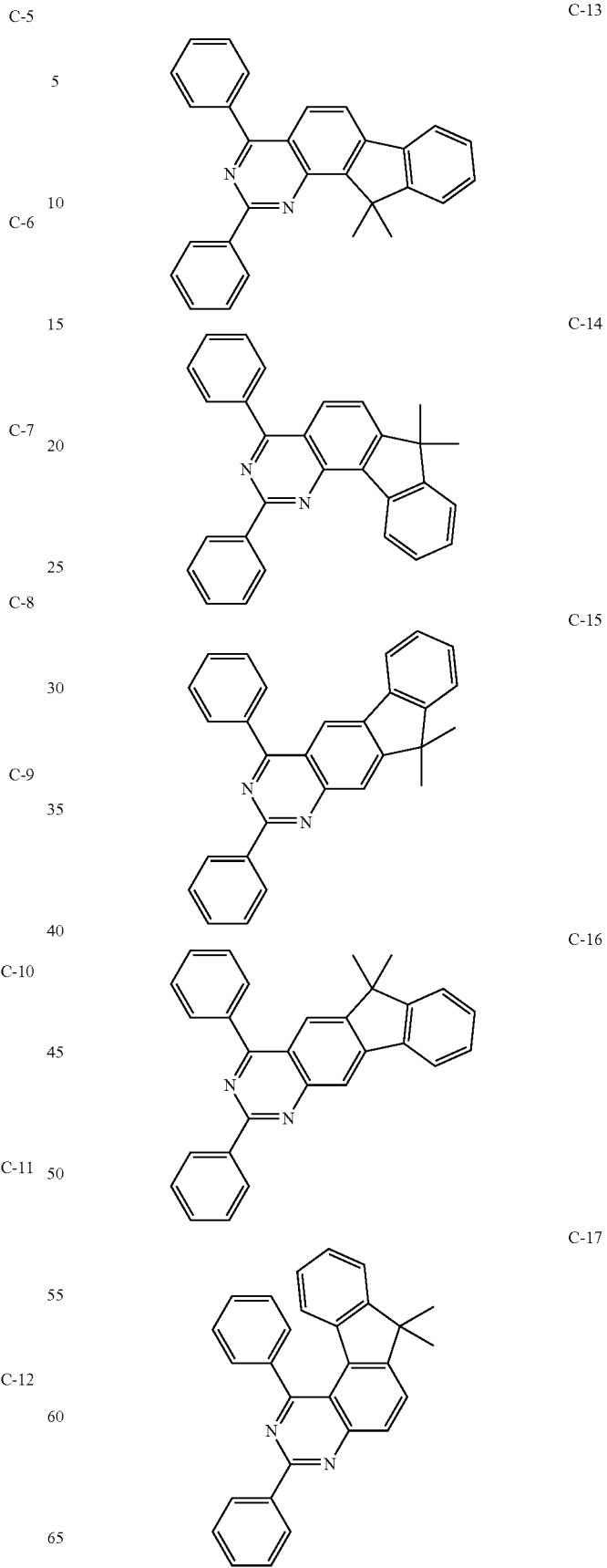

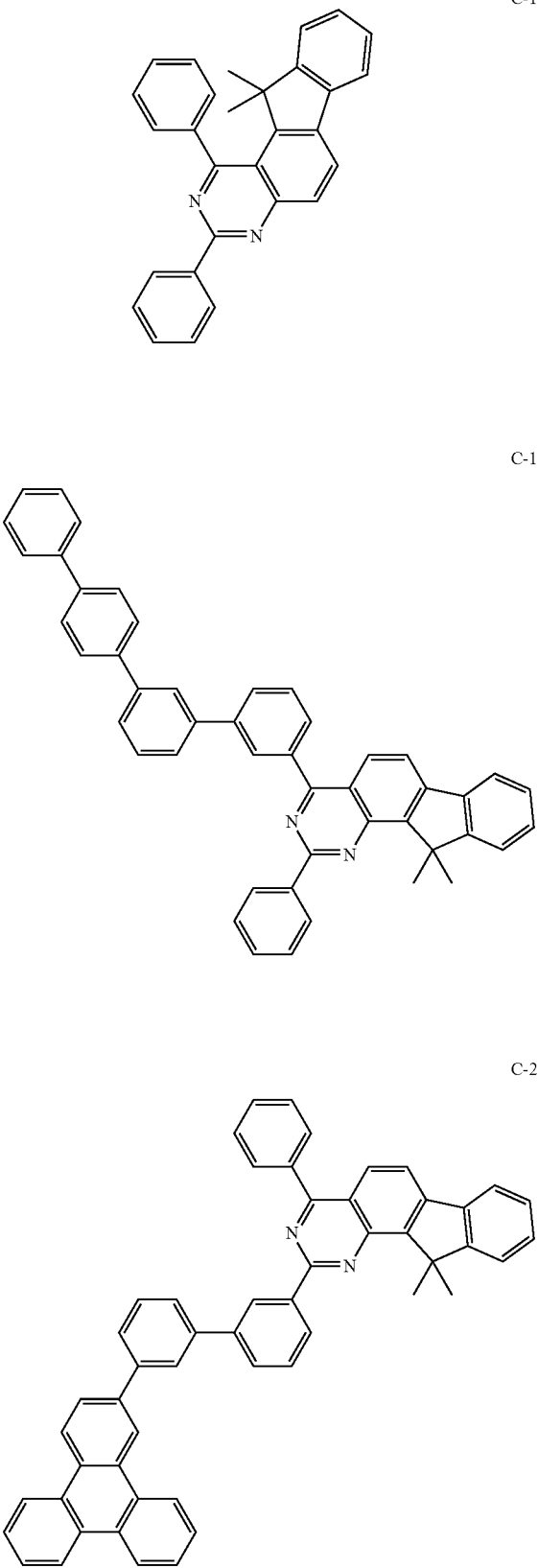
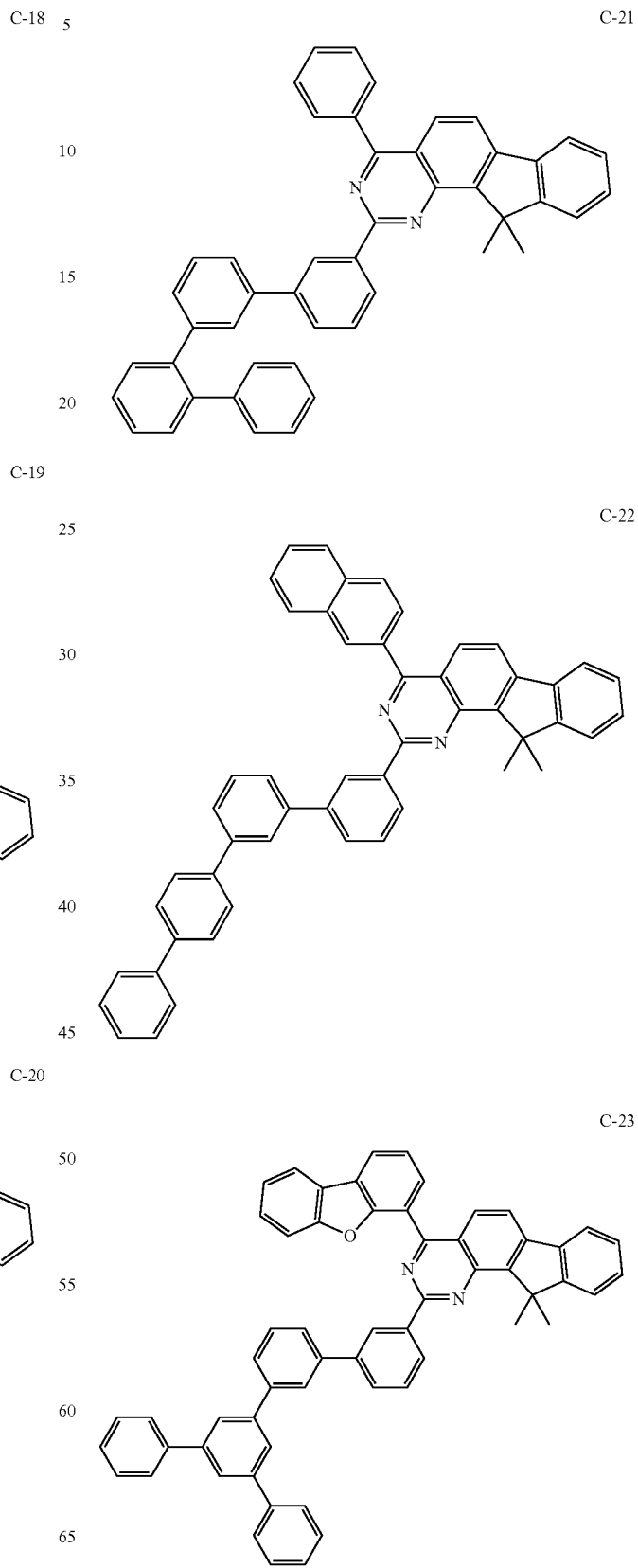

C-24
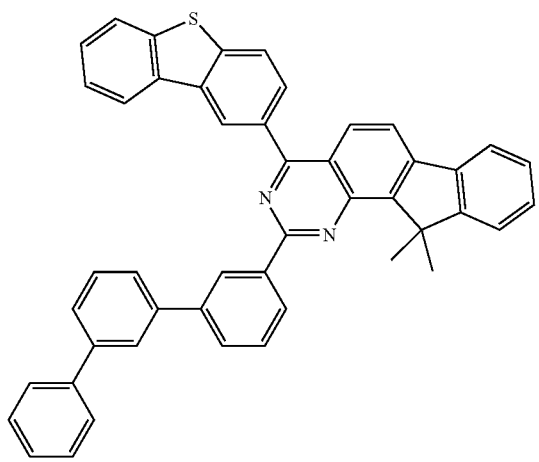
C-25
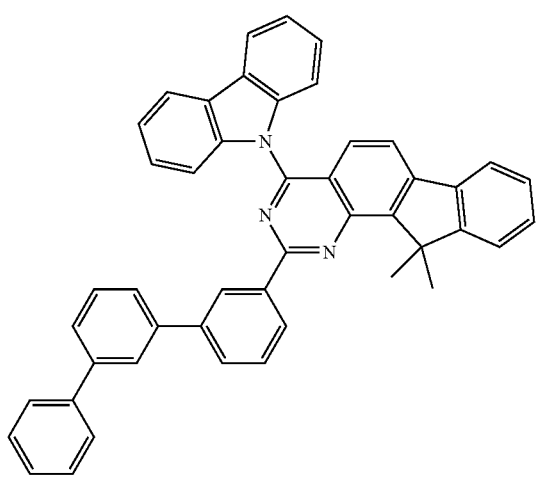
C-24
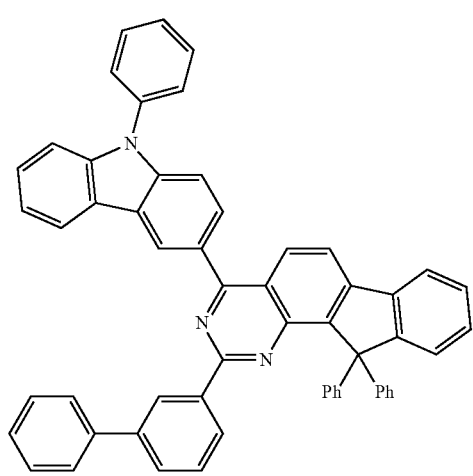
C-25
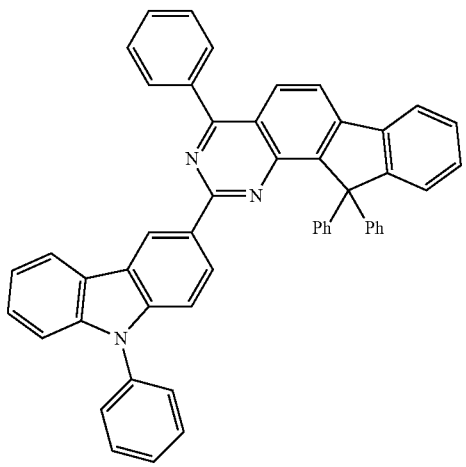
C-26
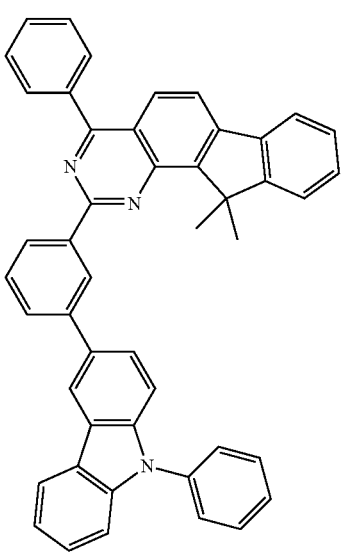
C-27
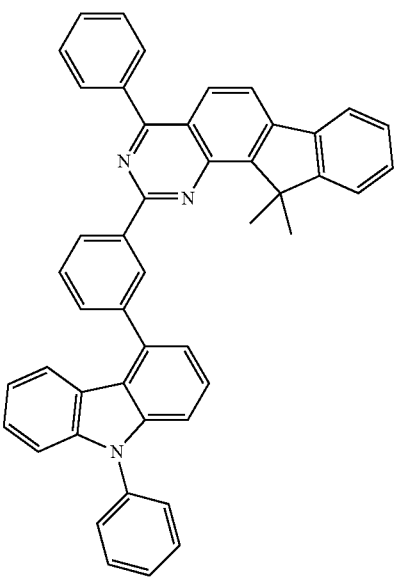

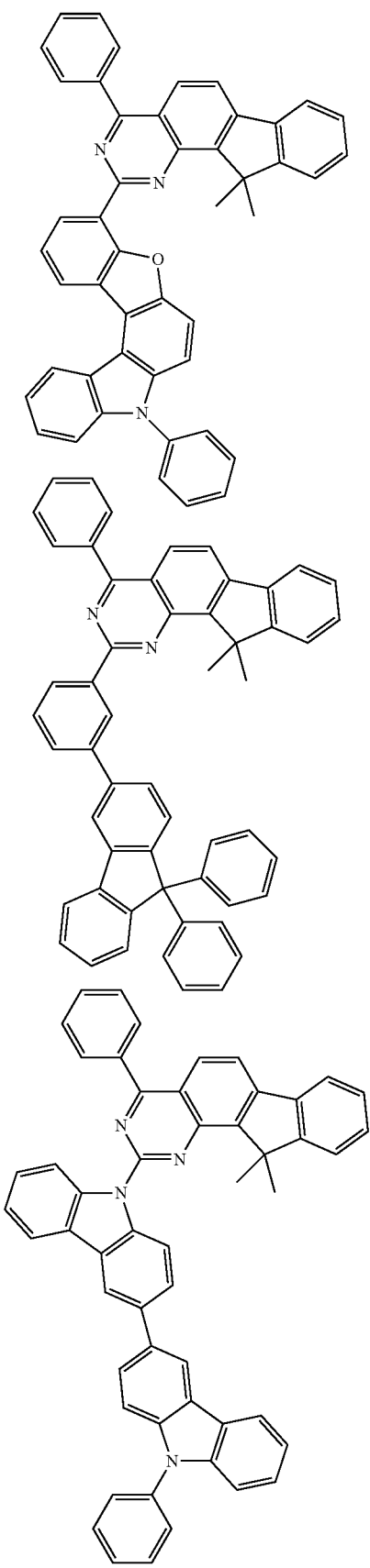
C-28
C-29
C-30
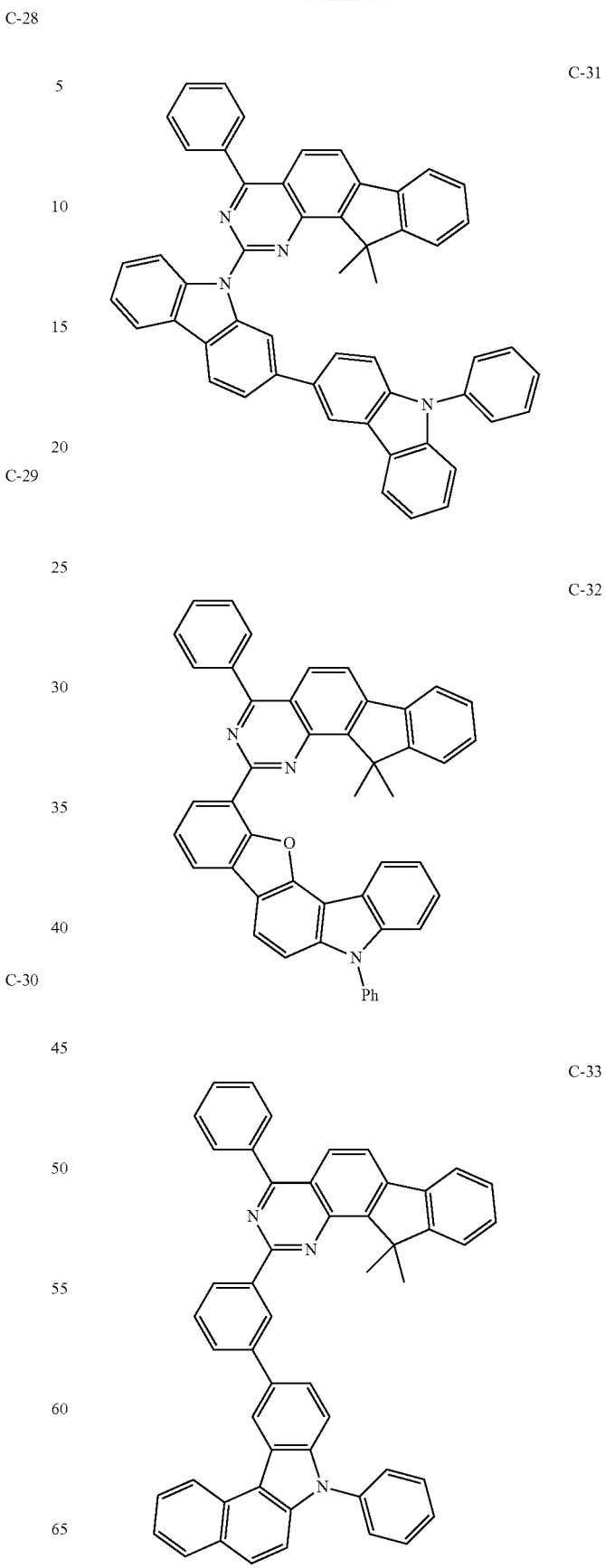
C-31
C-32
C-33

C-34
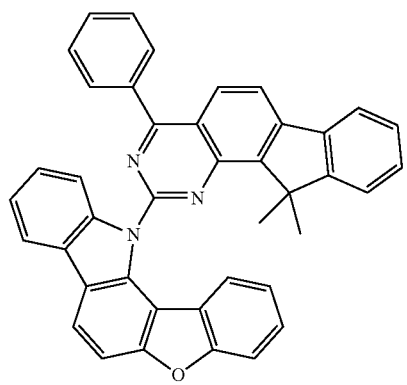
C-35
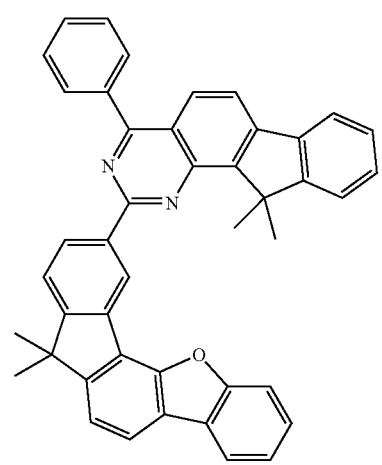
C-36
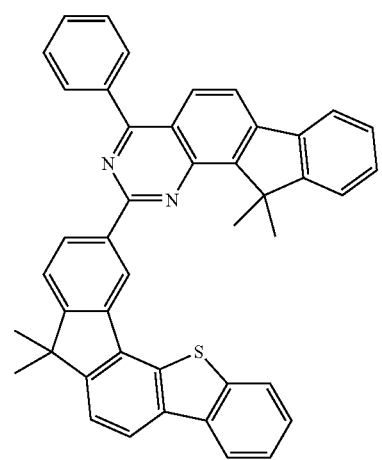
C-37
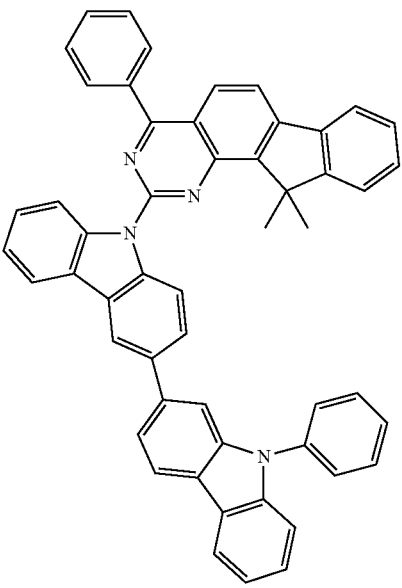
C-38
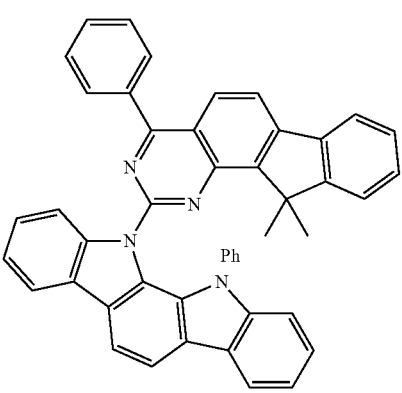
C-39
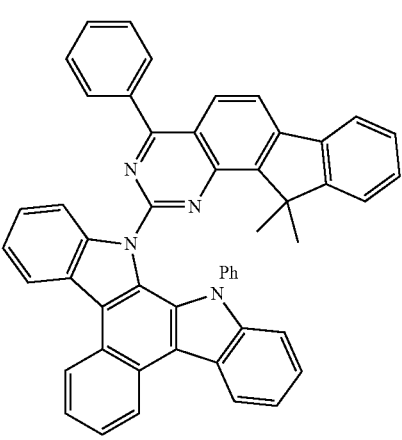

C-40
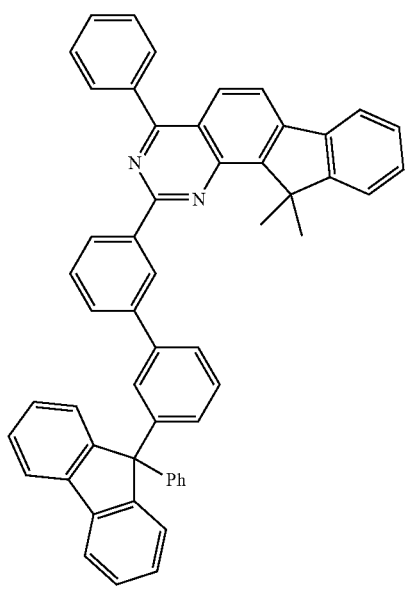
C-41
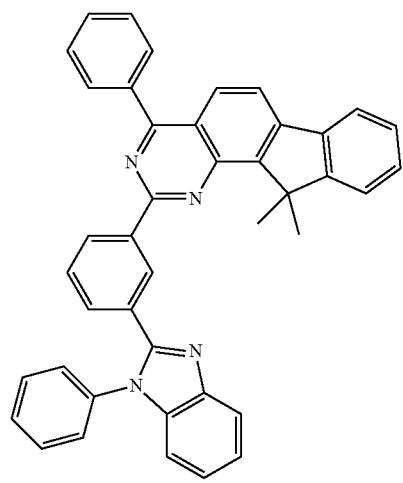
C-42
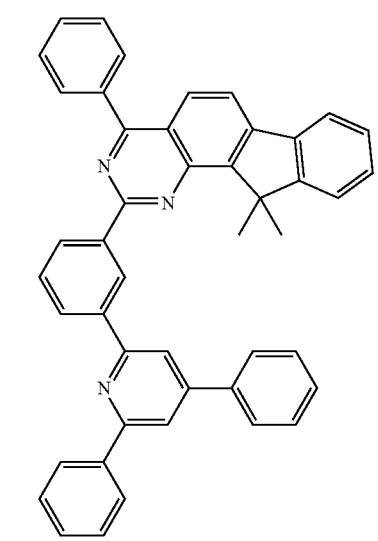
C-43
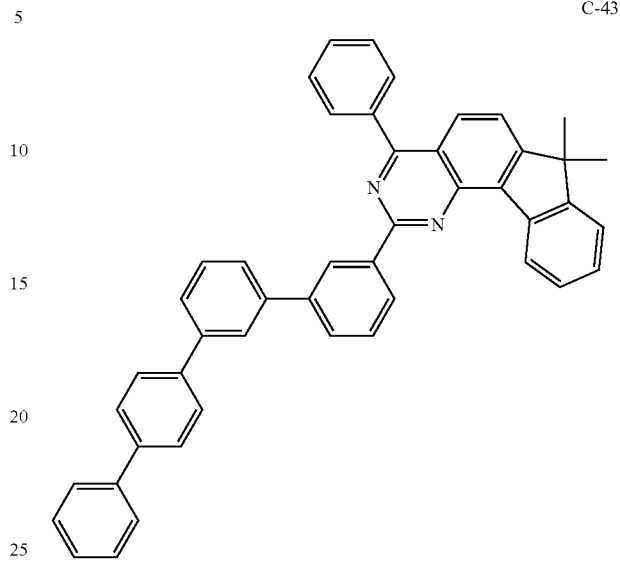
C-44
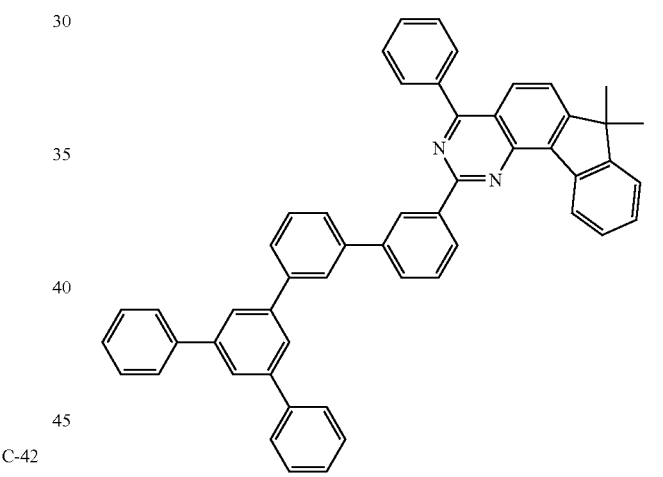
C-45
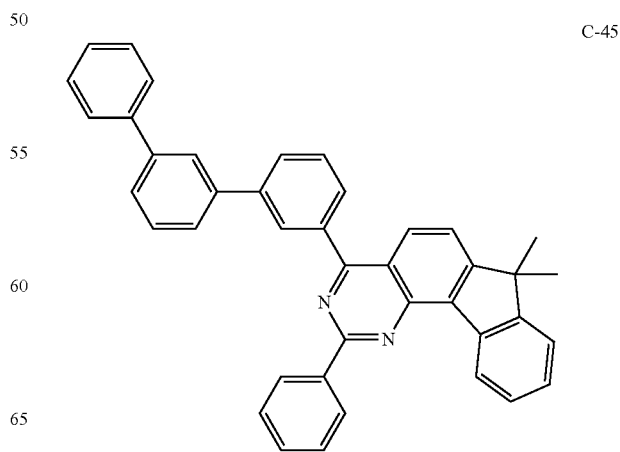

C-46
C-47
C-48
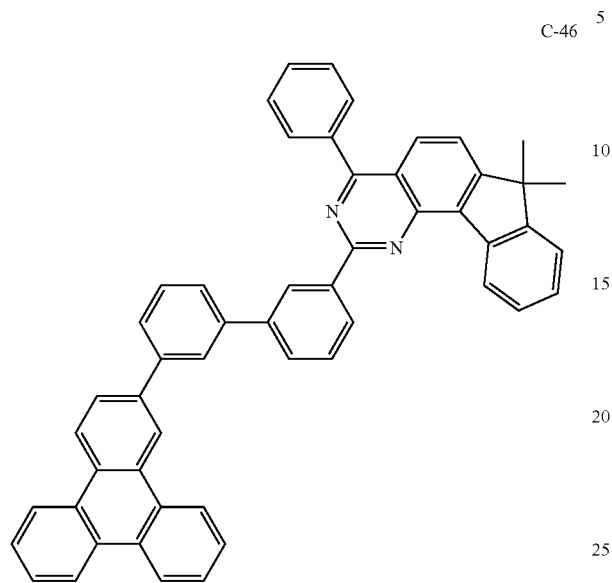
C-49
C-50
C-51
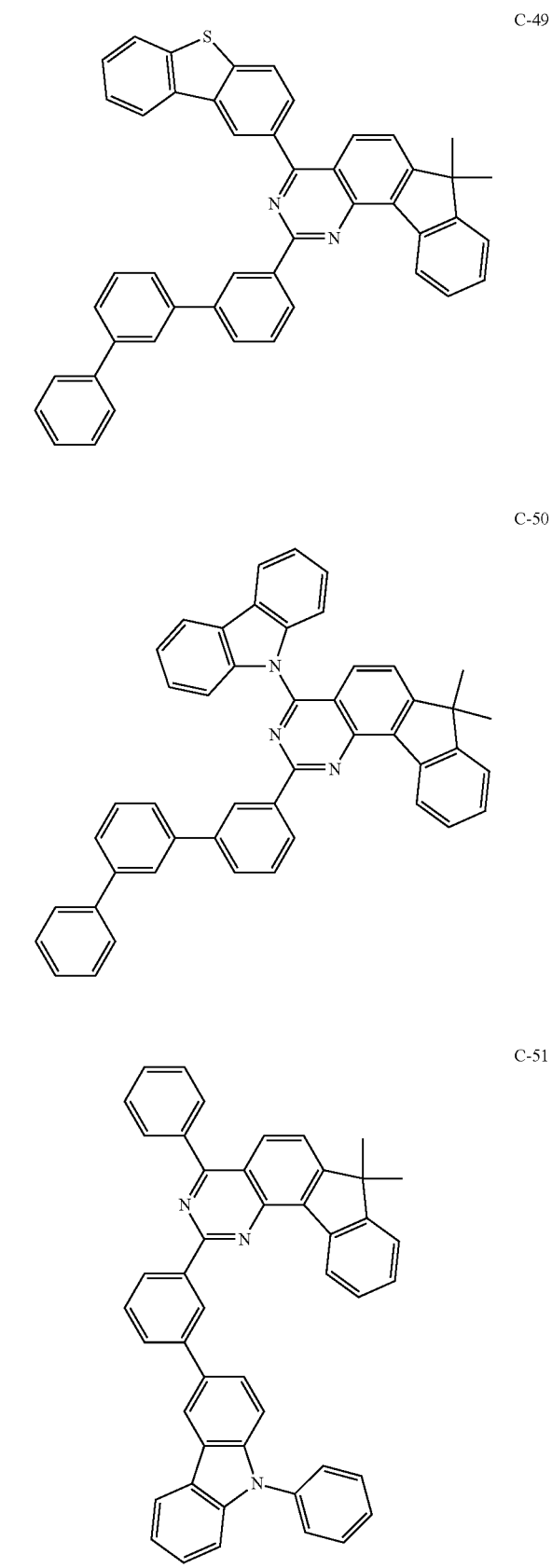

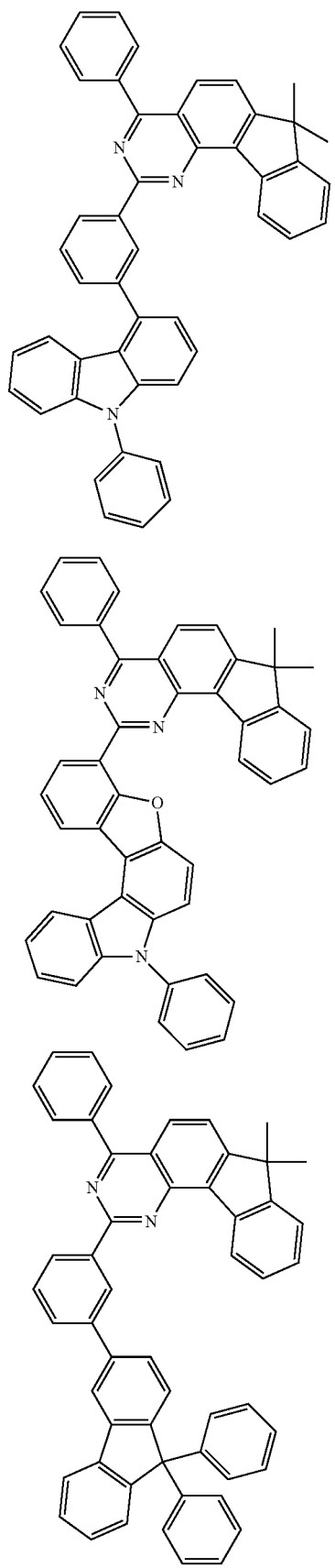
C-52
C-53
C-54
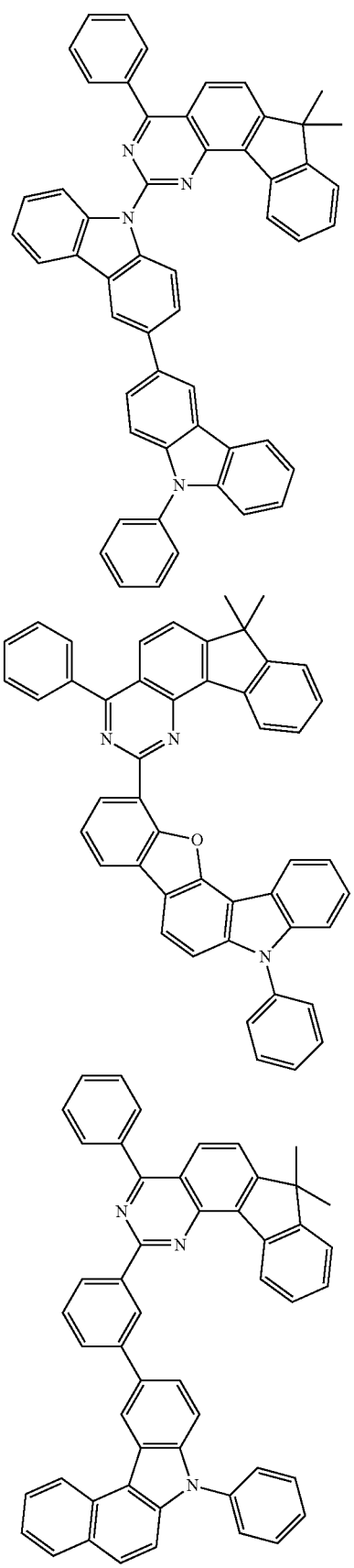
C-55
C-56
C-57

-continued
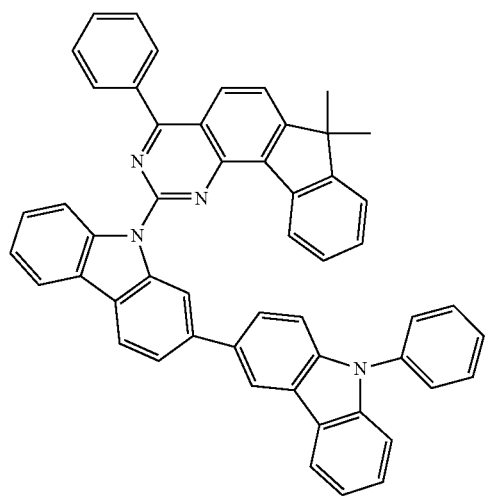
C-58
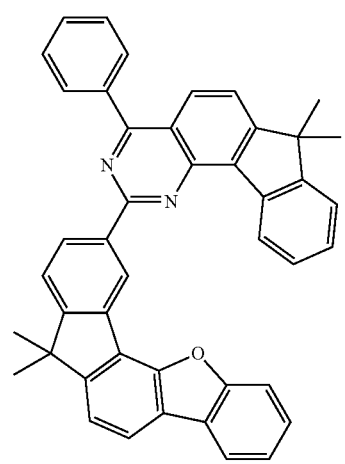
C-59
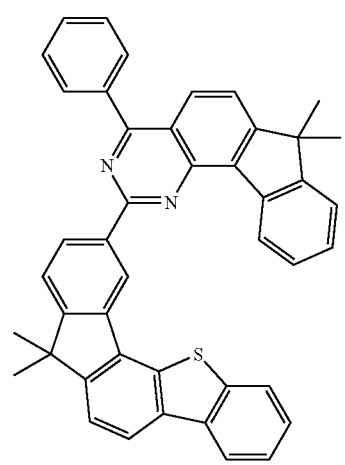
C-60
-continued
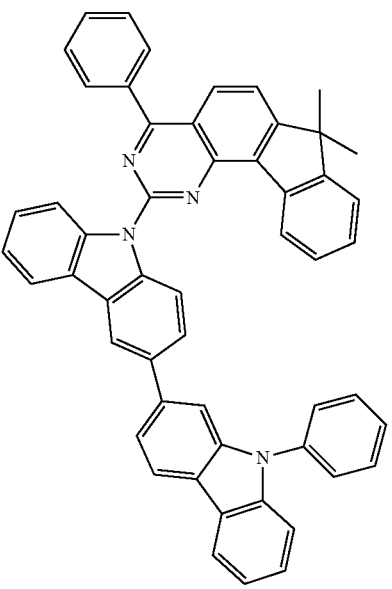
C-61
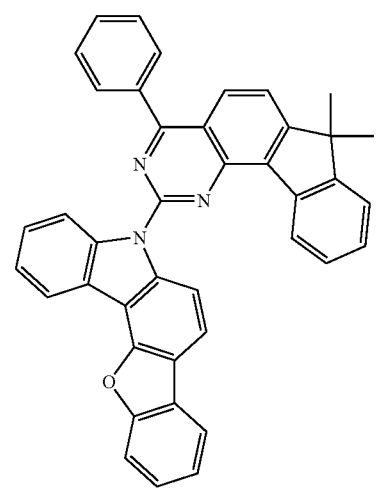
C-62
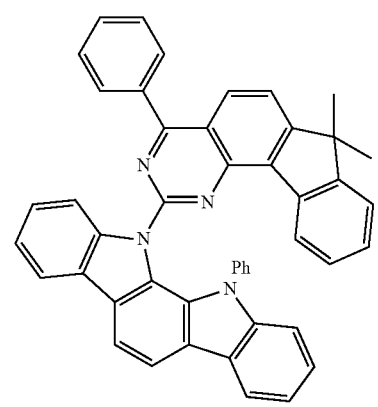
C-63

C-64
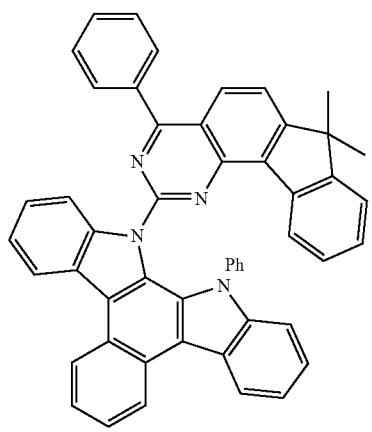
C-65
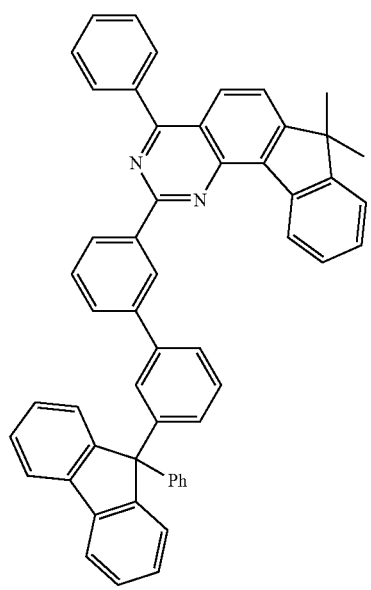
C-66
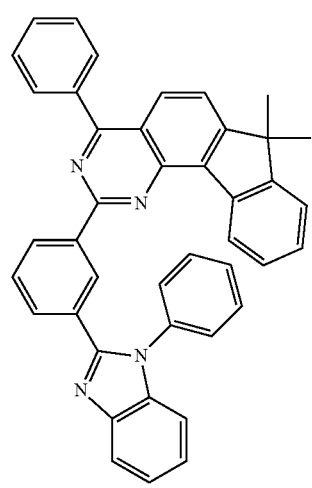
C-67
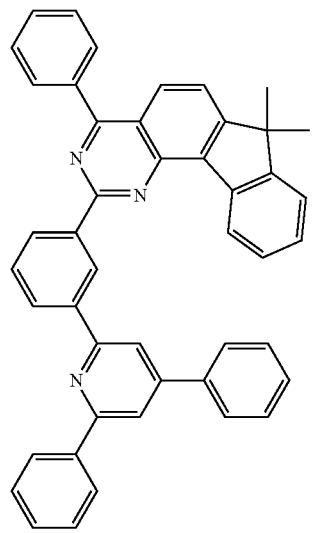
C-68
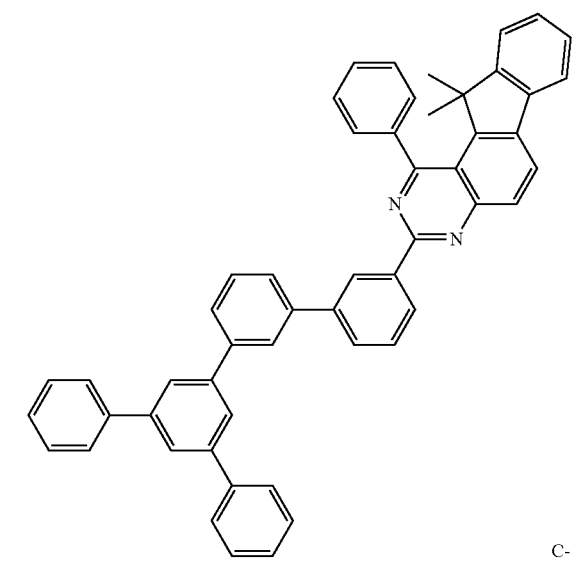
C-69
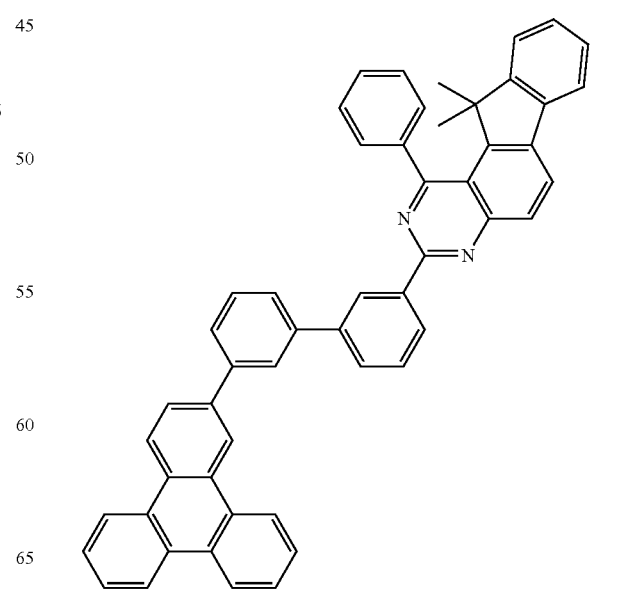

C-70
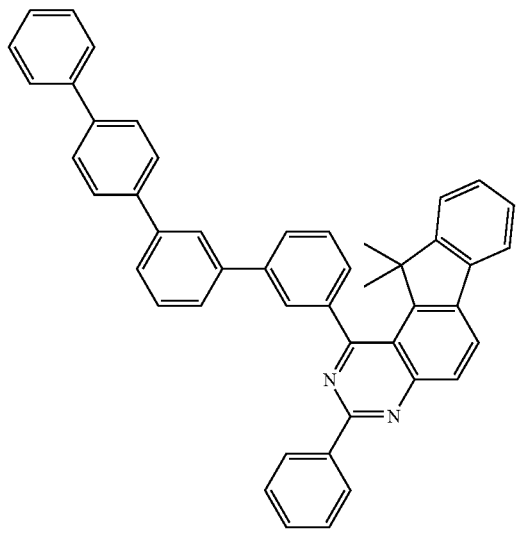
C-71
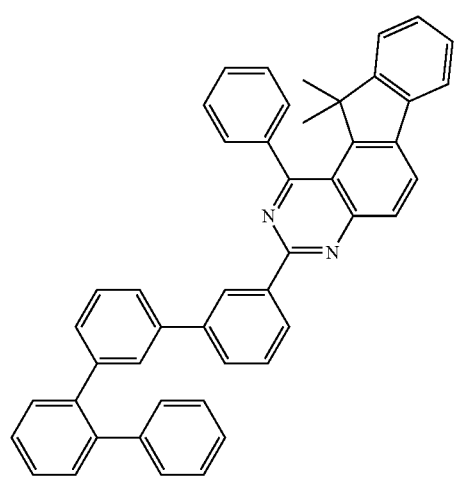
C-72
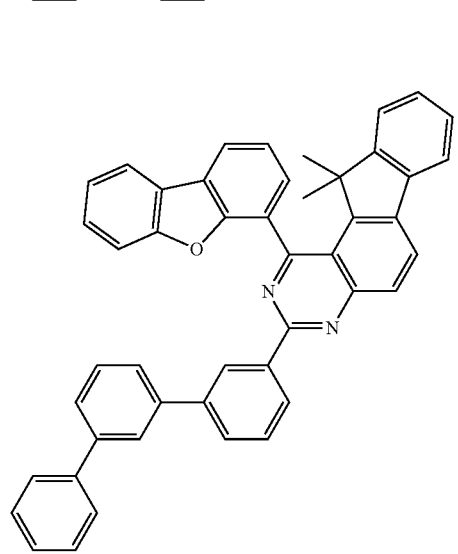
C-73
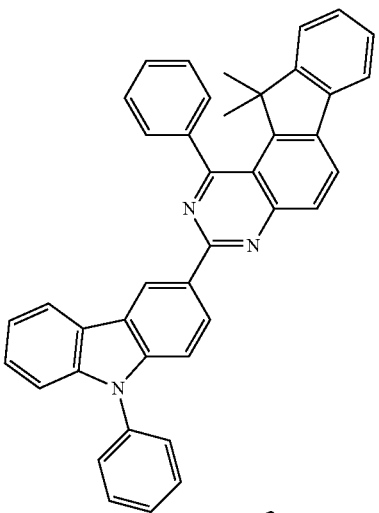
C-74
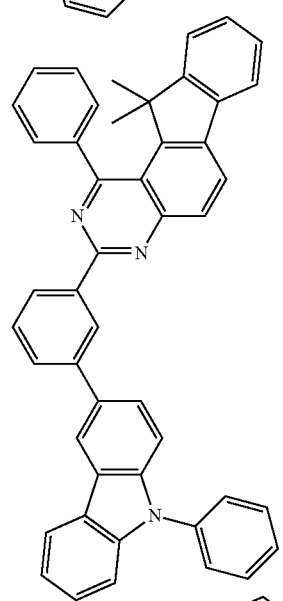
C-75
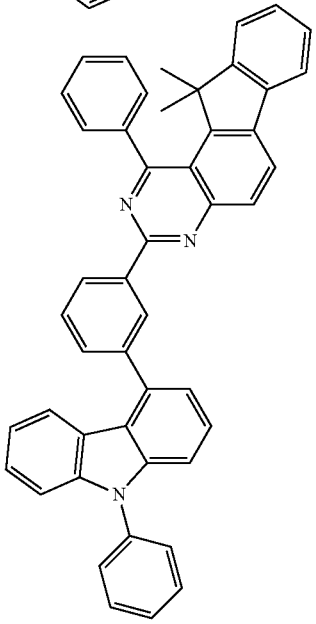

-continued
C-76
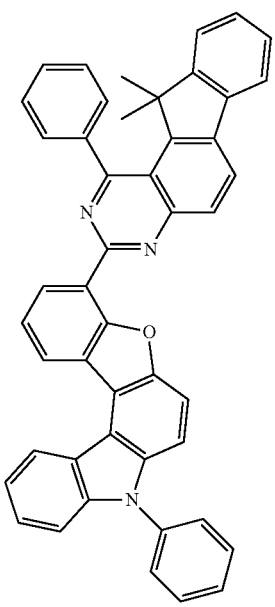
C-77
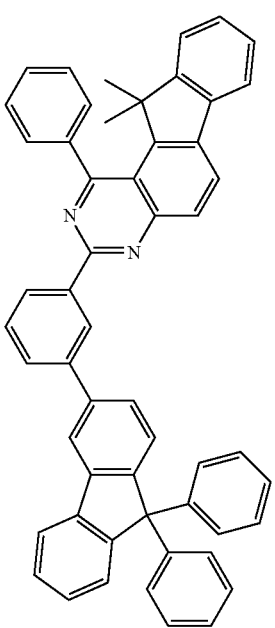
-continued
C-78
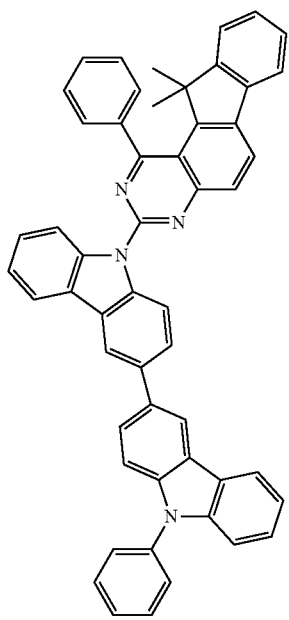
C-79
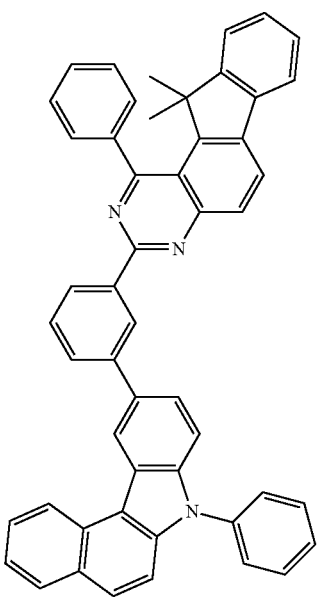

C-80
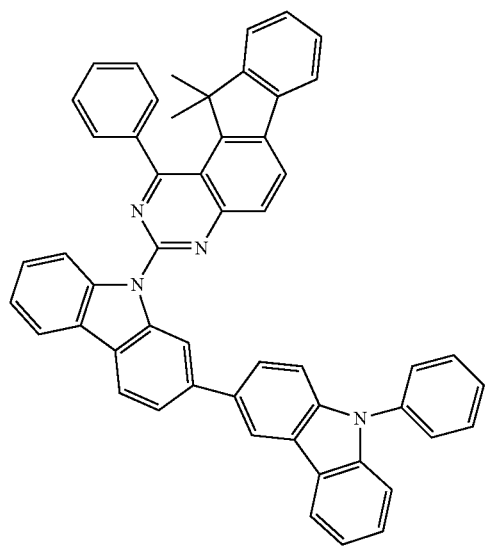
C-81
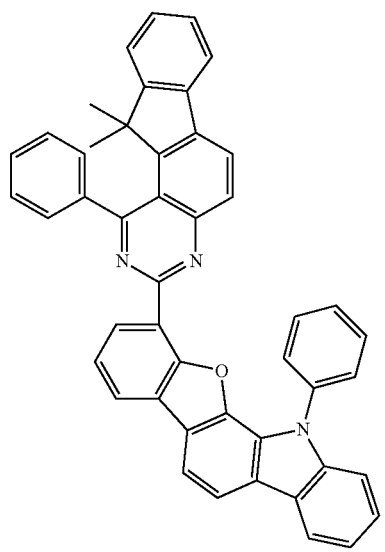
C-82
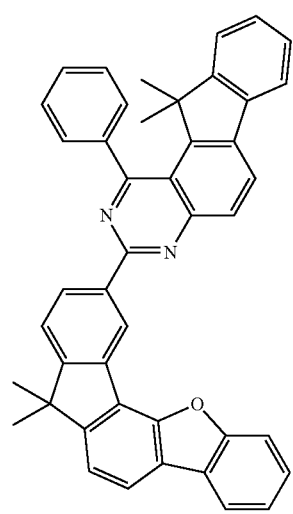
C-83
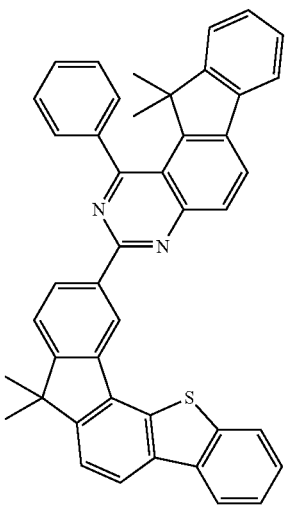
C-84
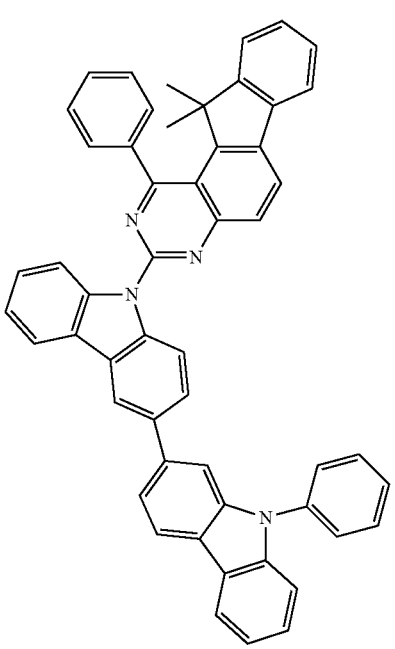
C-85
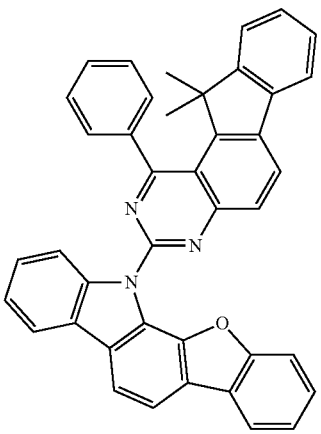

-continued
C-86
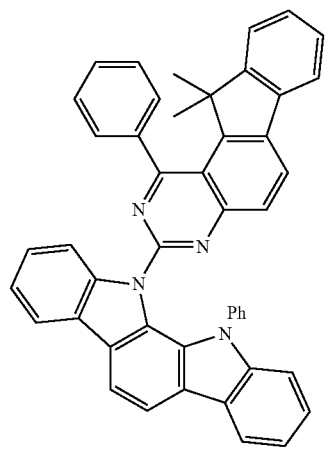
C-87
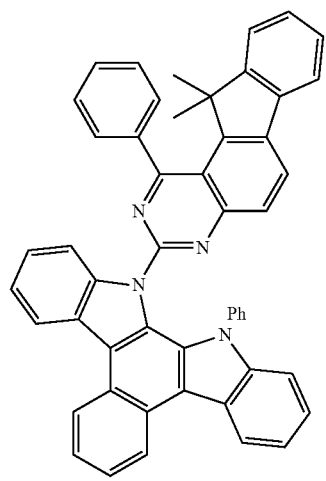
C-88
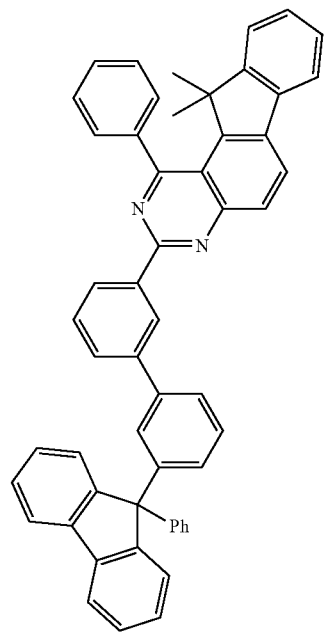
-continued
C-89
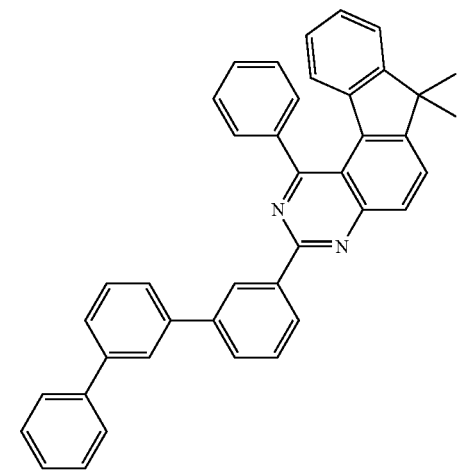
C-90
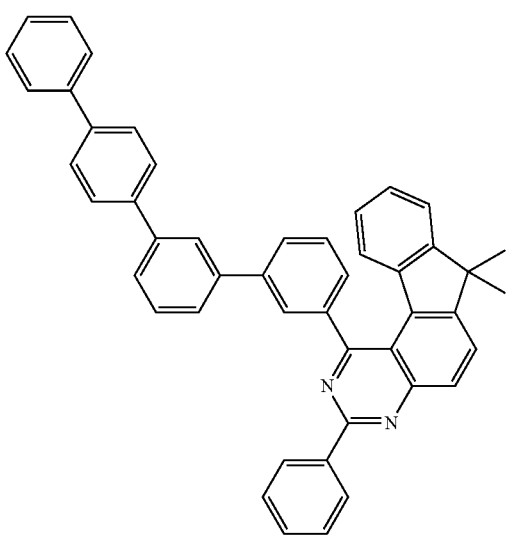
C-91
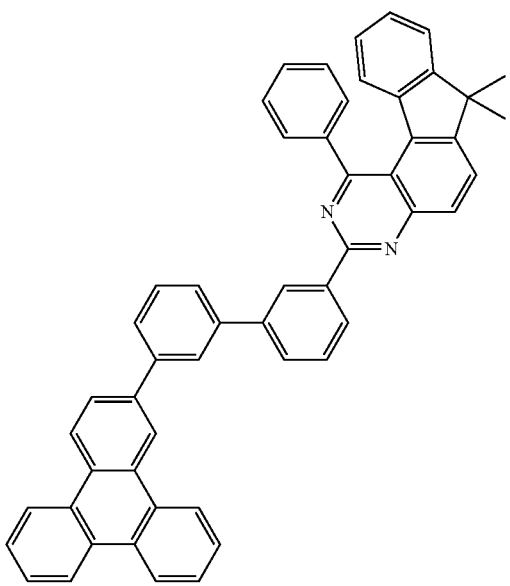

-continued
C-92
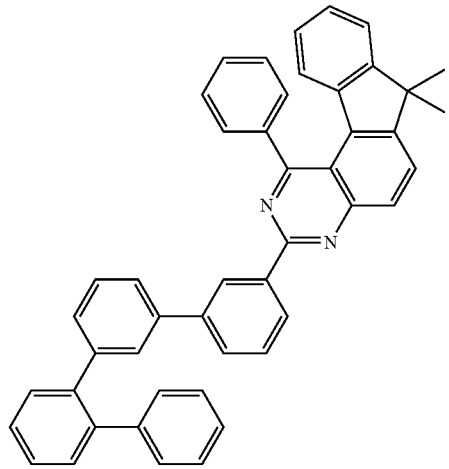
C-93
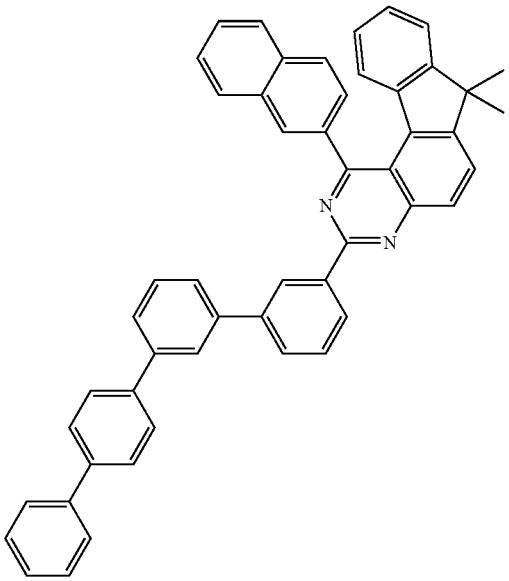
C-94
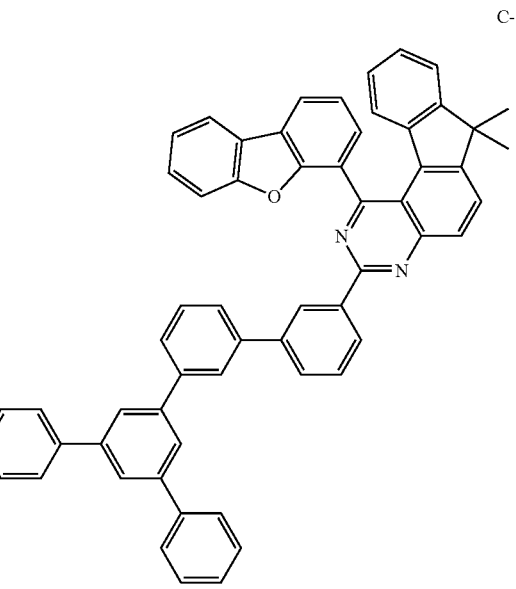
-continued
C-95
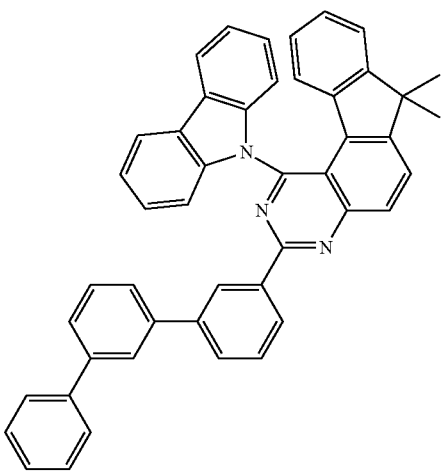
C-96
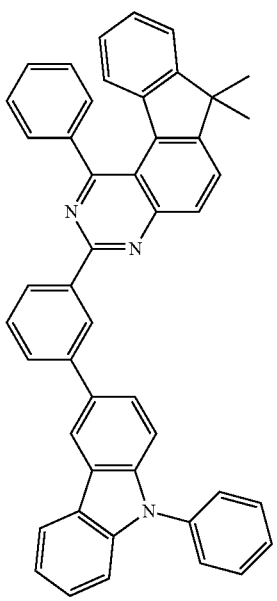
C-97
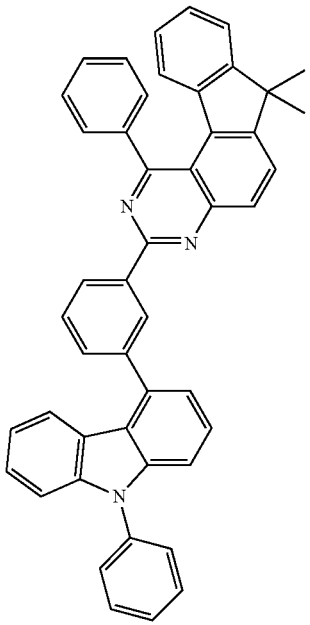

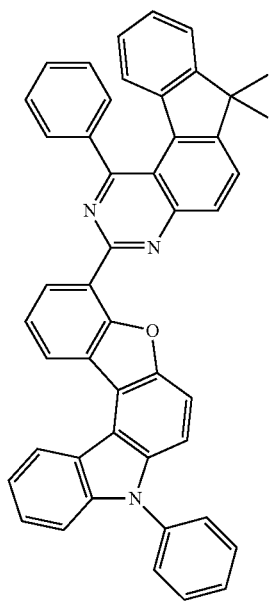
C-98
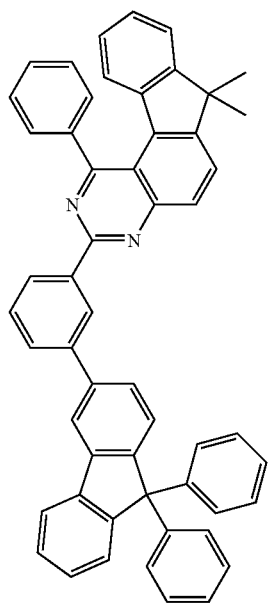
C-99
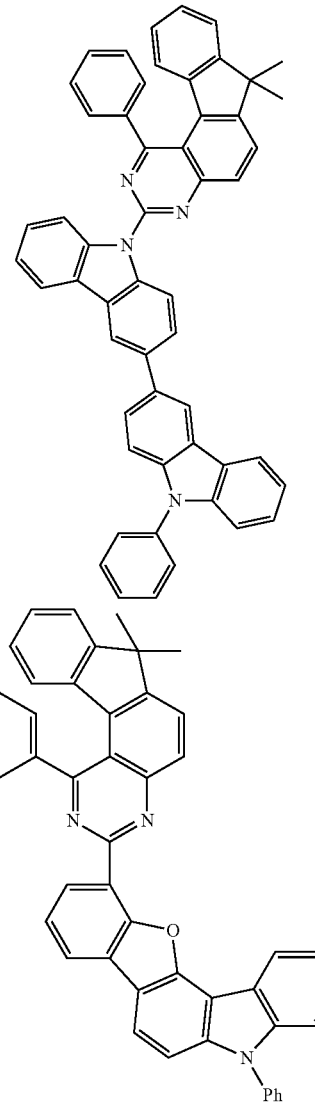
C-100
C-101
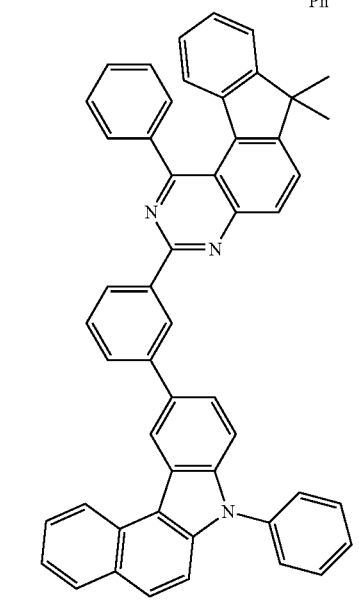
C-102

C-103
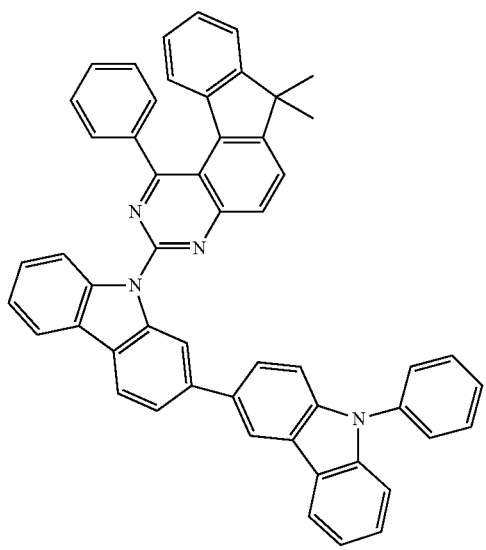
C-104
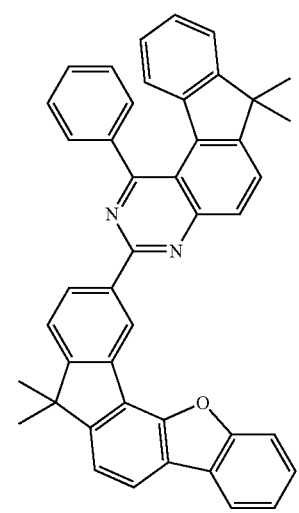
C-105
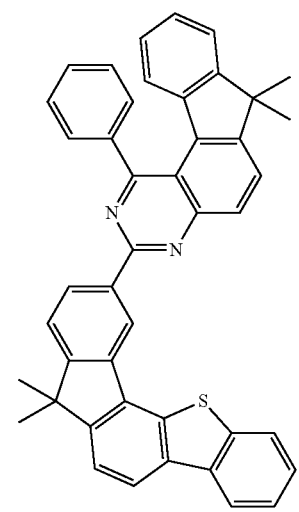
C-106
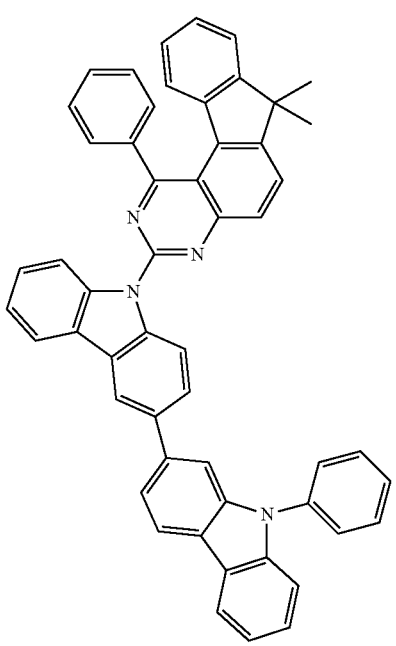
C-107
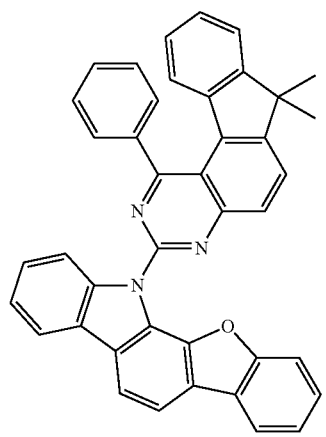
C-107
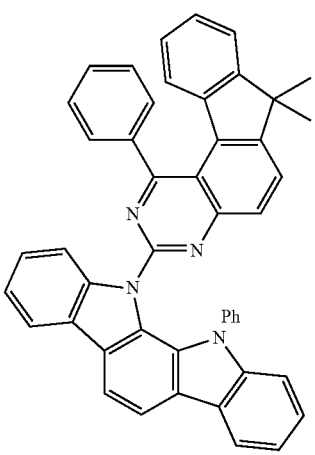

C-108
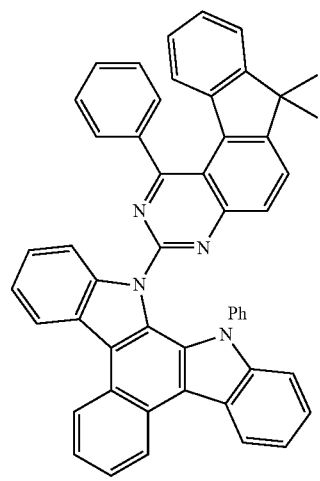
C-109
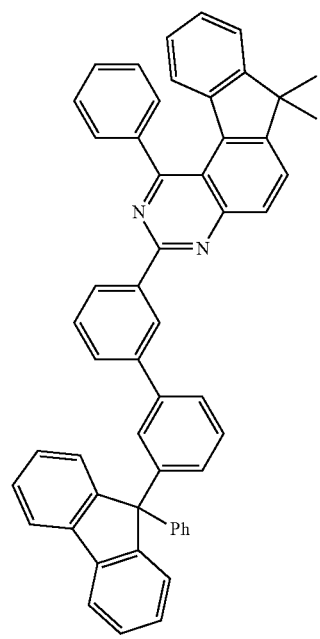
D-1
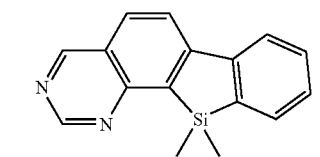
D-2
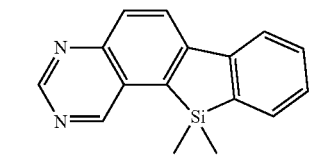
D-3
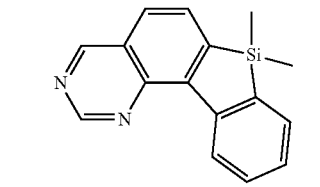
D-4
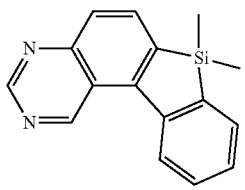
D-5
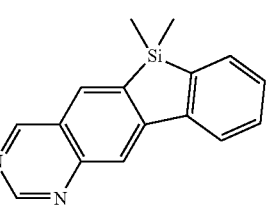
D-6
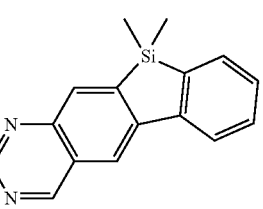
D-7
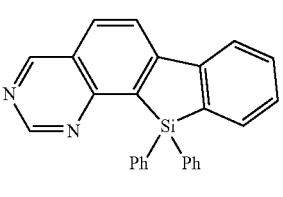
D-8
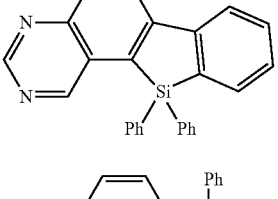
D-9
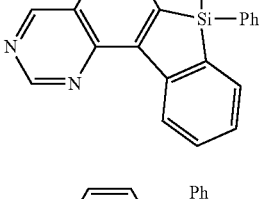
D-10
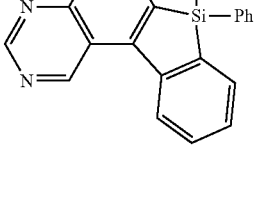
D-11
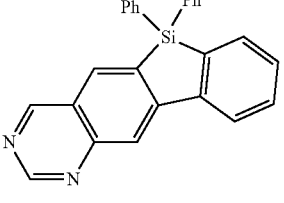

-continued
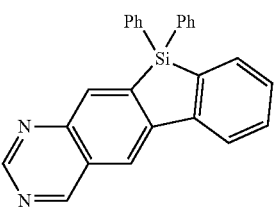
D-12
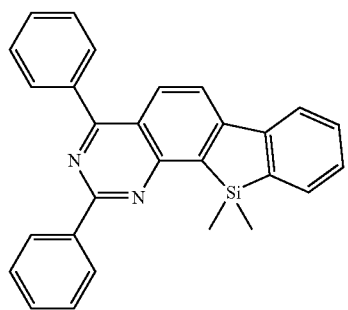
D-13
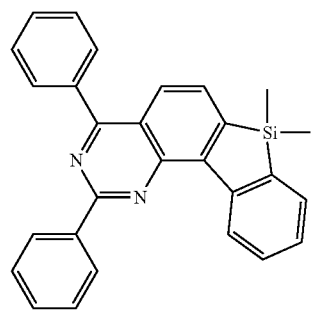
D-14
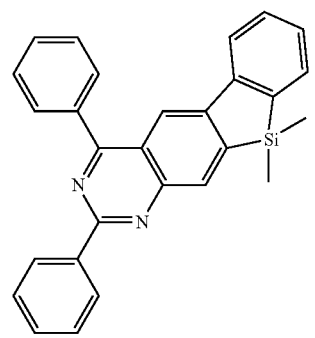
D-15
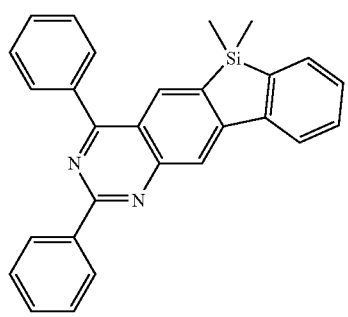
D-16
-continued
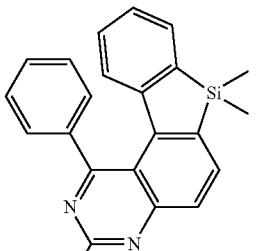
D-17
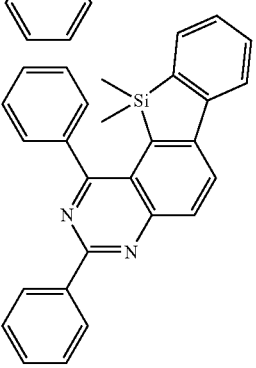
D-18
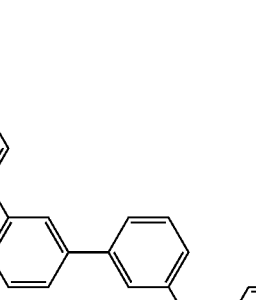
D-19
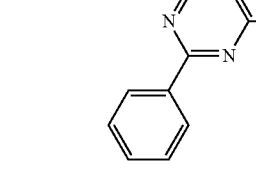
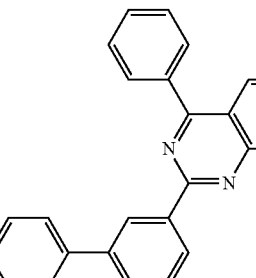
D-20
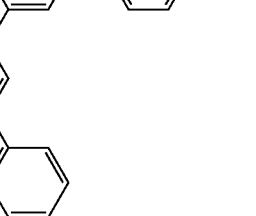

D-21
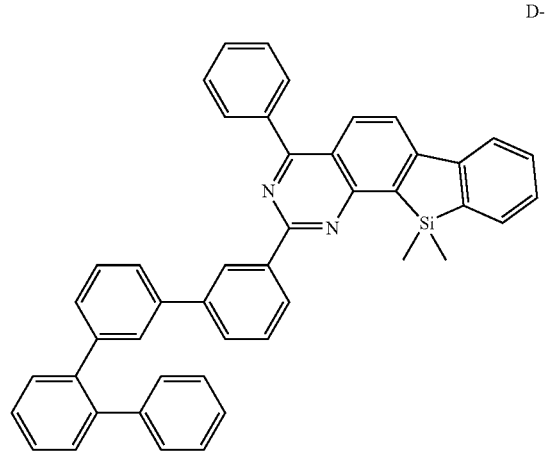
D-22
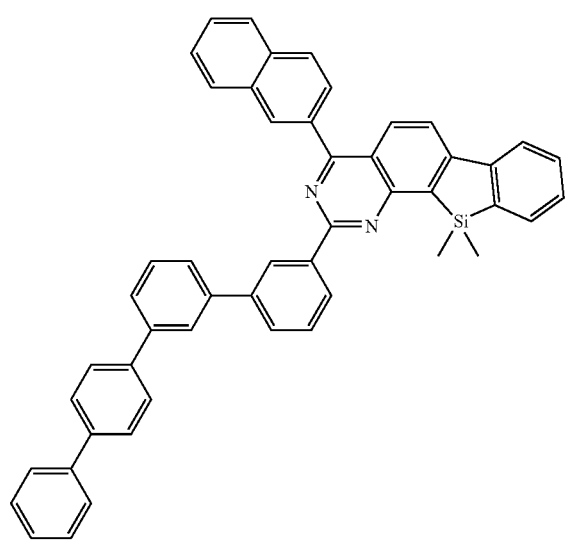
D-23
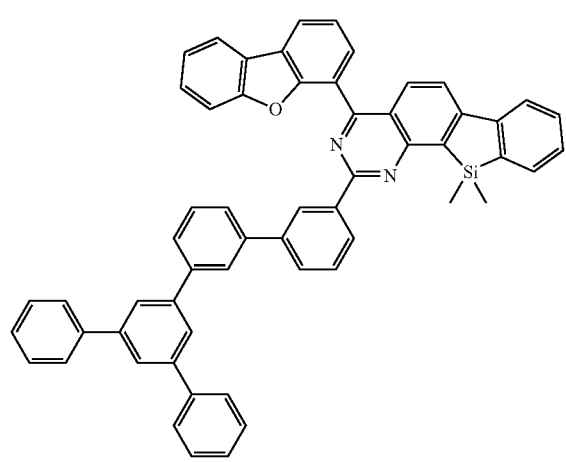
D-24
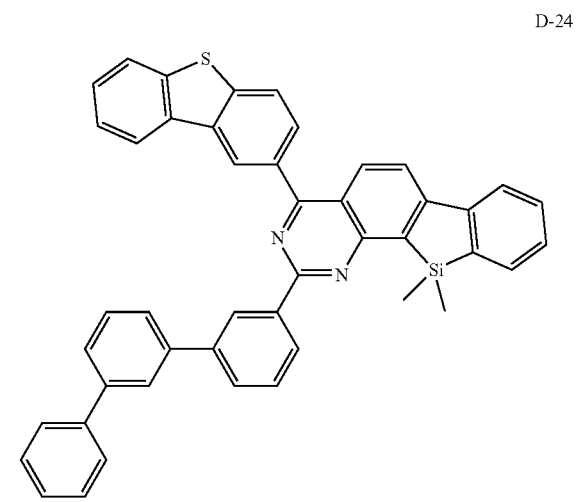
D-25
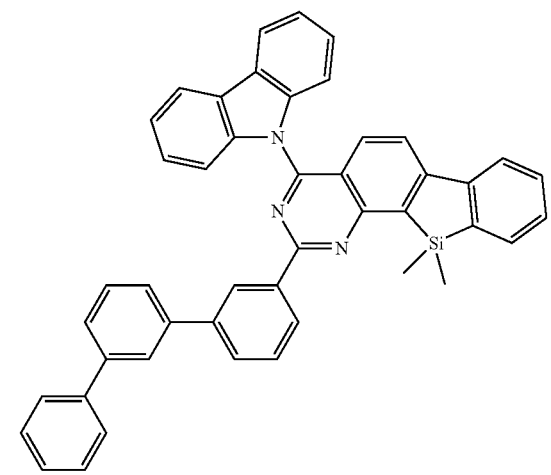
D-24
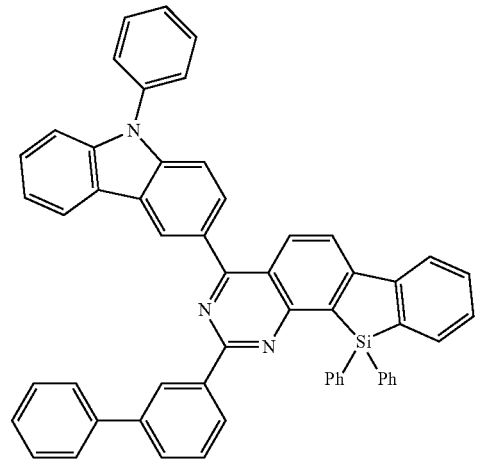

D-25
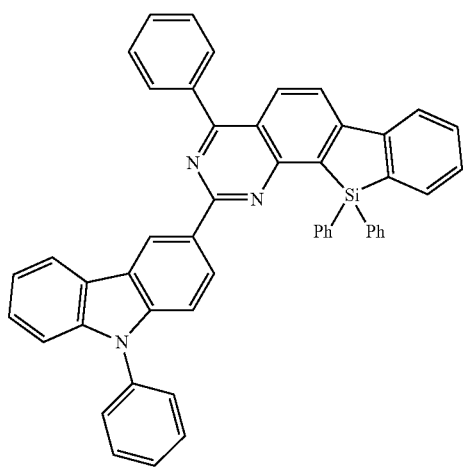
D-26
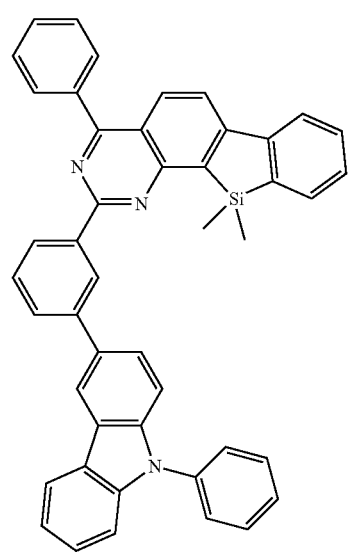
D-27
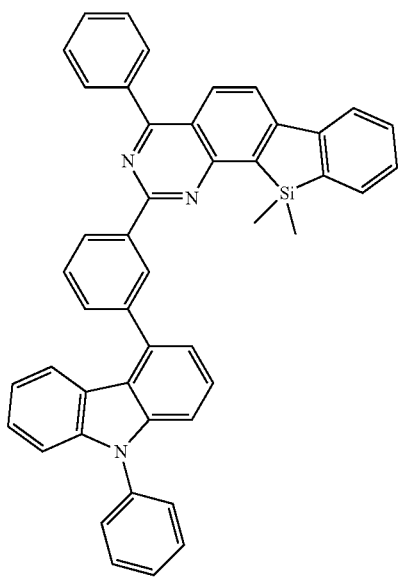
D-28
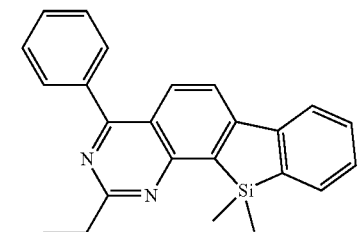
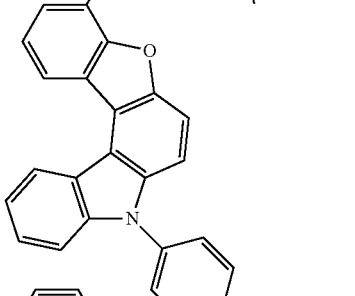
D-29
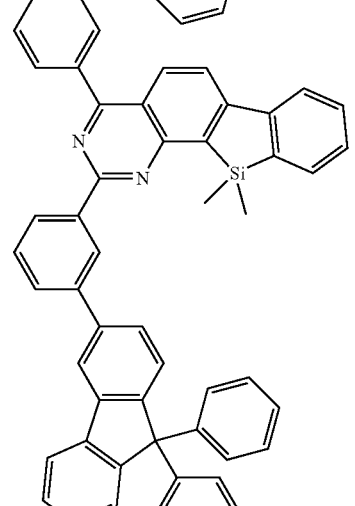
D-30
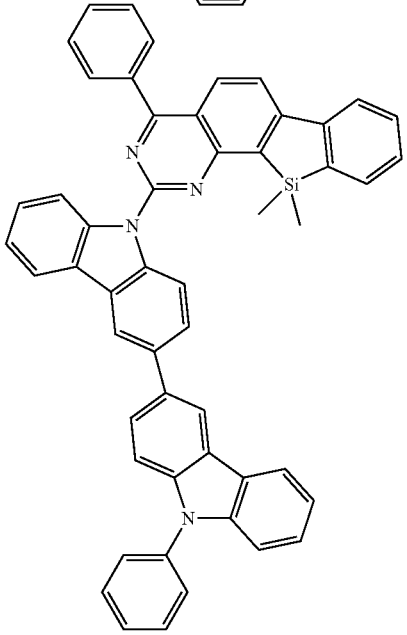

D-31
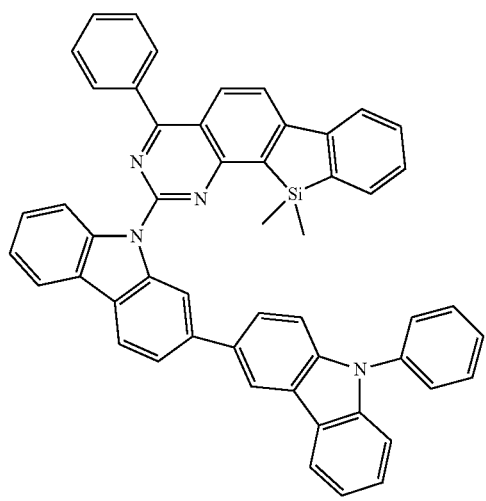
D-32
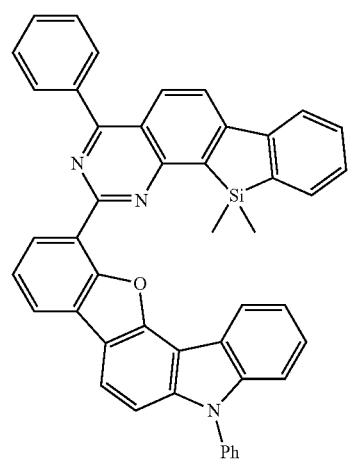
D-33
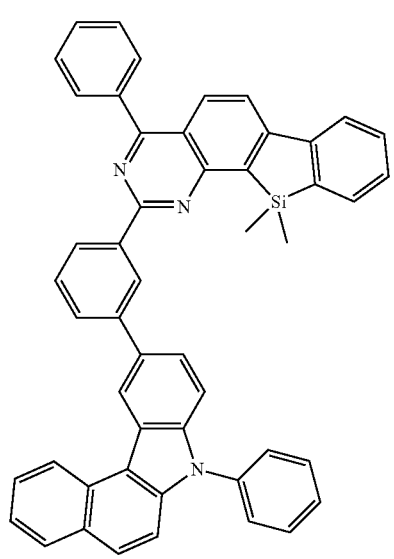
D-34
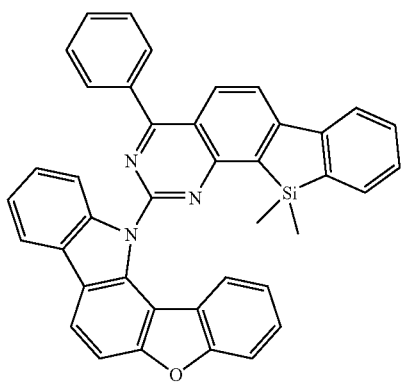
D-35
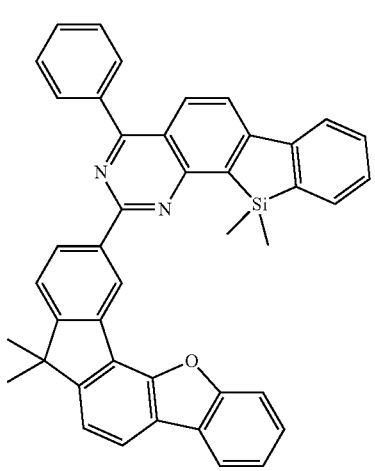
D-36
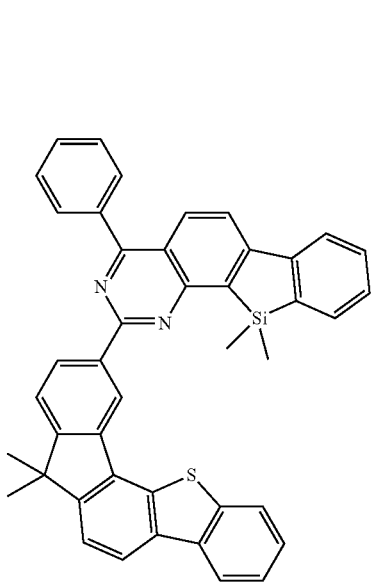

D-37
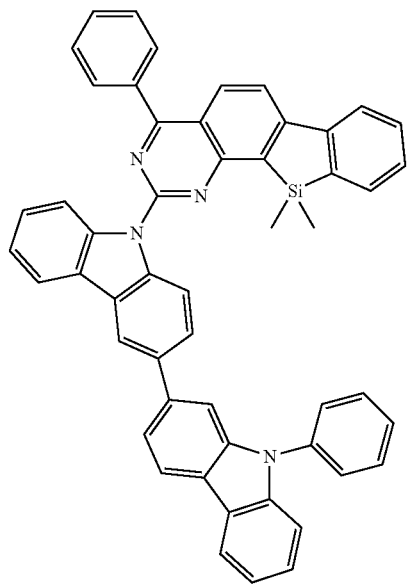
D-38
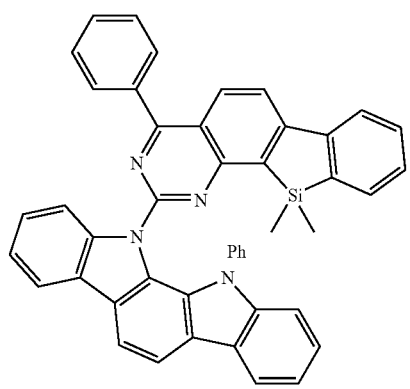
D-39
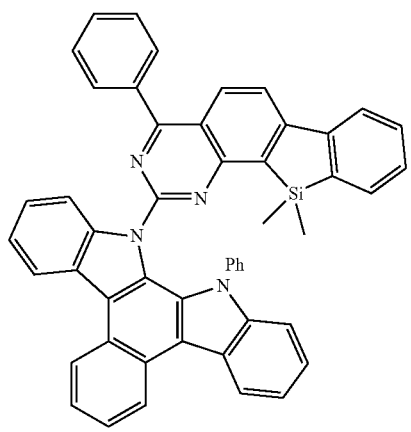
D-40
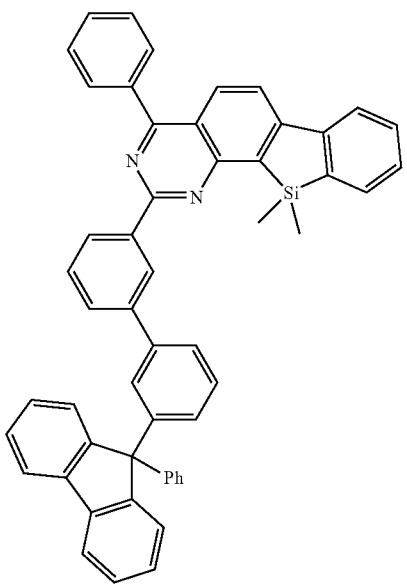
D-41
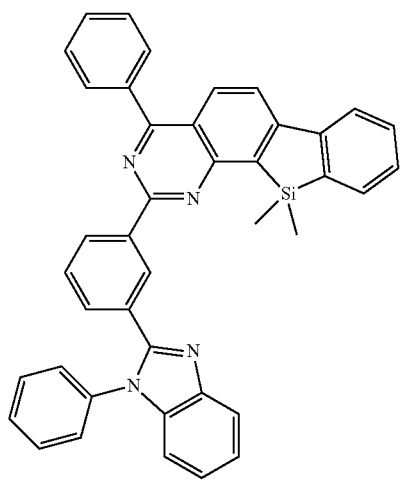
D-42
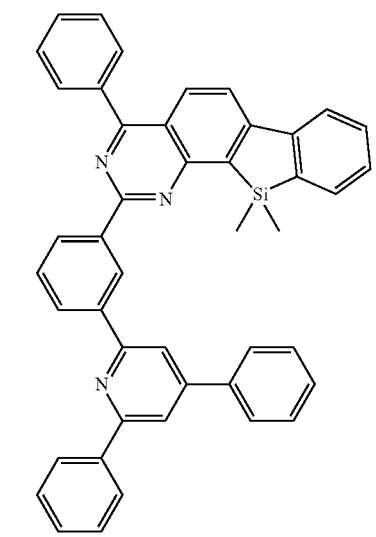

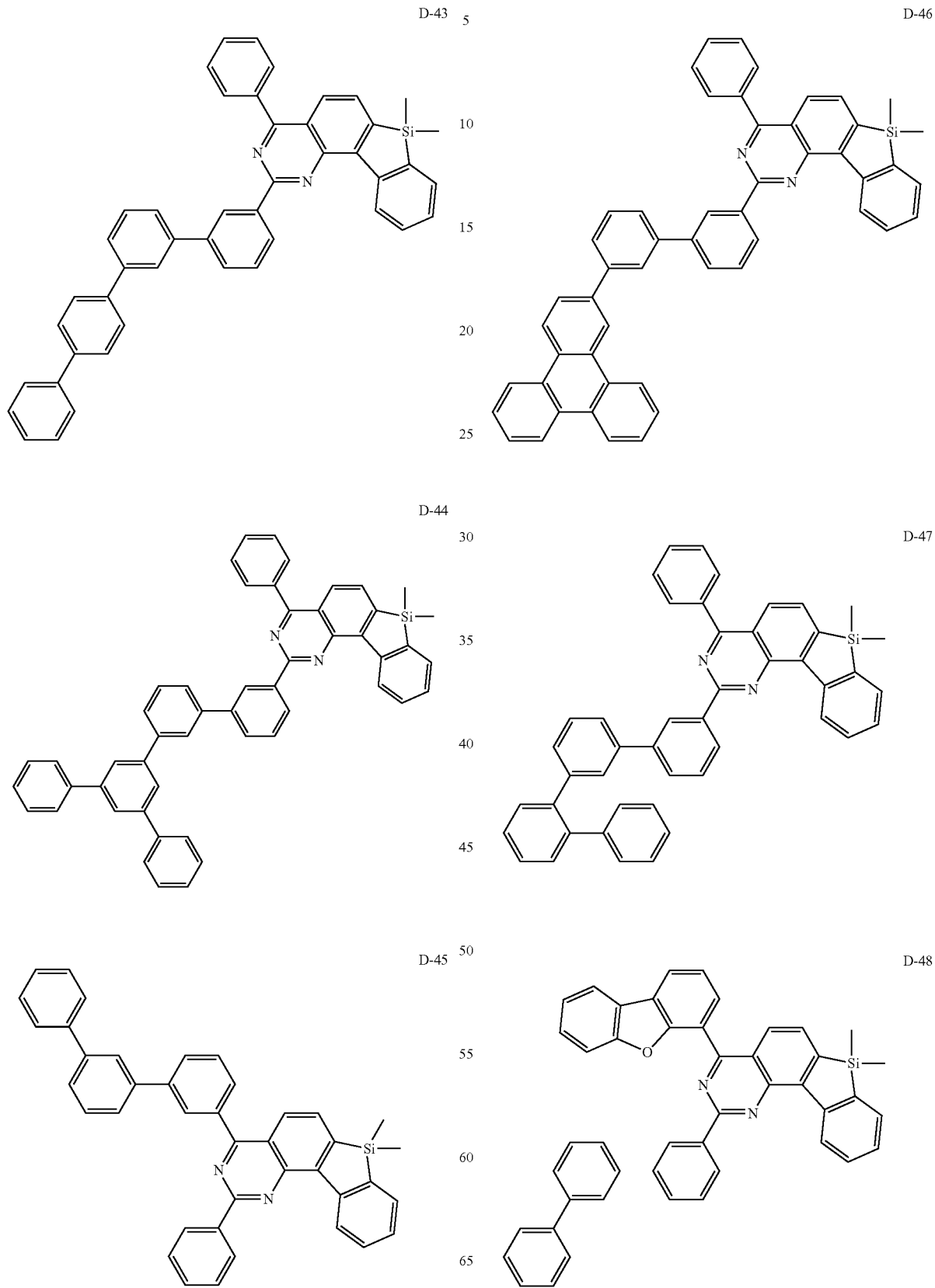

D-49
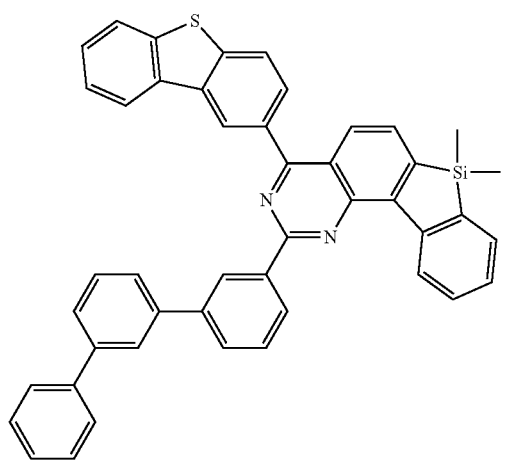
D-50
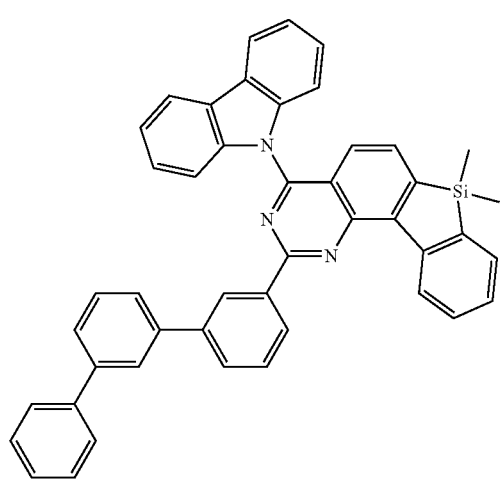
D-51
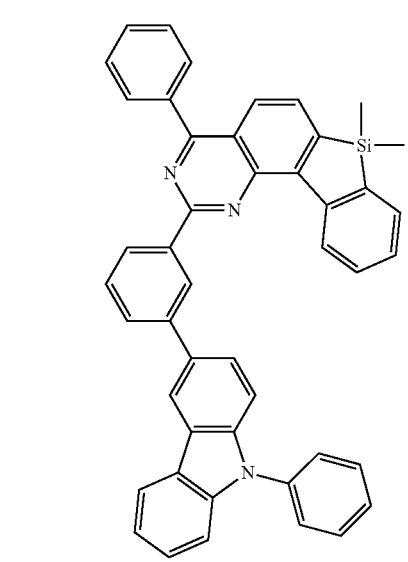
D-52
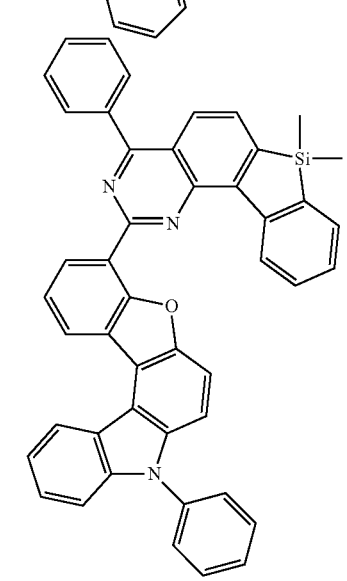
D-53
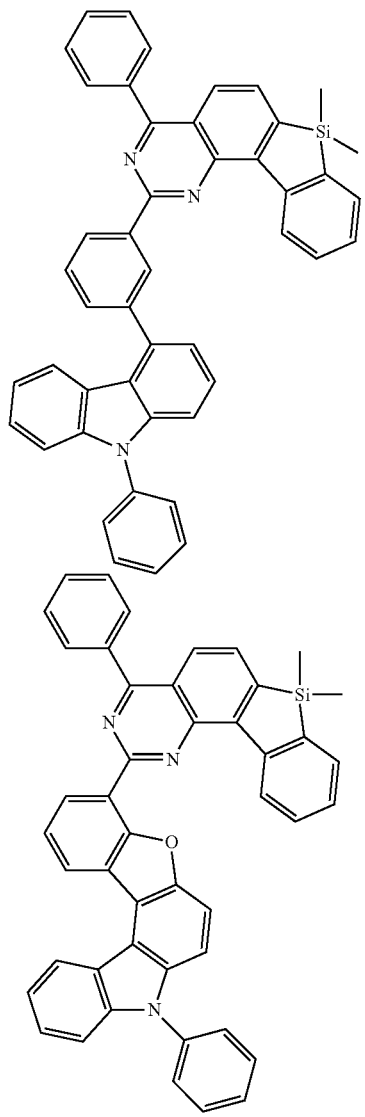
D-54
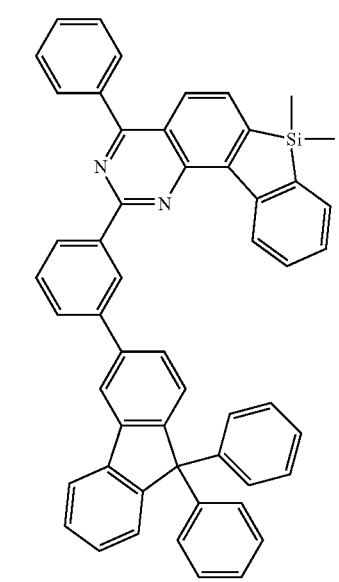

D-55
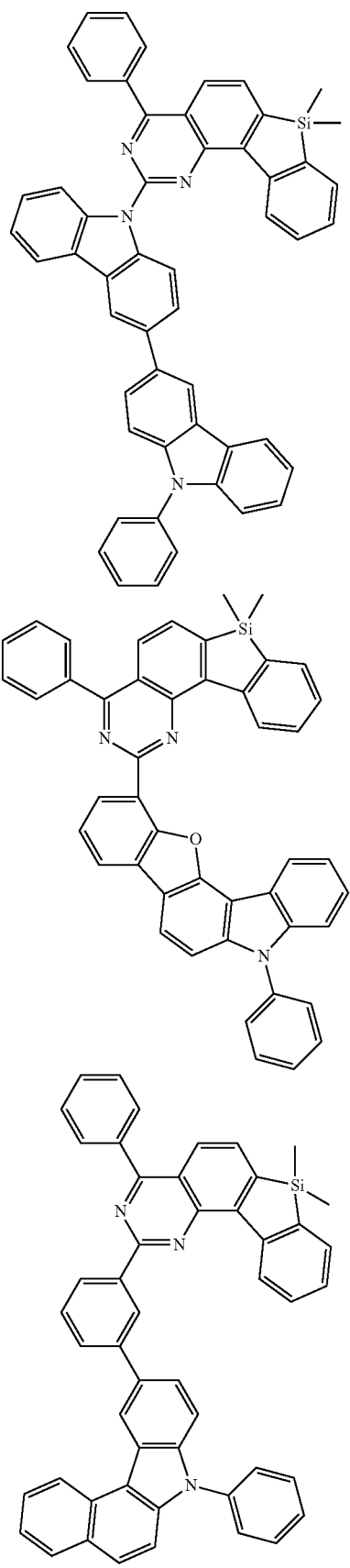
D-56
D-57
D-58
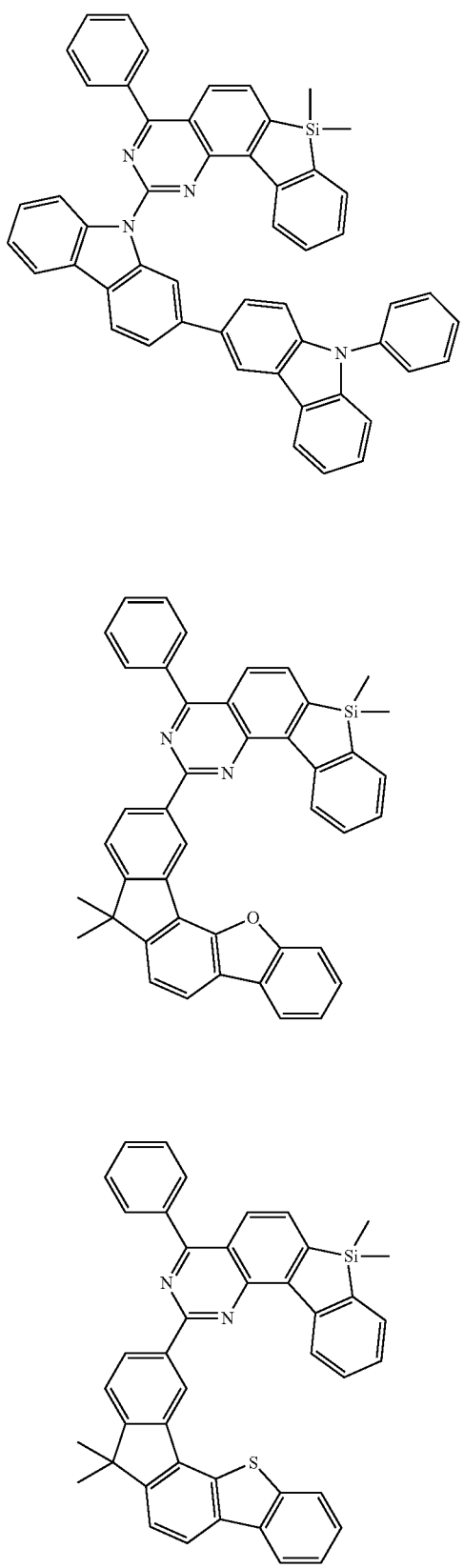
D-59
D-60

D-61
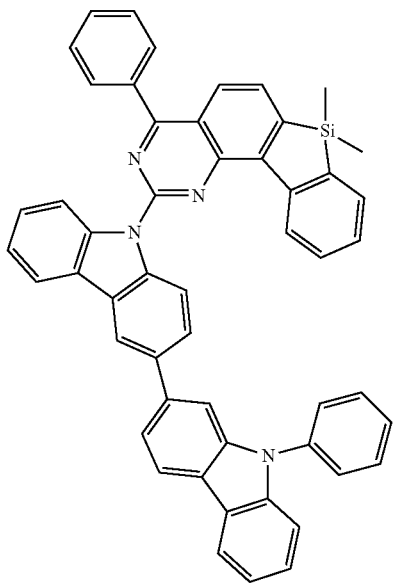
D-62
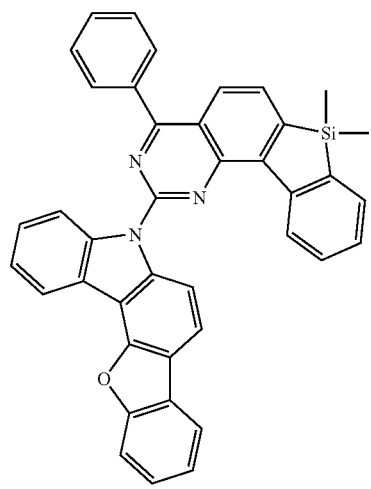
D-63
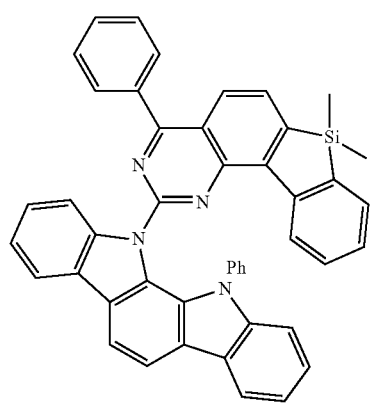
D-64
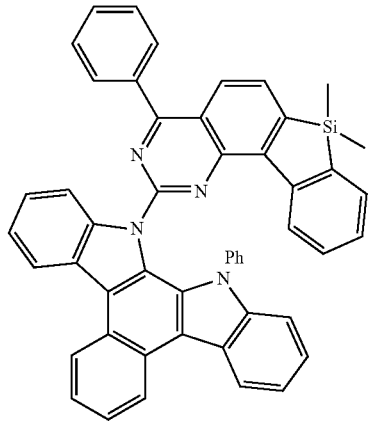
D-65
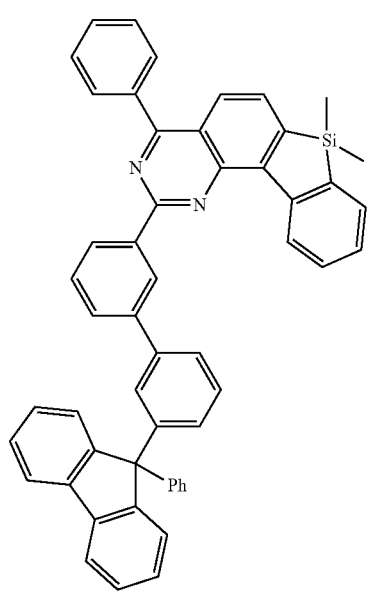
D-66
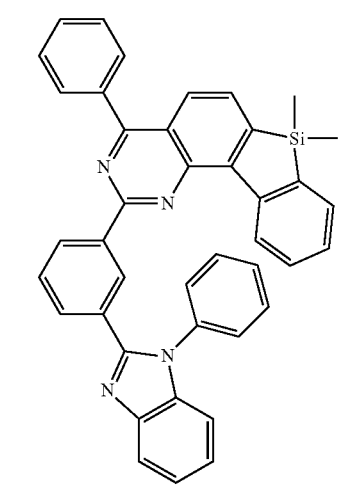

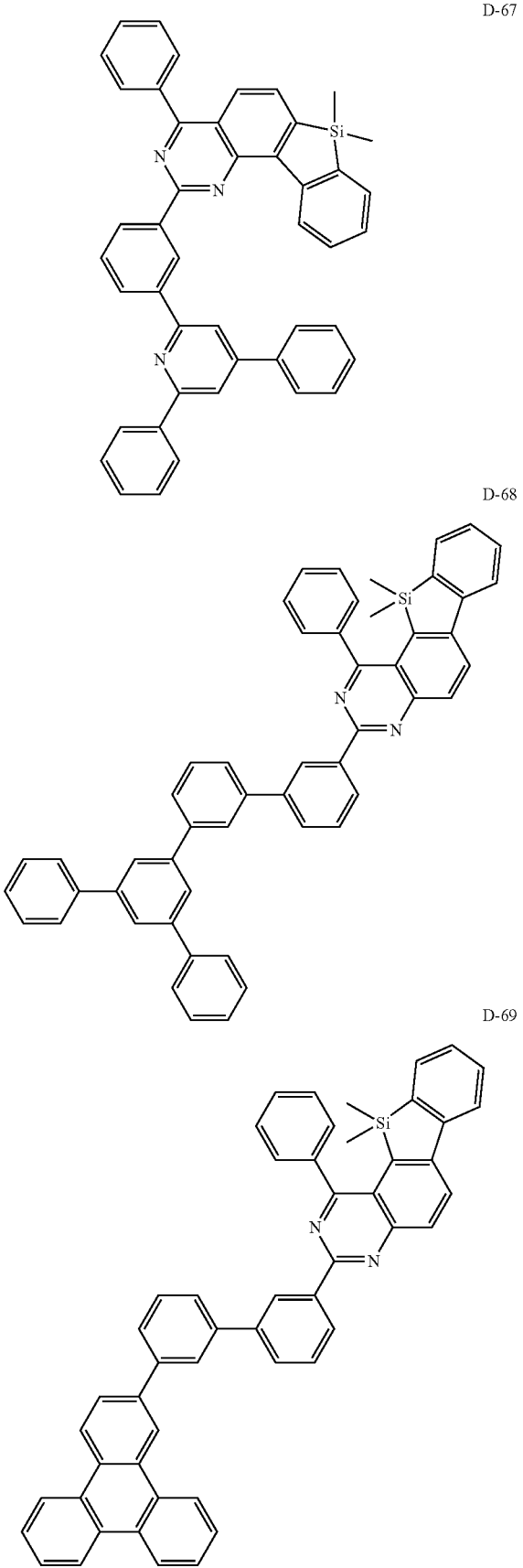
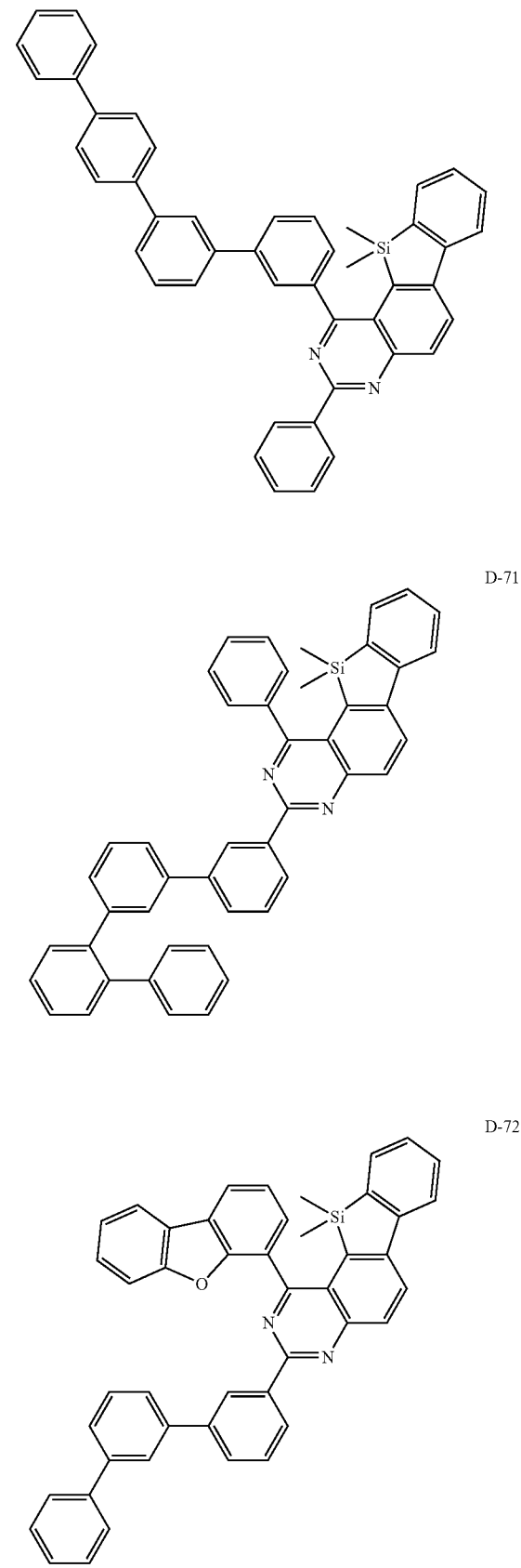

D-73
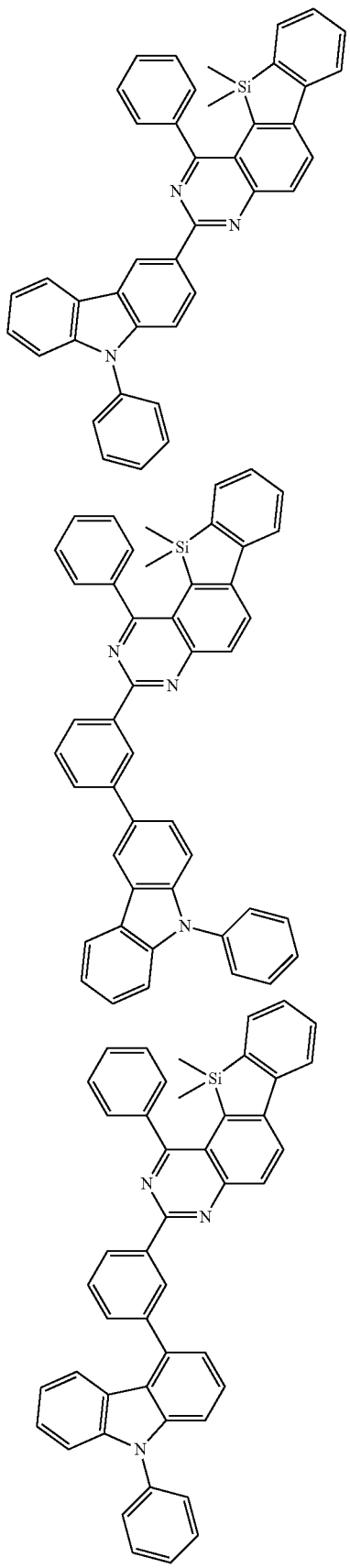
D-74
D-75
D-76
D-77

-continued
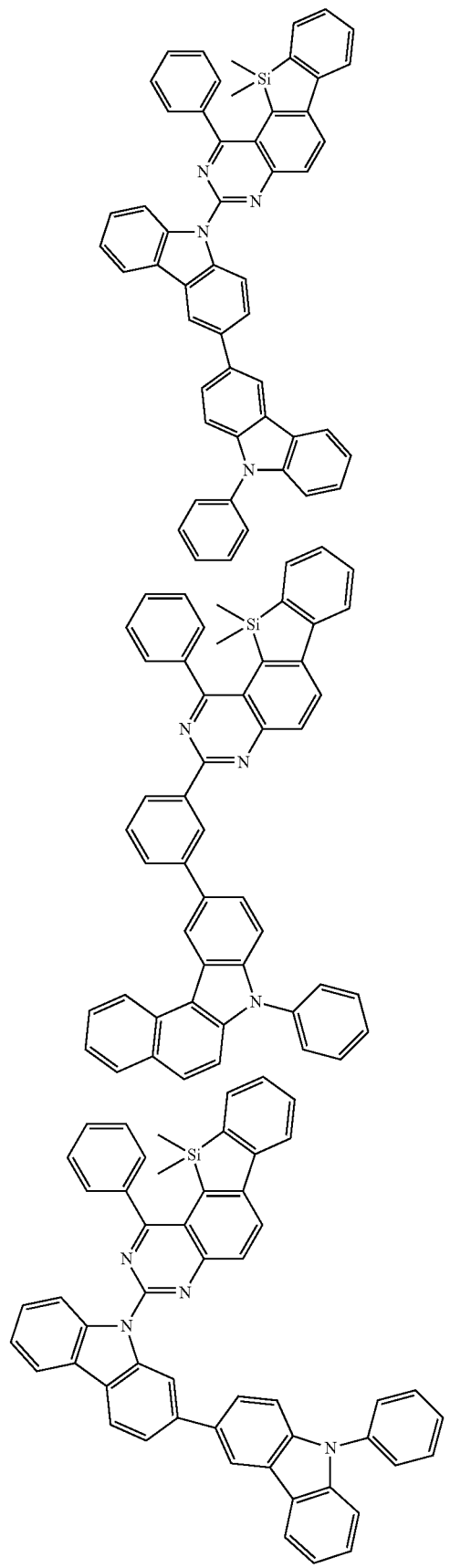
D-78
D-79
D-80
-continued
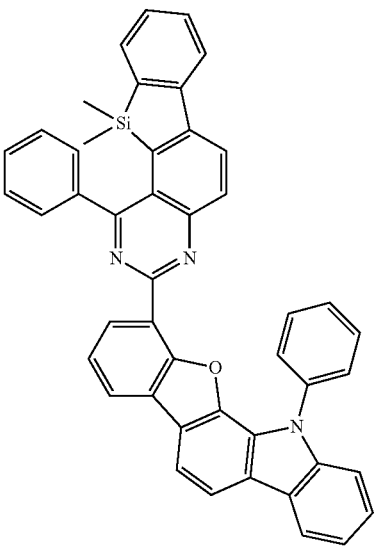
D-81
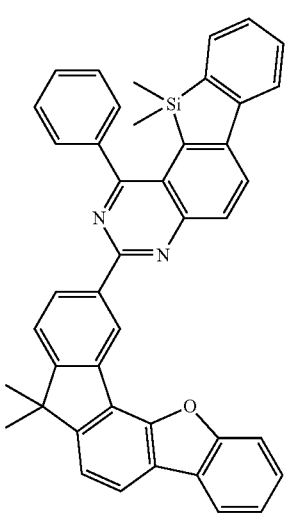
D-82
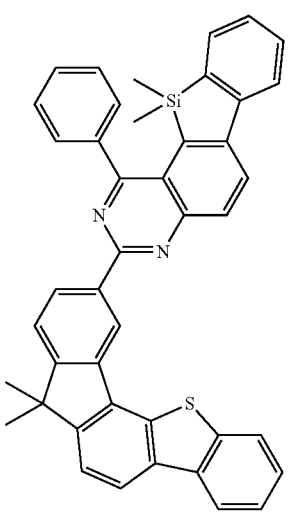
D-83

-continued
D-84
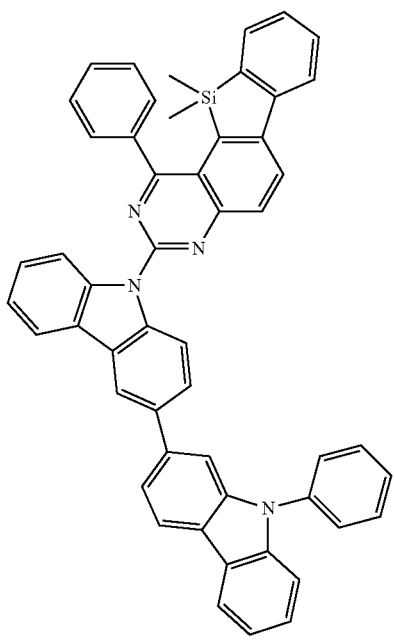
D-85
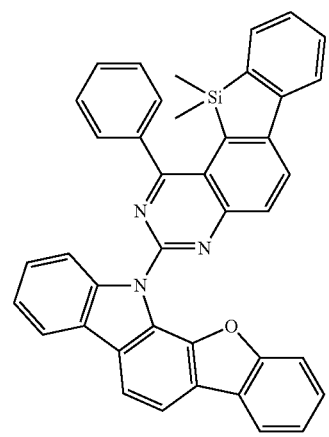
D-86
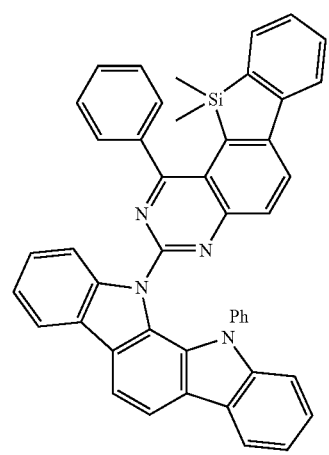
-continued
D-87
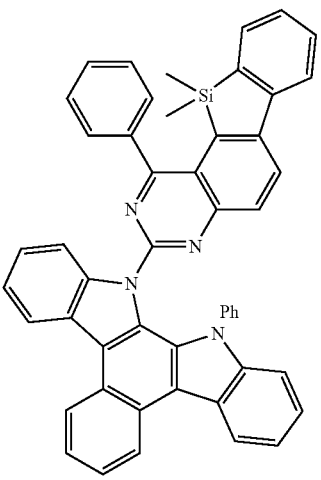
D-88
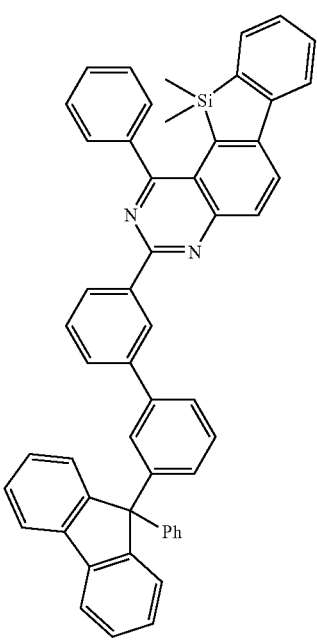
D-89
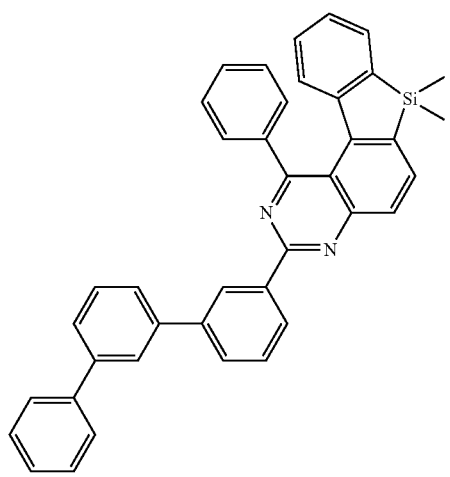

D-90
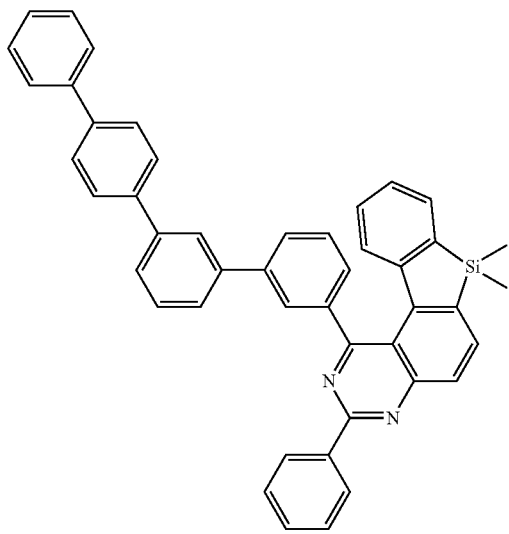
D-91
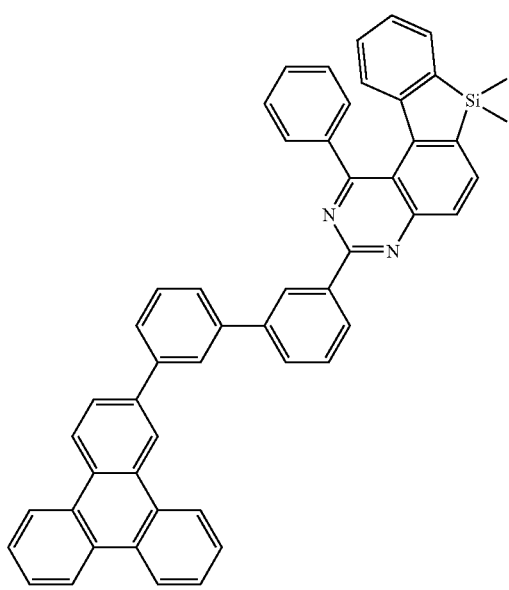
D-92
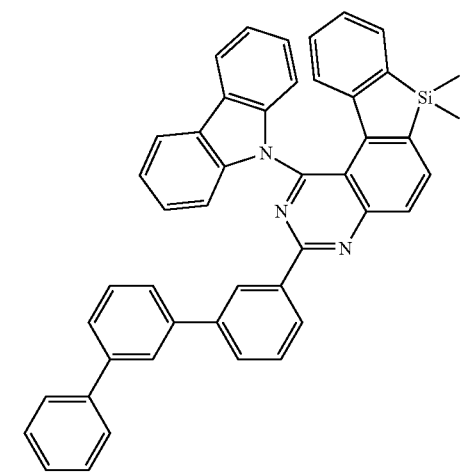
D-93
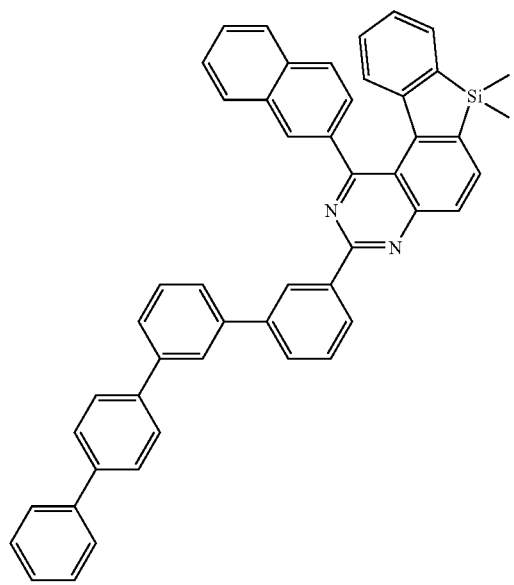
D-94 / D-95
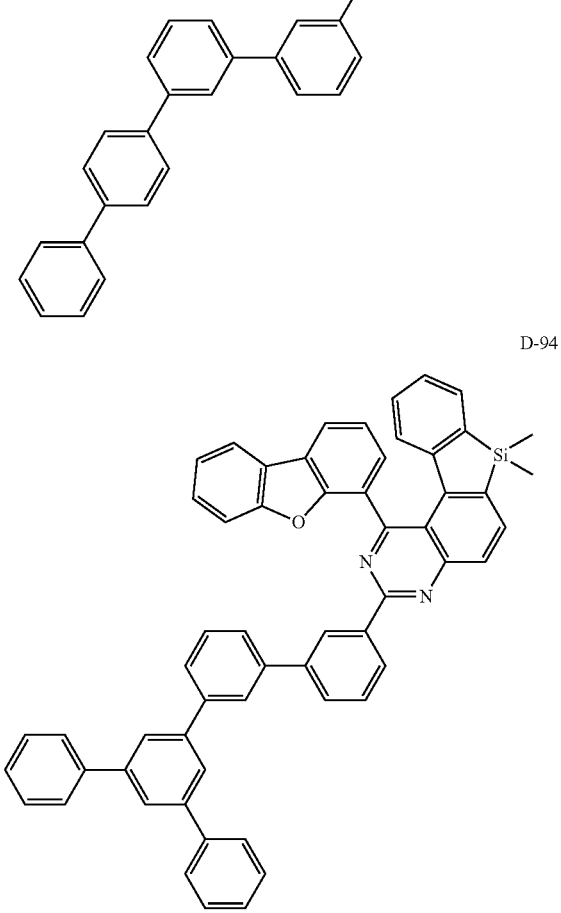

-continued
D-96
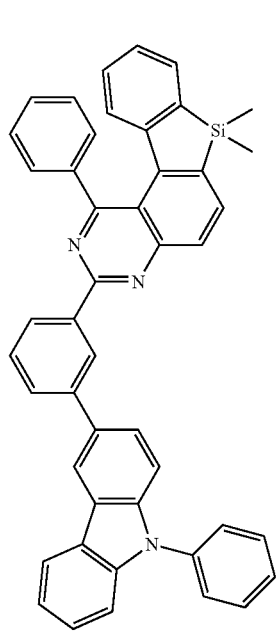
D-97
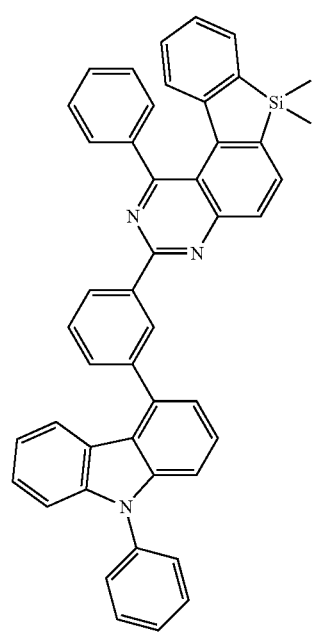
-continued
D-98
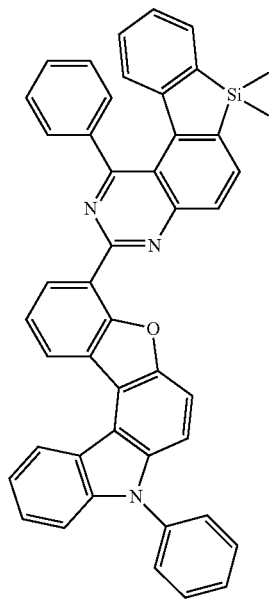
D-99
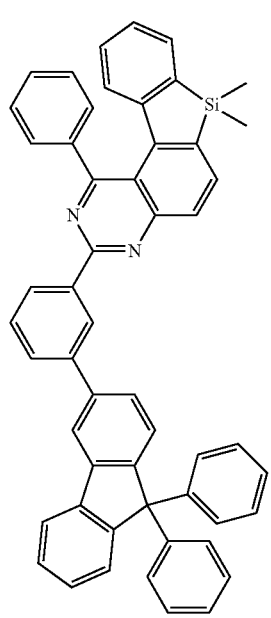

-continued
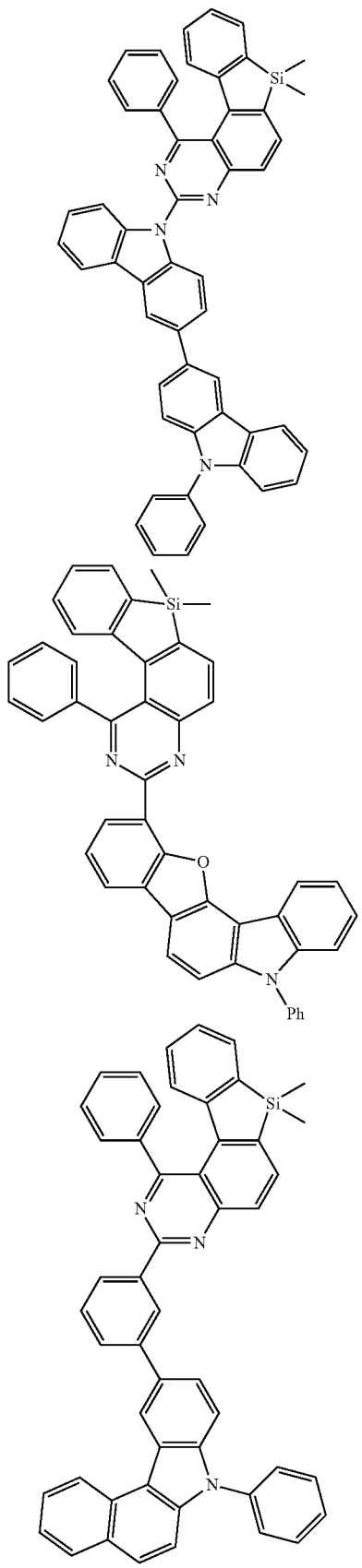
D-100
D-101
D-102
-continued
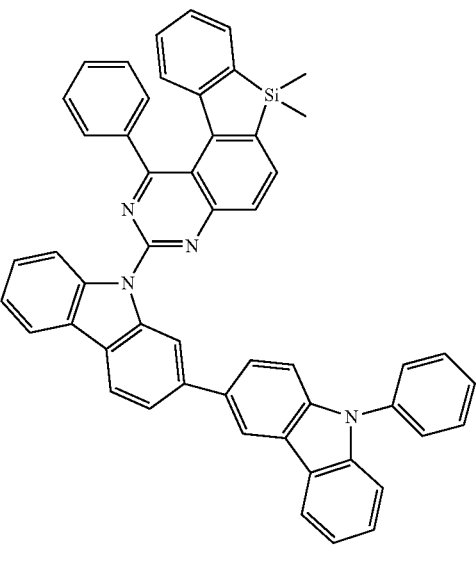
D-103
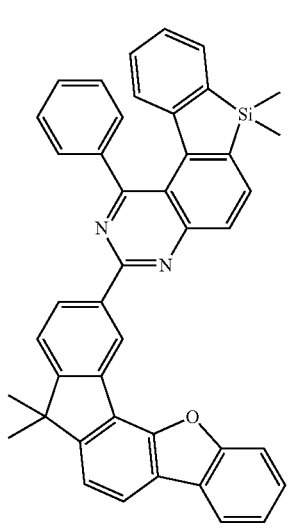
D-104
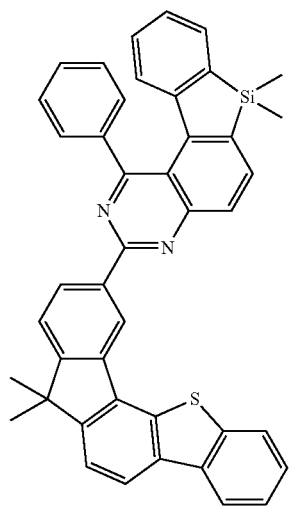
D-105

-continued

D-106
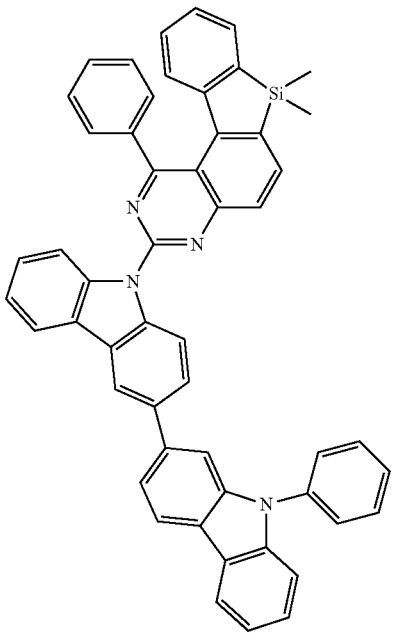

C-107
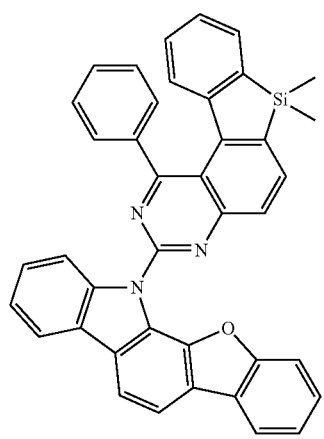

D-107
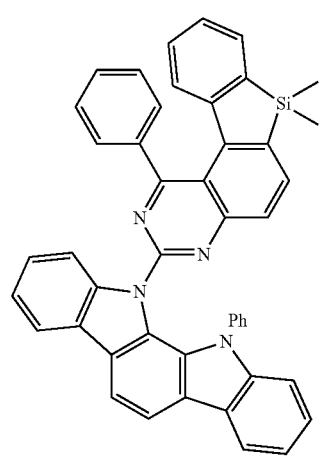

-continued

D-108
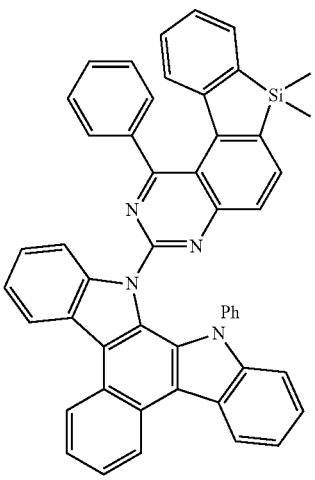

D-109
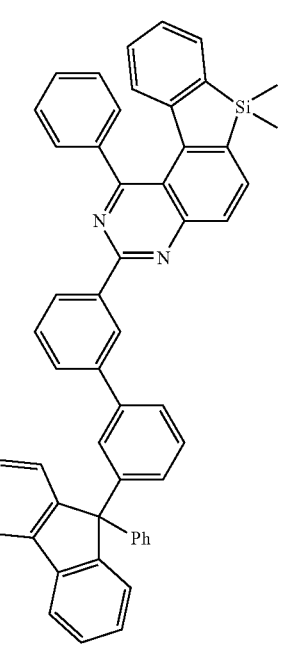

The compound for an organic optoelectronic diode may further include a dopant. The dopant may be a red, green, or blue dopant.

The dopant is a material in small amount to cause light emission and may be generally a material such as a metal complex that emits light by multiple excitation into a triplet or more. The dopant may be, for example an inorganic, organic, or organic/inorganic compound, and one or more kinds thereof may be used.

One example of the dopant may be a phosphorescent dopant and examples of the phosphorescent dopant may be an organometal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$$L_2MX \qquad \text{[Chemical Formula Z]}$$

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and L and X may be, for example a bidendate ligand.

Hereinafter, an organic optoelectronic diode including the compound for an organic optoelectronic diode is described.

The organic optoelectronic diode includes an anode and a cathode facing each other and at least one organic layer disposed between the anode and the cathode, wherein the organic layer includes the compound for an organic optoelectronic diode.

The organic layer includes a light emitting layer and the light emitting layer includes the compound for an organic optoelectronic diode of the present invention.

Specifically, the compound for an organic optoelectronic diode may be included as a host of the light emitting layer. For example, it may be included as a red host of the light emitting layer.

In an embodiment of the present invention, an organic optoelectronic diode includes the organic layer including at least one auxiliary layer selected from a hole injection layer, a hole transport layer, a hole transport auxiliary layer, an electron transport auxiliary layer, an electron transport layer, and an electron injection layer, wherein the auxiliary layer includes the compound for an organic optoelectronic diode. For example, it may be included in an electron transport auxiliary layer, an electron transport layer, or an electron injection layer.

The organic optoelectronic diode may be any device to convert electrical energy into photoenergy and vice versa without particular limitation, and may be, for example an organic photoelectric device, an organic light emitting diode, an organic solar cell, and an organic photo conductor drum.

Herein, an organic light emitting diode as one example of an organic optoelectronic diode is described referring to drawings.

FIGS. 1 and 2 are cross-sectional views of an organic light emitting diode according to an embodiment. Referring to FIG. 1, an organic optoelectronic diode 100 according to an embodiment includes an anode 120 and a cathode 110 and an organic layer 105 disposed between the anode 120 and the cathode 110.

The anode 120 may be made of a conductor having a large work function to help hole injection and may be for example made of a metal, a metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example made of a metal, a metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 105 includes a light emitting layer 130 including the compound for an organic optoelectronic diode.

The light emitting layer 130 may include, for example the compound for an organic optoelectronic diode alone, at least two kinds of the compound for an organic optoelectronic diode, or a mixture of the compound for an organic optoelectronic diode and other compounds. In case of the mixture of the compound for an organic optoelectronic diode and other compounds, for example they may be included as a host and a dopant, and the compound for an organic optoelectronic diode may be included, for example as a host. The host may be for example a phosphorescent host or a fluorescent host, for example a phosphorescent host.

When the compound is included as a host, the dopant may be an inorganic, organic, or organic/inorganic compound and may be selected from known dopants.

Referring to FIG. 2, an organic light emitting diode 200 further includes a hole auxiliary layer 140 in addition to a light emitting layer 230. The hole auxiliary layer 140 increases hole injection and/or hole mobility and blocks electrons between the anode 120 and the light emitting layer 130. The hole auxiliary layer 140 may be for example a hole transport layer, a hole injection layer, and/or an electron blocking layer, and may include at least one layer.

Even not shown in FIGS. 1 and 2, the organic layer 105 may further include an electron injection layer, an electron transport layer, an auxiliary electron transport layer, a hole transport layer, an auxiliary hole transport layer, a hole injection layer, or a combination thereof. The compound for an organic optoelectronic diode of the present invention may be included in these organic layers. The organic light emitting diodes 100 and 200 may be manufactured by forming an anode or a cathode on a substrate, forming an organic layer using a dry coating method such as evaporation, sputtering, plasma plating, and ion plating; or a wet coating method such as spin coating, dipping, and flow coating, and forming a cathode or an anode.

The organic light emitting diode may be applied to an organic light emitting display device.

Hereinafter, the embodiments are illustrated in more detail with reference to examples.

(Preparation of Compound for Organic Optoelectronic Device)

The compound for an organic optoelectronic diode as one specific examples of the present invention was synthesized through the following steps.

Synthesis of Intermediate

Synthesis Example 1: Synthesis of Intermediates G-7 and G-9

Intermediate G-7 as more specific examples of a compound according to the present invention was synthesized through five steps of [Reaction Scheme 1].

Intermediate G-9 was synthesized according to the same method as Reaction Scheme 1 by using a starting material G-8 as more specific examples of the compound according to the present invention.

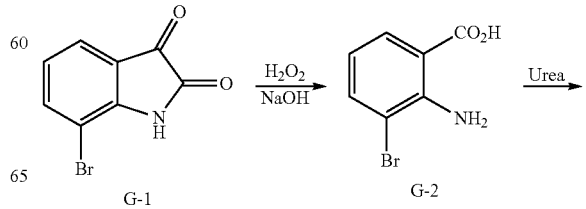

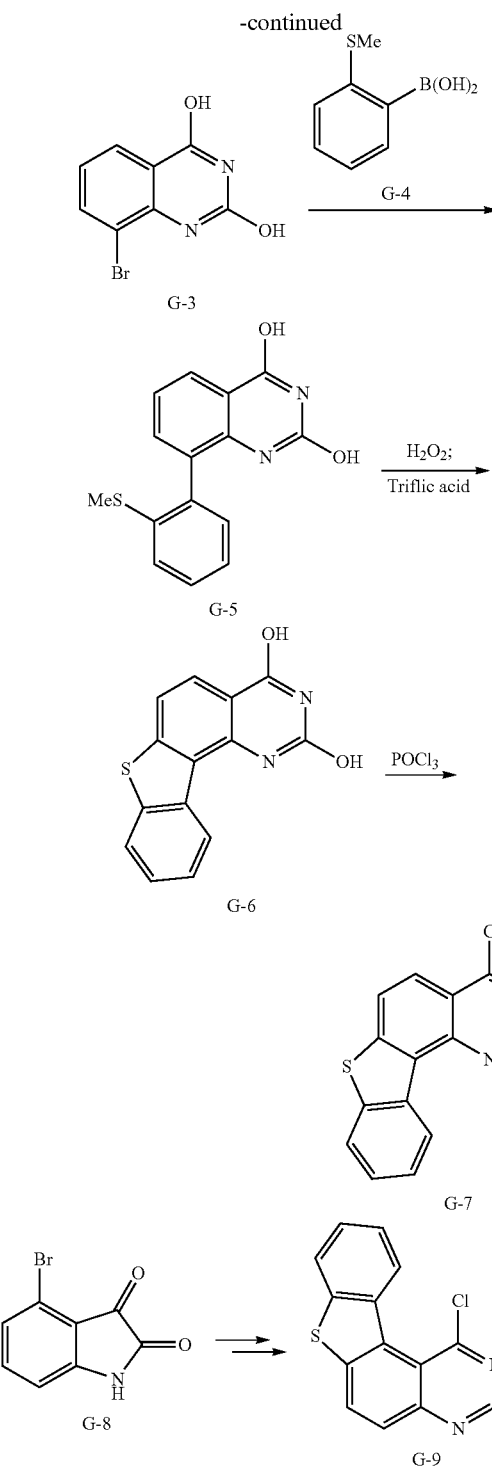

again, methanol (400 mL) was added thereto, and the mixture was stirred for 15 minutes and filtered. A filtrate therefrom was dried to synthesize an intermediate product (G-2, 23.9 g), and the intermediate product was used for the following reaction without additional purification.

calcd. $C_7H_6BrNO_2$: C, 38.92; H, 2.80; Br, 36.99; N, 6.48; O, 14.81. found: C, 38.94; H, 2.83; Br, 36.97; N, 6.46; O, 14.80.

Second Step: Synthesis of Intermediate Product G-3

Intermediate G-2 (23.9 g, 110.6 mmol) and urea (66.3 g, 1106 mmol) were put in 250 mL flask and then, heated at 180° C. for 12 hours under a nitrogen flow. When Intermediate G-2 all disappeared, the temperature was a little lowered, dichlorobenzene (100 mL) was added thereto, and the mixture was added to water (300 mL) and then, stirred therewith. A solid therefrom was filtered and dried to obtain Intermediate G-3 (16.0 g, yield of 60%).

calcd. $C_7H_6BrNO_2$: C, 38.92; H, 2.80; Br, 36.99; N, 6.48; O, 14.81. found: C, 38.90; H, 2.80; Br, 36.97; N, 6.49; O, 14.84.

Third Step: Synthesis of Intermediate Product G-5

Intermediate G-3 (16.0 g, 66.4 mmol), 2-methylthiophenylboronic acid (G-4, 12.3 g, 73.0 mmol), potassium carbonate ($K_2CO_3$, 22.9 g, 166 mmol), Pd $Pd(PPh_3)_4$ (tetrakis-(triphenylphosphine) palladium (0), 3.8 g, 3.3 mmol) were added to tetrahydrofuran (450 mL) and water (200 mL) in a 1000 mL flask, and the mixture was heated at 60° C. for 12 hours under a nitrogen flow. After removing an aqueous layer, an organic layer remaining there was concentrated, extracted with dichloromethane (300 mL), dried with anhydrous magnesium sulfate ($MgSO_4$), and filtered with silica gel/Celite, and after removing an appropriate amount of an organic solvent, methanol was used for recrystallization to obtain Compound G-5 (14.2 g, yield of 75%).

calcd. $C_{15}H_{12}N_2O_2S$: C, 63.36; H, 4.25; N, 9.85; O, 11.25; S, 11.28. found: C, 63.38; H, 4.27; N, 9.83; O, 11.24; S, 11.28.

Fourth Step: Synthesis of Intermediate Product G-6

Intermediate G-5 (14.2 g, 50.0 mmol) was dissolved in glacial acetic acid (300 mL) in a 1000 mL flask, and hydrogen peroxide (20%, 1 equivalent) dissolved in glacial acetic acid was slowly added thereto. The reactant was stirred at room temperature for 12 hours, and after removing acetic acid under a reduced pressure, a remainder there was dried to synthesis a sulfoxide intermediate. Subsequently, trifluorosulfonic acid (triflic acid) was added thereto without additional purification, the obtained mixture was stirred at room temperature for 24 hours. A potassium carbonate aqueous solution was added thereto to adjust pH into about 4, mL of methanol was poured thereinto, and the obtained mixture was stirred and filtered to synthesize Intermediate G-6 (9.6 g, yield of 72%).

Chemical Formula: $C_{14}H_8N_2O_2S$ calcd. C14H8N2O2S: C, 62.67; H, 3.01; N, 10.44; O, 11.93; S, 11.95. found: C, 62.67; H, 3.02; N, 10.42; O, 11.95; S, 11.94.

Fifth Step: Synthesis of Intermediate Product G-7

Intermediate G-6 (9.6 g, 35.8 mmol) was added to phosphorylchloride (23.5 mL, 429 mmol) in a 250 mL flask, and the mixture was heated at 120° C. for 4 hours under a nitrogen flow. The reaction mixture was slowly poured into an excessive amount of ice to complete a reaction, and a solid filtered therefrom was washed with water and methanol and dried to obtain Intermediate G-7 (9.6 g, yield of 88.0%).

First Step: Synthesis of Intermediate Product G-2

4-bromoindoline-2,3-dione (G-1, 25 g, 110.6 mmol) and 1.0 N sodium hydroxide an aqueous solution (220 mL) were put in a 1000 mL flask and then, stirred at 80° C. under a nitrogen flow. Hydrogen peroxide (20%, 16.7 mL) was added thereto through a dropping funnel for 15 minutes and the mixture was stirred at 80° C. for 1 hour. Subsequently, the reactant was cooled down to −10° C. and then, concentrated. HCl was slowly added thereto to adjust pH of the reactant in a range of 4 to 5, the reactant was concentrated calcd. $C_{14}H_6Cl_2N_2S$: C, 55.10; H, 1.98; Cl, 23.23; N, 9.18; S, 10.51. found: C, 55.12; H, 1.99; Cl, 23.22; N, 9.14; S, 10.53.

Synthesis Example 2: Synthesis of Intermediates H-6 and H-8, H-10, H-12

Intermediate H-6 (G-6) as more specific examples of a compound according to the present invention may be synthesized through five steps of [Reaction Scheme 2].

Intermediates H-8, H-10, and H-12 as more specific examples of a compound according to the present invention were synthesized according to the same method as the method of synthesizing Intermediate H-6 of [Reaction Scheme 2]. In addition, Intermediates H-8, H-10, and H-12 were manufactured by respectively using H-7, H-9, and H-11 instead of H-1 as a starting material in [Reaction Scheme 2].

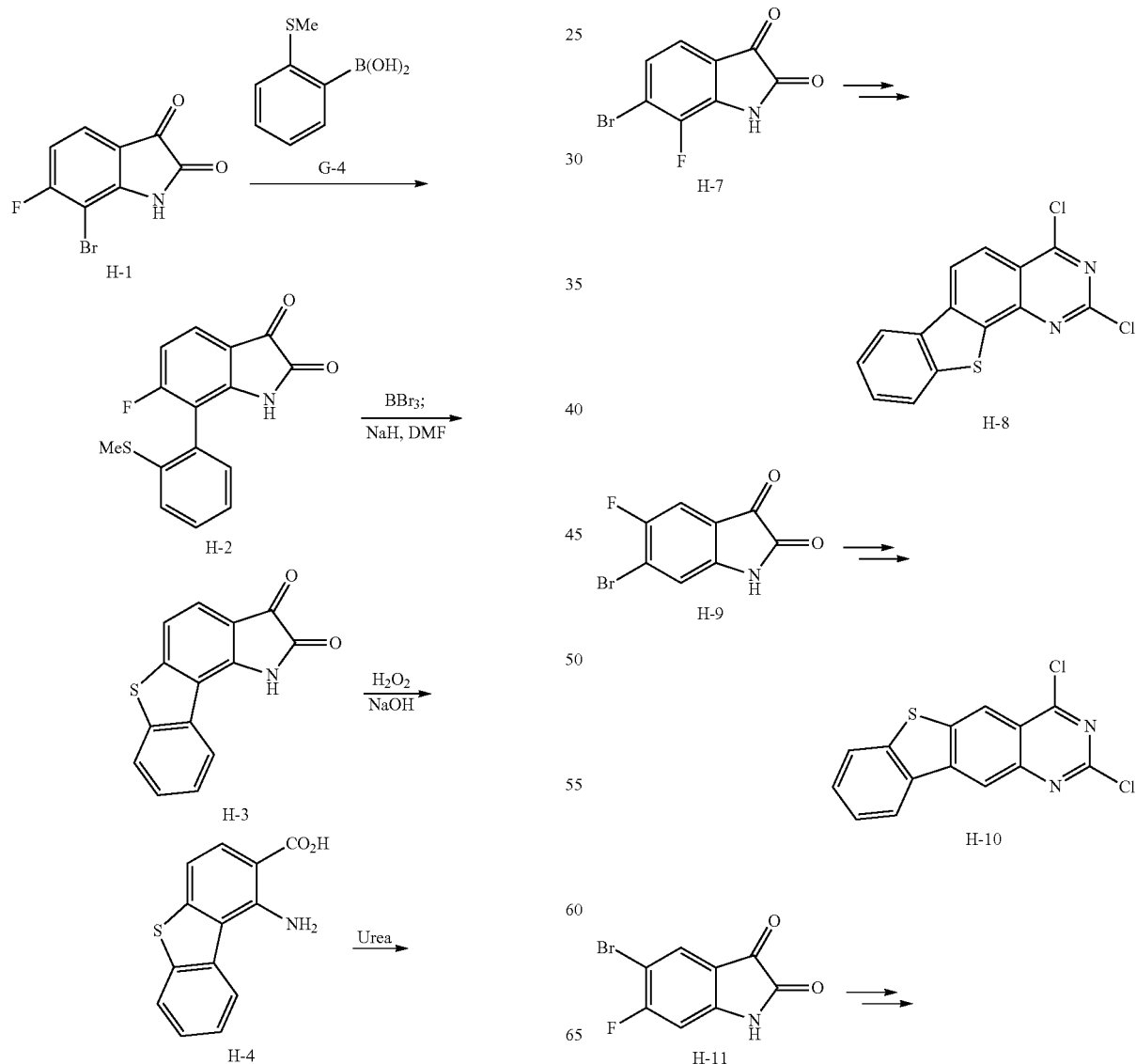

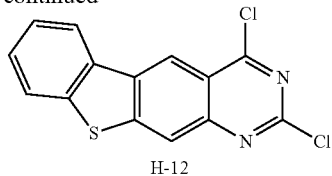

H-12

First Step: Synthesis of Intermediate H-2

4-bromo-3-fluoroindoline-2,3-dione (25 g, 102.4 mmol), 2-methylthiophenylboronic acid (G-4, 18.9 g, 112.7 mmol), potassium carbonate ($K_2CO_3$, 35.4 g, 256 mmol), Pd(PPh$_3$)$_4$ (tetrakis-(triphenylphosphine) palladium (0), 5.9 g, 5.1 mmol) were added to tetrahydrofuran (250 mL) and water (120 mL) in a 1000 mL flask, and the mixture was heated at 60° C. for 12 hours under a nitrogen flow. After removing an aqueous layer, an organic layer remaining there was concentrated, extracted by using dichloromethane (300 mL), dried with magnesium sulfate ($MgSO_4$), and filtered with silica gel/Celite, and after removing an appropriate amount of an organic solvent, methanol was used for recrystallization to obtain Compound H-2 (17.6 g, yield of 60%).

calcd. $C_{15}H_{11}FNO_2S$: C, 62.49; H, 3.85; F, 6.59; N, 4.86; O, 11.10; S, 11.12. found: C, 62.51; H, 3.83; F, 6.58; N, 4.89; O, 11.06; S, 11.13.

Second Step: Synthesis of Intermediate H-3

Intermediate H-2 (17.6 g, 61.4 mmol) was dissolved in dichloromethane (DCM, 300 mL) in a 1000 mL flask, and borane tribromide (BBr$_3$, 122.8 mL, 122.8 mmol) was slowly added in a dropwise fashion, while the mixture was maintained at 0° C.

When a reaction was complete, the mixture was washed with a sodium thiosulfate ($Na_2S_2O_3$) aqueous solution, and after removing an organic solvent, a remainder therein was dissolved in N,N-dimethylformalamide (DMF, 120 mL) at room temperature without additional purification, then, sodium hydride (60% NaH, 3.7 g, 92.1 mmol) was added thereto in an ice bath, and the mixture was stirred. The reactant was stirred at 100° C. for 1 hour, cooled down to room temperature, and dropped in 400 mL of water, and a solid produced therein was filtered and recrystallized with methanol to obtain Intermediate H-3 (11.7 g, yield of 75%).

calcd. $C_{14}H_8NO_2S$: C, 66.13; H, 3.17; N, 5.51; O, 12.58; S, 12.61. found: C, 66.11; H, 3.15; N, 5.53; O, 12.56; S, 12.64.

Third Step: Synthesis of Intermediate H-4

Intermediate H-3 (11.7 g, 46.1 mmol) and a 1.0 N sodium hydroxide aqueous solution (92 mL) were put in a 1000 mL flask and stirred under a nitrogen flow at 80° C. Hydrogen peroxide (20%, 7.0 mL) was added thereto through a dropping funnel for 15 minutes and the mixture was stirred at 80° C. for 1 hour. Then, the reactant was cooled down to −10° C. and concentrated. HCl was slowly added thereto to adjust the reactant pH in a range of 4 to 5, the mixture was concentrated again, methanol (200 mL) was added thereto, and the obtained mixture was stirred for 15 minutes and filtered. A filtrate therefrom was dried to synthesize an intermediate product H-4 (11.3 g), and the intermediate product H-4 was used for the following reaction without additional purification.

calcd. $C_{13}H_{10}NO_2S$: C, 63.92; H, 4.13; N, 5.73; O, 13.10; S, 13.13. found: C, 63.90; H, 4.11; N, 5.74; O, 13.11; S, 13.15.

Fourth Step: Synthesis of Intermediate H-5

Intermediate H-4 (11.3 g, 46.1 mmol) and urea (27.6 g, 461 mmol) were put in a 250 mL flask and then, heated under a nitrogen flow for 12 hours at 180° C. When Intermediate H-4 all disappeared, the temperature was a little lowered, dichlorobenzene (50 mL) and water (300 mL) were sequentially added thereto, and the mixture was stirred. A solid obtained therefrom was filtered and dried to obtain Intermediate H-5 (8.1 g, yield of 65%).

calcd. $C_{14}H_8N_2O_2S$: C, 62.67; H, 3.01; N, 10.44; O, 11.93; S, 11.95. found: C, 62.65; H, 3.00; N, 10.46; O, 11.91; S, 11.98.

Fifth Step: Synthesis of Intermediate Product H-6 Intermediate H-5 (8.1 g, 30.0 mmol) was added to phosphorylchloride (19.8 mL, 210 mmol) in a 250 mL flask, and the mixture was heated under a nitrogen flow for 4 hours at 120° C. The reaction mixture was poured onto an excessive amount of ice to complete a reaction, and a solid filtered therefrom was washed with water and methanol and dried to obtain Intermediate H-6 (8.3 g, yield of 90.0%).

calcd. $C_{14}H_6Cl_2N_2S$: C, 55.10; H, 1.98; Cl, 23.23; N, 9.18; S, 10.51. found: C, 55.12; H, 1.99; Cl, 23.22; N, 9.14; S, 10.53.

Synthesis Example 3: Synthesis of Intermediates I-6 and I-8, I-10, I-12

Intermediate I-6 was synthesized as more specific examples of a compound according to the present invention through 5 steps of [Reaction Scheme 3].

Intermediates I-7, I-8, and I-9 were synthesized as more specific examples of a compound according to the present invention according to the same method as the method of synthesizing Intermediate I-6 of [Reaction Scheme 3]. In addition, each intermediates I-7, I-8, and I-9 was manufactured by respectively using H-7, H-9, and H-11 instead of H-1 as a starting material in [Reaction Scheme 3].

[Reaction Scheme 3]

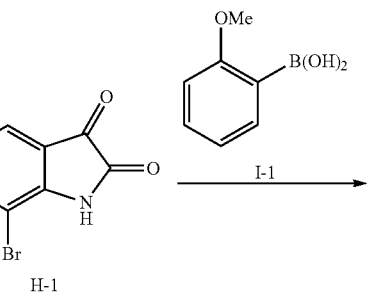

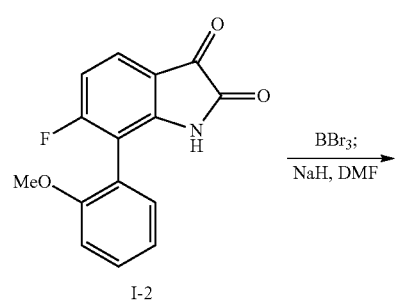

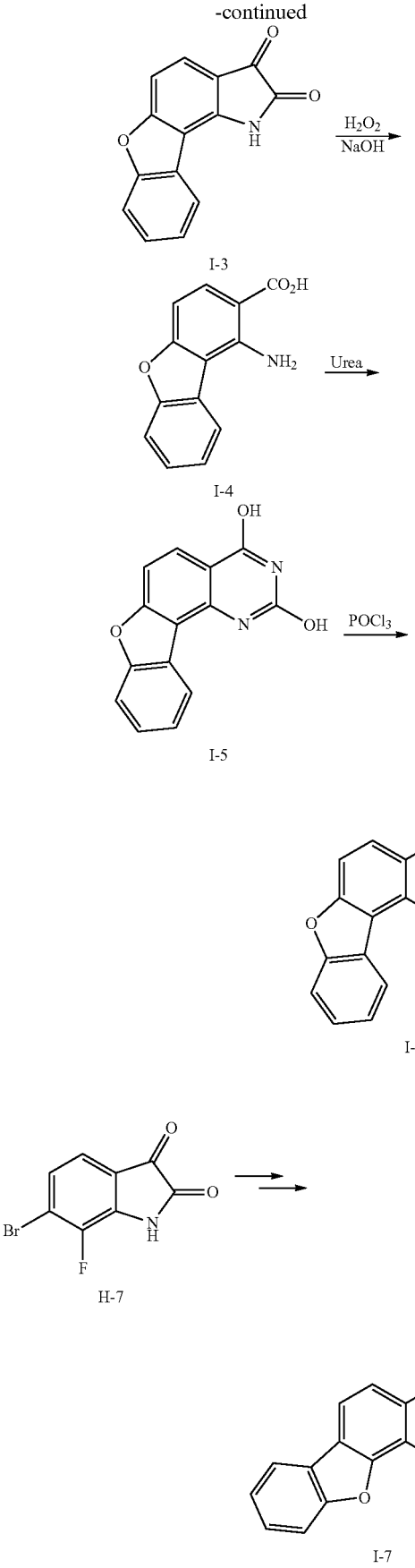

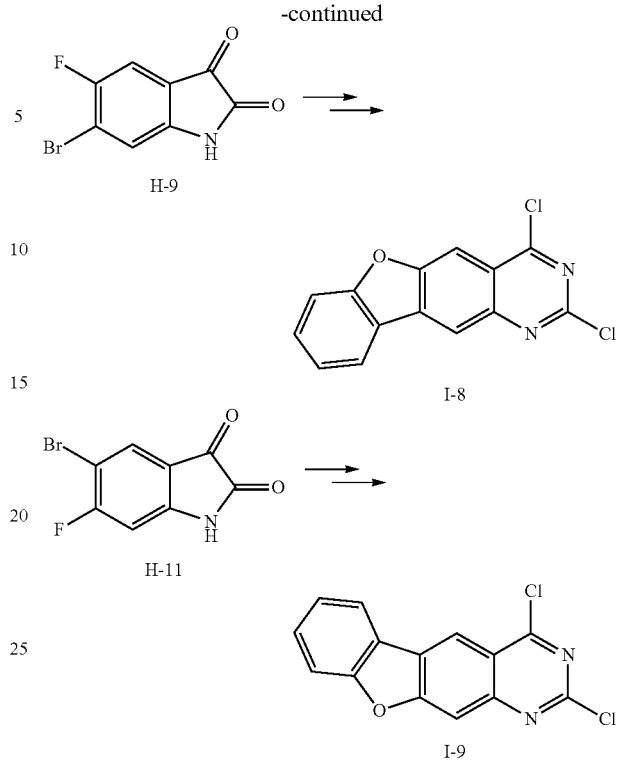

First Step: Synthesis of Intermediate I-2

4-bromo-3-fluoroindoline-2,3-dione (H-1, 25 g, 102.4 mmol), 2-methoxyphenylboronic acid (I-1, 17.1 g, 112.7 mmol), potassium carbonate ($K_2CO_3$, 35.4 g, mmol), and $Pd(PPh_3)_4$ (tetrakis-(triphenylphosphine) palladium (0), 5.9 g, 5.1 mmol) were added to tetrahydrofuran (250 mL) and water (120 mL) in a 1000 mL flask, and the mixture was heated under a nitrogen flow for 12 hours at 60° C. After removing an aqueous layer, an organic layer remaining there was concentrated, extracted by using dichloromethane (300 mL), dried with anhydrous magnesium sulfate ($MgSO_4$), and filtered with silica gel/Celite, and after removing an appropriate amount of an organic solvent, methanol was used for recrystallization to obtain Compound I-2 (19.4 g, yield of 70%).

calcd. $C_{15}H_{11}FNO_3$: C, 66.42; H, 3.72; F, 7.00; N, 5.16; O, 17.70. found: C, 66.40; H, 3.70; F, 7.00; N, 5.19; O, 17.71.

Second Step: Synthesis of Intermediate I-3

Intermediate I-2 (19.4 g, 71.7 mmol) was dissolved in dichloromethane (DCM, 350 mL) in a 1000 ml, flask, and borane tribromide ($BBr_3$, 143.4 mL, 143.4 mmol) was slowly added thereto in a dropwise fashion, while the mixture was maintained at 0° C. When a reaction was complete, the resulting mixture was washed with a sodium thiosulfate ($Na_2S_2O_3$) aqueous solution, after removing an organic solvent, a remainder therein was dissolved in N,N-dimethylamide (DMF, 140 mL) at room temperature without additional purification, sodium hydride (60% NaH, 4.3 g, 107.5 mmol) was added thereto in an ice bath, and the obtained mixture was stirred. The reactant was stirred at 100° C. for 1 hour, cooled down to room temperature, and dropped in water (400 mL), and a solid produced therein was filtered and recrystallized with methanol to obtain Intermediate I-3 (13.6 g, yield of 80%).

calcd. $C_{14}H_8NO_3$: C, 70.89; H, 2.97; N, 5.90; O, 20.23. found: C, 70.91; H, 2.99; N, 5.90; O, 20.20.

Third Step: Synthesis of Intermediate I-4

Intermediate I-3 (13.6 g, 57.4 mmol) and a 1.0 N sodium hydroxide aqueous solution (115 mL) were put in a 1000 mL flask and then, stirred at 80° C. under a nitrogen flow. Hydrogen peroxide (20%, 8.7 mL) was added thereto through a dropping funnel for 15 minutes and the obtained mixture was stirred at 80° C. for 1 hour. The reactant was cooled down to −10° C. and concentrated. Subsequently, HCl was slowly added thereto to adjust pH of the reactant in a range of 4 to 5, the mixture was concentrated again, methanol (200 mL) was added thereto, and the obtained mixture was stirred for 15 minutes and filtered. A filtrate therefrom was dried to synthesize Intermediate I-4 (13.0 g), and Intermediate I-4 was used for the following reaction without additional purification.

calcd. $C_{13}H_{10}NO_3$: C, 68.72; H, 3.99; N, 6.16; O, 21.12. found: C, 68.70; H, 3.96; N, 6.19; O, 21.15.

Fourth Step: Synthesis of Intermediate I-5

Intermediate I-4 (13.0 g, 57.4 mmol) and urea (34.4 g, 574 mmol) were put in a 250 mL flask and then, heated at 180° C. under a nitrogen flow for 12 hours. When Intermediate H-4 all disappeared, the temperature was a little lowered, dichlorobenzene (50 mL) and water (300 mL) were subsequently added thereto, and the mixture was stirred. A solid obtained therefrom was filtered and dried to obtain Intermediate I-5 (8.6 g, yield of 60%).

calcd. $C_{14}H_8N_2O_3$: C, 66.67; H, 3.20; N, 11.11; O, 19.03. found: C, 66.63; H, 3.17; N, 11.15; O, 19.05.

Fifth Step: Synthesis of Intermediate Product I-6

Intermediate I-5 (8.6 g, 34.2 mmol) was dissolved in phosphorylchloride (22.6 mL, mmol) in a 250 mL flask, and the mixture was heated under a nitrogen flow for 4 hours at 120° C. The reaction mixture was slowly poured into an excessive amount of ice to complete a reaction, a solid therein was filtered, washed with water and methanol, and dried to obtain Intermediate I-6 (8.3 g, yield of 90.0%).

calcd. $C_{14}H_6C_{12}N_3$: C, 58.16; H, 2.09; Cl, 24.53; N, 9.69; O, 5.53. found: C, 58.19; H, 2.03; Cl, 24.57; N, 9.69; O, 5.53.

Synthesis Example 4: Synthesis of Intermediates H-17 and I-13

Intermediates H-17 and I-13 were synthesized as more specific examples of a compound according to the present invention through 4 steps of [Reaction Scheme 4].

Herein, Intermediates H-17 and I-13 were synthesized from common Intermediate H-13, but Intermediate I-13 was synthesized according to the same method as above except for using I-1 as a reactant in the second step.

[Reaction Scheme 4]

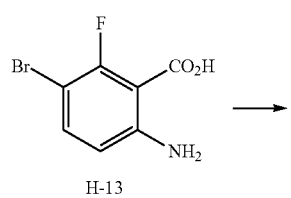

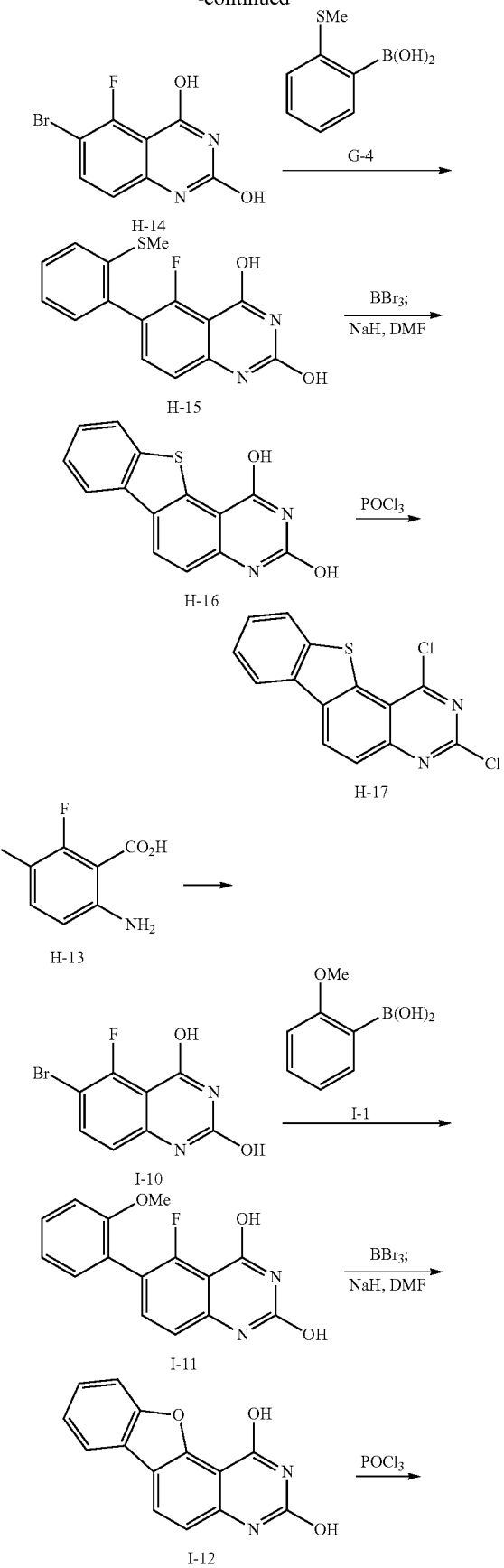

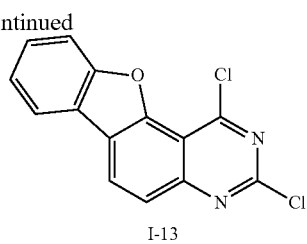

I-13

First Step: Synthesis of Intermediate H-14

Intermediate H-13 (15.0 g, 64.1 mmol) and urea (38.4 g, 641 mmol) were put in a 250 mL flask and heated at 180° C. under a nitrogen flow for 12 hours. When Intermediate H-4 all disappeared, the temperature was a little lowered, dichlorobenzene (50 mL) and water (300 mL) were added thereto, and the mixture was stirred. A solid obtained therefrom was filtered and dried to obtain Intermediate H-14 (10.0 g, yield of 60%).

calcd. $C_8H_4BrFN_2O_2$: C, 37.09; H, 1.56; Br, 30.85; F, 7.33; N, 10.81; O, 12.35. found: C, 37.06; H, 1.53; Br, 30.87; F, 7.31; N, 10.85; O, 12.38.

Second Step: Synthesis of Intermediate H-15

Intermediate H-14 (10.0 g, 38.5 mmol), 2-methylthiophenylboronic acid G-4 (7.1 g, 42.3 mmol), potassium carbonate ($K_2CO_3$, 13.3 g, 96 mmol), and $Pd(PPh_3)_4$ (tetrakis-(triphenylphosphine) palladium (0), 2.2 g, 1.9 mmol) were added to tetrahydrofuran (200 mL) and water (100 mL) in a 1000 mL flask, and the mixture was heated under a nitrogen flow for 12 hours at 60° C. After removing an aqueous layer, an organic layer remaining there was concentrated, extracted with dichloromethane (150 mL), dried with anhydrous magnesium sulfate ($MgSO_4$), and filtered with silica gel/Celite, and after removing an appropriate amount of an organic solvent, methanol was used for recrystallization to obtain Compound H-15 (8.1 g, yield of 70%).

calcd. $C_{15}H_{11}FN_2O_2S$: 59.59; H, 3.67; F, 6.28; N, 9.27; O, 10.58; S, 10.61. found: 59.56; H, 3.63; F, 6.32; N, 9.25; O, 10.59; S, 10.65.

Third Step Synthesis of Intermediate H-16

Intermediate H-15 (8.1 g, 27.0 mmol) was dissolved in dichloromethane (DCM, 150 mL) in a 1000 mL flask, borane tribromide ($BBr_3$, 54.0 mL, 54.0 mmol) was slowly added thereto in a dropwise fashion, while the mixture was maintained at 0° C. When a reaction was complete, the mixture was washed with a sodiumthiosulfate ($Na_2S_2O_3$) aqueous solution, a remainder after removing an organic solvent was dissolved in N,N-dimethylformamide (DMF, 60 mL) at room temperature without additional purification, sodium hydride (60% NaH, 1.6 g, 40.5 mmol) was added thereto in an ice bath, and the mixture was stirred. The reactant was stirred at 100° C. for 1 hour, cooled down to room temperature, and dropped into water (200 mL), and a solid obtained therefrom was filtered and recrystallized with methanol to obtain Intermediate H-16 (5.4 g, yield of 75%).

calcd. $C_{14}H_8NO_2S$: C, 62.67; H, 3.01; N, 10.44; O, 11.93; S, 11.95. found: C, 62.69; H, 3.04; N, 10.45; O, 11.90; S, 11.92.

Fourth Step: Synthesis of Intermediate Product H-17

Intermediate H-16 (5.4 g, 20.3 mmol) was dissolved in phosphorylchloride (13.2 mL, mmol) in a 100 mL flask and then, heated at 120° C. under a nitrogen flow for 4 hours. The reaction mixture was slowly poured into an excessive amount of ice to complete a reaction, and a solid filtered therefrom was washed with water and methanol and dried to obtain Intermediate H-17 (5.6 g, yield of 90.0%).

calcd. $C_{14}H_6C_{12}N_2S$: C, 55.10; H, 1.98; Cl, 23.23; N, 9.18; S, 10.51. found: C, 55.09; H, 1.99; Cl, 23.26; N, 9.16; S, 10.51.

Synthesis Example 5: Synthesis of Intermediate J-6

Intermediate J-6 as more specific examples of a compound according to the present invention was synthesized through 4 steps of [Reaction Scheme 5].

[Reaction Scheme 5]

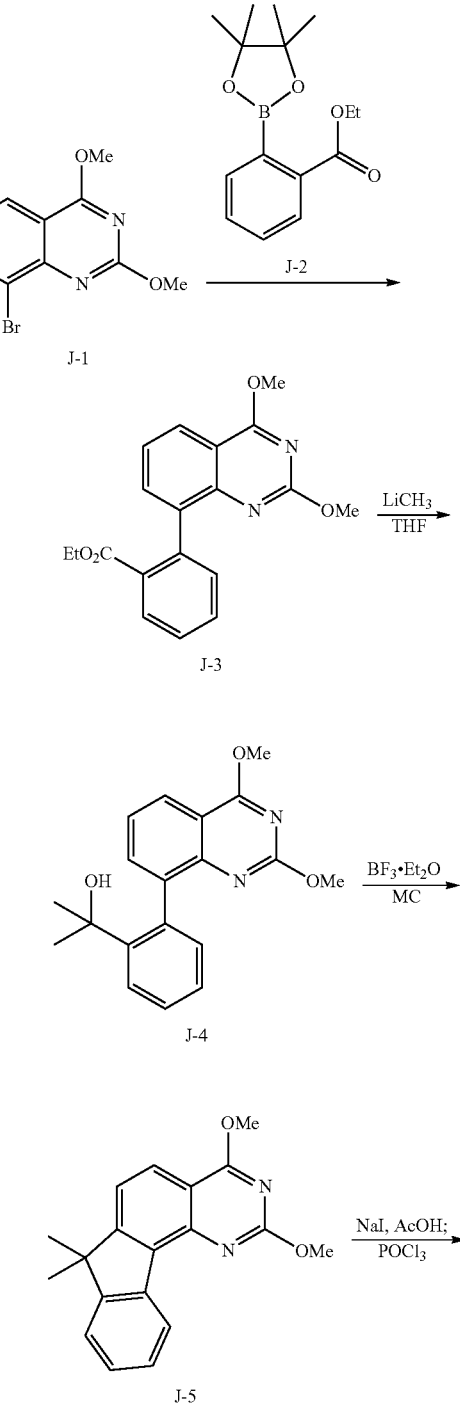

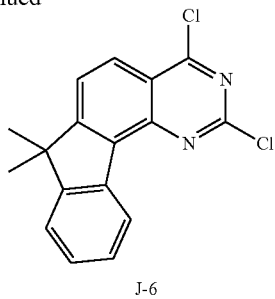

J-6

First Step: Synthesis of Intermediate J-3

Intermediates of quinazoline J-1 (synthesis reference, Organic Letters, 13(4), 676-679; 2011) (30.0 g, 111.0 mmol) and boron ester J-2 (purchasable, Oakwood Chemical Product List) (33.7 g, 122.1 mmol), potassium carbonate (38.4 g, 277.5 mmol), and tetrakis (triphenylphosphine)palladium (6.4 g, 5.6 mmol) were added to 1,4-dioxane (300 mL) and water (150 mL) in a 2000 mL flask, and the mixture was heated and refluxed under a nitrogen flow for 12 hours. The obtained mixture was added to methanol (750 mL), a solid crystallized therein was filtered, dissolved in monochlorobenzene, and filtered with silica gel/Celite, and after removing an appropriate amount of an organic solvent, methanol was used for a recrystallization to obtain Intermediate J-3 (26.7 g, yield of 71%).

Calcd. $C_{19}H_{18}N_2O_4$: C, 67.44; H, 5.36; N, 8.28; O, 18.91. found: C, 67.42; H, 5.35; N, 8.26; O, 18.95.

Second Step: Synthesis of Intermediate J-4

Intermediate J-3 (26.7 g, 78.8 mmol) was added to anhydrous tetrahydrofuran (300 mL) in a 1000 mL flask, a 1.5 M methyllithium solution (108 ml) in diethyl ether was added thereto in a dropwise fashion at −70° C., and the mixture was stirred at the same temperature for 2 hours. When a reaction was complete, 100 ml of ice water and 200 mL of a saturated ammonium chloride aqueous solution were added thereto. An organic layer was separated, twice washed with distilled water, dried, and then, evaporated under vacuum. A colorless solid remaining there was recrystallized from heptane/toluene to obtain Intermediate J-4 (21.7 g, yield of 85%).

calcd. C17H14Cl2N2O: C, 61.28; H, 4.23; Cl, 21.28; N, 8.41; O, 4.80. found: C, 61.11; H, 4.03; Cl, 21.24; N, 8.40; O, 4.78.

Third Step: Synthesis of Intermediate J-5

Intermediate J-4 (21.7 g, 67.0 mmol) was dissolved in anhydrous 1,2-dichloromethane (MC, 300 mL) in a 1000 mL flask, and boron trifluoride-diethyletherate (10.5 g, 73.7 mmol) was slowly added thereto in a dropwise fashion for 10 minutes. The mixture was heated up to 50° C. and stirred for 2 hours. The resultant was cooled down to room temperature, distilled water was added thereto, and the mixture was three times extracted with diethylether. An organic layer obtained therefrom was dried with anhydrous magnesium sulfate. A residue concentrated after removing a solvent was separated and purified through silica gel chromatography to obtain Intermediate J-5 (11.3 g, yield of 55%).

calcd. $C_{19}H_{18}N_2O_2$: C, 74.49; H, 5.92; N, 9.14; O, 10.44. found: C, 74.46; H, 5.91; N, 9.16; O, 10.47.

Fourth Step: Synthesis of Intermediate J-6

Intermediate J-4 (21.7 g, 67.0 mmol) was dissolved in glacial acetic acid (200 mL) in a 1000 mL flask, sodium iodide (NaI, 268 mmol) was added thereto, and the mixture was stirred. After maintaining the reactant at 60° C. for 1 hour, a solvent therein was removed under a reduced pressure. A residue concentrated therefrom was dissolved in dichloromethane (DCM, 200 mL) and then, washed with a sodium thiosulfate ($Na_2S_2O_3$) aqueous solution. An organic layer therefrom was dried with anhydrous magnesium sulfate ($MgSO_4$) and concentrated under a reduced pressure. The resultant was added to phosphorylchloride (44.5 mL, 470 mmol) in a 250 mL flask without additional purification, and the mixture was heated at 120° C. under a nitrogen flow for 4 hours. The reaction mixture was slowly poured into an excessive amount of ice to complete a reaction, and a solid filtered therefrom was washed with water and methanol and dried to obtain Intermediate J-6 (19.0 g, yield of 90.0%).

calcd. $C_{17}H_{12}Cl_2N_2$: C, 64.78; H, 3.84; Cl, 22.50; N, 8.89. found: C, 64.75; H, 3.82; Cl, 22.53; N, 8.90.

Synthesis Example 6: Synthesis of Intermediate K-4

Intermediate K-4 was synthesizes as more specific examples of a compound according to the present invention through 3 steps of [Reaction Scheme 6].

[Reaction Scheme 6]

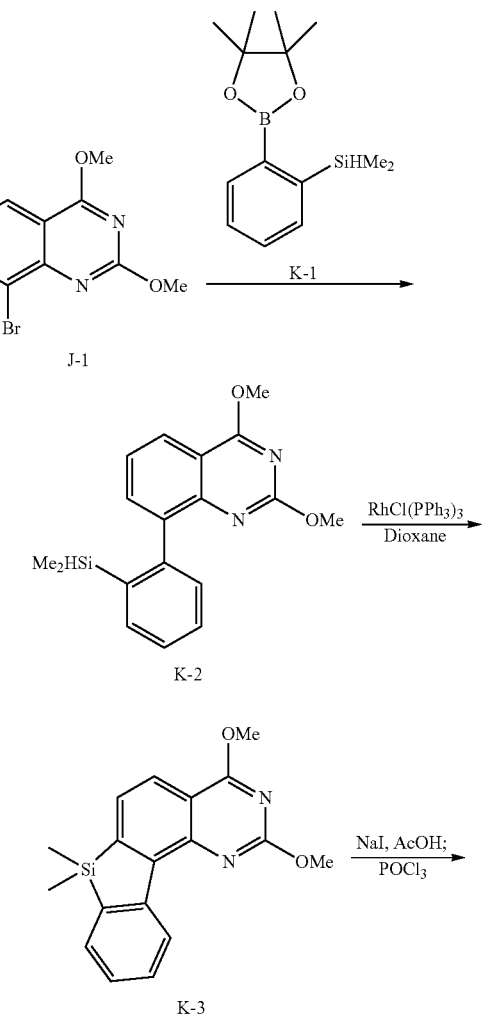

-continued

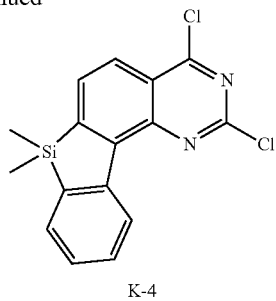

K-4

First Step: Synthesis of Intermediate K-2

Intermediates of quinazoline J-1 (30.0 g, 111.0 mmol) and boronester K-1 (synthesis reference, Chemistry Letters, 36(3), 362-363; 2007) (32.0 g, 122.1 mmol), potassium carbonate (38.4 g, 277.5 mmol), and tetrakis (triphenylphosphine)palladium (6.4 g, 5.6 mmol) were added to 1,4-dioxane (300 mL) and water (150 mL) in a 2000 mL flask, and the mixture was heated and refluxed under a nitrogen flow for 12 hours. The obtained mixture was added to methanol (750 mL), a solid crystallized therein was dissolved in monochlorobenzene, filtered with silica gel/Celite, and after removing an appropriate amount of an organic solvent, recrystallized with methanol to obtain Intermediate K-2 (27.0 g, yield of 75%).

Calcd. $C_{18}H_{20}N_2O_2Si$: C, 66.63; H, 6.21; N, 8.63; O, 9.86; Si, 8.66. found: C, 66.60; H, 6.22; N, 8.65; O, 9.85; Si, 8.68.

Second Step: Synthesis of Intermediate K-3

Intermediate K-2 (27.0 g, 83.3 mmol), $RhCl(PPh_3)_3$ (389 mg, 0.42 mmol), and 1,4-dioxane (100 mL) were put in a 250 mL sealed tube and then, stirred at 135° C. for 1 hour. When a reaction was complete, the resultant was treated through silica gel column chromatography (Hex:DCM=2:1) after removing a solvent under a reduced pressure to obtain Intermediate K-3 (21.7 g, yield of 81%).

calcd. $C_{18}H_{18}N_2O_2Si$: C, 67.05; H, 5.63; N, 8.69; O, 9.92; Si, 8.71. found: C, 67.01; H, 5.64; N, 8.67; O, 9.93; Si, 8.75.

Fourth Step: Synthesis of Intermediate K-4

Intermediate K-3 (21.7 g, 67.5 mmol) was dissolved in glacial acetic acid (200 mL) in a 1000 mL flask, sodiumiodide (NaI, 268 mmol) was added thereto, and the mixture was stirred. After maintaining the reactant at 60° C. for 1 hour, a solvent therein was removed under a reduced pressure. A residue concentrated therefrom was dissolved in dichloromethane (DCM=MC (methylenechloride), 200 mL) and then, washed with a sodium thiosulfate ($Na_2S_2O_3$) aqueous solution. An organic layer therein was dried with anhydrous magnesium sulfate ($MgSO_4$) and concentrated under a reduced pressure. The resultant was added to phosphorylchloride (44.5 mL, 470 mmol) without additional purification in a 250 mL flask and heated at 120° C. under a nitrogen flow for 4 hours. The reaction mixture was slowly poured into an excessive amount of ice to complete a reaction, a solid therefrom was filtered, washed with water and methanol, and dried to obtain Intermediate K-4 (16.3 g, yield of 73.0%).

calcd. $C_{17}H_{12}Cl_2N_2$: C, 64.78; H, 3.84; Cl, 22.50; N, 8.89. found: C, 64.75; H, 3.82; Cl, 22.53; N, 8.90.

Synthesis of Compound

Synthesis Example 7: Synthesis of Compound A-65

Compound A-65 was synthesized as more specific examples of a compound according to the present invention through 2 steps of Reaction Scheme 7.

[Reaction Scheme 7]

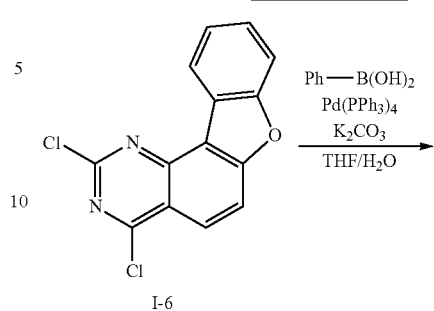

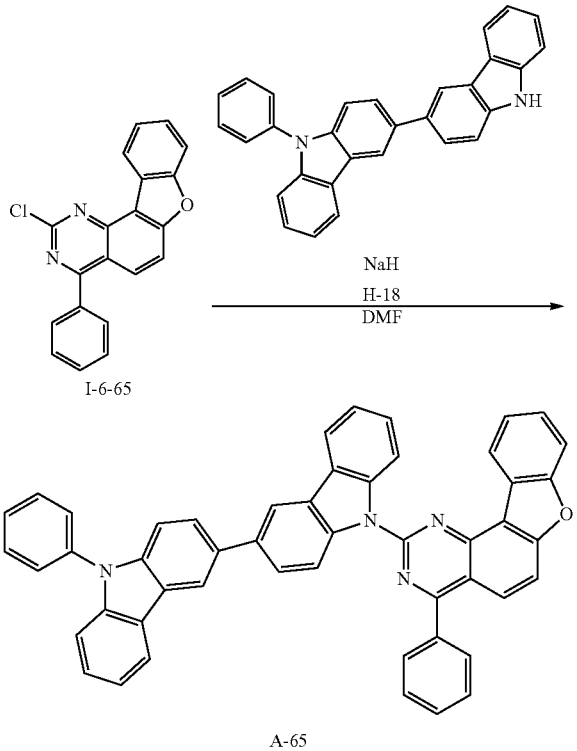

First Step: Synthesis of Intermediate I-6-65

Intermediate I-6 (8.67 g, 30.0 mmol), phenylboronic acid (5.4 g, 31.5 mmol), potassium carbonate (10.4 g, 75.0 mmol), and tetrakis (triphenylphosphine)palladium (1.15 g, 1.0 mmol) were added to tetrahydrofuran (100 mL) and water (50 mL) in a 500 mL flask, and the mixture was heated and refluxed under a nitrogen flow for 12 hours. The obtained mixture was added to methanol (200 mL), a solid crystallized therein was filtered, dissolved in monochlorobenzene, filtered with silica gel/Celite, and after removing an appropriate amount of an organic solvent, recrystallized with methanol to obtain Intermediate I-6-65 (7.44 g, yield of 75%).

Calcd. $C_{20}H_{11}ClN_2O$: C, 72.62; H, 3.35; Cl, 10.72; N, 8.47; O, 4.84. found: C, 72.60; H, 3.33; Cl, 10.77; N, 8.45; O, 4.85.

Second Step: Synthesis of Compound A-65

Intermediate I-6-65 (6.6 g, 20.0 mmol), 3,3-biscarbazole H-18 (8.2 g, 20.0 mmol), and sodium hydride (a 60% mineral dispersion, 0.96 g, 24.0 mmol) were added to anhydrous N,N-dimethyl formamide (DMF, 60 mL) in a 250 mL round flask, and the mixture was stirred under a nitrogen flow for 6 hours. The obtained mixture was added to methanol (200 mL), and a solid crystallized therein was filtered, dissolved in dichlorobenzene, filtered with silica gel/Celite, and after removing an appropriate amount of an organic solvent, recrystallized with methanol to obtain Compound A-65 (12.7 g, yield of 90%).

calcd. $C_{50}H_{30}N_4O$: C, 85.45; H, 4.30; N, 7.97; O, 2.28. found: C, 85.43; H, 4.27; N, 7.99; O, 2.30.

Synthesis Example 8: Synthesis of Compound A-74

Compound A-74 was synthesized as more specific examples of a compound according to the present invention through 1 step of Reaction Scheme 8.

[Reaction Scheme 8]

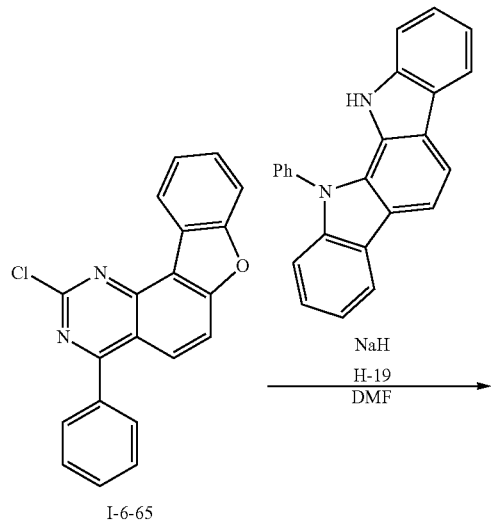

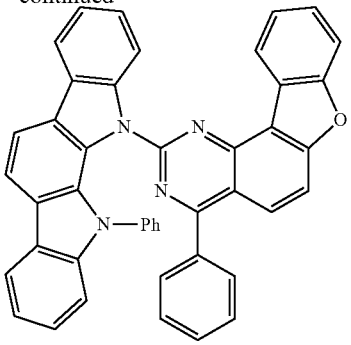

A-74

First Step: Synthesis of Compound A-74

Intermediate I-6-65 (6.6 g, 20.0 mmol), indolocarbazole H-19 (6.65 g, 20.0 mmol), and sodium hydride (a 60% mineral dispersion, 0.96 g, 24.0 mmol) were added to anhydrous N,N-dimethyl formamide (DMF, 60 mL) in a 250 mL round flask and then, stirred under a nitrogen flow for 6 hours. The obtained mixture was added to methanol (200 mL), and a solid crystallized therein was filtered, dissolved in dichlorobenzene, and filtered with silica gel/Celite, and after removing an appropriate amount of an organic solvent, recrystallized with methanol to obtain Compound A-74 (11.5 g, yield of 92%).

calcd. $C_{44}H_{26}N_4O$: C, 84.33; H, 4.18; N, 8.94; O, 2.55. found: C, 84.33; H, 4.18; N, 8.94; O, 2.55.

Synthesis Example 9: Synthesis of Compound A-32

Compound A-32 was synthesized as more specific examples of a compound according to the present invention through 2 steps of Reaction Scheme 9.

[Reaction Scheme 9]

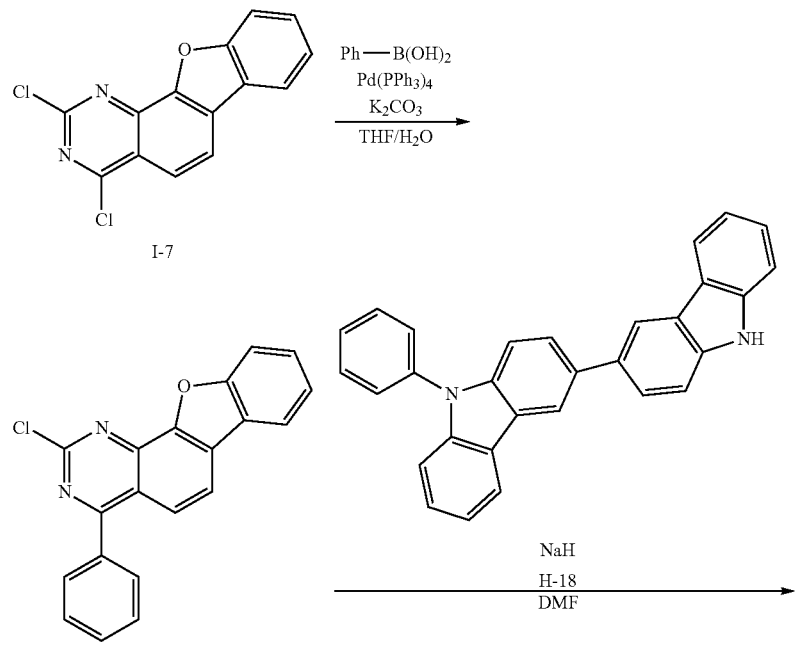

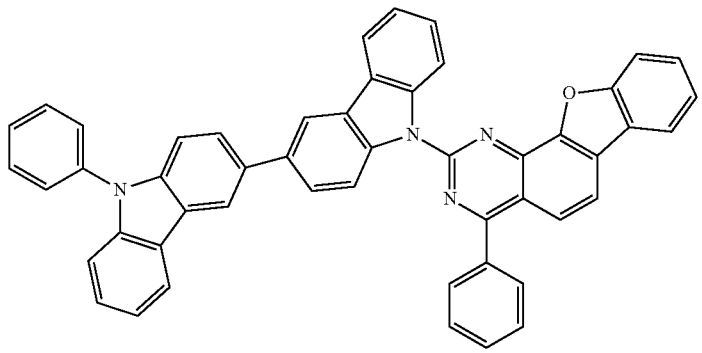

A-32

First Step: Synthesis of Intermediate I-7-32

Intermediate I-7 (8.67 g, 30.0 mmol), phenylboronic acid (5.4 g, 31.5 mmol), potassium carbonate (10.4 g, 75.0 mmol), and tetrakis (triphenylphosphine)palladium (1.15 g, 1.0 mmol) were added to tetrahydrofuran (100 mL) and water (50 mL) in a 500 mL flask and then, heated and refluxed under a nitrogen flow for 12 hours. The obtained mixture was added to methanol (200 mL), and a solid crystallized therein was filtered, dissolved in monochlorobenzene, filtered with silica gel/Celite, and after removing an appropriate amount of an organic solvent, recrystallized with methanol to obtain Intermediate I-7-32 (7.74 g, yield of 78%).

Calcd. $C_{20}H_{11}ClN_2O$: C, 72.62; H, 3.35; Cl, 10.72; N, 8.47; O, 4.84. found: C, 72.60; H, 3.33; Cl, 10.77; N, 8.46; O, 4.83.

Second Step: Synthesis of Compound A-32

Intermediate I-7-32 (6.6 g, 20.0 mmol), 3,3-biscarbazole H-18 (8.2 g, 20.0 mmol), and sodium hydride (a 60% mineral dispersion, 0.96 g, 24.0 mmol) were added to anhydrous N,N-dimethyl formamide (DMF, 60 mL) in a 250 mL round flask, and the mixture was stirred under a nitrogen flow for 6 hours. This obtained mixture was added to methanol (200 mL), and a solid crystallized therein was filtered, dissolved in dichlorobenzene, filtered with silica gel/Celite, and after removing an appropriate amount of an organic solvent, recrystallized with methanol to obtain Compound A-32 (12.8 g, yield of 93%).

calcd. $C_{50}H_{30}N_4O$: C, 85.45; H, 4.30; N, 7.97; O, 2.28. found: C, 85.42; H, 4.27; N, 7.97; O, 2.33.

Synthesis Example 10: Synthesis of Compound A-41

Compound A-41 was synthesized as more specific examples of a compound according to the present invention through 1 step of Reaction Scheme 10.

[Reaction Scheme 10]

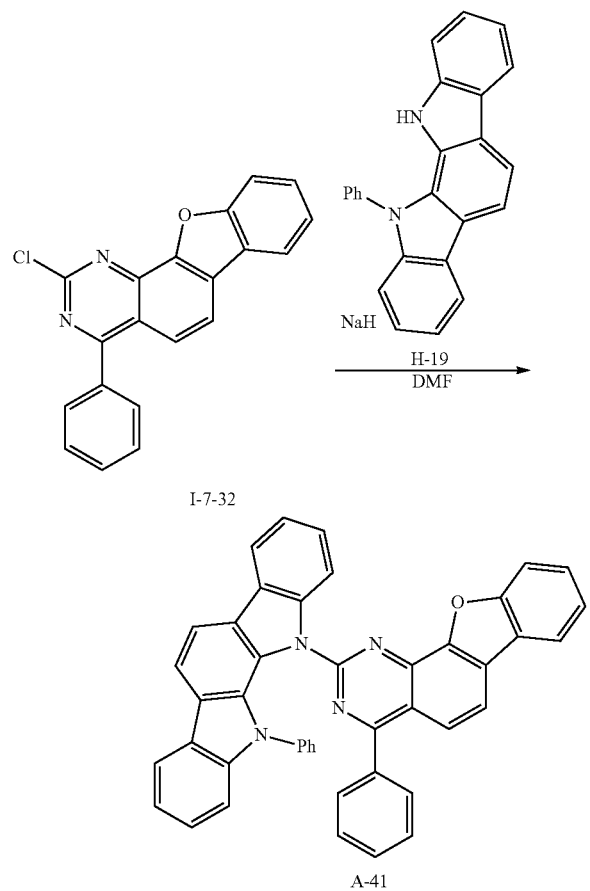

First Step: Synthesis of Compound A-41

Intermediate I-7-32 (6.6 g, 20.0 mmol), indolocarbazole H-19 (6.65 g, 20.0 mmol), and sodium hydride (a 60% mineral dispersion, 0.96 g, 24.0 mmol) were added to anhydrous N,N-dimethyl formamide (DMF, 60 mL) in a 250 mL round flask, and the mixture was stirred under a nitrogen flow for 6 hours. This obtained mixture was added to methanol (200 mL), and a solid crystallized therein was filtered, dissolved in dichlorobenzene, and filtered with silica gel/Celite, and after removing an appropriate amount of an organic solvent, recrystallized with methanol to obtain Compound A-41 (11.0 g, yield of 88%).

calcd. $C_{44}H_{26}N_4O$: C, 84.33; H, 4.18; N, 8.94; O, 2.55. found: C, 84.33; H, 4.18; N, 8.94; O, 2.55.

Synthesis Example 11: Synthesis of Compound A-98

Compound A-98 was synthesized as more specific examples of a compound according to the present invention through 2 steps of Reaction Scheme 11.

chlorobenzene, filtered with silica gel/Celite, and after removing an appropriate amount of an organic solvent, recrystallized with methanol to obtain Intermediate I-13-98 (7.70 g, yield of 78%).

Calcd. $C_{20}H_{11}ClN_2O$: C, 72.62; H, 3.35; Cl, 10.72; N, 8.47; O, 4.84. found: C, 72.60; H, 3.33; Cl, 10.79; N, 8.45; O, 4.82.

Second Step: Synthesis of Compound A-98

Intermediate I-13-98 (6.6 g, 20.0 mmol), 3,3-biscarbazole H-18 (8.2 g, 20.0 mmol), and sodium hydride (a 60% mineral dispersion, 0.96 g, 24.0 mmol) were added to anhydrous N,N-dimethyl formamide (DMF, 60 mL) in a 250

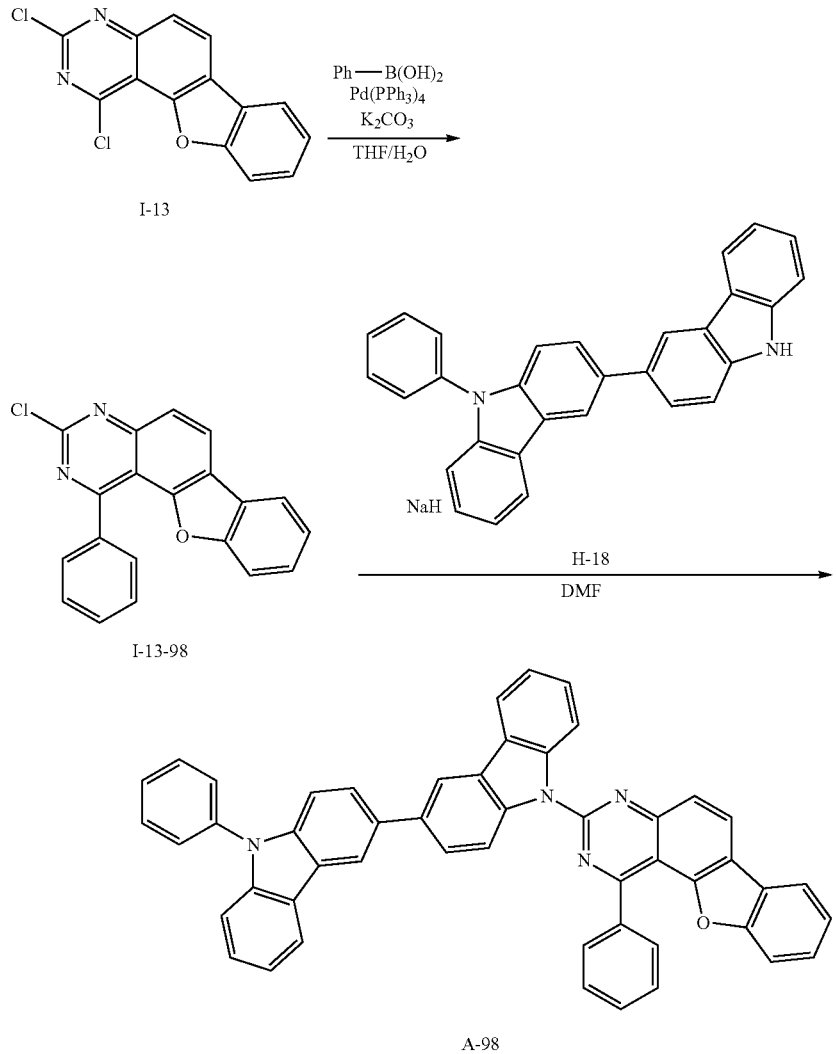

[Reaction Scheme 11]

First Step: Synthesis of Intermediate I-13-98

Intermediate I-13 (8.67 g, 30.0 mmol), phenylboronic acid (5.4 g, 31.5 mmol), potassium carbonate (10.4 g, 75.0 mmol), and tetrakis (triphenylphosphine)palladium (1.15 g, 1.0 mmol) were added to tetrahydrofuran (100 mL) and water (50 mL) in a 500 mL flask, and the mixture was heated and refluxed under a nitrogen flow for 12 hours. This obtained mixture was added to methanol (200 mL), and a solid crystallized therein was filtered, dissolved in monomL round flask, and the mixture was stirred under a nitrogen flow for 6 hours. This obtained mixture was added to methanol (200 mL), and a solid crystallized therein was filtered, dissolved in dichlorobenzene, filtered with silica gel/Celite, and after removing an appropriate amount of an organic solvent, recrystallized with methanol to obtain Compound A-98 (12.5 g, yield of 90%).

calcd. $C_{50}H_{30}N_4O$: C, 85.45; H, 4.30; N, 7.97; O, 2.28. found: C, 85.41; H, 4.26; N, 7.96; O, 2.36.

Synthesis Example 12: Synthesis of Compound B-65

Compound B-65 was synthesized as more specific examples of a compound according to the present invention through 2 steps of Reaction Scheme 12.

[Reaction Scheme 12]

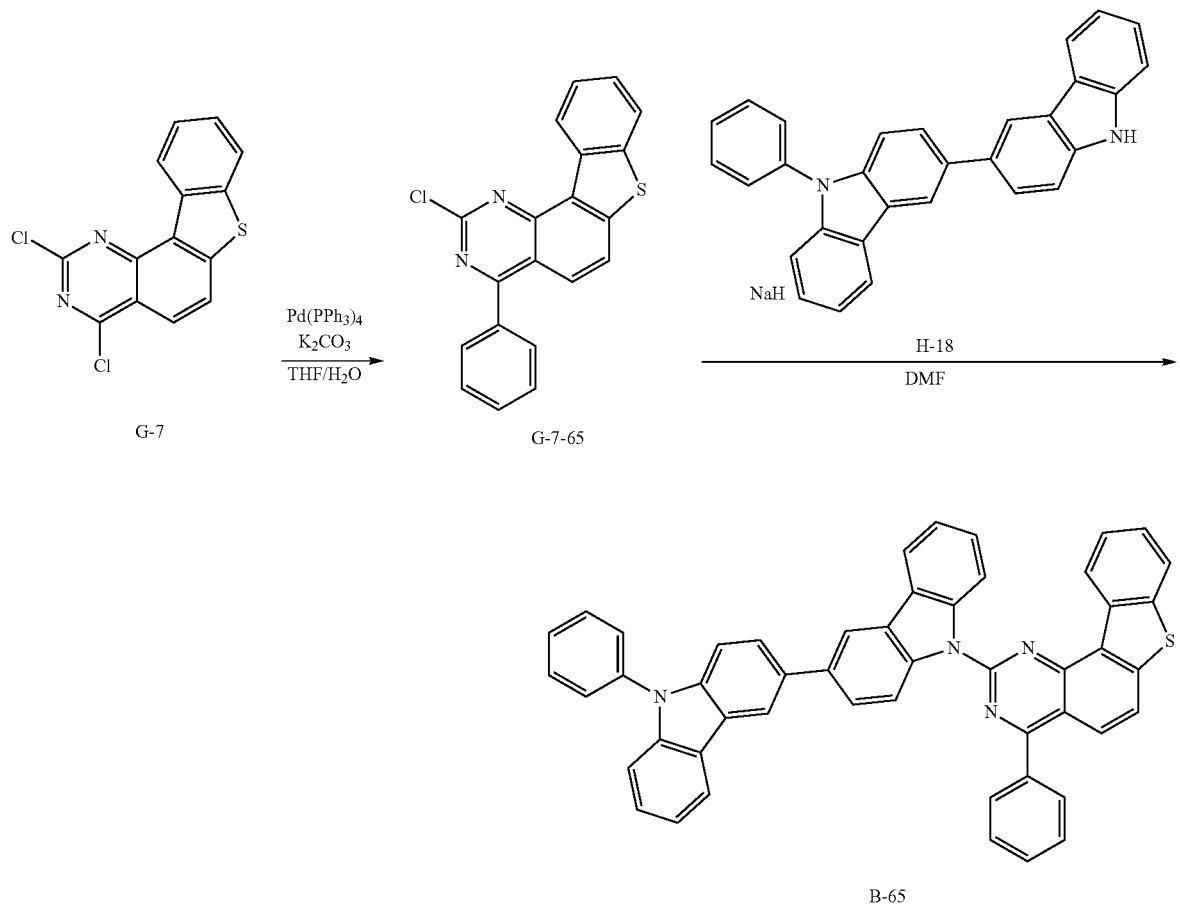

First Step: Synthesis of Intermediate G-7-65

Intermediate G-7 (9.16 g, 30.0 mmol), phenylboronic acid (5.4 g, 31.5 mmol), potassium carbonate (10.4 g, 75.0 mmol), and tetrakis (triphenylphosphine)palladium (1.15 g, 1.0 mmol) were added to tetrahydrofuran (100 mL) and water (50 mL) in a 500 mL flask, and the mixture was heated and refluxed under a nitrogen flow for 12 hours. The obtained mixture was added to methanol (200 mL), and a solid crystallized therein was filtered, dissolved in monochlorobenzene, filtered with silica gel/Celite, and after removing an appropriate amount of an organic solvent, recrystallized with methanol to obtain Intermediate G-7-65 (8.3 g, yield of 80%).

Calcd. $C_{20}H_{11}ClN_2S$: C, 69.26; H, 3.20; Cl, 10.22; N, 8.08; S, 9.25. found: C, 69.23; H, 3.18; Cl, 10.29; N, 8.07; S, 9.23.

Second Step: Synthesis of Compound B-65

Intermediate G-7-65 (6.94 g, 20.0 mmol), 3,3-biscarbazole H-18 (8.2 g, 20.0 mmol), and sodium hydride (a 60% mineral dispersion, 0.96 g, 24.0 mmol) were added to anhydrous N,N-dimethyl formamide (DMF, 60 ml) in a 250 mL round flask, and the mixture was stirred under a nitrogen flow for 6 hours. This obtained mixture was added to methanol (200 mL), and a solid crystallized therein was filtered, dissolved in dichlorobenzene, filtered with silica gel/Celite, and after removing an appropriate amount of an organic solvent, recrystallized with methanol to obtain Compound B-65 (12.9 g, yield of 90%).

calcd. $C_{50}H_{30}N_4S$: C, 83.54; H, 4.21; N, 7.79; S, 4.46. found: C, 83.56; H, 4.18; N, 7.77; S, 4.49.

Synthesis Example 13: Synthesis of Compound B-74

Compound B-74 was synthesized as more specific examples of a compound according to the present invention through one step of Reaction Scheme 13.

[Reaction Scheme 13]

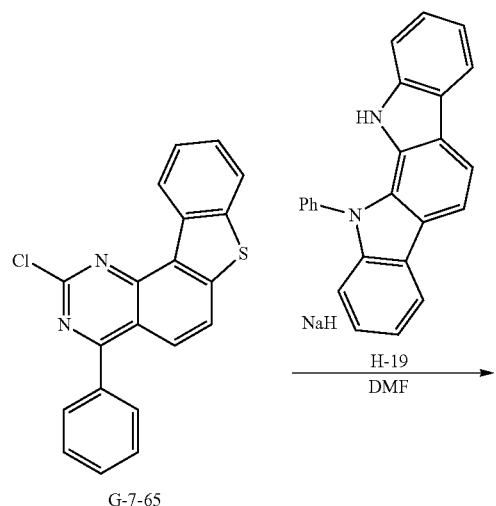

[Reaction Scheme 14]

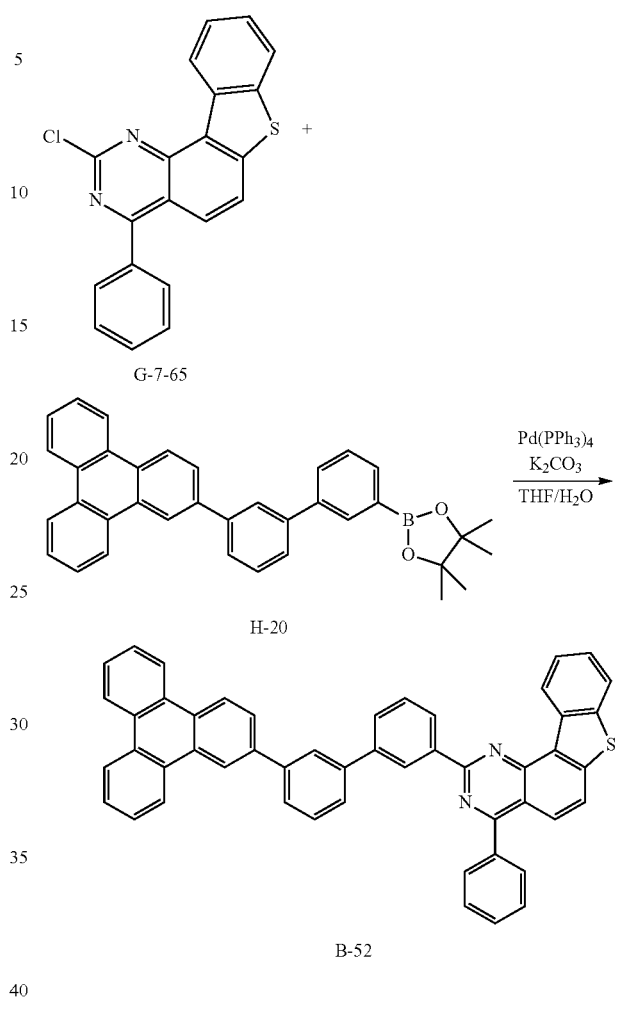

First Step: Synthesis of Compound B-74

Intermediate G-7-65 (6.94 g, 20.0 mmol), indolocarbazole H-19 (6.65 g, 20.0 mmol), and sodium hydride (a 60% mineral dispersion, 0.96 g, 24.0 mmol) were added to anhydrous N,N-dimethyl formamide (DMF, 60 mL) in a 250 mL round flask, and the mixture was stirred under a nitrogen flow for 6 hours. This obtained mixture was added to methanol (200 mL), and a solid crystallized therein was filtered, dissolved in dichlorobenzene, filtered with silica gel/Celite, and after removing an appropriate amount of an organic solvent, recrystallized with methanol to obtain Compound B-74 (11.0 g, yield of 88%).

calcd. $C_{44}H_{26}N_4O$: C, 84.33; H, 4.18; N, 8.94; O, 2.55. found: C, 84.33; H, 4.18; N, 8.94; O, 2.55.

Synthesis Example 14: Synthesis of Compound B-52

Compound B-52 was synthesized as more specific examples of a compound according to the present invention through one step of Reaction Scheme 14.

First Step: Synthesis of Compound B-52

Intermediate G-7-65 (6.94 g, 20.0 mmol), boronester H-20 (Intermediate I-7 according to a synthesis method of Synthesis Example 7 of WO 2014/185598, 10.6 g, 21.0 mmol), potassium carbonate (6.9 g, 50.0 mmol), and tetrakis (triphenylphosphine)palladium (0.76 g, 0.66 mmol) were added to tetrahydrofuran (60 mL) and water (30 mL) in a 500 mL flask, and the mixture was heated and refluxed under a nitrogen flow for 12 hours. This obtained mixture was added to methanol (200 mL), and a solid crystallized therein was filtered, dissolved in monochlorobenzene, filtered with silica gel/Celite, and after removing an appropriate amount of an organic solvent, recrystallized with monochlorobenzene to obtain Compound B-52 (10.5 g, yield of 76%).

Calcd. $C_{50}H_{30}N_2S$: C, 86.93; H, 4.38; N, 4.05; S, 4.64. found: C, 86.91; H, 4.35; N, 4.07; S, 4.66.

Synthesis Example 15: Synthesis of Compound B-48

Compound B-48 was synthesized as more specific examples of a compound according to the present invention through one step of Reaction Scheme 15.

[Reaction Scheme 15]

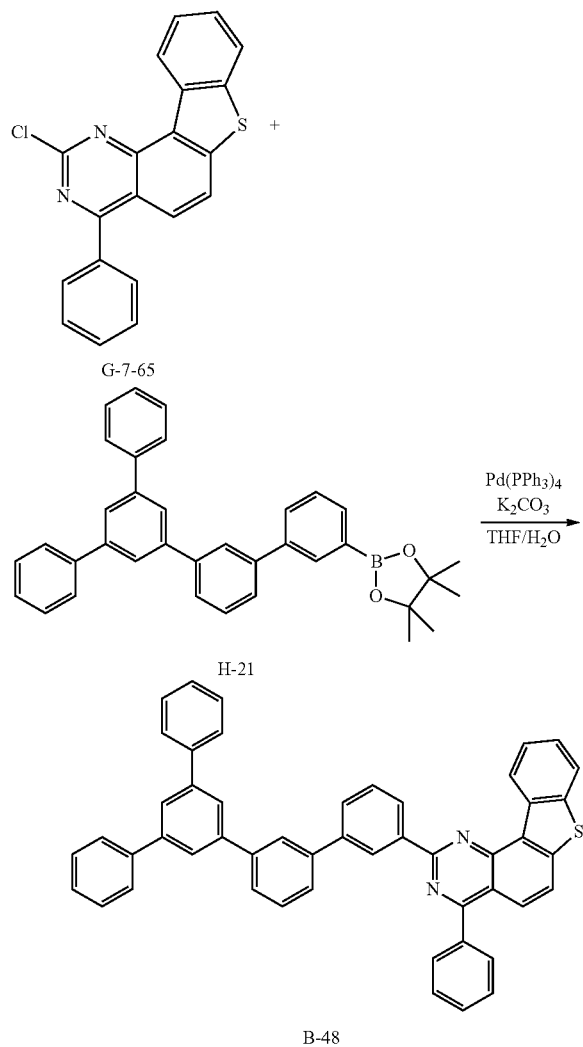

B-48

[Reaction Scheme 16]

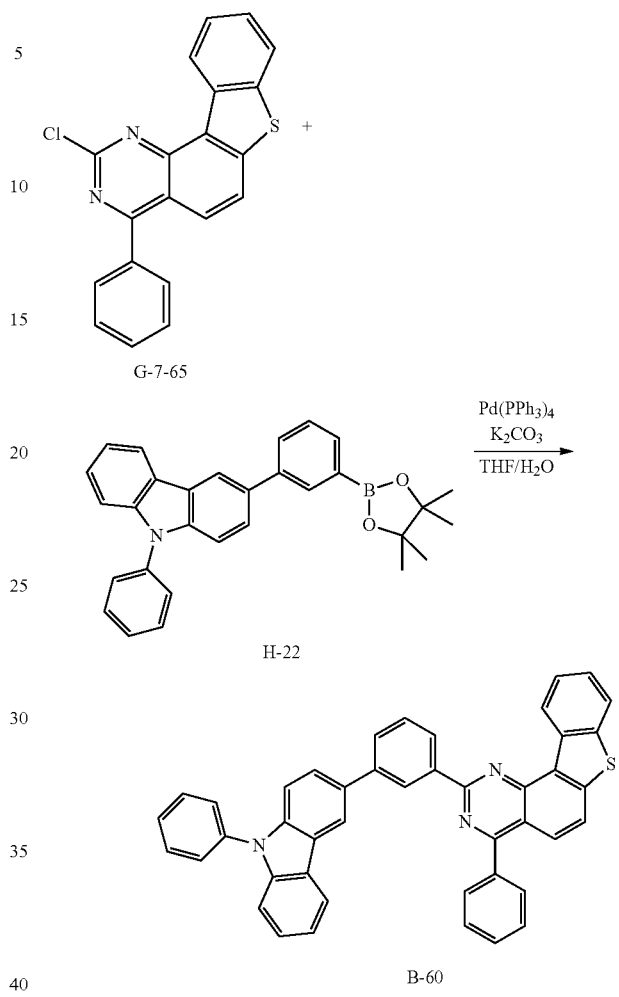

B-60

First Step: Synthesis of Compound B-48

Intermediate G-7-65 (6.94 g, 20.0 mmol), boronester H-21 (changing a starting material according to a synthesis method of Intermediate I-7 of WO 2014/185598, 10.7 g, 21.0 mmol), potassium carbonate (6.9 g, 50.0 mmol), and tetrakis(triphenylphosphine)palladium (0.76 g, 0.66 mmol) were added to tetrahydrofuran (60 mL) and water (30 mL) in a 500 mL flask, and the mixture was heated and refluxed under a nitrogen flow for 12 hours. The obtained mixture was added to methanol (200 mL), and a solid crystallized therein was filtered, dissolved in monochlorobenzene, filtered with silica gel/Celite, and after removing an appropriate amount of an organic solvent, recrystallized with monochlorobenzene to obtain Compound B-48 (9.0 g, yield of 65%).

Calcd. $C_{50}H_{30}N_2S$: C, 86.67; H, 4.66; N, 4.04; S, 4.63. found: C, 86.87; H, 4.32; N, 4.09; S, 4.69.

Synthesis Example 16: Synthesis of Compound B-60

Compound B-60 was synthesized as more specific examples of a compound according to the present invention through one step of Reaction Scheme 16.

First Step: Synthesis of Compound B-60

Intermediate G-7-65 (6.94 g, 20.0 mmol), boronester H-22 (synthesis reference, U.S. Pat. Appl. Publ., 20140284584, 25 Sep. 2014) (9.4 g, 21.0 mmol), potassium carbonate (6.9 g, 50.0 mmol), and tetrakis(triphenylphosphine)palladium (0.76 g, 0.66 mmol) were added to tetrahydrofuran (60 mL) and water (30 mL) in a 500 mL flask, and the mixture was heated and refluxed under a nitrogen flow for 12 hours. This obtained mixture was added to methanol (200 mL), and a solid crystallized therein was filtered, dissolved in monochlorobenzene, filtered with silica gel/Celite, and after removing an appropriate amount of an organic solvent, recrystallized with monochlorobenzene to obtain Compound B-60 (8.7 g, yield of 69%).

Calcd. $C_{44}H_{27}N_3S$: C, 83.91; H, 4.32; N, 6.67; S, 5.09. found: C, 83.89; H, 4.30; N, 6.66; S, 5.13.

Synthesis Example 17: Synthesis of Compound B-32

Compound B-32 was synthesized as more specific examples of a compound according to the present invention through two steps of Reaction Scheme 17.

[Reaction Scheme 17]

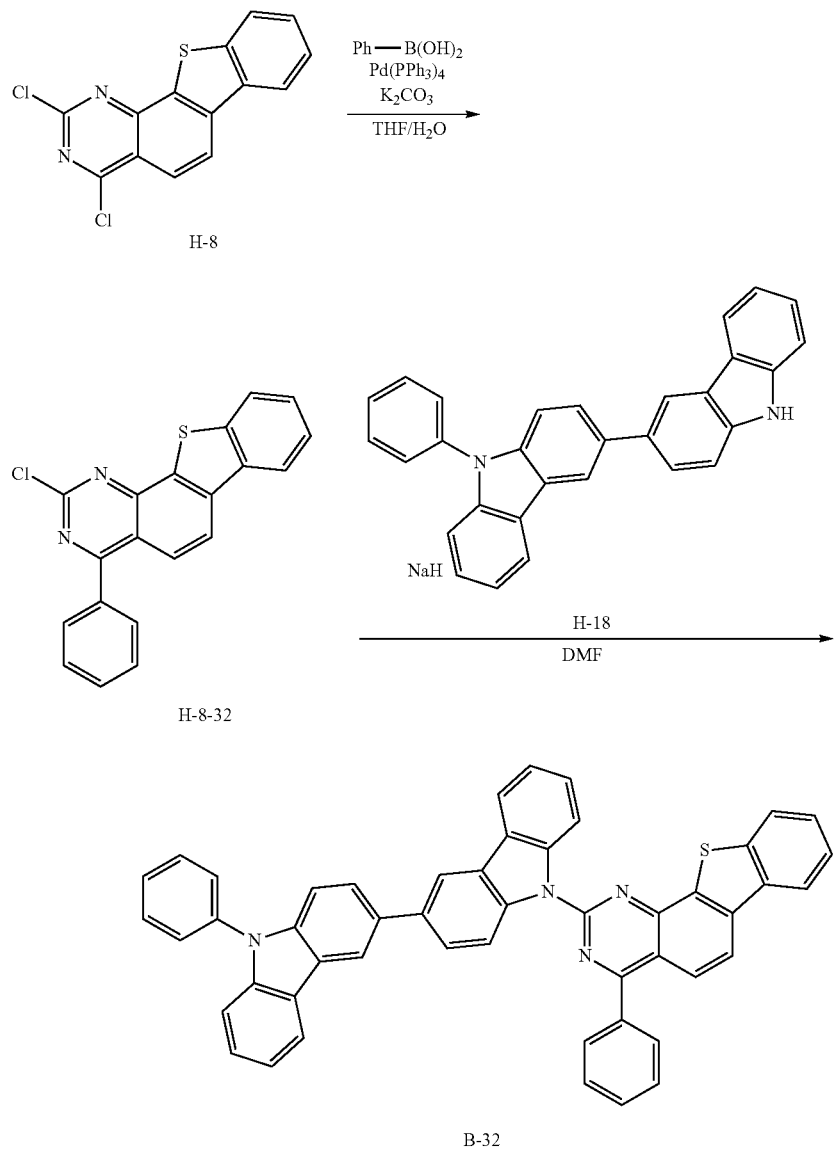

First Step: Synthesis of Intermediate H-8-32

Intermediate H-8 (9.16 g, 30.0 mmol), phenylboronic acid (5.4 g, 31.5 mmol), potassium carbonate (10.4 g, 75.0 mmol), and tetrakis (triphenylphosphine)palladium (1.15 g, 1.0 mmol) were added to tetrahydrofuran (100 mL) and water (50 mL) in a 500 mL flask, and the mixture was heated and refluxed under a nitrogen flow for 12 hours. This obtained mixture was added to methanol (200 mL), and a solid crystallized therein was filtered in monochlorobenzene, filtered with silica gel/Celite, and after removing an appropriate amount of an organic solvent, recrystallized with methanol to obtain Intermediate H-8-32 (7.6 g, yield of 73%).

Calcd. $C_{20}H_{11}ClN_2S$: C, 69.26; H, 3.20; Cl, 10.22; N, 8.08; S, 9.25. found: C, 69.21; H, 3.18; Cl, 10.29; N, 8.10; S, 9.22.

Second Step: Synthesis of Compound B-32

Intermediate H-8-32 (6.94 g, 20.0 mmol), 3,3-biscarbazole H-18 (8.2 g, 20.0 mmol), and sodium hydride (a 60% mineral dispersion, 0.96 g, 24.0 mmol) were added to anhydrous N,N-dimethyl formamide (DMF, 60 mL) in a 250 mL round flask, and the mixture was stirred under a nitrogen flow for 6 hours. This obtained mixture was added to methanol (200 mL), and a solid crystallized therein was filtered, dissolved in dichlorobenzene, filtered with silica gel/Celite, and after removing an appropriate amount of an organic solvent, recrystallized with methanol to obtain Compound B-32 (13.4 g, yield of 93%).

calcd. $C_{50}H_{30}N_4S$: C, 83.54; H, 4.21; N, 7.79; S, 4.46. found: C, 83.56; H, 4.16; N, 7.75; S, 4.52.

Synthesis Example 18: Synthesis of Compound B-98

Compound B-98 was synthesized as more specific examples of a compound according to the present invention through two steps of Reaction Scheme 18.

[Reaction Scheme 18]

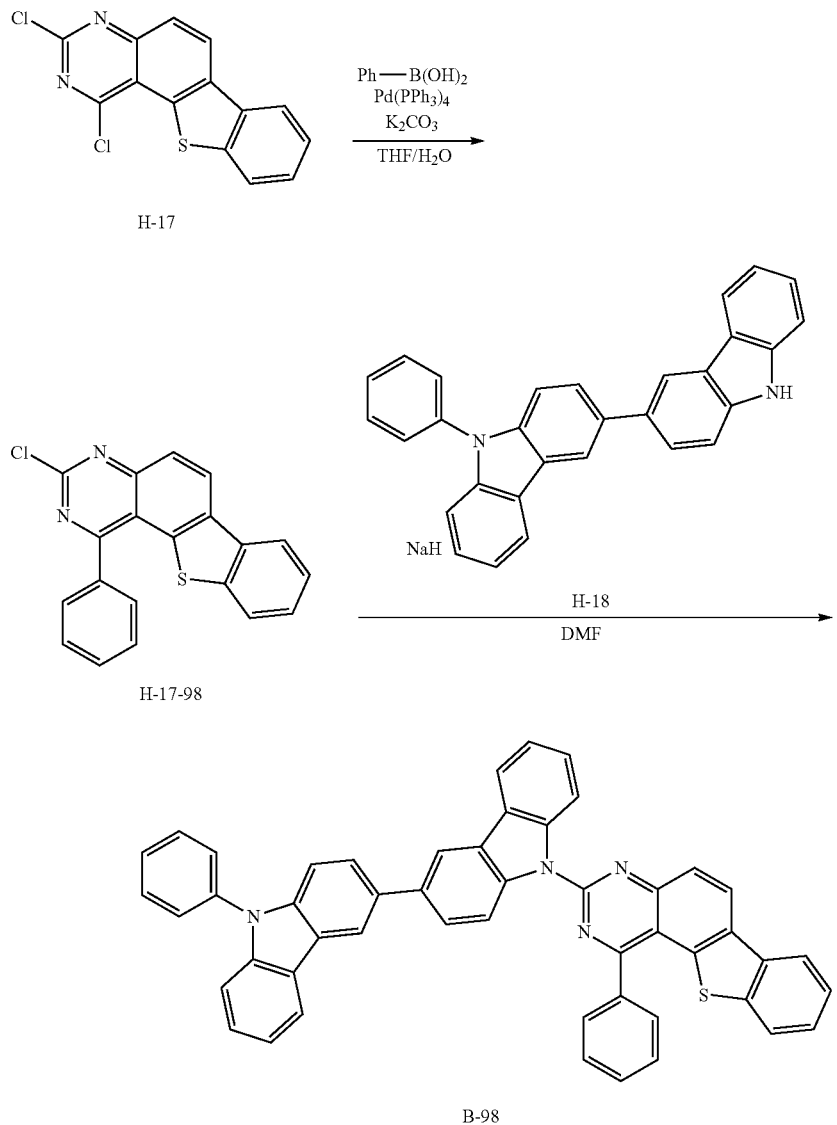

First Step: Synthesis of Intermediate H-17-98

Intermediate H-17 (9.16 g, 30.0 mmol), phenylboronic acid (5.4 g, 31.5 mmol), potassium carbonate (10.4 g, 75.0 mmol), and tetrakis (triphenylphosphine)palladium (1.15 g, 1.0 mmol) were added to tetrahydrofuran (100 mL) and water (50 mL) in a 500 mL flask, and the mixture was heated and refluxed under a nitrogen flow for 12 hours. The obtained mixture was added to methanol (200 mL), and a solid crystallized therein was filtered, dissolved in monochlorobenzene, filtered with silica gel/Celite, and after removing an appropriate amount of an organic solvent, recrystallized with methanol to obtain Intermediate H-17-98 (7.0 g, yield of 67%).

Calcd. $C_{20}H_{11}ClN_2S$: C, 69.26; H, 3.20; Cl, 10.22; N, 8.08; S, 9.25. found: C, 69.21; H, 3.16; Cl, 10.26; N, 8.10; S, 9.27.

Second Step: Synthesis of Compound B-98

Intermediate H-17-98 (6.94 g, 20.0 mmol), 3,3-biscarbazole H-18 (8.2 g, 20.0 mmol), and sodium hydride (a 60% mineral dispersion, 0.96 g, 24.0 mmol) were added to anhydrous N,N-dimethyl formamide (DMF, 60 mL) in a 250 mL round flask, and the mixture was stirred under a nitrogen flow for 6 hours. This obtained mixture was added to methanol (200 mL), and a solid crystallized therein was filtered, dissolved in dichlorobenzene, filtered with silica gel/Celite, and after removing an appropriate amount of an organic solvent, recrystallized with methanol to obtain Compound B-98 (12.2 g, yield of 85%).

calcd. $C_{50}H_{30}N_4S$: C, 83.54; H, 4.21; N, 7.79; S, 4.46. found: C, 83.53; H, 4.15; N, 7.74; S, 4.56.

Synthesis Example 19: Synthesis of Compound B-131

Compound B-131 was synthesized as more specific examples of a compound according to the present invention through 2 steps of Reaction Scheme 19.

[Reaction Scheme 19]

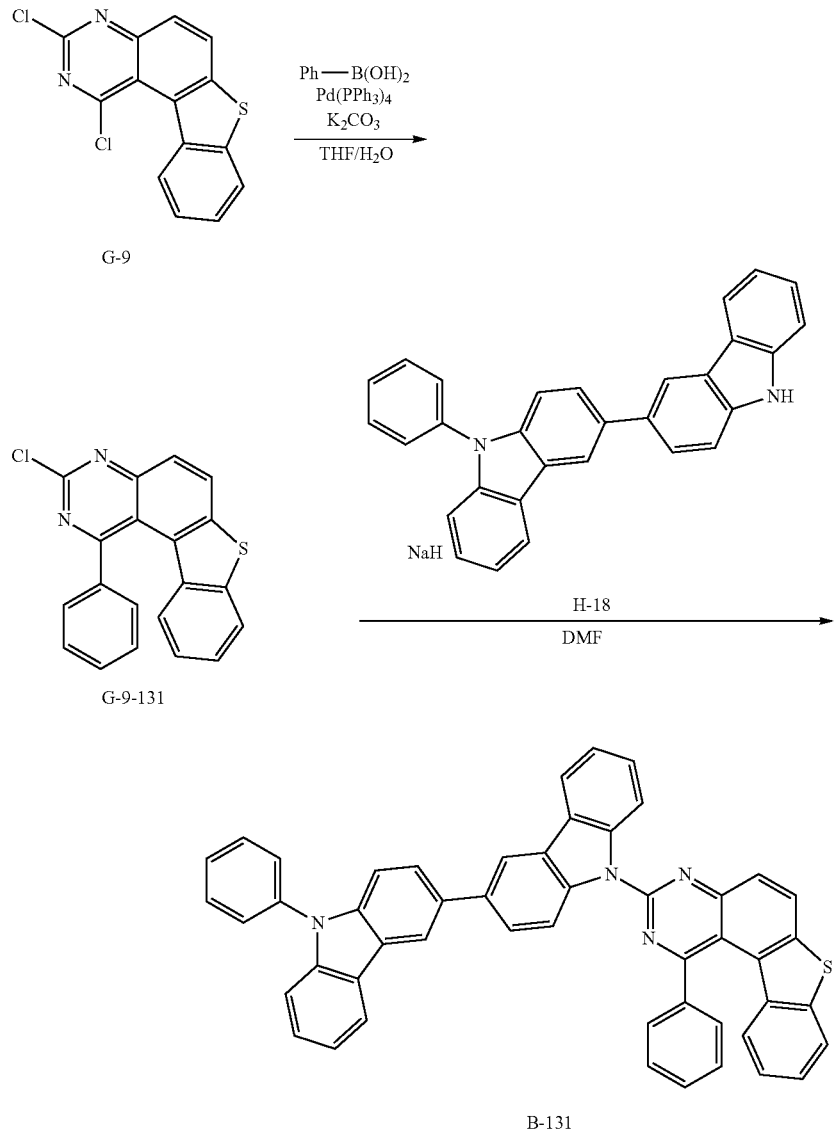

First Step: Synthesis of Intermediate G-9-131

Intermediate G-9 (9.16 g, 30.0 mmol), phenylboronic acid (5.4 g, 31.5 mmol), potassium carbonate (10.4 g, 75.0 mmol), and tetrakis (triphenylphosphine)palladium (1.15 g, 1.0 mmol) were added to tetrahydrofuran (100 mL) and water (50 mL) in a 500 mL flask, and the mixture was heated and refluxed under a nitrogen flow for 12 hours. This obtained mixture was added to methanol (200 mL), and a solid crystallized therein was filtered, dissolved in monochlorobenzene, filtered with silica gel/Celite, and after removing an appropriate amount of an organic solvent, recrystallized with methanol to obtain Intermediate G-9-131 (7.0 g, yield of 67%).

Calcd. $C_{20}H_{11}ClN_2S$: C, 69.26; H, 3.20; Cl, 10.22; N, 8.08; S, 9.25. found: C, 69.21; H, 3.18; Cl, 10.29; N, 8.10; S, 9.22.

Second Step: Synthesis of Compound B-131

Intermediate G-9-131 (6.94 g, 20.0 mmol), 3,3-biscarbazole H-18 (8.2 g, 20.0 mmol), and sodium hydride (a 60% mineral dispersion, 0.96 g, 24.0 mmol) were added to anhydrous N,N-dimethyl formamide (DMF, 60 mL) in a 250 mL round flask, and the mixture was stirred under a nitrogen flow for 6 hours. This obtained mixture was added to methanol (200 mL), and a solid crystallized therein was filtered, dissolved in dichlorobenzene, filtered with silica gel/Celite, and after removing an appropriate amount of an organic solvent, recrystallized with methanol to obtain Compound B-131 (12.1 g, yield of 84%).

calcd. $C_{50}H_{30}N_4S$: C, 83.54; H, 4.21; N, 7.79; S, 4.46. found: C, 83.53; H, 4.17; N, 7.75; S, 4.54.

Synthesis Example 20: Synthesis of Compound C-55

Compound C-55 was synthesized as more specific examples of a compound according to the present invention through two steps of Reaction Scheme 20.

[Reaction Scheme 20]

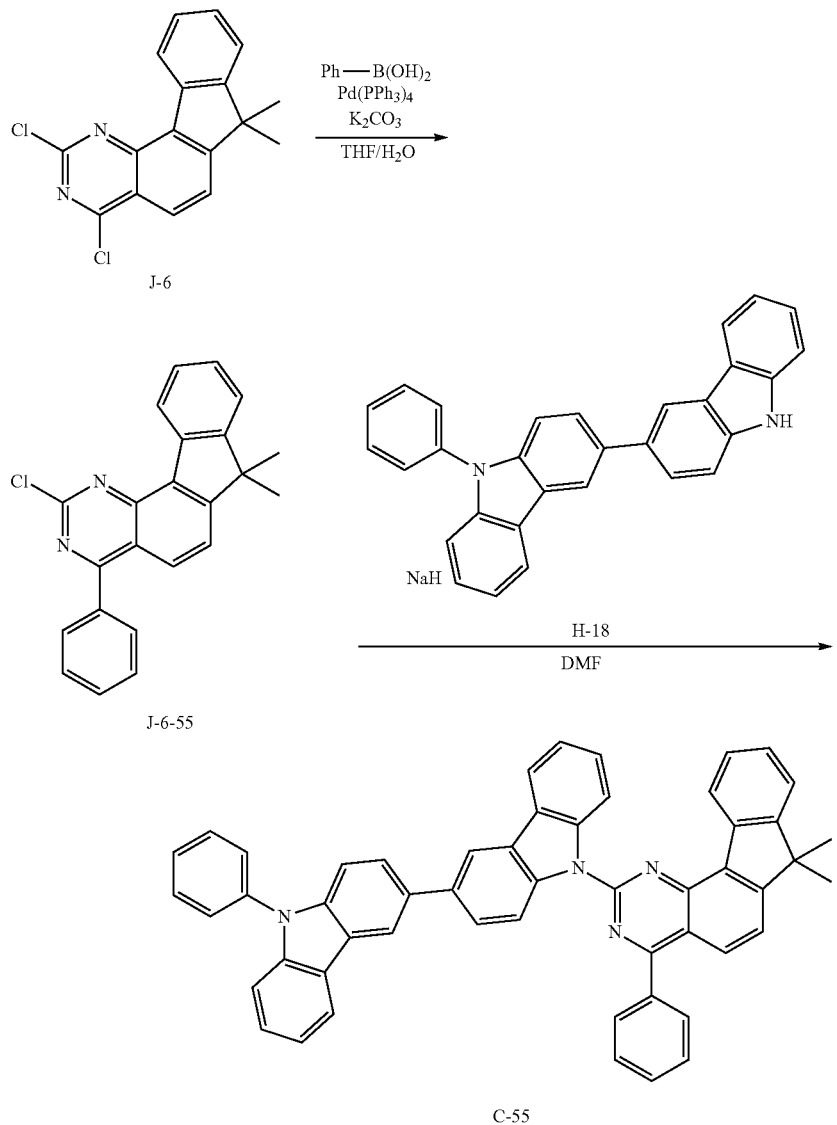

First Step: Synthesis of Intermediate J-6-55

Intermediate J-6 (9.46 g, 30.0 mmol), phenylboronic acid (5.4 g, 31.5 mmol), potassium carbonate (10.4 g, 75.0 mmol), and tetrakis (triphenylphosphine)palladium (1.15 g, 1.0 mmol) were added to tetrahydrofuran (100 mL) and water (50 mL) in a 500 mL flask, and the mixture was heated and refluxed under a nitrogen flow for 12 hours. This obtained mixture was added to methanol (200 mL), and a solid crystallized therein was filtered, dissolved in monochlorobenzene, filtered with silica gel/Celite, and after removing an appropriate amount of an organic solvent, recrystallized with methanol to obtain Intermediate J-6-55 (8.8 g, yield of 82%).

Calcd. $C_{23}H_{17}ClN_2$: C, 77.41; H, 4.80; Cl, 9.94; N, 7.85. found: C, 77.38; H, 4.82; Cl, 9.98; N, 7.82.

Second Step: Synthesis of Compound C-55

Intermediate J-6-55 (7.14 g, 20.0 mmol), 3,3-biscarbazole H-18 (8.2 g, 20.0 mmol), and sodium hydride (a 60% mineral dispersion, 0.96 g, 24.0 mmol) were added to anhydrous N,N-dimethyl formamide (DMF, 60 mL) in a 250 mL round flask, and the mixture was stirred under a nitrogen flow for 6 hours. This obtained mixture was added to methanol (200 mL), and a solid crystallized therein was filtered, dissolved in dichlorobenzene, filtered with silica gel/Celite, and after removing an appropriate amount of an organic solvent, recrystallized with methanol to obtain Compound C-55 (11.7 g, yield of 80%).

calcd. $C_{53}H_{36}N_4$: C, 87.33; H, 4.98; N, 7.69. found: C, 87.35; H, 4.96; N, 7.69.

Synthesis Example 21: Synthesis of Compound D-55

Compound D-55 was synthesized as more specific examples of a compound according to the present invention through two steps of Reaction Scheme 21.

[Reaction Scheme 21]

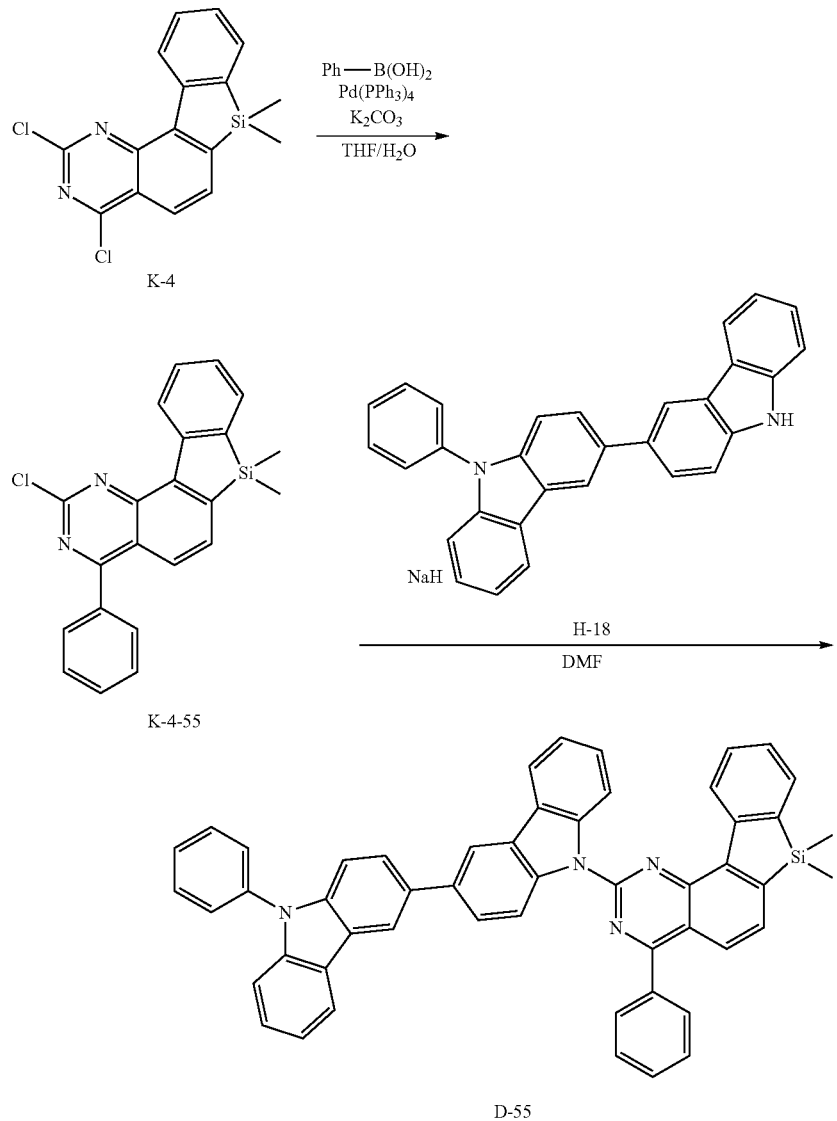

First Step: Synthesis of Intermediate K-4-55

Intermediate K-4 (9.94 g, 30.0 mmol), phenylboronic acid (5.4 g, 31.5 mmol), potassium carbonate (10.4 g, 75.0 mmol), and tetrakis (triphenylphosphine)palladium (1.15 g, 1.0 mmol) were added to tetrahydrofuran (100 mL) and water (50 mL) in a 500 mL flask, and the mixture was heated and refluxed under a nitrogen flow for 12 hours. This obtained mixture was added to methanol (200 mL), and a solid crystallized therein was filtered, dissolved in monochlorobenzene, filtered with silica gel/Celite, and after removing an appropriate amount of an organic solvent, recrystallized with methanol to obtain Intermediate K-4-55 (7.8 g, yield of 70%).

Calcd. $C_{22}H_{17}ClN_2Si$: C, 70.86; H, 4.59; Cl, 9.51; N, 7.51; Si, 7.53. found: C, 70.85; H, 4.58; Cl, 9.47; N, 7.50; Si, 7.59.

Second Step: Synthesis of Compound D-55

Intermediate K-4-55 (7.46 g, 20.0 mmol), 3,3-biscarbazole H-18 (8.2 g, 20.0 mmol), and sodium hydride (a 60% mineral dispersion, 0.96 g, 24.0 mmol) were added to anhydrous N,N-dimethyl formamide (DMF, 60 mL) in a 250 mL round flask, and the mixture was stirred under a nitrogen flow for 6 hours. This obtained mixture was added to methanol (200 mL), and a solid crystallized therein was filtered, dissolved in dichlorobenzene, filtered with silica gel/Celite, and after removing an appropriate amount of an organic solvent, recrystallized with methanol to obtain Compound D-55 (10.7 g, yield of 72%).

calcd. $C_{52}H_{36}N_4Si$: C, 83.84; H, 4.87; N, 7.52; Si, 3.77. found: C, 83.82; H, 4.85; N, 7.53; Si, 3.80.

Comparative Example 1: CBP

A compound represented by Chemical Formula a was synthesized according to the same method as a method described in International Patent Laid Open WO 2013032035.

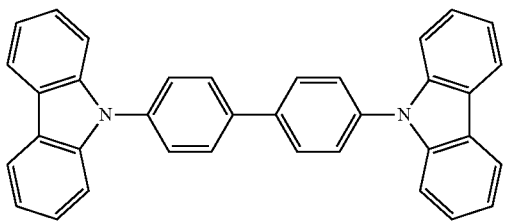 [SMILES: c1ccc2c(c1)c1ccccc1n2-c1ccc(-c2ccc(-n3c4ccccc4c4ccccc43)cc2)cc1]

Comparative Example 2

Compounds E-1, E-2, E-3, E-4, E-5, and E-6 were introduced for energy comparison.

E-1

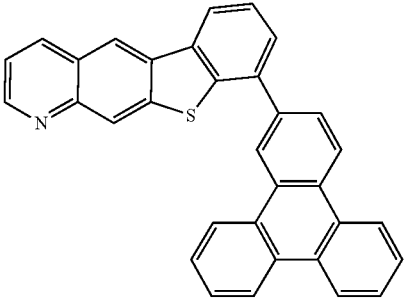

E-2

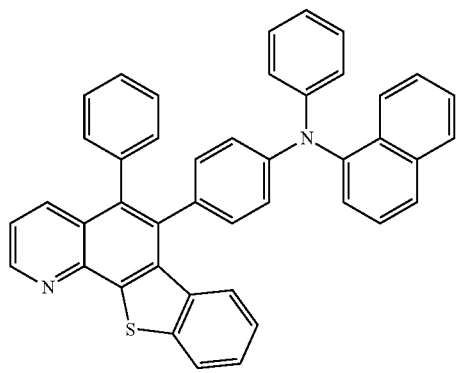

E-3

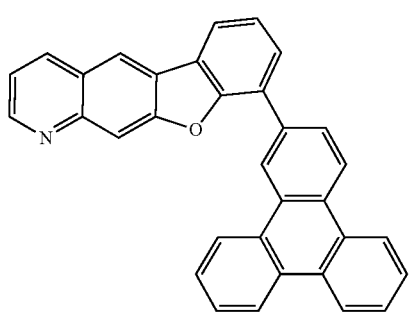

E-4

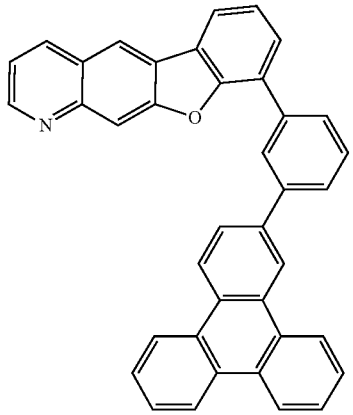

E-5

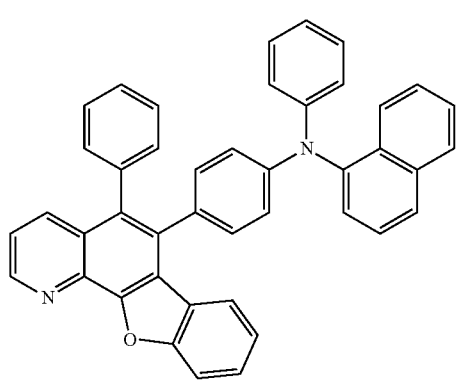

E-6

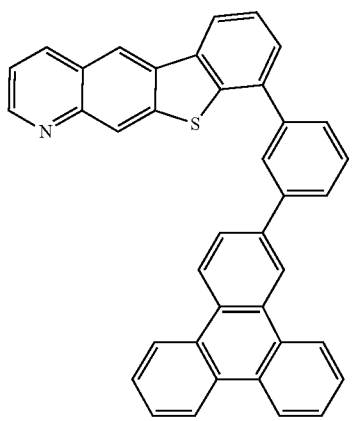

(Simulation Characteristics Comparison of Compounds)

An energy level of each material was calculated in a Gaussian 09 method by using a super computer GAIA (IBM power 6), and the results are shown in Table 1.

TABLE 1

| Compounds | HOST | LUMO (eV) |
| --- | --- | --- |
| Comparative Example 1 | CBP | −1.231 |
| Comparative Example 2 | E-1 | −1.481 |
|  | E-2 | −1.37 |
|  | E-3 | −1.748 |
|  | E-4 | −1.726 |
|  | E-5 | −1.715 |
|  | E-6 | −1.71 |
| Synthesis Example 7 | A-65 | −1.96 |
| Synthesis Example 8 | A-74 | −1.922 |
| Synthesis Example 9 | A-32 | −1.951 |
| Synthesis Example 10 | A-41 | −1.941 |
| Synthesis Example 11 | A-98 | −1.927 |
| Synthesis Example 12 | B-65 | −2.01 |

TABLE 1-continued

| Compounds | HOST | LUMO (eV) |
| --- | --- | --- |
| Synthesis Example 13 | B-74 | −1.961 |
| Synthesis Example 14 | B-52 | −1.989 |
| Synthesis Example 15 | B-48 | −2.013 |
| Synthesis Example 16 | B-60 | −1.945 |
| Synthesis Example 17 | B-32 | −2.018 |
| Synthesis Example 18 | B-98 | −1.937 |
| Synthesis Example 19 | B-131 | −2.105 |
| Synthesis Example 20 | C-55 | −1.966 |
| Synthesis Example 21 | D-55 | −2.052 |

Compounds of Examples of Table 1 should balance an energy level with a dopant in order to be used as a light emitting layer material. LUMO may have an energy level ranging from −1.4 to −2.2 but appropriately from −1.8 to −2.2, considering that the lower the energy level is, the more improved electron transport characteristics are. Referring to the results through a simulation, CBP of Comparison Example 1 showed too a high LUMO energy level, but E-1 to E-6 of Comparison Example 2 also showed a little high LUMO energy level ranging from −1.3 to −1.7. When HOST has a high LUMO energy level in a range of −1.3 to 1.7, HOST may have difficulties in terms of election injection and thus an unbalance between holes and electrons and show low efficiency. On the contrary, when HOST has a low LUMO energy level in a range of −1.8 to −2.2, HOST may have a smooth electron injection and thus sufficient efficiency, and particularly, when used as a red host, the LUMO energy level may be appropriately in a range of −1.9 to −2.0. Synthesis Examples 7 to 21 satisfy the aforementioned condition and thus are expected to increase red host or ETL electron transport capability due to rapid electron injection and transport characteristics and the like and thus lower an operation of an entire device.

Manufacture of Organic Light Emitting Diode

Manufacture of Organic Light Emitting Diode

Example 1

An organic light emitting diode was manufactured using Compound A-65 of Synthesis Example 7 as a host and $(piq)_2Ir(acac)$ as a dopant.

As for an anode, 1000 Å-thick ITO was used, and as for a cathode, 1000 Å-thick aluminum was used. Specifically, illustrating a method of manufacturing the organic light emitting diode, the anode is manufactured by cutting an ITO glass substrate having 15 $\Omega/cm^2$ of a sheet resistance into a size of 50 mm×50 mm×0.7 mm, ultrasonic wave-cleaning them in each acetone, isopropylalcohol, and pure water for 15 minutes respectively, and UV ozone cleaning them for 30 minutes.

On the substrate, an 800 Å-thick hole transport layer was formed by depositing N4,N4'-di(naphthalen-1-yl)-N4,N4'-diphenylbiphenyl-4,4'-diamine (NPB) (80 nm) under a vacuum degree of $650×10^{-7}$ Pa at a deposition rate of 0.1 to 0.3 nm/s. Subsequently, a 300 Å-thick light emitting layer was formed by using A-65 of Synthesis Example 7 under the same vacuum deposition condition, and a phosphorescent dopant of $(piq)_2Ir(acac)$ was simultaneously deposited. Herein, the phosphorescent dopant was deposited to be 3 wt % based on 100 wt % of the total weight of the light emitting layer by adjusting the deposition rate.

On the light emitting layer, a 50 Å-thick hole blocking layer was formed by depositing bis(2-methyl-8-quinolinolate)-4-(phenylphenolato)aluminum (BAlq) under the same vacuum deposition condition. Subsequently, a 200 Å-thick electron transport layer was formed by depositing Alq3 under the same vacuum deposition condition. On the electron transport layer, a cathode is formed by sequentially depositing LiF and Al to manufacture an organic optoelectronic diode.

The organic light emitting diode has a structure of ITO/NPB (80 nm)/EML (A-65 (97 wt %)+$(piq)_2Ir(acac)$ (3 wt %), 30 nm)/Balq (5 nm)/Alq3 20 nm/LiF (1 nm)/Al 100 nm.

Example 2

An organic light emitting diode was manufactured according to the same method as Example 1 except for using Compound A-74 of Synthesis Example 8 instead of Compound A-65 of Synthesis Example 7 as a host material.

Example 3

An organic light emitting diode was manufactured according to the same method as Example 1 except for using Compound A-32 of Synthesis Example 9 instead of Compound A-65 of Synthesis Example 7 as a host material.

Example 4

An organic light emitting diode was manufactured according to the same method as Example 1 except for using Compound A-41 of Synthesis Example 10 instead of Compound A-65 of Synthesis Example 7 as a host material.

Example 5

An organic light emitting diode was manufactured according to the same method as Example 1 except for using Compound A-98 of Synthesis Example 11 instead of Compound A-65 of Synthesis Example 7 as a host material.

Example 6

An organic light emitting diode was manufactured according to the same method as Example 1 except for using Compound B-65 of Synthesis Example 12 instead of Compound A-65 of Synthesis Example 7 as a host material.

Example 7

An organic light emitting diode was manufactured according to the same method as Example 1 except for using Compound B-74 of Synthesis Example 13 instead of Compound A-65 of Synthesis Example 7 as a host material.

Example 8

An organic light emitting diode was manufactured according to the same method as Example 1 except for using Compound B-52 of Synthesis Example 14 instead of Compound A-65 of Synthesis Example 7 as a host material.

Example 9

An organic light emitting diode was manufactured according to the same method as Example 1 except for using Compound B-48 of Synthesis Example 15 instead of Compound A-65 of Synthesis Example 7 as a host material.

Example 10

An organic light emitting diode was manufactured according to the same method as Example 1 except for using Compound B-60 of Synthesis Example 16 instead of Compound A-65 of Synthesis Example 7 as a host material.

Example 11

An organic light emitting diode was manufactured according to the same method as Example 1 except for using Compound B-32 of Synthesis Example 17 instead of Compound A-65 of Synthesis Example 7 as a host material.

Example 12

An organic light emitting diode was manufactured according to the same method as Example 1 except for using Compound B-98 of Synthesis Example 18 instead of Compound A-65 of Synthesis Example 7 as a host material.

Example 13

An organic light emitting diode was manufactured according to the same method as Example 1 except for using Compound B-131 of Synthesis Example 19 instead of Compound A-65 of Synthesis Example 7 as a host material.

Example 14

An organic light emitting diode was manufactured according to the same method as Example 1 except for using Compound C-55 of Synthesis Example 20 instead of Compound A-65 of Synthesis Example 7 as a host material.

Example 15

An organic light emitting diode was manufactured according to the same method as Example 1 except for using Compound D-55 of Synthesis Example 21 instead of Compound A-65 of Synthesis Example 7 as a host material.

Comparative Example 3

An organic light emitting diode was manufactured according to the same method as Example 1 except for using CBP instead of Compound A-65 of Synthesis Example 7 as a host material.

The structures of NPB, BAlq, CBP, and (piq)$_2$Ir(acac) used to manufacture the organic light emitting diodes are as follows.

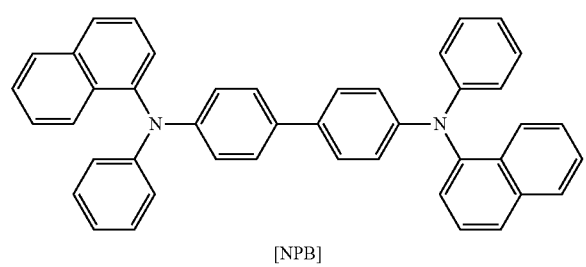

[NPB]

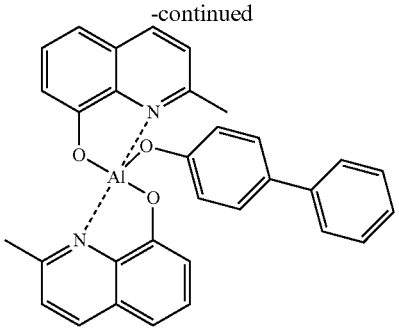

[BAlq]

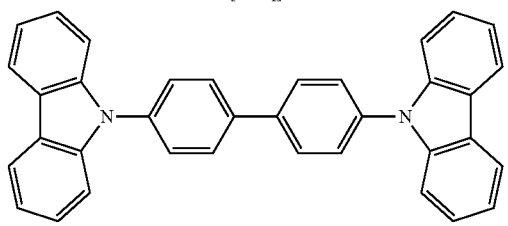

[CBP]

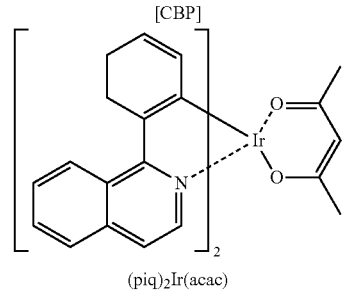

(piq)$_2$Ir(acac)

(Performance Measurement of Organic Light Emitting Diode)

Current density and luminance changes depending on a voltage and luminous efficiency of each organic light emitting diode according to Examples 1, 2, 3, 4, 5, 6, 7, 8, 9, 10, 11, 12, 13, 14, and 15 and Comparative Example 3 were measured.

Specific measurement methods are as follows, and the results are shown in Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

Life-span was obtained by measuring time taken until current efficiency (cd/A) decreased down to 90% while luminance (cd/m$^2$) was maintained at 5000 cd/m$^2$.

TABLE 2

| Nos. | Light emitting layer | Driving voltage (V) | Color (EL color) | Efficiency (cd/A) | 90% life-span (h) at 5000 cd/m² |
|---|---|---|---|---|---|
| Comparative Example 3 | CBP | 6.0 | red | 5.8 | 20 |
| Example 1 | A-65 | 4.1 | red | 17.5 | 130 |
| Example 2 | A-74 | 4.2 | red | 16.3 | 110 |
| Example 3 | A-32 | 4.5 | red | 17.3 | 130 |
| Example 4 | A-41 | 4.1 | red | 16.5 | 100 |
| Example 5 | A-98 | 4.5 | red | 15.6 | 80 |
| Example 6 | B-65 | 4.4 | red | 16.3 | 120 |
| Example 7 | B-74 | 4.3 | red | 17.5 | — |
| Example 8 | B-52 | 4.2 | red | 17.3 | 40 |
| Example 9 | B-48 | 4.2 | red | 16.3 | 45 |
| Example 10 | B-60 | 4.4 | red | 14.9 | 130 |
| Example 11 | B-32 | 4.3 | red | 18.2 | 100 |
| Example 12 | B-98 | 4.6 | red | 15.9 | 70 |
| Example 13 | B-131 | 4.7 | red | 15.4 | 60 |
| Example 14 | C-55 | 5.8 | red | 18.3 | — |
| Example 15 | D-55 | 6.3 | red | 14.8 | — |

As shown in Table 2, the compound of the present invention showed improved characteristics in terms of a driving voltage, luminous efficiency, and/or power efficiency, and a life-span compared with the compound of Comparative Example 3.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

<Description of Symbols>

100: organic light emitting diode  200: organic light emitting diode
105: organic layer
110: cathode
120: anode
130: light emitting layer  230: light emitting layer
140: hole auxiliary layer

The invention claimed is:

1. A compound for an organic optoelectronic diode, the compound represented by a combination of Chemical Formula 1 and Chemical Formula 2:

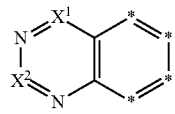

[Chemical Formula 1]

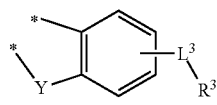

[Chemical Formula 2]

wherein, in Chemical Formulas 1 and 2,
$X^1$ is N or $C-L^1-R^1$,
$X^2$ is N or $C-L^2-R^2$,
Y is O, S, $CR^aR^b$, or $SiR^cR^d$,
$L^1$ to $L^3$ are independently a single bond, C6 to C30 arylene group, a substituted or unsubstituted C2 to C30 heteroarylene group, or a combination thereof,
$R^1$ and $R^2$ are each independently a substituted or unsubstituted C6 to C30 aryl group, a substituted or unsubstituted C2 to C30 heterocyclic group, or a combination thereof,
$R^3$ and $R^a$ to $R^d$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heterocyclic group, a substituted or unsubstituted C6 to C30 arylamine group, a substituted or unsubstituted C1 to C30 alkoxy group, a substituted or unsubstituted C3 to C40 silyl group, a halogen, a halogen-containing group, a cyano group, a hydroxyl group, an amino group, a nitro group, a carboxyl group, a ferrocenyl group, or a combination thereof, and
in Chemical Formula 1, each * represents carbon, and in Chemical Formula 2, each * represents a link to Chemical Formula 1, two adjacent *'s of Chemical Formula 1 being linked by the *'s of Chemical Formula 2 to form a fused ring,
wherein "substituted" refers to replacement of at least one hydrogen by deuterium, a halogen, a hydroxy group, an amino group, C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

2. The compound for an organic optoelectronic diode as claimed in claim 1, wherein Chemical Formula 1 is represented by one of Chemical Formulas 3 to 8:

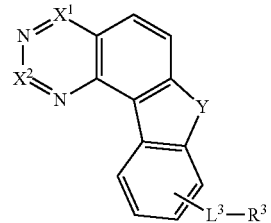

[Chemical Formula 3]

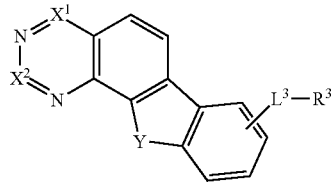

[Chemical Formula 4]

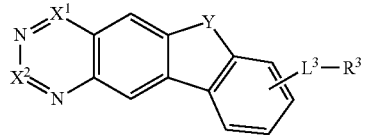

[Chemical Formula 5]

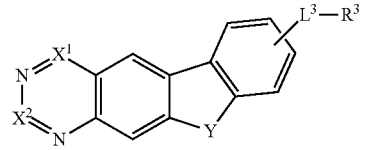

[Chemical Formula 6]

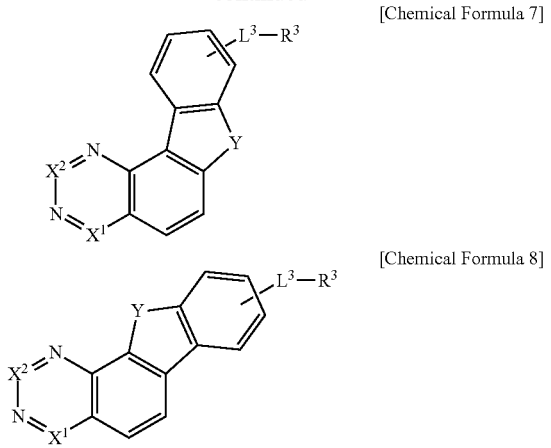

[Chemical Formula 7]

[Chemical Formula 8]

wherein, in Chemical Formulas 3 to 8, $X^1$ is N or $C\text{-}L^1\text{-}R^1$, $X^2$ is N or $C\text{-}L^2\text{-}R^2$, Y is O, S, $CR^aR^b$, or $SiR^cR^d$, $L^1$ to $L^3$ are independently a single bond, C6 to C30 arylene group, a substituted or unsubstituted C2 to C30 heteroarylene group, or a combination thereof, and $R^1$ and $R^2$ are each independently a substituted or unsubstituted C6 to C30 aryl group, a substituted or unsubstituted C2 to C30 heterocyclic group, or a combination thereof, $R^3$ and $R^a$ to $R^d$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heterocyclic group, a substituted or unsubstituted C6 to C30 arylamine group, a substituted or unsubstituted C1 to C30 alkoxy group, a substituted or unsubstituted C3 to C40 silyl group, a halogen, a halogen-containing group, a cyano group, a hydroxyl group, an amino group, a nitro group, a carboxyl group, a ferrocenyl group, or a combination thereof, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

3. The compound for an organic optoelectronic diode as claimed in claim 1, wherein the $X^1$ is $C\text{-}L^1\text{-}R^1$ and $X^2$ is $C\text{-}L^2\text{-}R^2$.

4. The compound for an organic optoelectronic diode as claimed in claim 1, wherein:

the $R^1$ and $R^2$ are independently a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted triphenylene group, a substituted or unsubstituted fluorenyl group, a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted azaphenanthrenyl group, a substituted or unsubstituted phenanthrolinyl group, a substituted or unsubstituted phenazinyl group, a substituted or unsubstituted carbazolyl group, a substituted or unsubstituted dibenzofuranyl group, a substituted or unsubstituted dibenzothiophenyl group, a substituted or unsubstituted benzofuropyrimidinyl group, a substituted or unsubstituted benzothienopyrimidinyl group, a substituted or unsubstituted benzocarbazolyl group, a substituted or unsubstituted benzofurocarbazolyl group, a substituted or unsubstituted indolocarbazolyl group, a substituted or unsubstituted benzofurofluorenyl group, a substituted or unsubstituted benzothienofluorenyl group, a substituted or unsubstituted indolodibenzofuranyl group, a substituted or unsubstituted benzoindolocarbazolyl group, or a combination thereof, and the $R^3$ is hydrogen, deuterium, a substituted or unsubstituted C6 to C30 arylamine group, a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted triphenylene group, a substituted or unsubstituted fluorenyl group, a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted azaphenanthrenyl group, a substituted or unsubstituted phenanthrolinyl group, a substituted or unsubstituted phenazinyl group, a substituted or unsubstituted carbazolyl group, a substituted or unsubstituted dibenzofuranyl group, a substituted or unsubstituted dibenzothiophenyl group, a substituted or unsubstituted benzofuropyrimidinyl group, a substituted or unsubstituted benzothienopyrimidinyl group, a substituted or unsubstituted benzocarbazolyl group, a substituted or unsubstituted benzofurocarbazolyl group, a substituted or unsubstituted indolocarbazolyl group, a substituted or unsubstituted benzofurofluorenyl group, a substituted or unsubstituted benzothienofluorenyl group, a substituted or unsubstituted indolodibenzofuranyl group, a substituted or unsubstituted benzoindolocarbazolyl group, or a combination thereof.

5. The compound for an organic optoelectronic diode as claimed in claim 1, wherein the $R^3$ is hydrogen, and the $R^1$ and $R^2$ are independently selected from groups of Group I:

[Group 1]

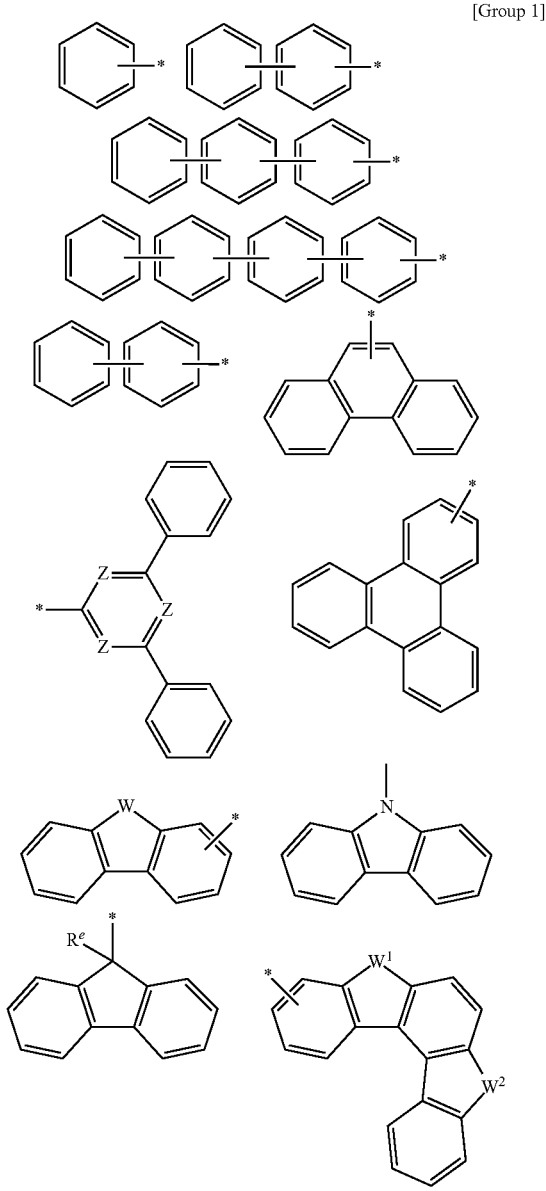

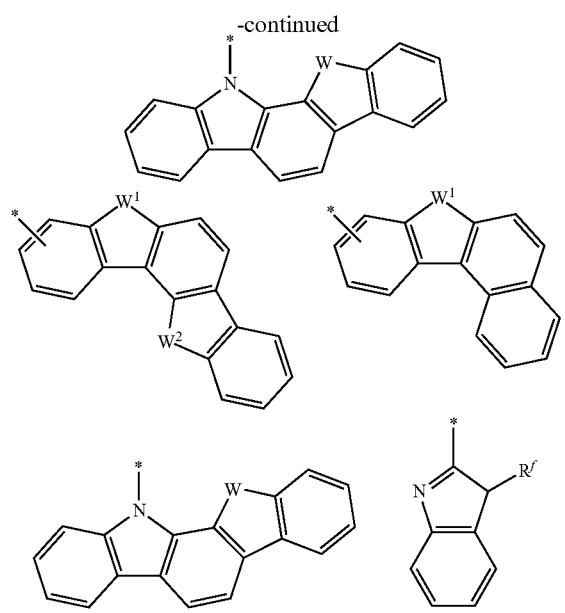

wherein, in Group I,

Z is N, or $CR^g$,

W, $W^1$, and $W^2$ are independently O, S, $NR^h$, $CR^iR^j$, $R^e$ to $R^j$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, or a substituted or unsubstituted C2 to C30 heteroaryl group, and

* is a linking point and is positioned at one element of elements consisting of the functional group.

6. The compound for an organic optoelectronic diode as claimed in claim 5, wherein the substituted or unsubstituted groups of Group I is represented by one of groups of Group I-1:

[Group I-1]

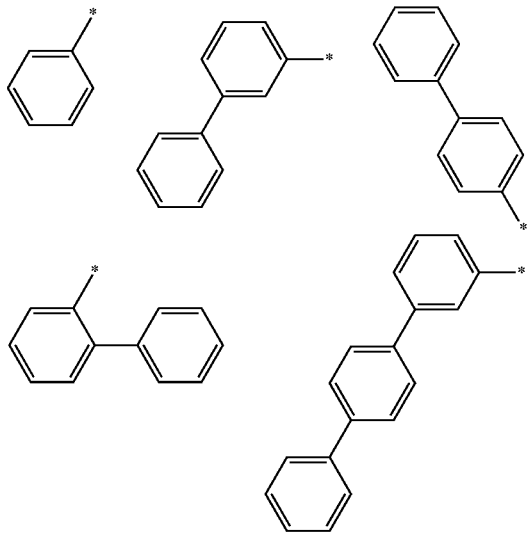

-continued
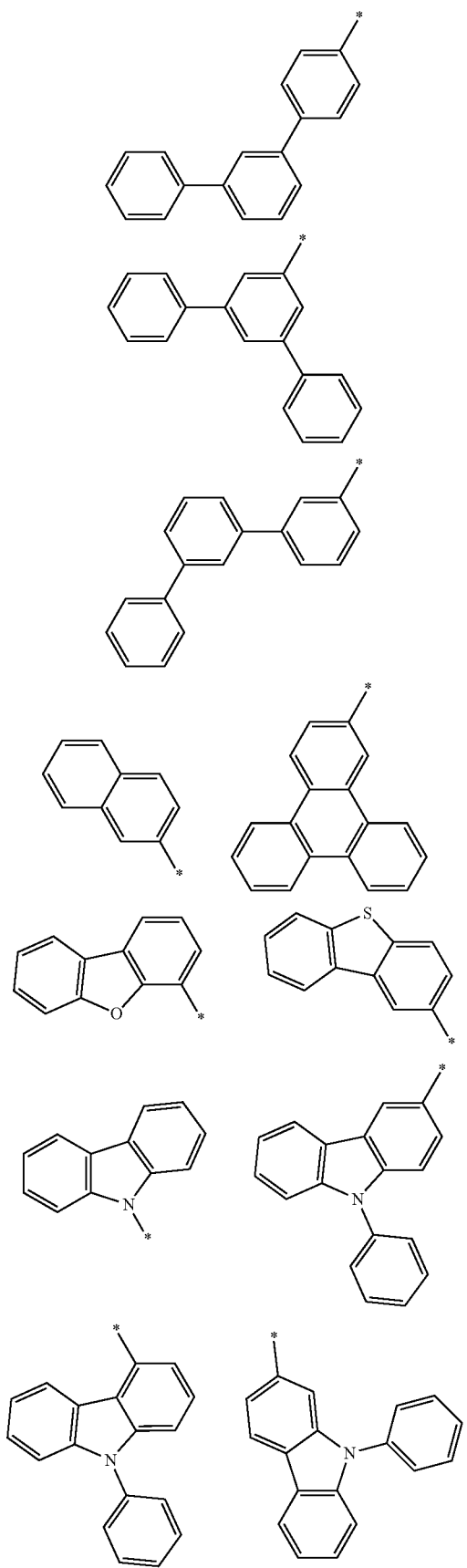
-continued
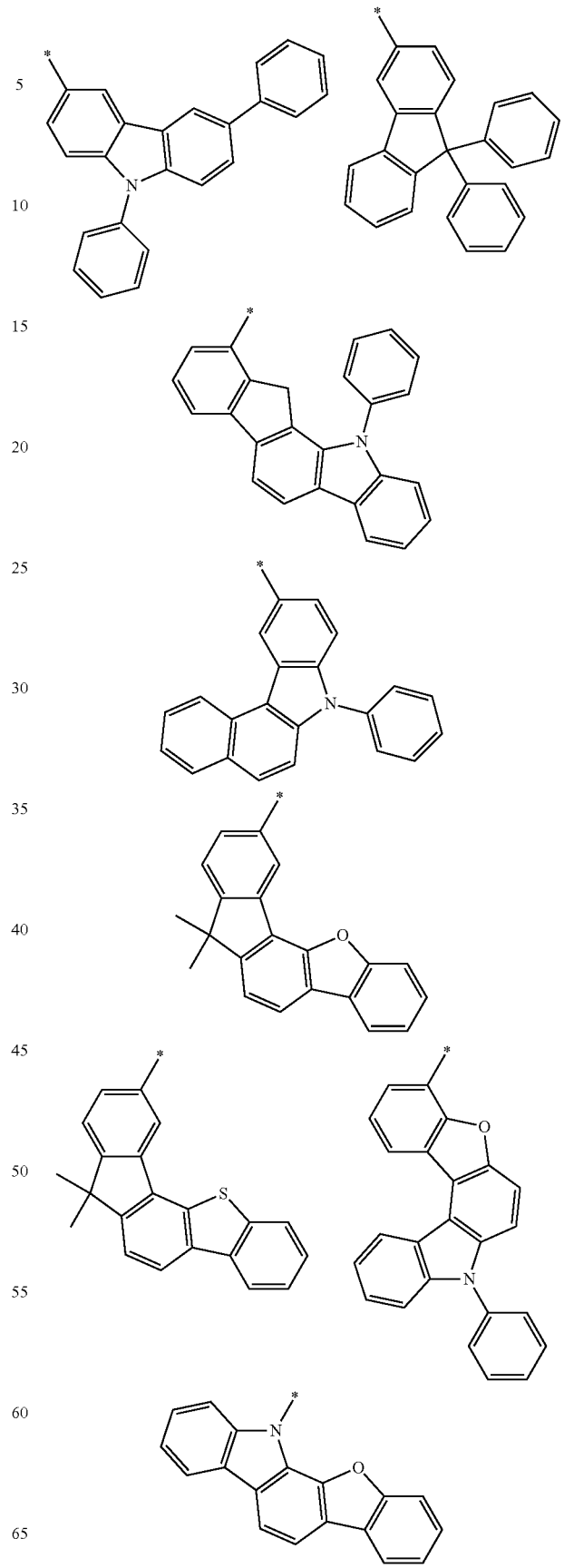

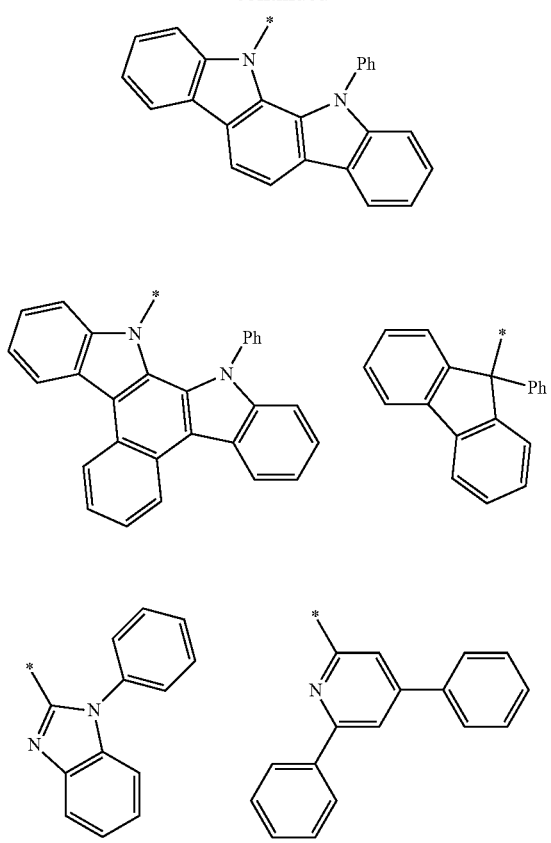

wherein, in Group I-1, * is a linking point.

7. The compound for an organic optoelectronic diode as claimed in claim 1, wherein the $L^1$ to $L^3$ are independently a single bond, a substituted or unsubstituted C6 to C30 arylene group, or a substituted or unsubstituted C2 to C30 heteroarylene group.

8. The compound for an organic optoelectronic diode as claimed in claim 1, wherein the $L^1$ to $L^3$ are independently a single bond, a substituted or unsubstituted phenylene group, a substituted or unsubstituted biphenylene group, a substituted or unsubstituted terphenylene group, a substituted or unsubstituted carbazolylene group, or a substituted or unsubstituted fluorenyl group.

9. The compound for an organic optoelectronic diode as claimed in claim 1, wherein the $L^1$ to $L^3$ are independently a single bond, or a group selected from substituted or unsubstituted groups of Group II:

[Group II]

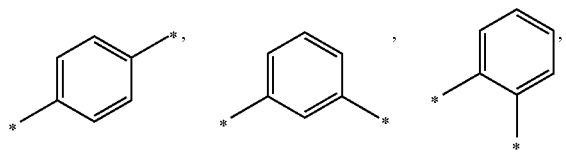

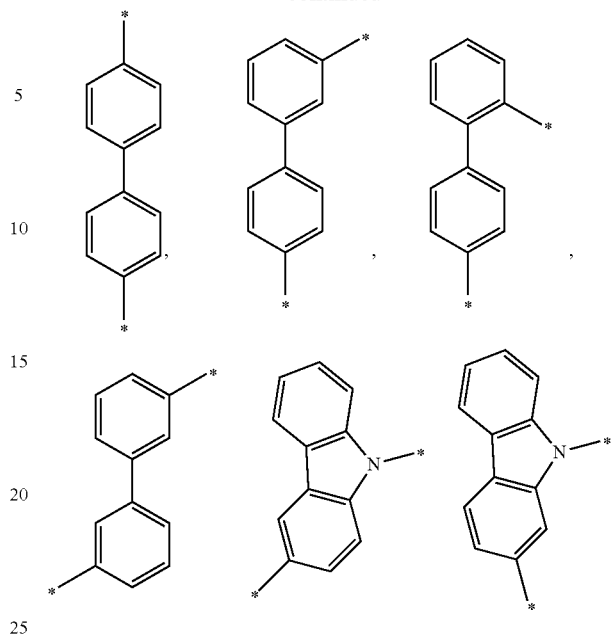

wherein, in Group II,

* is a linking point, wherein "substituted" refers to replacement of at least one hydrogen by deuterium, a C1 to C40 silyl group, a C1 to C30 alkyl group, a C3 to C30 cycloalkyl group, a C2 to C30 heterocycloalkyl group, a C6 to C30 aryl group, carbazolyl group, a dibenzofuranyl group, a dibenzothiophenyl group, or a fluorenyl group.

10. The compound for an organic optoelectronic diode as claimed in claim 2, wherein the $L^1$ to $L^3$ are independently a single bond, a substituted or unsubstituted phenylene group, a substituted or unsubstituted biphenylene group, a substituted or unsubstituted terphenylene group, a substituted or unsubstituted carbazolylene group, or a substituted or unsubstituted fluorenyl group, the $R^3$ is hydrogen, and the $R^1$ and $R^2$ are independently selected from groups of Group I,

[Group 1]

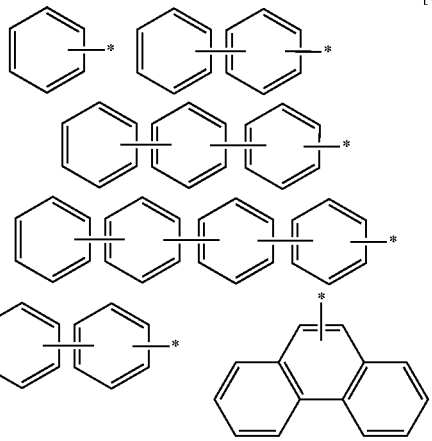

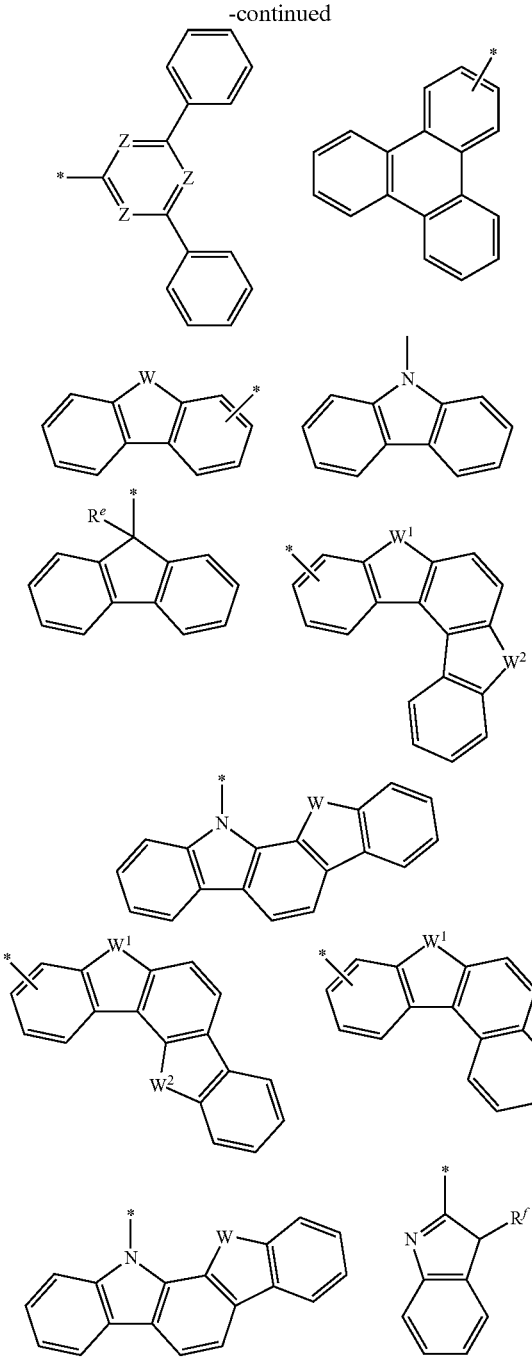

wherein, in Group I,

Z is N, or CR$^g$,

W, W$^1$, and W$^2$ are independently O, S, NR$^h$, or CR$^i$R$^j$,

R$^e$ to R$^j$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, or a substituted or unsubstituted C2 to C30 heteroaryl group, and

* is a linking point and may be positioned at one element of elements consisting of the functional group.

11. An organic optoelectronic diode, comprising:
an anode and a cathode facing each other, and
an organic layer disposed between the anode and the cathode,
wherein the organic layer includes the compound for an organic optoelectronic diode as claimed in claim 1.

12. The organic optoelectronic diode as claimed in claim 11, wherein the organic layer includes a light emitting layer, and
the light emitting layer includes the compound for an organic optoelectronic diode.

13. The organic optoelectronic diode as claimed in claim 12, wherein the compound for an organic optoelectronic diode is included as a host of the light emitting layer.

14. The organic optoelectronic diode as claimed in claim 11, wherein the organic layer includes at least one auxiliary layer selected from a hole injection layer, a hole transport layer, a hole transport auxiliary layer, an electron transport auxiliary layer, an electron transport layer, and an electron injection layer, and
the auxiliary layer includes the compound for an organic optoelectronic diode.

15. A display device comprising the organic optoelectronic diode as claimed in claim 11.

16. The compound for an organic optoelectronic diode as claimed in claim 1, wherein the compound is one of the following compounds:

A-65
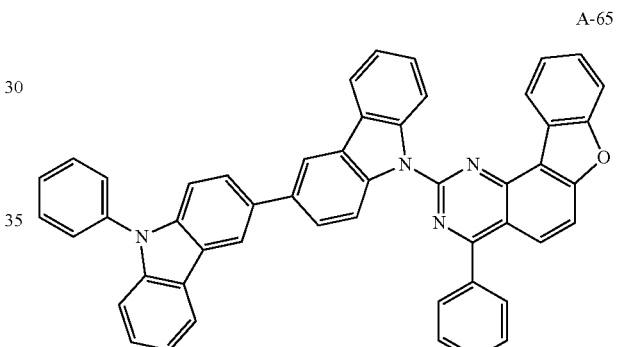

A-74
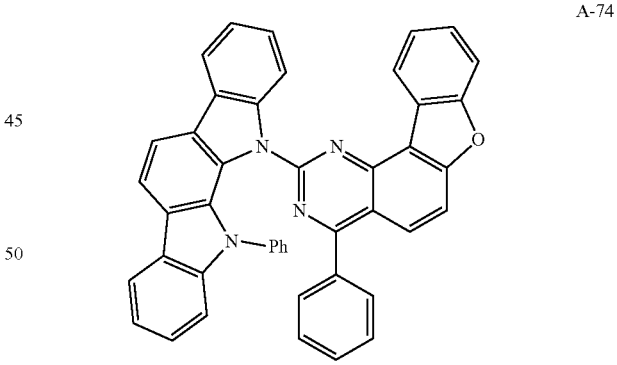

A-32
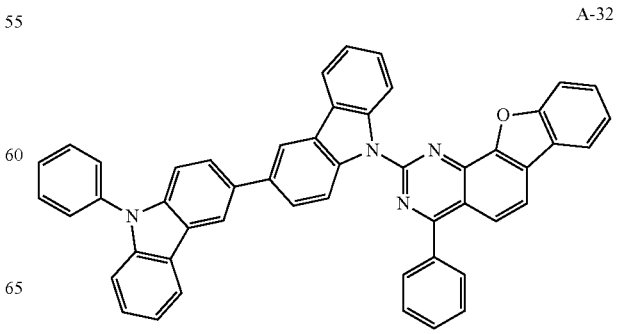

A-41
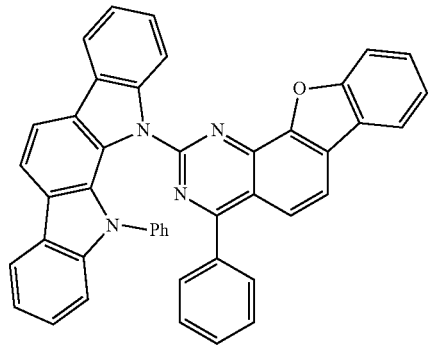
B-52
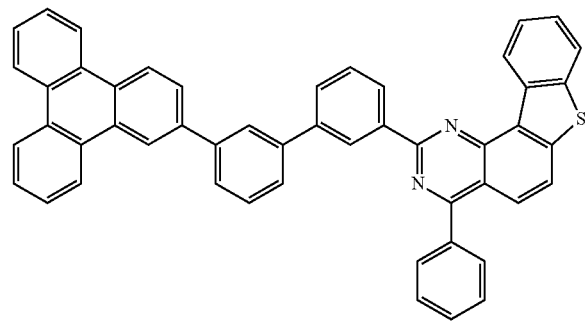
A-98
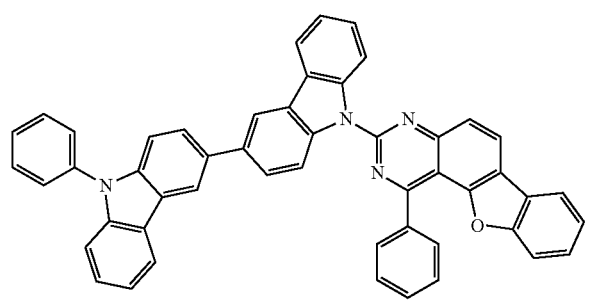
B-48
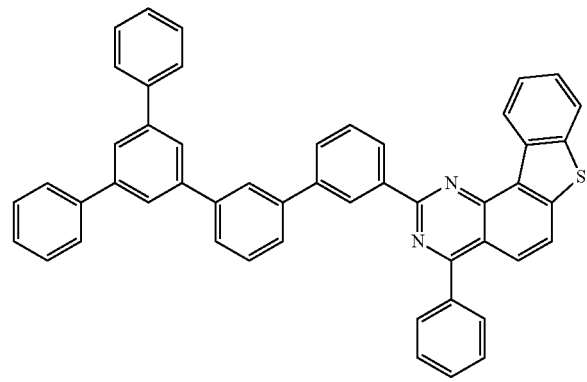
B-65
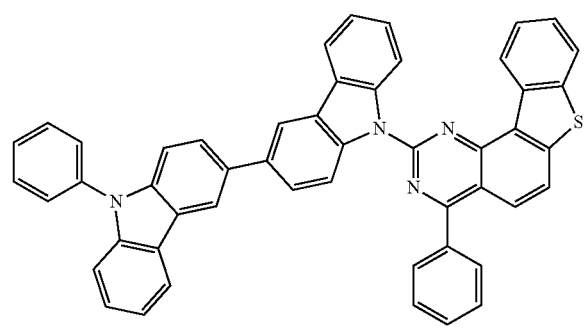
B-60
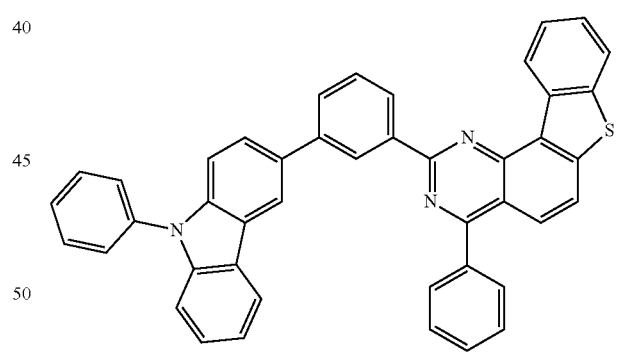
B-74
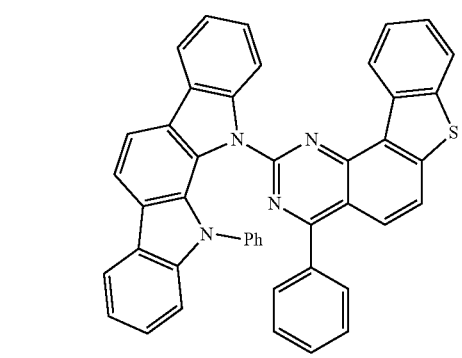
B-32
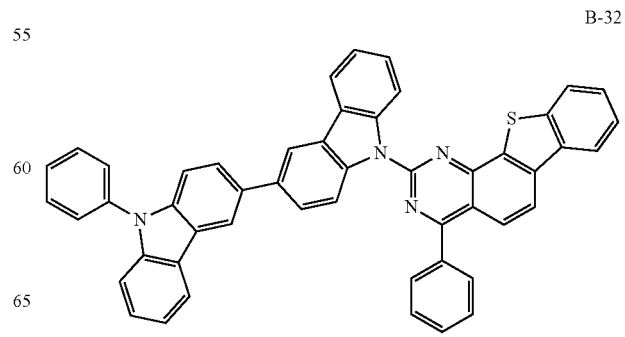

-continued
B-98
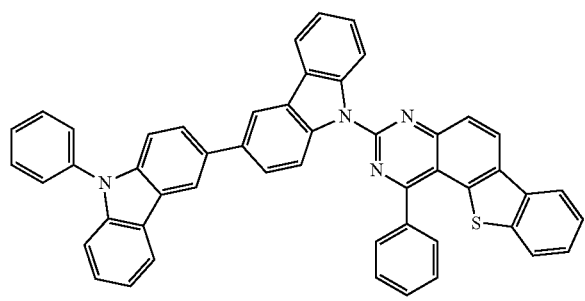
B-131
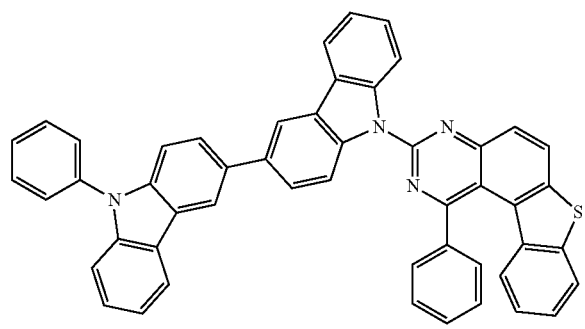
-continued
C-55
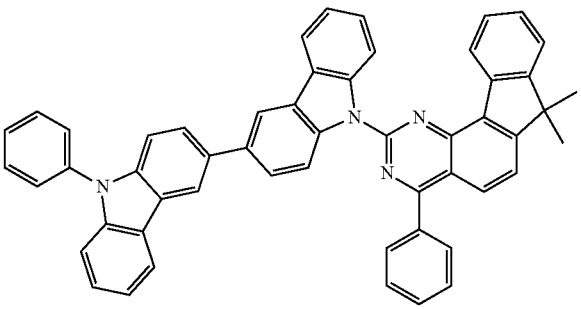
D-55
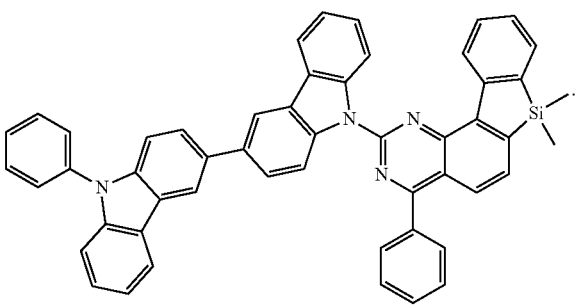
* * * * *